US007365196B2

(12) United States Patent
Belanger et al.

(10) Patent No.: US 7,365,196 B2
(45) Date of Patent: Apr. 29, 2008

(54) SULPHONAMIDO-SUBSTITUTED BRIDGED BICYCLOALKYL DERIVATIVES

(75) Inventors: Patrice Charles Belanger, Dollard-des-Ormeaux (CA); Ian James Collins, Ware (GB); Joanne Claire Hannam, Stanstead (GB); Timothy Harrison, Great Dunmow (GB); Stephen John Lewis, East Barnet (GB); Andrew Madin, Sawbridgeworth (GB); Edward Giles McIver, Bishops Stortford (GB); Alan John Nadin, Sawbridgeworth (GB); Joseph George Neduvelil, East Barnet (GB); Mark Steven Shearman, Bishops Stortford (GB); Adrian Leonard Smith, Simi Valley, CA (US); Timothy Jason Sparey, London (GB); Graeme Irvine Stevenson, Saffron Walden (GB); Martin Richard Teall, Bishops Stortford (GB)

(73) Assignees: Merck Sharp & Dohme Ltd., Hoddesdom, Hertfordshire (GB); Merck Frosst Canada & Co., Kirkland, Quebec (CA)

( * ) Notice: Subject to any disclaimer, the term of this patent is extended or adjusted under 35 U.S.C. 154(b) by 779 days.

(21) Appl. No.: 10/239,233

(22) PCT Filed: Mar. 15, 2001

(86) PCT No.: PCT/GB01/01154

§ 371 (c)(1),
(2), (4) Date: Feb. 5, 2003

(87) PCT Pub. No.: WO01/70677

PCT Pub. Date: Sep. 27, 2001

(65) Prior Publication Data

US 2004/0029862 A1 Feb. 12, 2004

(30) Foreign Application Priority Data

Mar. 20, 2000 (GB) ............................. 0006717.3
Nov. 2, 2000 (GB) ............................. 0026827.6

(51) Int. Cl.
C07D 413/14 (2006.01)
C07D 413/12 (2006.01)
C07D 213/71 (2006.01)
C07D 213/52 (2006.01)
C07D 333/34 (2006.01)
C07D 409/14 (2006.01)
C07D 409/12 (2006.01)
C07D 249/12 (2006.01)
C07D 233/84 (2006.01)
C07D 207/48 (2006.01)
C07D 277/16 (2006.01)
C07D 307/64 (2006.01)
A61P 25/28 (2006.01)

(52) U.S. Cl. .................... 544/131; 549/59; 549/65; 549/75; 549/366; 549/469; 549/471; 549/479; 564/90; 564/91; 564/92; 564/93; 564/95; 564/96; 564/97; 564/98; 564/99; 560/10; 548/145; 548/186; 548/213; 548/266.2; 548/269.4; 548/302.4; 548/315.1; 548/323.5; 548/346.1; 548/538; 548/569; 546/16; 546/172; 546/213; 546/203; 546/232; 546/269.4; 546/280.1; 546/285; 544/380; 544/133; 544/146; 544/154; 544/234; 544/350; 544/364; 544/379; 540/509; 540/520; 540/579; 540/581; 540/593

(58) Field of Classification Search ............. 514/232.8, 514/295, 248, 211.12, 211.09, 239.2, 325, 514/428, 237.8, 340, 252.12, 398; 546/93, 546/203, 269.4, 16, 172, 213, 232, 280.1, 546/285; 540/593, 579, 509, 520, 581; 548/569, 548/346.1, 145, 186, 213, 266.2, 269.4, 302.4, 548/315.1, 323.5, 538; 544/154, 380, 234, 544/131, 133, 146, 350, 364, 379; 560/10; 564/90, 91, 92, 93, 95, 96, 97, 98, 99; 549/59, 549/65, 75, 366, 469, 471, 479

See application file for complete search history.

(56) References Cited

U.S. PATENT DOCUMENTS 3,406,184 A 10/1968 Raasch
3,715,362 A 2/1973 Dominianni
5,168,101 A * 12/1992 Arai et al. ................... 514/530

(Continued)

FOREIGN PATENT DOCUMENTS

WO WO 98/38156 9/1998

OTHER PUBLICATIONS

Solvolysis of 7-anti-bromo-2-exo-benzensulfonamidobicyclo(2.2.1)heptane. An example of solvolytic ring opening. Zalkow et al., Journal of the American Chemical Society, 1964, vol. 86(19), pp. 4208-4209.*
The structure and reactions of the 1:1 adduct of benzenesulfonyl azide and bicyclo(2.2.1)heptene. Franz et al., Research Dept. Organic Chemical Division, Monsanto Co, 1963, vol. 29, pp. 2922-2927.*
Bridged ring compounds. XIII. The reaction of N,N-dibromobenzenesulfonamide with bicyclo(2.2.1)heptene, bicyclo(2.2.2)octene, and endo-bicyclo(2.2.1)-5-heptene-2,3-dicarboxylic anhydride. Oehschlager et al., Department of Chem, Oklahoma, 1965.*

(Continued)

Primary Examiner—Mark L Berch
(74) Attorney, Agent, or Firm—William Krovatin; John C. Todaro

(57) ABSTRACT

A class of compounds is disclosed, comprising sulphonamido-substituted bridged bicycloalkyl structures. The compounds are inhibitors of gamma-secretase, and hence are useful in the treatment of and/or prevention of Alzheimer's disease.

10 Claims, No Drawings

U.S. PATENT DOCUMENTS

| | | | | |
|---|---|---|---|---|
| 5,663,417 | A | * | 9/1997 | Hamanaka et al. ......... 560/121 |
| 5,703,129 | A | | 12/1997 | Felsenstein et al. |
| 5,994,398 | A | * | 11/1999 | John et al. ................. 514/485 |
| 6,172,113 | B1 | * | 1/2001 | Ohtani et al. ............... 514/562 |
| 6,559,162 | B2 | * | 5/2003 | Bjorsne et al. ............. 514/299 |
| 6,610,734 | B2 | * | 8/2003 | Kreft et al. ................. 514/445 |
| 6,713,650 | B2 | * | 3/2004 | Ibrahim et al. ............. 564/188 |
| 6,852,761 | B2 | * | 2/2005 | South et al. ................ 514/637 |
| 7,138,400 | B2 | * | 11/2006 | Collins et al. ........... 514/234.2 |
| 7,144,910 | B2 | * | 12/2006 | Madin et al. ............... 514/406 |
| 7,183,303 | B2 | * | 2/2007 | Castro Pineiro et al. .... 514/372 |
| 7,205,434 | B2 | * | 4/2007 | Hannam et al. ............. 564/80 |
| 2004/0006050 | A1 | * | 1/2004 | Kreft et al. ................. 514/150 |
| 2005/0245573 | A1 | * | 11/2005 | Neitzel et al. .............. 514/317 |

OTHER PUBLICATIONS

Charles Glabe, Science 314, 602-603 (Oct. 27, 2006).*
Zalkow, Tet. Letters 26(10) 2149 (1975).*
J. E. Franz, et al.: *Journal of Organic Chemistry*, vol. 29, No. 10, Oct. 1964, pp. 2922-2927.
R. Huisgen, et al.: *Chemische Berichte*, vol. 98, No. 12, Dec. 1965, pp. 3992-4013.
S. Itsuno, et al.: *Journal of the Chemical Society, Perkin Transactions 1*, No. 10, Jul. 15, 1999 pp. 2011-2016.
M. Narisada, et al.: *Journal of Medicinal Chemistry*, vol. 31, No. 9, Sep. 1988, pp. 1847-1854.
G. M. Rishton, et al.: *Journal of Medicinal Chemistry*, vol. 43, No. 12, May 23, 2000, pp. 2297-2299.
K. B. Sharpless, et al.: *Journal of Organic Chemistry*, vol. 41, No. 1, Jan. 9, 1976, pp. 176-177.
Y. Yamaguchi, et al.: *Xenobiotica*, vol. 26, No. 6, Jun. 1996, pp. 613-626.
L. H. Zalkow, et al.: *Journal of the American Chemical Society*, vo. 86, No. 19, Oct. 5, 1964.
L. H. Zalkow, et al.: *Journal of Organic Chemistry*, vol. 28, No. 12, Dec. 1963, pp. 3303-3309.

* cited by examiner

SULPHONAMIDO-SUBSTITUTED BRIDGED BICYCLOALKYL DERIVATIVES

CROSS REFERENCE TO RELATED APPLICATIONS

This application is a U.S. National Phase application under 35 U.S.C. § 371 of PCT Application No. PCT/GB01/01154, filed Mar. 15, 2001, which claims priority under 35 U.S.C. § 119 from GB Application No. 0006717.3, filed Mar. 20, 2000, and GB Application No. 0026827.6, filed Nov. 2, 2000.

The present invention relates to a novel class of compounds their salts, pharmaceutical compositions comprising them, processes for making them and their use in therapy of the human body. In particular, the invention relates to compounds which are inhibitors of γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although their exact role in the onset and progress of AD is not fully understood, it is generally accepted that suppressing or attenuating their formation is a likely means of alleviating or preventing the condition. (See, for example, ID *research alert* 1996 1(2):1-7; ID *research alert* 1997 2(1):1-8; Current Opinion in CPNS Investigational Drugs 1999 1(3):327-332; and Chemistry in Britain, Jan. 2000, 28-31.)

Aβ is a peptide comprising 39-43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_S$). Proteases which release APP and its fragments from the membrane are termed "secretases". Most $APP_S$ is released by a putative α-secretase which cleaves within the Aβ domain (between residues $Lys^{16}$ and $Leu^{17}$) to release α-$APP_S$ and precludes the release of intact Aβ. A minor portion of $APP_S$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

A limited number of phenylsulphonylamino-substituted bridged bicycloalkane derivatives are disclosed in a non-pharmaceutical context in *J. Org. Chem.*, 30(12), 4205-11 (1965).

The present invention provides a novel class of non-peptidic compounds which are useful in the treatment or prevention of AD by inhibiting the activity of the putative γ-secretase, thus arresting the production of Aβ and preventing the formation of insoluble plaques.

According to the invention, there is provided a pharmaceutical composition comprising, in a pharmaceutically acceptable carrier, a therapeutically effective amount of one or more compounds of formula I:

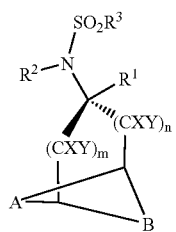

wherein:

A and B are independently selected from $-(CXY)_p-$; $-(CXY)_qCY=CY(CXY)_r-$; $-(CXY)_xNR^{13}(CXY)_y-$;

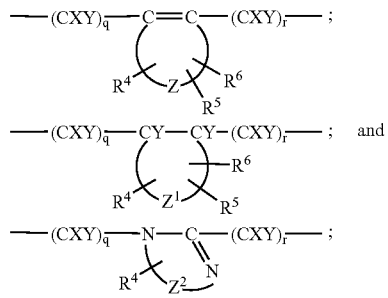

X represents halogen, $R^9$, $-OR^9$, $-SR^9$, $-S(O)_tR^{10}$ where t is 1 or 2, $-OSO_2R^9$, $-N(R^9)_2$, $-COR^9$, $-CO_2R^9$, $-OCOR^{10}$, $-OCO_2R^{11}$, $-CON(R^9)_2$, $-SO_2N(R^9)_2$, $-OSO_2N(R^9)_2$, $-NR^9COR^{10}$, $-NR^9CO_2R^{10}$ or $-NR^9SO_2R^{10}$;

Y represents H or $C_{1-6}$alkyl;

or X and Y together represent $=O$, $=S$, $=N-OR^{11}$ or $=CHR^{11}$;

provided neither A nor B comprises more than one $-CXY$-moiety which is other than $-CH_2-$;

Z completes an aromatic ring system of 5 to 10 atoms, of which 0 to 3 are selected from nitrogen, oxygen and sulfur and the remainder are carbon, or Z completes a non-aromatic ring system of 5 to 10 atoms, of which 0 to 3 are independently selected from oxygen, nitrogen and sulphur and the remainder are carbon;

$Z^1$ completes a non-aromatic ring system of 5 to 10 atoms, of which 0 to 3 are independently selected from oxygen, nitrogen and sulphur and the remainder are carbon;

$Z^2$ completes a 5- or 6-membered heteroaryl ring;

m and n are independently 1 or 0;

p is an integer from 1-6;

q and r are independently 0, 1 or 2;

x and y are independently 0, 1 or 2;

provided that when m=n=0, at least one of A and B comprises a chain of 2 or more atoms, such that the ring completed by A and B contains at least 5 atoms;

$R^1$ represents H, $C_{1-4}$alkyl, or $C_{2-4}$alkenyl;

$R^2$ represents H, $C_{1-6}$alkyl, $C_{6-10}$aryl, $C_{6-10}$-aryl$C_{1-6}$alkyl, $C_{3-6}$cycloalkyl or $C_{2-6}$acyl which is optionally substituted with a carboxylic acid group or with an amino group;

$R^3$ represents $C_{1-16}$alkyl, $C_{3-10}$cycloalkyl, $C_{2-16}$alkenyl, $C_{2-16}$alkynyl, $C_{6-10}$aryl$C_{1-6}$alkyl, heteroaryl$C_{1-6}$alkyl, $C_{6-10}$aryl$C_{2-6}$alkenyl, heteroaryl$C_{2-6}$alkenyl, $C_{6-10}$aryl, bi($C_{6-10}$aryl), heteroaryl, bi(heteroaryl) or heterocyclyl; wherein the alkyl, cycloalkyl, alkenyl and alkynyl groups represented by $R^3$ or forming part of a group represented by $R^3$ optionally bear up to 3 substituents independently selected from halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkyl$NR^7COR^8$, —$NR^7CO_2R^8$ and —$NR^7SO_2R^8$; and the aryl, heteroaryl and heterocyclic groups represented by $R^3$ or forming part of a group represented by $R^3$ optionally bear up to 5 substituents independently selected from $R^8$, halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkyl$NR^7COR^8$, —$NR^7CO_2R^8$ and —$NR^7SO_2R^8$;

$R^4$, $R^5$ and $R^6$ independently represent $R^9$, halogen, CN, $NO_2$, —$OR^9$, —$SR^9$, $S(O)_tR_{10}$ where t is 1 or 2, —$N(R^9)_2$, —$COR^9$, —$CO_2R^9$, —$OCOR^{10}$, —$CON(R^9)_2$, —$SO_2N(R^9)_2$, —$NR^9COR^{10}$, —$NR^9CO_2R^{10}$, —$NR^9SO_2R^{10}$, —CH═CHCH$_2$N($R^{16}$)$_2$, —CH$_2$OR$^{10}$, —CH$_2$N($R^{16}$)$_2$, —NHCOCH$_2$OR$^{10}$ or —NHCOCH$_2$N($R^{16}$)$_2$;

$R^7$ represents H or $R^8$; or two $R^7$ groups together with a nitrogen atom to which they are mutually attached may complete a pyrrolidine, piperidine, piperazine or morpholine ring;

$R^8$ represents $C_{1-10}$alkyl, perfluoro$C_{1-6}$alkyl, $C_{3-10}$cycloalkyl, $C_{3-6}$cycloalkyl$CO_{1-6}$alkyl, $C_{2-10}$alkenyl, $C_{2-10}$alkynyl, Ar or —$CO_{1-6}$alkylAr;

$R^9$ represents H or $R^{10}$; or two $R^9$ groups together with a nitrogen atom to which they are mutually attached may complete a pyrrolidine, piperidine, piperazine or morpholine ring which is optionally substituted by $R^{12}$, —$COR^{12}$ or —$SO_2R^{12}$;

$R^{10}$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, $C_{6-10}$aryl$C_{2-6}$alkenyl, or heteroaryl$C_{2-6}$alkenyl, wherein the alkyl, cycloalkyl, alkenyl and alkynyl groups optionally bear one substituent selected from halogen, $CF_3$, $NO_2$, CN, —$OR^{11}$, —$SR^{11}$, —$SO_2R^{12}$, —$COR^{11}$, —$CO_2R^{11}$, —$ON(R^{11})_2$, —$OCOR^{12}$, —$N(R^{11})_2$ and —$NR^{11}COR^{12}$; and the aryl, heteroaryl and heterocyclic groups optionally bear up to 3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^{11}$ represents H or $R^{12}$;

$R^{12}$ represents $C_{1-6}$alkyl, perfluoro$C_{1-6}$alkyl, $C_{3-7}$cycloalkyl, $C_{2-6}$alkenyl, $C_{2-6}$alkynyl, Ar, —$C_{1-6}$alkylAr or ArO$C_{1-6}$alkyl; or two $R^{12}$ groups together with a nitrogen atom to which they are mutually attached may complete a heterocyclic ring system of 3-10 atoms, 0-2 of which (in addition to said nitrogen atom) are selected from O, N and S, said ring system bearing 0-2 substituents selected from halogen, CN, $NO_2$, $R^{12}$, $OR^{11}$, $NHR^{11}$, and $COR^{11}$.

$R^{13}$ represents $R^9$, —$COR^{10}$, —$CO_2R^{10}$, —$SO_2R^{10}$, —$CON(R^9)_2$ or —$SO_2N(R^9)_2$;

each $R^{16}$ independently represents H or $R^{10}$, or two $R^{16}$ groups together with the nitrogen to which they are mutually attached complete a mono- or bicyclic heterocyclic ring system of 5-10 ring atoms selected from C, N, O and S, said ring system optionally having an additional aryl or heteroaryl ring fused thereto, said heterocyclic system and/or additional fused ring bearing 0-3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy;

"heterocyclyl" at every occurrence thereof means a cyclic or polycyclic system of up to 10 ring atoms selected from C, N, 0 and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom is other than C;

or a pharmaceutically acceptable salt thereof

In a subset of the compounds according to formula I, $R^{12}$ represents $C_{1-6}$alkyl, perfluoro$C_{1-6}$alkyl, $C_{3-7}$cycloalkyl, $C_{2-6}$alkenyl, $C_{2-6}$alkynyl, Ar, —$C_{1-6}$alkylAr or ArO$C_{1-6}$alkyl.

In a further subset of the compounds of formula I,

A represents —(CXY)$_p$—; —(CX)$_q$CY═CY(CXY)$_r$—;

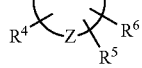

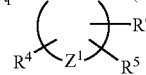

B represents —(CXY)$_s$— or —(CXY)$_q$CY═CY(CXY)$_r$—;

X represents halogen, $R^9$, —$OR^9$, —$SR^9$, —$S(O)_tR^{10}$ where t is 1 or 2, —$N(R^9)_2$, —$COR^9$, —$CO_2R^9$, —$OCOR^{10}$, —$CON(R^9)_2$, —$SO_2N(R^9)_2$, —$NR^9COR^{10}$, —$NR^9CO_2R^{10}$ or —$NR^9SO_2R^{10}$;

Y represents H or $C_{1-6}$alkyl;

or X and Y together represent ═O or ═CH$_2$;

provided neither A nor B comprises more than one —CXY— moiety which is other than —CH$_2$—;

Z completes an aromatic ring system of 6 to 10 atoms, of which 0 to 2 are nitrogen and the remainder are carbon, or Z completes a non-aromatic ring system of 5 to 10 atoms, of which 0 to 3 are independently selected from oxygen, nitrogen and sulphur and the remainder are carbon;

$Z^1$ completes a non-aromatic ring system of 5 to 10 atoms, of which 0 to 3 are independently selected from oxygen, nitrogen and sulphur and the remainder are carbon;

m and n are independently 1 or 0;

p is an integer from 1-6;

q and r are independently 0, 1 or 2;
s is an integer from 1-6;

provided that when m=n=0, at least one of p and s is greater than 1;

$R^1$ represents H or $C_{1-4}$alkyl;

$R^2$ represents H, $C_{1-6}$alkyl, $C_{6-10}$aryl, $C_{6-10}$aryl$C_{1-6}$alkyl or $C_{3-6}$cycloalkyl;

$R^3$ represents $C_{1-16}$alkyl, $C_{3-10}$cycloalkyl, $C_{2-16}$alkenyl, $C_{2-16}$alkynyl, $C_{6-10}$aryl$C_{1-6}$alkyl, heteroaryl$C_{1-6}$alkyl, $C_{6-10}$aryl, bi($C_{6-10}$aryl), heteroaryl, bi(heteroaryl) or heterocyclyl; wherein the alkyl, cycloalkyl, alkenyl and alkynyl groups represented by $R^3$ or forming part of a-group represented by $R^3$ optionally bear up to 3 substituents independently selected from halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkylNR$^7$COR$^8$, —$NR^7CO_2R^8$ and —$NR^7SO_2R^8$; and the aryl, heteroaryl and heterocyclic groups represented by $R^3$ or forming part of a group represented by $R^3$ optionally bear up to 5 substituents independently selected from $R^8$, halogen, CN, $NO_2$, —$OR^7$, —$SR^7$, —$S(O)R^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkylNR$^7$COR$^8$, —$NR^7CO_2R^8$ and —$NR^7SO_2R^8$;

$R^4$, $R^5$ and $R^6$ are independently $R^9$, halogen, CN, $NO_2$, —$OR^9$, —$SR^9$, —$S(O)_tR^{10}$ where t is 1 or 2, —$N(R^9)_2$, —$COR^9$, —$CO_2R^9$, —$OCOR^{10}$, —$CON(R^9)_2$, —$SO_2N(R^9)_2$, —$NR^9COR^{10}$, —$NR^9CO_2R^{10}$ or —$NR^9SO_2R^{10}$;

$R^7$ is H or $R^8$; or two $R^7$ groups together with a nitrogen atom to which they are mutually attached may complete a piperidine, piperazine or morpholine ring;

$R^8$ is $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, Ar or —$C_{1-6}$alkylAr;

$R^9$ is H or $R^{10}$; or two $R^9$ groups together with a nitrogen atom to which they are mutually attached may complete a piperidine, piperazine or morpholine ring which is optionally substituted by $R^{12}$, —$COR^{12}$ or —$SO_2R^{12}$;

$R^{10}$ is $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, or heteroaryl$C_{1-6}$alkyl, wherein the alkyl, cycloalkyl, alkenyl and alkynyl groups optionally bear one substituent selected from halogen, $CF_3$, $NO_2$, CN, —$OR^{11}$, —$SR^{11}$, —$SO_2R^{12}$, —$COR^{11}$, —$CO_2R^{11}$, —$OCOR^{12}$, —$N(R^{11})_2$ and —$NR^{11}COR^{12}$; and the aryl, heteroaryl and heterocyclic groups optionally bear up to 3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$OCOR^{12}$, —$N(R^{11})_2$ and —$NR^{11}COR^{12}$;

$R^{11}$ is H or $R^{12}$;

$R^{12}$ is $C_{1-6}$alkyl, perfluoro$C_{1-6}$alkyl, $C_{2-6}$alkenyl, $C_{2-6}$alkynyl, Ar or —$C_{1-6}$alkylAr; and Ar is phenyl or heteroaryl either of which optionally bears up to 3 substituents independently selected from halogen, $CF_3$, $NO_2$, CN, $C_{1-6}$alkyl and $C_{1-6}$alkoxy;

where "heterocyclyl" and "heteroaryl" are as defined previously.

In a further aspect, the invention provides a compound of formula I as defined above, or a pharmaceutically acceptable salt thereof, with the proviso that:

when A=B=—$CH_2CH_2$—, $R^1$=$R^2$=H. $R^3$=phenyl and m=0, $(CXY)_n$ is other than —$CH_2$—, —CH(Br)— or —CH(SPh)—; and when m=n=0, $R^1$=$R^2$=H, $R^3$=phenyl and B=—$CH_2CH_2$—, A is other than —CH(Br)$CH_2CH_2$—.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl"$C_{1-6}$alkyl, "$C_{2-6}$alkynyl" and "$C_{1-6}$alkoxy" are to be construed in an analogous manner.

The expression "perfluoro$C_{1-6}$alkyl" as used herein refers to alkyl groups as defined above comprising at least one —$CF_2$— or —$CF_3$ group.

The expression "$C_{3-10}$cycloalkyl" as used herein refers to nonaromatic monocyclic or fused bicyclic hydrocarbon ring systems comprising from 3 to 10 ring atoms. Examples include cyclopropyl, cyclobutyl, cyclopentyl, cyclohexyl, cyclohexenyl and decalinyl.

The expression "$C_{3-6}$ cycloalkyl($C_{1-6}$)alkyl" as used herein includes cyclopropylmethyl, cyclobutylmethyl, cyclopentylmethyl and cyclohexylmethyl.

The expression "$C_{2-6}$acyl" as used herein refers to ($C_{1-5}$alkyl)carbonyl groups, such as acetyl, propanoyl and butanoyl, including cycloalkyl derivatives such as cyclopentanecarbonyl and cyclobutanecarbonyl.

$C_{6-10}$aryl groups include phenyl and naphthyl, preferably phenyl.

The expression "bi($C_{6-10}$aryl)" refers to two aryl groups as defined above linked by a single bond, an example being biphenyl.

The expression "$C_{6-10}$aryl$C_{1-6}$alkyl," as used herein includes benzyl, phenylethyl, phenylpropyl and naphthylmethyl.

The expression "heterocyclyl" as used herein means a cyclic or polycyclic system of up to 10 ring atoms selected from C, N, O and S, wherein none of the constituent rings is aromatic and wherein at least one ring atom is other than carbon. Preferably not more than 3 ring atoms are other than carbon. Suitable heterocyclyl groups include azetidinyl, pyrrolidinyl, terahydrofuryl, piperidinyl, piperazinyl, morpholinyl and thiomorpholinyl.

Further examples of heterocyclic ring systems include 2,5-diazabicyclo [2.2.1]heptane and 2-aza-5-oxabicyclo [2.2.1]heptane.

The expression "heteroaryl" as used herein means a cyclic or polycyclic system of up to 10 ring atoms selected from C, N, O and S, wherein at least one of the constituent rings is aromatic and wherein at least one ring atom is other than carbon. Preferably not more than 3 ring atoms are other than carbon. Where a heteroaryl ring comprises two or more atoms which are not carbon, not more than one of said atoms may be other than nitrogen. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of suitable heteroaryl ring systems include 1,2,4-triazine, 1,3,5-triazine, 1,2,3,4-tetrahydroisoquinoline, imidazo[2,1-b]thiazole and benzo[1,4]dioxin.

A heteroaryl or heterocyclic group containing a nitrogen atom may be in the form of the corresponding N-oxide.

The term "bi(heteroaryl)" as used herein refers to two heteroaryl groups as defined above (which may be the same or different) linked by a single bond, for example 5-(pyridin-2-yl)thiophene-2-yl.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Regardless of the presence or absence of asymmetric centres, certain compounds in accordance with the invention exist as enantiomers by virtue of the asymmetry of the molecule as a whole. For example, many of the compounds of formula I in which A comprises a monosubstituted fused benzene ring lack a plane of symmetry, and hence exist as pairs of enantiomers, the interconversion of which is prevented by the rigidity of the bridged bicycloalkyl ring structure. It is to be understood that all such isomers and mixtures thereof in any proportion are encompassed within the scope of the present invention, and that structural formulae depicting asymmetric molecules of this type shall be representative of both of the possible enantiomers, unless otherwise indicated.

The compounds of formula I are sulphonamido-substituted bridged bicycloalkyl derivatives, optionally comprising a further fused ring system.

In formula I, m and n are independently 0 or 1, but preferably at least one of m and n is 0, and most preferably m and n are both 0.

p is an integer from 1 to 6, preferably from 2 to 5, and most preferably is 3 or 4.

q and r are independently 0, 1 or 2 but are preferably both 1 or both 0.

s is an integer from 1 to 4, and is preferably 2 or 3, most preferably 2.

x and y are independently 0, 1 or 2, but are preferably not both 0.

When m=n=0, at least one of A and B comprises a chain of 2 or more atoms, such that the ring completed by A and B contains at least 5 atoms. Thus, for example, if m=n=0 and A and B represent —(CXY)$_p$— and —(CXY)$_x$—NR$^{13}$—(CXY)$_y$— respectively, then p must be greater than 1 or at least one of x and y must be greater than 0.

X represents halogen, R$^9$, —OR$^9$, —SR$^9$, —S(O)$_t$R$^{10}$ where t is 1 or 2, —OSO$_2$R$^9$, —N(R$^9$)$_2$, —COR$^9$, —CO$_2$R$^9$, —OCOR$^{10}$, —OCO$_2$R$^{10}$, —CON(R$^9$)$_2$, —SO$_2$N(R$^9$)$_2$, —OSO$_2$N(R$^9$)$_2$, —NR$^9$COR$^{10}$, —NR$^9$CO$_2$R$^{10}$ or —NR$^9$SO$_2$R$^{10}$; wherein R$^9$ and R$^{10}$ are as defined above. Alternatively, X and Y together may represent =O, =S, =N—OR$^{11}$ or =CHR$^{11}$. In a subset of the compounds of the invention, X represents halogen, R$^9$, —OR$^9$, —SR$^9$, —S(O)$_t$R$^{10}$, —N(R$^9$)$_2$, —COR$^9$, —CO$_2$R$^9$, —OCOR$^{10}$, —CON(R$^9$)$_2$, —SO$_2$N(R$^9$)$_2$, —NR$^9$COR$^{10}$, —NR$^9$CO$_2$R$^{10}$ or —NR$^9$SO$_2$R$^{10}$; or together with Y represents =O or =CH$_2$. Typically, X represents H, C$_{1-4}$alkyl, substituted C$_{1-4}$alkyl, —OR$^{9a}$, —COR$^{9a}$, —CO$_2$R$^{9a}$, OCOR$^{10a}$, —N(R$^{9a}$)$_2$, —CON(R$^{9a}$)$_2$, —OCO$_2$R$^{10a}$, —OSO$_2$R$^{10a}$ or (in combination with Y) =O, =S, =N—OR$^{11}$, =CHAr or =CH$_2$, where R$^{9a}$ is H or R$^{10a}$, and R$^{10a}$ is C$_{1-6}$alkyl, C$_{2-6}$alkenyl, Ar (especially phenyl) or benzyl. Preferred embodiments of X include H, methyl, hydroxymethyl, —CO$_2$Et, —CONHCH$_2$Ph, —OCOMe, —OCO$_2$Me, methanesulfonyloxy, p-toluenesulfonyloxy, 2-nitrobenzoyloxy, 3,4-dimethoxybenzoyloxy, 2-methylthionicotinoyloxy, and (in combination with Y) =O, =S, =N—OMe, =N—OEt, =N—OPh, =N—OCH$_2$Ph, =CHPh and =CH$_2$.

Y may represent H or C$_{1-6}$alkyl, or may combine with X as indicated above. Preferably, Y represents H or together with X represents =O, =S, =N—OMe, =N—OEt, =N—OPh, =N—OCH$_2$Ph, =CHPh or =CH$_2$.

Neither A nor B may comprise more than one —CXY— moiety which is other than —CH$_2$—.

When A and/or B comprises a —NR$^{13}$— moiety, R$^{13}$ preferably represents H, optionally-substituted C$_{1-6}$alkyl, C$_{2-6}$alkenyl or C$_{6-10}$arylC$_{1-6}$alkyl. Particular values for R$^{13}$ include H, methyl, ethyl, allyl, cyanomethyl, carbamoylmethyl, methoxycarbonylmethyl, benzyl, cblorobenzyl and methoxybenzyl. Preferably, A and B do not both comprise a —NR$^{13}$— moiety.

Suitable embodiments of A and B include:
—CXY—, —CH$_2$CXY—, —CH$_2$CXYCH$_2$—, —CH$_2$CH$_2$CXYCH$_2$—, —CH=CH—, —CH$_2$CH=CHCXY—, —CH$_2$NR$^{13}$CXY—, —CH$_2$CH$_2$NR$^{13}$CXY—, —CH$_2$CXYNR$^{13}$CH$_2$—, —CXYCH$_2$NR$^{13}$CH$_2$—, —NR$^{13}$CXY—,

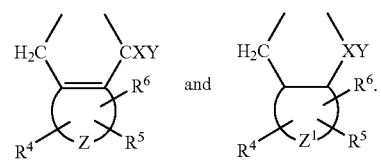

Preferred embodiments of A include —CH$_2$CH$_2$CH$_2$—, —CH$_2$CH$_2$—, —CH$_2$CH$_2$CH$_2$CH$_2$—, —CH$_2$CH=CHCH$_2$—,

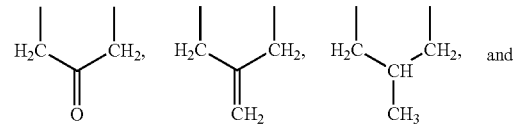

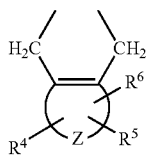

Typical embodiments of B include —CH$_2$—, —CH$_2$CH$_2$—, —CH$_2$CH$_2$CH$_2$—, —CH$_2$NR$^{13}$CH$_2$—, —NR$^{13}$CH$_2$—, —CH$_2$CH$_2$CH$_2$CH$_2$—, —CH═CH—, and —CH$_2$CH═CHCH$_2$—, and preferred embodiments of B include —CH$_2$CH$_2$— and —CH$_2$CH$_2$CH$_2$—.

Z completes an aromatic ring system containing 5-10 atoms, of which 0-3 are selected from nitrogen, oxygen and sulfur and the remainder are carbon (in particular, an aromatic ring system containing 6-10 atoms, of which 0-2 are nitrogen and the remainder are carbon), or Z completes a non-aromatic ring system containing 5-10 atoms, of which 0-3 are independently selected from oxygen, nitrogen and sulphur and the remainder are carbon. Examples of aromatic ring systems completed by Z include benzene, naphthalene, pyridine, quinoline, isoquinoline, pyrazine, pyrimidine, pyrrole, furan, thiophene, indole, benzofuran, benzothiophene, oxazole, isoxazole, thiazole, isothiazole and triazole. Examples of non-aromatic ring systems completed by Z include cyclohexane, cyclopentane, indane, tetralin, decalin, piperidine, piperazine, morpholine, tetrahydrofuran and tetrahydrothiophene. Preferably, Z completes a benzene ring or a pyridine ring.

Z$^1$ completes a non-aromatic ring system containing 5-10 atoms, of which 0-3 are independently selected from oxygen, nitrogen and sulphur and the remainder are carbon. Examples of ring systems completed by Z$^1$ include cyclohexane, cyclopentane, indane, tetralin, decalin, piperidine, piperazine, morpholine, tetrahydrofuran and tetrahydrothiophene.

Z$^2$ completes a heteroaromatic ring comprising 5 or 6 atoms, such as imidazole, triazole or pyrimidine.

A fused ring (as indicated by Z, Z$^1$ or Z$^2$) may form part of A or B, but A and B preferably do not both comprise such a ring. Typically, such fused rings (if present) form part of A.

Examples of structures completed by A and B include (but are not restricted to):

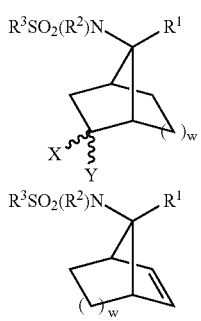
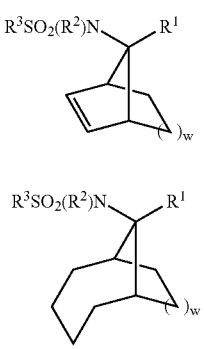
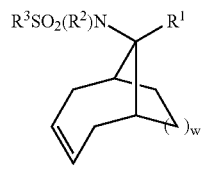
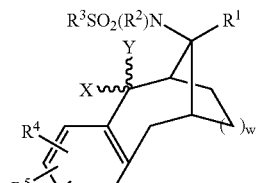
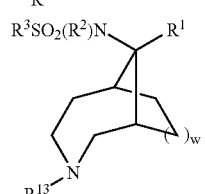
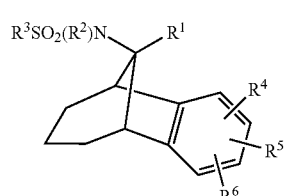
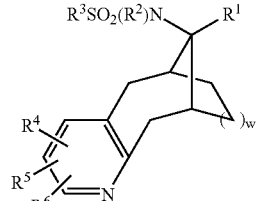
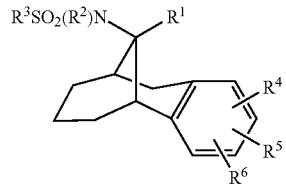
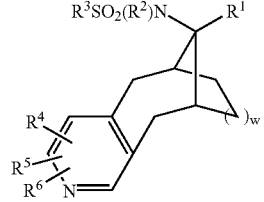

where w is 1 or 2, and X, Y, R$^1$-R$^6$ and R$^{13}$ have the same meanings as before.

R$^1$ represents H, C$_{1-4}$alkyl (such as methyl, ethyl, isopropyl or t-butyl), or C$_{2-4}$alkenyl (such as allyl). In a subset of the compounds of formula I, $R^1$ represents H or $C_{1-4}$alkyl. Preferably, $R^1$ represents H, methyl or allyl. Most preferably, $R^1$ represents H.

$R^2$ represents H, $C_{1-6}$alkyl (such as methyl, ethyl, propyl or butyl), $C_{6-10}$aryl (such as phenyl or naphthyl), $C_{6-10}$aryl$C_{1-6}$alkyl (such as benzyl), $C_{3-6}$cycloalkyl (such as cyclopropyl, cyclopentyl or cyclohexyl), or $C_{2-6}$acyl which is optionally substituted with $-CO_2H$ (such as acetyl, malonoyl, succinoyl or glutaroyl), or with an amino group, in particular a primary amino group or an alkyl- or dialkylamino group in which the alkyl group(s) comprise(s) up to 4 carbons. Preferably, $R^2$ is H.

$R^3$ represents $C_{1-16}$alkyl, $C_{3-10}$cycloalkyl, $C_{2-16}$alkenyl, $C_{2-16}$alkynyl, $C_{6-10}$aryl$C_{1-6}$alkyl, heteroaryl$C_{1-6}$alkyl, $C_{6-10}$aryl$C_{2-6}$alkenyl, heteroaryl$C_{2-6}$alkenyl, $C_{6-10}$aryl, $C_{6-10}$aryloxy$C_{6-10}$aryl, bi($C_{6-10}$aryl), heteroaryl, bi(heteroaryl), or heterocyclyl. In a subset of the compounds of formula I, $R^3$ represents $C_{1-16}$alkyl, $C_{3-10}$cycloalkyl, $C_{2-16}$alkenyl, $C_{2-16}$alkynyl, $C_{6-10}$aryl$C_{1-6}$alkyl, heteroaryl$C_{1-6}$alkyl, $C_{6-10}$aryl, $C_{6-10}$aryloxy$C_{6-10}$aryl, bi($C_{6-10}$aryl), heteroaryl, bi(heteroaryl) or heterocyclyl.

Alkyl, cycloalkyl, alkenyl and alkynyl groups represented by $R^3$ or forming part of a group represented by $R^3$ may bear up to 3 substituents (but preferably not more than one substituent) independently selected from halogen, CN, $NO_2$, $-OR^7$, $-SR^7$, $-S(O)_tR^8$ where t is 1 or 2, $-N(R^7)_2$, $-COR^7$, $-CO_2R^7$, $-OCOR^8$, $-CON(R^7)_2$, $-NR^7COR^8$, $-C_{1-6}$alkyl$NR^7COR^8$, $-NR^7CO_2R^8$ and $-NR^7SO_2R^8$; where $R^7$ and $R^8$ are as defined previously. Typical substituents include halogen, $-OR^7$, $-SR^7$ and $-SO_2R^8$.

Aryl, heteroaryl and heterocyclic groups represented by $R^3$ or forming part of a group represented by $R^3$ may bear up to 5 substituents independently selected from halogen, $R^8$, CN, $NO_2$, $-OR^7$, $-SR^7$, $-S(O)_tR^8$ where t is 1 or 2, $-N(R^7)_2$, $-COR^7$, $-CO_2R^7$, $-OCOR^8$, $-CON(R^7)_2$, $-NR^7COR^8$, $-C_{1-6}$alkyl$NR^7COR^8$, $-NR^7CO_2R^8$ and $-NR^7SO_2R^8$; where $R^7$ and $R^8$ are as defined previously. Generally not more than 3 (preferably not more than two) such substituents are present. Typical substituents include halogen, $R^8$, CN, $NO_2$, $-OR^7$, $-SR^7$, $-S(O)_2R^8$, $-N(R^7)_2$, $-COR^7$, $-CO_2R^7$, $-NR^7COR^8$ and $-C_{1-6}$alkyl$NR^7COR^8$. Preferred substituents include F, Cl, methyl, methoxy and $NO_2$.

$R^7$ represents H or $R^8$; or two $R^7$ groups together with a nitrogen atom to which they are mutually attached may complete a pyrrolidine, piperidine, piperazine or morpholine ring, while $R^8$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, Ar or $-C_{1-6}$alkylAr, where Ar represents phenyl or heteroaryl either of which optionally bears up to 3 substituents independently selected from halogen, $CF_3$, $NO_2$, CN, $C_{1-6}$alkyl and $C_{1-6}$alkoxy. Preferably, $R^7$ and $R^8$ are independently selected from H, $C_{1-6}$alkyl (especially methyl, ethyl, n-propyl or isopropyl), perfluoro$C_{1-6}$alkyl (especially trifluoromethyl or 2,2,2-trifluoroethyl), Ar (especially phenyl optionally bearing up to 3 substituents independently selected from halogen, $CF_3$, $NO_2$, CN, $C_{1-6}$alkyl and $C_{1-6}$alkoxy) and $-C_{1-6}$alkylAr (especially benzyl optionally bearing up to 3 substituents independently selected from halogen, $CF_3$, $NO_2$, CN, $C_{1-6}$alkyl and $C_{1-6}$alkoxy), with the proviso that $R^8$ cannot be H.

Typical examples of alkyl and substituted alkyl groups represented by $R^3$ include methyl, trifluoromethyl, ethyl, n-propyl, isopropyl, n-octyl, n-dodecyl, n-decyl, n-butyl, miethanesulphonylmethyl, 2-ethoxyethyl, 2-ethanethioethyl, 3-chloropropyl, 2,2,2-trichloroethyl and 2,2,2-tifluoroethyl.

Typical examples of cycloalkyl groups represented by $R^3$ include cyclopropyl, cyclopentyl and cyclohexyl.

Typical examples of alkenyl and substituted alkenyl groups represented by $R^3$ include vinyl, allyl and 2-phenylethenyl.

Typical examples of alkynyl groups represented by $R^3$ include propargyl.

Typical examples of arylalkyl groups represented by $R^3$ include benzyl, 2-nitrobenzyl, and 2-phenylethyl.

Typical examples of heteroarylalkyl groups represented by $R^3$ include pyridylmethyl, 2-(2-thienyl)ethyl and 2-furylethyl.

Typical examples of aryl groups represented by $R^3$ include phenyl, 1-naphthyl, 2-naphthyl, 2,5-dichlorophenyl, 2-nitrophenyl, 3-nitrophenyl, 4-nitrophenyl, 2,4,6-trimethylphenyl, 2-fluorophenyl, 3-fluorophenyl, 4-fluorophenyl, 2-chlorophenyl, 3-chlorophenyl, 4-chlorophenyl, 4-methoxyphenyl, 4-trifluoromethylphenyl, 3,4-dichlorophenyl, 3,4-dimethoxyphenyl, 4-acetylphenyl, 5-dimethylaminonaphth-1-yl, pentafluorophenyl, 2,4,6-tris(isopropyl)phenyl, 4-bromophenyl, o-tolyl, m-tolyl, p-tolyl, pentamethylphenyl, 2,3,5,6-tetramethylphenyl, 3,5-bis(trifluoromethyl)phenyl, 2,3,4-trichlorophenyl, 2,5-dimethoxyphenyl, 3-chloro-4-fluorophenyl, 4-ethylphenyl, 4-n-propylphenyl, 4-isopropylphenyl, 4-bromo-2,5-difluorophenyl, 4-trifluoromethoxyphenyl, 3-trifluoromethylphenyl, 2,4-difluorophenyl, 4-chloro-2,5-dimethylphenyl, 2-methyl-5-nitrophenyl, 2-trifluoromethylphenyl, 3,5-dichlorophenyl, 2-chloro-6-methylphenyl, 2,3-dichlorophenyl, 2-bromophenyl, 3-chloro-2-methylphenyl, 2,6-dichlorophenyl, 3-bromophenyl, 2-cyanophenyl, 4-n-butoxyphenyl, 2,4-dichlorophenyl, 2-chloro-4-fluorophenyl, 3-fluoro-6-methylphenyl, -2,4,6-trichlorophenyl, 4-iodophenyl, 4-t-butylphenyl, 2-methoxycarbonylphenyl, 4-methylsulphonylphenyl, 2-methylsulphonylphenyl, 4-(1,1-dimethylpropyl)phenyl, 2-chloro-5-trifluoromethylphenyl, 2-trifluoromethoxyphenyl, 4-acetamido-3-chlorophenyl, 5-chloro-2-methoxyphenyl, 2,6-difluorophenyl, 4-methyl-3-nitrophenyl, 4-n-butylphenyl, 4-(2-chloro-6-nitrophenoxy)phenyl, 4-(3-chloro-2-cyanophenoxy)phenyl, 2,5-bis(trifluoromethoxy)phenyl, 2-chloro-4-trifluoromethylphenyl, 3-carboxy-4-hydroxyphenyl, 2,3,4-trifluorophenyl, 3,4-difluorophenyl, 4-n-pentylphenyl, 3-chloro-4-methylphenyl, 4-bromo-2-ethylphenyl, 2,6-dichloro-4-trifluoromethylphenyl, 2-iodophenyl and 4-cyanophenyl.

Typical examples of biaryl groups represented by $R^3$ include 4-biphenyl.

Heterocyclyl groups represented by $R^3$ may be bonded through carbon or nitrogen (if present). Typical examples of heterocyclyl groups represented by $R^3$ include 1-pyrrolidinyl, 4-morpholinyl, 1-piperidinyl, 1-piperazinyl, tetrahydrothiophenyl and tetrahydrofuryl.

Typical examples of heteroaryl groups represented by $R^3$ include 2- and 3-thienyl, 4,5-dibromo-2-thienyl, 4-bromo-2,5-dichloro-3-thienyl, 2,5-dichloro-3-thienyl, 4,5-dichloro-2-thienyl, 2-trifluoroacetyl-1,2,3,4-tetrahydro-7-isoquinolinyl, 3,5-dimethyl-4-isoxazolyl, 5-bromo-2-thienyl, 4-bromo-5-chloro-2-thienyl, 3-bromo-5-chloro-2-thienyl, 5-chloro-1,3-dimethyl-1H-pyrazol-4-yl, benzo[1,2,5]thiadiazol-4-yl, 1-methyl-1H-imidazol-4-yl, benzo[1,2,5]oxadiazol-4-yl, 2-methoxycarbonyl-3-thienyl, 5-(N-(4-chlorobenzoyl)aminomethyl)-2-thienyl, 6-chloro-imidazo[2,1-b]thiazol-5-yl, 1,2-dimethyl-1H-imidazol-4-yl, 4-ethoxycarbonyl-3-pyridyl, 2,5-dichloro-4-nitro-3-thienyl, 2-pyridyl, 3-pyridyl, 5-chloro-2-thienyl, 2-furyl, 2-thiazolyl and 2-chlorothiazol-5-yl.

Further examples of heteroaryl groups represented by $R^3$ include 2-(morpholin-4-yl)thiazol-5-yl, 6-chloropyrid-3-yl, pyrrol-3-yl, 1-methylpyrrol-3-yl and isothiazol-5-yl.

Typical examples of bi(heteroaryl) groups represented by $R^3$ include 5-(1-methyl-5-trifluoromethyl-1H-pyrazol-3-yl)-2-thienyl, 5-pyridin-2-yl-2-thienyl, 5-isoxazol-3-yl-2-thienyl, 5-(2-methylthiopyrimidin-4-yl)-2-thienyl, 5-(2-methylthiazol-4-yl)-2-thienyl, 5-(2-methyl-5-trifluoromethyl-2H-pyrazol-3-yl)-2-thienyl and 5-(5-trifluoromethylisoxazol-3-yl)-2-thienyl.

Examples of preferred groups represented by $R^3$ include phenyl, thiophene, substituted thiophene (in particular 5-chloro-2-thienyl) and n-butyl.

Further examples of preferred groups represented by $R^3$ include 2-, 3- and 4-fluorophenyl, 2,4-difluorophenyl, 2,3,4-trifluorophenyl, 4-chlorophenyl, pyrid-3-yl, 6-chloropyrid-3-yl and isothiazol-5-yl.

$R^4$, $R^5$ and $R^6$ are independently $R^9$, halogen, CN, $NO_2$, $-OR^9$, $-SR^9$, $-S(O)_tR^{10}$ where t is 1 or 2, $-N(R^9)_2$, $-COR^9$, $-CO_2R^9$, $-OCOR^{10}$, $-CON(R^9)_2$, $-SO_2N(R^9)_2$, $-NR^9COR^{10}$, $-NR^9CO_2R^{10}$, $-CH=CHCH_2N(R^{16})_2$, $-NR^9SO_2R^{10}$, $-CH_2OR^9$, $-CH_2N(R^{16})_2$, $-NHCOCH^2OR^{10}$ or $-NHCOCH_2N(R^{16})_2$; where $R^9$, $R^{10}$ and $R^{16}$ are as defined previously. When the group A or B comprises a non-aromatic ring completed by Z or $Z^1$, $R^4$, $R^5$ and $R^6$ preferably all represent hydrogen. When A or B comprises an aromatic ring completed by Z, $R^4$, $R^5$ and $R^6$ are preferably independently selected from $R^9$, halogen, CN, $NO_2$, $-OR^9$, $-N(R^9)_2$, $-NR^9COR^{10}$, $-NR^9CO_2R^{10}$, $-CH=CHCH_2N(R^{16})_2$, $-CH_2OR^9$, $-CH_2N(R^{16})_2$, $-NHCOCH^2OR^{10}$ and $-NHCOCH_2N(R^{16})_2$, but preferably at least one of $R^5$ and $R^6$ represents H, and most preferably both $R^5$ and $R^6$ represent H.

When A or B comprises a heteroaromatic ring completed by $Z^2$, $R^4$ preferably represents H.

$R^9$ represents H or $R^{10}$; or two $R^9$ groups together with a nitrogen atom to which they are mutually attached may complete a pyrrolidine, piperidine, piperazine or morpholine ring which is optionally substituted by $R^{12}$, $-COR^{12}$ or $-SO_2R^{12}$, while $R^{10}$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, $C_{6-10}$aryl$C_{2-6}$alkenyl or heteroaryl$C_{2-6}$alkenyl, wherein the alkyl, cycloalkyl, alkenyl and alkynyl groups optionally bear one substituent selected from halogen, $CF_3$, $NO_2$, CN, $-OR^{11}$, $-SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$; and the aryl, heteroaryl and heterocyclic groups optionally bear up to 3 substituents independently selected from halogen, $NO_2$, CN, $R^{12}$, $-OR^{11}$, $-SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$, where $R^{11}$ and $R^{12}$ are as defined previously. Preferably, $R^9$ and $R^{10}$ independently represent H, $C_{1-10}$alkyl, perfluoro$C_{1-6}$alkyl, $C_{3-6}$cycloalkyl$C_{1-6}$alkyl, $C_{2-10}$alkenyl, $C_{2-10}$alkynyl, $C_{6-10}$aryl, heteroaryl, $C_{6-10}$aryl$C_{1-6}$alkyl, $C_{6-10}$aryl$C_{2-6}$alkenyl, heteroaryl$C_{2-6}$alkenyl or heteroaryl$C_{1-6}$alkyl, wherein the alkyl, cycloalkyl, alkenyl and alkynyl groups are unsubstituted or substituted by CN, $OR^{11}$, $-COR^{11}$, $-CO_2R^{11}$ or $-CON(R^{11})_2$, and wherein the aryl and heteroaryl groups bear not more than two substituents selected from halogen, $NO_2$, CN, $R^{12}$, $-OR^{11}$ and $-SO_2R^{12}$, with the proviso that $R^{10}$ cannot represent H.

$R^{11}$ represents H or $R^{12}$, while $R^{12}$ represents $C_{1-6}$alkyl, $C_{3-7}$cycloalkyl, perfluoro$C_{1-6}$alkyl, $C_{2-6}$alkenyl, $C_{2-6}$alkynyl, ArO$C_{1-6}$alkyl, Ar or $-C_{1-6}$alkylAr, where Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy, or two $R^{12}$ groups together with a nitrogen atom to which they are mutually attached may complete a heterocyclic ring system of 3-10 atoms, 0-2 of which (in addition to said nitrogen atom) are selected from O, N and S, said ring system bearing 0-2 substituents selected from halogen, CN, $NO_2$, $R^{12}$, $OR^{11}$, $NHR^{11}$, and $COR^{11}$. Preferably, $R^{11}$ and $R^{12}$ independently represent H, $C_{1-6}$alkyl, perfluoro$C_{1-6}$alkyl, $C_{2-6}$alkenyl, $C_{2-6}$alkynyl, phenyl (optionally bearing up to 2 substituents independently selected from halogen, $CF_3$, $NO_2$, CN, $C_{1-6}$alkyl and $C_{1-6}$alkoxy), heteroaryl (especially thiazolyl, optionally substituted by halogen, $CF_3$ or $C_{1-6}$alkyl) or benzyl (optionally bearing up to 2 substituents independently selected from halogen, $CF_3$, $NO_2$, CN, $C_{1-6}$alkyl and $C_{1-6}$alkoxy), with the proviso that $R^{12}$ cannot represent H.

Examples of heterocyclic rings represented by $N(R^{12})_2$ include pyrrolidine, piperidine, piperazine, morpholine, thiomorpholine, 2,5-diazabicyclo[2.2.1]heptane and 2-aza-5-oxabicyclo[2.2.1]heptane, any of which may be substituted, e.g. by halogen, $CF_3$, methyl, hydroxymethyl, methoxymethyl or hydroxy.

Each $R^{16}$ independently represents H or $R^{10}$, or two $R^{16}$ groups together with the nitrogen to which they are mutually attached complete a mono- or bicyclic heterocyclic ring system of 5-10 ring atoms selected from C, N, O and S, said ring system optionally having an additional aryl or heteroaryl ring fused thereto, said heterocyclic system and/or additional fused ring bearing 0-3 substituents independently selected from halogen, $NO_2$, CN, $R^{12}$, $-OR^{11}$, $SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$. Examples of heterocyclic ring systems represented by $-N(R^{16})_2$ include pyrrolidine, piperidine, piperazine, morpholine, thiomorpholine, 2,5-diazabicyclo[2,2,1]heptane, 5,6-dihydro-8H-imidazo[1,2-a]pyrazine and spiro[isobenzofuran-1(3H),4'-piperidine]. Preferably, the heterocyclic ring system bears at most one substituent. Preferred substituents are halogen and $R^{12}$ groups, in particular alkyl, $CF_3$, phenoxyalkyl and phenyl, wherein the phenyl groups optionally bear up to 2 substituents selected from halogen (especially chlorine or fluorine), $C_{1-6}$alkyl and $C_{1-6}$alkoxy.

$R^4$ very aptly represents halogen (especially chlorine, bromine or fluorine), nitro, CN, phenyl, substituted phenyl (such as 3,5-bis(trifluoromethyl)phenyl, o-anisyl, 2-fluorophenyl, 3-fluorophenyl and 4-fluorophenyl), heteroaryl (such as 5-phenyl-1,2,4-oxadiazol-3-yl, 5-pyridyl-1,2,4-oxadiazol-3-yl, 3-thienyl, 2-thienyl, 2-benzofuryl, 2-pyridyl, 4-pyridyl, 3-pyridyl and 6-methoxy-3-pyridyl), amino represented by $-N(R^9)_2$, amido represented by $-NR^9COR^{10}$, carbamate represented by $-NR^9CO_2R^{10}$, alkoxy, aryloxy or heteroaryloxy represented by $-OR^{10}$, optionally substituted alkenyl, including $-CH=CHCH_2N(R^{16})_2$ $C_{6-10}$aryl$C_{2-6}$alkenyl and heteroaryl$C_{2-6}$alkenyl, substituted acetamido represented by $-NHCOCH_2(NR^{16})_2$, and substituted methyl represented by $-CH_2OR^9$.

Preferred amino groups represented by $R^4$ include $N(R^9)_2$ wherein the two $R^9$ groups complete a piperidine or piperazine ring which is optionally substituted in the 4-position by Ar, and $NHR^{10}$ wherein $R^{10}$ is selected from $C_{6-10}$aryl$C_{1-6}$alkyl (especially benzyl or substituted benzyl), heteroaryl$C_{1-6}$alkyl, and $C_{1-6}$alkyl which is substituted by $OR^{10}$ or $N(R_{11})_2$ (especially ethyl which is substituted by OAr or $N(R_{12})_2$ wherein the $R^{12}$ groups complete a heterocyclic ring).

Typical examples of amino groups represented by $R^4$ include $NH_2$, (3-pyridylmethyl)amino, 4-phenoxybenzylamino, 4-benzyloxybenzylamino, 2-methoxybenzylamino, 3-methoxybenzylamino, 4-methoxybenzylamino, 3,3-dimethylbutylamino, (cyclohexylmethyl)amino, 3-methylbutylamino, (4-pyridylmethyl)amino, 2-benzyloxyethylamino, 2-phenylpropylamino, (2,3-dihydrobenzo[1,4]dioxin-6-ylmethyl)amino, 4-t-butylbenzylamino, 3-phenylbutylamino, 4-isopropoxybenzylamino, (benzofuran-2-ylmethyl)amino, 3-phenylpropylamino, 4-n-pentylbenzylamino, 4-methanesulphonylbenzylamino, 3-(4-t-butylphenoxy)benzylamino, 3-(4-methoxyphenoxy)benzylamino, 3-trifluoromethoxybenzylamino, 4-cyanobenzylamino, 3-fluorobenzylamino, 4-fluorobenzylamino, 3-chlorobenzylamino, 3-trifluoromethylbenzylamino, 3-(3,4-dichlorophenoxy)benzylamino, 4-(4-t-butylthiazol-2-yl)benzylamino, 4-(hex-1-ynyl)benzylamino, 3-benzyloxybenzylamino and 4-phenylpiperidin-1-yl.

Further examples of amino groups represented by $R^4$ include 2-(4-fluorophenoxy)ethylamino, 2-(4-chlorophenoxy)ethylamino, 2-(4-fluoroanilino)ethylamino, 2-(4-morpholinyl)ethylamino, 4-(4-fluorophenyl)piperazin-1-yl, 4-(2-methoxyphenyl)piperazin-1-yl and 4-(pyridin-2-yl)piperazin-1-yl.

Typical examples of amido groups represented by $R^4$ include benzamido, phenylacetamido, 3,5-difluorophenylacetamido, 4-fluorobenzamido, acetamido, propionamido, butyramido, pentanamido, hexanamido, isobutyramido, 3-methylbutyramido, 2-methylbutyramido, 2-methylpentanamido, 3-methylpentanamido, 4-methylpentanamido, 2,2-dimethylbutyramido, 2-ethylbutyramido, cyclopentylacetamido, 2,2-dimethylpent-4-enamido, cyclopropylacetamido, 4-methyloctanamido, 3,5,5-trimethylhexanamido, 2-methylhexanamido, 2,2-dimethylpentanamido, 5-methylhexanamido, 3-phenylpropionamido, isonicotinamido, pyridine-2-carboxamido and nicotinamido.

Typical examples of carbamate groups represented by $R^4$ include phenoxycarbonylamino, 4-chlorophenoxycarbonylamino, methoxycarbonylamino, benzyloxycarbonylamino, isobutoxycarbonylamino, allyloxycarbonylamino, 4-methylphenoxycarbonylamino, 4-bromophenoxycarbonylamino, 4-fluorophenoxycarbonylamino, 4-methoxyphenoxycarbonylamino and 2,2-dimethylpropoxycarbonylamino.

When $R^4$ represents an alkoxy, aryloxy or heteroaryloxy group $—OR^{10}$, $R^{10}$ preferably represents $C_{6-10}arylC_{1-6}alkyl$ (such as benzyl, chlorobenzyl, fluorobenzyl and methoxybenzyl), heteroaryl$C_{1-6}$alkyl (such as pyridylmethyl), $C_{1-6}$alkyl (such as methyl), heterocyclyl (such as 1-t-butoxycarbonylpiperidin-4-yl), heteroaryl (such as pyridin-4-yl), or $C_{1-6}$alkyl which is substituted by $—OR^{11}$, $—CON(R^{11})_2$ or $—N(R^{11})_2$, especially an ethyl group substituted by $—OAr$. Particularly preferred alkoxy groups represented by $R^4$ include phenoxyethoxy, 4-chlorophenoxyethoxy and 4-fluorophenoxyethoxy. Further preferred alkoxy groups represented by $R^4$ include methoxy substituted with $7CON(R^{12})_2$ and ethoxy or propoxy substituted with $—N(R^{12})_2$, in particular 2-(morpholin-4-yl)ethoxy, 2-(2-methylpyrrolidin-1-yl)ethoxy, 2-(2-hydroxymethyl)pyrrolidin-1-ylethoxy, 2-(2-methoxymethyl)pyrrolidin-1-ylethoxy, 2-(3-hydroxypyrrolidin-1-yl)ethoxy, 2-(2-aza-5-oxa-[2.2.1]bicyclohept-2-yl)ethoxy, 2-(piperidin-1-yl)ethoxy, 2-(4-hydroxypiperidin-1-yl)ethoxy and 2-(2-methylpiperidin-1-yl)ethoxy and 3-(morpholin-4-yl)propoxy.

Typical examples of $C_{6-10}arylC_{2-6}$alkenyl groups represented by $R^4$ include 4-phenylbut-1-enyl, styryl, 4-methoxystyryl, 4-fluorostyryl, 4-chlorostyryl and 4-bromostyryl.

Typical examples of heteroaryl$C_{2-6}$alkenyl groups represented by $R^4$ include 3-(imidazol-1-yl)propenyl and 3-(1,2,4-triazol-1-yl)propenyl.

Typical examples of alkenyl and substituted alkenyl groups represented by $R^4$ include, vinyl, cyanovinyl, 3-(N,N-dimethylamino)prop-1-enyl, 3-hydroxyprop-1-enyl, methoxycarbonylethenyl and benzoylethenyl.

A special class of alkenyl groups represented by $R^4$ have the formula $—CH=CHCH_2N(R^{16})_2$. Typical examples include 3-(N,N-dimethylamino)propenyl, 3-(piperidin-1-yl)propenyl, 3-(morpholin-4-yl)propenyl and the corresponding N-oxide, 3-(4-methypiperazin-1-yl)propenyl, 3-(4-phenylpiperazin-1-yl)propenyl and 3-(N-2-methoxyethyl-N-methylamino)propenyl.

Typical examples of substituted acetamido groups represented by $—NHCOCH_2(NR^{16})_2$ include 2-(diethylamino)acetamido, 2-(N-benzyl-N-methylamino)acetamido, 2-(pyrrolidin-1-yl)acetamido, 2-[4-(4-fluorophenyl)piperazin-1-yl]acetamido, 2-[5-(4-fluorophenyl)-2,5-diazabicyclo[2.2.1]hept-2-yl]acetamido, 2-(4-phenylpiperazin-1-yl)acetamido, 2-(piperidin-1-yl)acetamido, 2-(4-methylpiperazin-1-yl)acetamido, 2-(morpholin-4-yl)acetamido, 2-(4-phenylpiperidin-1-yl)acetamido, 2-[4-(2-methoxyphenyl)piperidin-1-yl]acetamido, 2-(2-phenoxymethylmorpholin-4-yl)acetamido, 2-[(4-phenylmorpholin-2-ylmethyl)amino]acetamido, 2-(3-phenyl-5,6-dihydro-8H-imidazo[1,2-a]pyrazin-7-yl)acetamido and 2-[4-(2-methoxyphenyl)piperazin-1-yl]acetamido.

Typical examples of substituted acetamido groups represented by $—NHCOCH_2OR^{10}$ include 2-methoxyacetamido, 2-phenoxyacetamido, and the corresponding 2-, 3- and 4-fluorophenoxy derivatives and 2-, 3- and 4-chlorophenoxy derivatives.

Typical examples of substituted methyl groups represented by $—CH_2OR^9$ include hydroxymethyl, phenoxymethyl, 2-, 3- and 4-chlorophenoxymethyl, 2-, 3- and 4-fluorophenoxymethyl, 2-, 3- and 4-methoxyphenoxymethyl, 4-trifluoromethylphenoxymethyl, 4-t-butylphenoxymethyl, 4-[1,2,4]triazol-1-ylphenomethyl, quinolin-5-yloxymethyl, 4-trifluoromethoxyphenoxymethyl and 4-(4-acetylpiperazin-1-yl)phenoxymethyl.

A subclass of the compounds of formula I is defined by formula II:

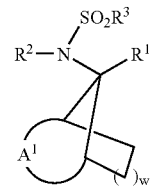

II wherein:

w is 1 or 2;

$A^1$ represents $—CH_2CXY—$, $—CH_2CH_2CH_2CH_2—$, $—CH_2CH=CHCH_2—$ or $—CH_2CXYCH_2—$; and X, Y, $R^1$, $R^2$ and $R^3$ have the same meanings as before.

In a subset of the compounds of formula II, $A^1$ represents $—CH_2CH_2CH_2—$, $—CH_2CH_2CH_2CH_2—$, $—CH_2CH=CHCH_2—$ or $—CH_2CXYCH_2—$.

In preferred compounds of formula II, w is 1; $R^1$ and $R^2$ are both H; Y is H or together with X represents $=O$, $=N—OR^{11}$ or $=CH_2$; and X is selected from H, $C_{1-6}$alkyl, $—CO_2R^9$, $—OCOR^{10}$, $—OCO_2R^{10}$, $—OSO_2R^9$, and $—CON(R^9)_2$, or together with Y represents $=O$, $=N—OR^{11}$ or $=CH_2$, where $R^9$ and $R^{11}$ have the same meaning as before.

Examples of compounds within this subclass include:

endo-N-bicyclo [4.2.1]non-3-en-9-yl-4-methyl-benzenesulfonamide;
endo-N-bicyclo[4.2.1]non-3-en-9-yl-4-fluoro-benzenesulfonamide;
endo-N-bicyclo[4.2.1]non-3-en-9-yl-benzenesulfonamide;
endo-thiophene-2-sulfonic acid bicyclo[4.2.1]non-3-en-9-ylamide;
endo-5-chloro-thiophene-2-sulfonic acid bicyclo[4.2.1]non-3-en-9-ylamide;
endo-5-chloro-thiophene-2-sulfonic acid bicyclo [4.2.1] non-9-ylamide; and
endo-8-(5-chloro-thiophene-2-sulfonylamino)-bicyclo [3.2.1]octane-endo-3-carboxylic acid ethyl ester.

Further examples of compounds within this sub class include:
(syn, exo)-7-{[(5-chlorothien-2-yl)sulfonyl]amino}bicyclo [2.2.1]hept-2-yl acetate;
(syn, exo)-7-{[(5-chlorothien-2-yl)sulfonyl]amino}bicyclo [2.2.1]hept-2-yl 2-(methylthio)nicotinate;
(syn, exo)-7-{[(5-chlorothien-2-yl)sulfonyl]amino}bicyclo [2.2.1]hept-2-yl 3,4-dimethoxybenzoate;
(syn, exo)-7-(5-chlorothiophene-2-sulfonylamino)-bicyclo [2.2.1]hept-2-yl 2-nitrobenzoate;
(syn, exo)-7-{[(5-chlorothien-2-yl)sulfonyl]amino}bicyclo [2.2.1]hept-2-yl methyl carbonate;
(syn, exo)-7-(5-chlorothiophene-2-sulfonylamino)-bicyclo [2.2.1]hept-2-yl methanesulfonate;
(syn, exo)-7-(5-chlorothiophene-2-sulfonylamino)-bicyclo [2.2.1]hept-2-yl toluene-4-sulfonate;
(syn)-5-chloro-N-(2-methylenebicyclo[2.2.1]hept-7-yl) thiophene-2-sulfonamide;
(syn, endo)-7-{[(5-chlorothien-2-yl)sulfonyl]amino}bicyclo [2.2.1]hept-2-yl acetate;
[9-endo]-N-(9-methylbicyclo[4.2.1]non-3-en-9-yl)benzenesulfonamide;
[9-endo]-5-chloro-N-(9-methylbicyclo[4.2.1]non-3-en-9-yl) thiophene-2-sulfonamide; and
[9-endo]-N-(9-allylbicyclo[4.2.1]non-3-en-9-yl)-5-chlorothiophene-2-sulfonamide.

Still further compounds within this subclass include:
5-chloro-thiophene-2-sulfonic acid (3-methylbicyclo[3.2.1] oct-8-yl)-amide;
endo-5-chloro-thiophene-2-sulfonic acid (3-methylene-bicyclo[3.2.1]oct-8-yl)-amide;
endo-5-chloro-thiophene-2-sulfonic acid (3-oxo-bicyclo [3.2.1]oct-8-yl)-amide;
endo-5-chloro-thiophene-2-sulfonic acid (3-methoxyimino-bicyclo[3.2.1]oct-8-yl)-amide;
endo-butane-1-sulfonic acid (3-methylene-bicyclo[3.2.1] oct-8-yl)-amide;
endo-N-(3-methylene-bicyclo[3.2.1]oct-8-yl)-benzenesulfonamide;
endo-thiophene-2-sulfonic acid (3-methylene-bicyclo[3.2.1] oct-8-yl)-amide;
endo-4-methyl-N-(3-methylene-bicyclo[3.2.1]oct-8-yl)-benzenesulfonamide;
endo-4-fluoro-N-(3-methylene-bicyclo[3.2.1]oct-8-yl)-benzenesulfonamide;
endo-2-fluoro-N-(3-methylene-bicyclo[3.2.1]oct-8-yl)-benzenesulfonamide;
endo-3-fluoro-N-(3-methylene-bicyclo[3.2.1]oct-8-yl)-benzenesulfonamide;
endo-4-chloro-N-(3-methylene-bicyclo[3.2.1]oct-8-yl)-benzenesulfonamide;
endo-4-bromo-N-(3-methylene-bicyclo[3.2.1]oct-8-yl)-benzenesulfonamide;
endo-5-bromo-thiophene-2-sulfonic acid (3-methylene-bicyclo [3.2.1]oct-8-yl)-amide;
endo-4-iodo-N-(3-methylene-bicyclo[3.2.1]oct-8-yl)-benzenesulfonamide; and
endo-5-chloro-thiophene-2-sulfonic acid (3-benzylidene-bicyclo[3.2.1]oct-8-yl)-amide.

A second subclass of the compounds of formula I is defined by formula IIA:

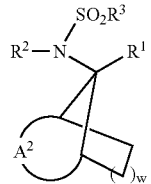

IIA wherein:
$A^2$ represents —$CH_2$—$NR^{13}$—CXY—$CH_2$— or

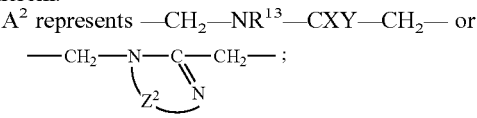

and w, X, Y, $Z^2$, $R^1$, $R^2$, $R^3$ and $R^{13}$ have the same meanings as before.

In preferred embodiments of formula IIA, $R^1$ and $R^2$ are both H, w is 1, X and Y are both H or together represent =S, $Z^2$ completes an imidazole ring, and $R^{13}$ is selected from H, 2,2,2-trifluoroethyl, benzyl, chlorobenzyl, methoxybenzyl, methoxycarbonylbenzyl, methoxycarbonylmethyl, benzoylmethyl and aminocarbonylmethyl.

Examples of compounds within this subclass include:

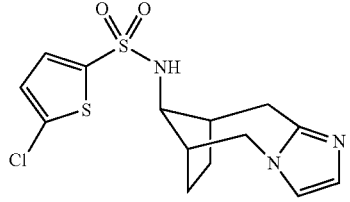

and

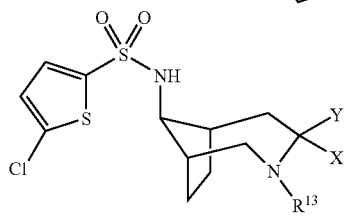

in which X, Y and $R^{13}$ are as indicated in the following table:

| X | Y | $R^{13}$ |
|---|---|----------|
| H | H | Benzyl |
| =O | | H |
| =S | | H |
| H | H | H |
| H | H | $CF_3CH_2$ |
| H | H | $PhCOCH_2$ |
| H | H | $MeOCOCH_2$ |
| H | H | $PhCH_2CH_2$ |
| H | H | $PhCH_2CH_2CH_2$ |
| H | H | $H_2NCOCH_2$ |
| H | H | 2-chlorobenzyl |
| H | H | 3-chlorobenzyl |
| H | H | 4-chlorobenzyl |
| H | H | 2-methoxybenzyl |

-continued

| X | Y | R¹³ |
|---|---|---|
| H | H | 3-methoxybenzyl |
| H | H | 4-methoxybenzyl |
| H | H | 3-MeOCOC₆H₄CH₂ |
| H | H | 4-MeOCOC₆H₄CH₂ |

A third subclass of the compounds of formula I is defined by formula III:

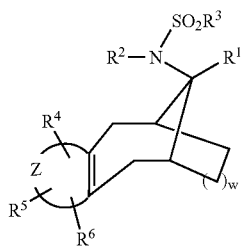

III wherein w, Z, $R^1$, $R^2$, $R^3$, $R^4$, $R^5$ and $R^6$ have the same meanings as before.

In this subclass, w is preferably 1; $R^1$ is preferably H or methyl; $R^2$ is preferably H; $R^5$ and $R^6$ are preferably H; and Z preferably completes an aromatic ring system.

A fourth subclass of the compounds of formula I is defined by formula IIIA:

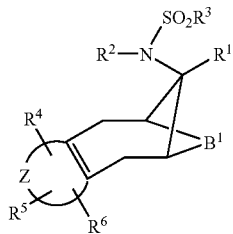

IIIA wherein:

$B^1$ represents —$(CH_2)_u$—$NR^{13}$—CXY—$(CH_2)_v$—;

u and v are independently 0 or 1; and

X, Y, $R^1$, $R^2$, $R^3$, $R^4$, $R^5$, $R^6$ and $R^{13}$ have the same meanings as before.

Preferably, $R^1$ and $R^2$ are both H, $R^5$ and $R^6$ are both H, Z completes an aromatic ring, X and Y are both H and one of u and v is 0 and the other is 1.

A preferred subclass of the compounds of formula III is defined by formula IV:

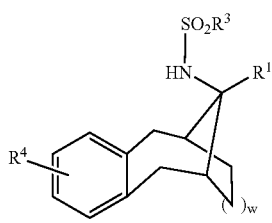

IV wherein w, $R^1$, $R^3$ and $R^4$ have the same meanings as before.

Examples of compounds within this subclass include:
endo-4-methyl-N-tricyclo[8.2.1.0³,⁸]trideca-3(8),4,6-trien-13-yl-benzenesulfonamide;
endo-4-fluoro-N-tricyclo[8:2.1.0³,⁸]trideca-3(8),4,6-trien-13-yl-benzenesulfonamide;
endo-4-chloro-N-tricyclo[8.2.1.0³,⁸]trideca-3(8),4,6-trien-13-yl-benzenesulfonamide;
endo-4-nitro-N-tricyclo[8.2.1.0³,⁸]trideca-3(8),4,6-trien-13-yl-benzenesulfonamide;
endo-propane-1-sulfonic acid tricyclo[8.2.1.0³,⁸]trideca-3(8),4,6-trien-13-ylamide;
endo-4-bromo-N-tricyclo[8.2.1.0³,⁸]trideca-3(8),4,6-trien-13-yl-benzenesulfonamide;
endo-4-iodo-N-tricyclo[8.2.1.0³,⁸]trideca-3(8),4,6-trien-13-yl-benzenesulfonamide;
endo-4,5-dibromo-thiophene-2-sulfonic acid tricyclo[8.2.1.0³,⁸]trideca-3(8),4,6-trien-13-ylamide;
endo-3-chloro-4-fluoro-N-tricyclo[8.2.1.0³,⁸]trideca-3(8),4,6-trien-13-yl-benzenesulfonamide;
endo-4-ethyl-N-tricyclo[8.2.1.0³,⁸]trideca-3(8),4,6-trien-13-yl-benzenesulfonamide;
endo-2,3,4,5,6-pentafluoro-N-tricyclo[8.2.1.0³,⁸]trideca-3(8),4,6-trien-13-yl-benzenesulfonamide;
endo-N-tricyclo[8.2.1.0³,⁸]trideca-3(8),4,6-trien-13-yl-4-trifluoromethyl-benzenesulfonamide;
endo-2,4-difluoro-N-tricyclo[8.2.1.0³,⁸]trideca-3(8),4,6-trien-13-yl-benzenesulfonamide;
endo-2-chloro-N-tricyclo[8.2.1.0³,⁸]trideca-3(8),4,6-trien-13-yl-benzenesulfonamide;
endo-2,5-dichloro-thiophene-3-sulfonic acid tricyclo[8.2.1.0³,⁸]trideca-3(8),4,6-trien-13-ylamide;
endo-2,3-dichloro-N-tricyclo[8.2.1.0³,⁸]trideca-3(8),4,6-trien-13-yl-benzenesulfonamide;
endo-4,5-dichloro-thiophene-2-sulfonic acid tricyclo[8.2.1.0³,⁸]trideca-3(8),4,6-trien-13-ylamide;
endo-2-cyano-N-tricyclo[8.2.1.0³,⁸]trideca-3(8),4,6-trien-13-yl-benzenesulfonamide;
endo-thiophene-2-sulfonic acid tricyclo[8.2.1.0³,⁸]trideca-3(8),4,6-trien-13-ylamide;
endo-3-fluoro-N-tricyclo[8.2.1.0³,⁸]trideca-3(8),4,6-trien-13-yl-benzenesulfonamide;
endo-5-bromo-thiophene-2-sulfonic acid tricyclo[8.2.1.0³,⁸]trideca-3(8),4,6-trien-13-ylamide;
endo-2,6-difluoro-N-tricyclo[8.2.1.0³,⁸]trideca-3(8),4,6-trien-13-yl-benzenesulfonamide;
endo-4-bromo-5-chloro-thiophene-2-sulfonic acid tricyclo[8.2.1.0³,⁸]trideca-3(8),4,6-trien-13-ylamide;
endo-3-bromo-5-chloro-thiophene-2-sulfonic acid tricyclo[8.2.1.0³,⁸]trideca-3(8),4,6-trien-13-ylamide;
endo-2,3,4-trifluoro-N-tricyclo[8.2.1.0³,⁸]trideca-3(8),4,6-trien-13-yl-benzenesulfonamide;
endo-3,4-difluoro-N-tricyclo[8.2.1.0³,⁸]trideca-3(8),4,6-trien-13-yl-benzenesulfonamide;
endo-4-cyano-N-tricyclo[8.2.1.0³,⁸]trideca-3(8),4,6-trien-13-yl-benzenesulfonamide;
endo-N-tricyclo[8.2.1.0³,⁸]trideca-3(8),4,6-trien-13-yl-benzenesulfonamide;
endo-2-fluoro-N-tricyclo[8.2.1.0³,⁸]trideca-3(8),4,6-trien-13-yl-benzenesulfonamide;
endo-pyridine-2-sulfonic acid tricyclo[8.2.1.0³,⁸]trideca-3(8),4,6-trien-13-ylamide;
endo-butane-1-sulfonic acid tricyclo[8.2.1.0³,⁸]trideca-3(8),4,6-trien-13-ylamide;
endo-5-chloro-thiophene-2-sulfonic acid tricyclo[8.2.1.0³,⁸]trideca-3(8),4,6-trien-13-ylamide;
endo-N-(5-fluoro-tricyclo[8.2.1.0³,⁸]trideca-3(8),4,6-trien-13-yl)-benzenesulfonamide;
endo-5-chloro-thiophene-2-sulfonic acid (5-fluoro-tricyclo[8.2.1.0³,⁸]trideca-3(8),4,6-trien-13-yl)-amide;
endo-5-chloro-thiophene-2-sulfonic acid (4-fluoro-tricyclo[8.2.1.0³,⁸]trideca-3(8),4,6-trien-13-yl)-amide;

endo-5-chloro-thiophene-2-sulfonic acid (5-chloro-tricyclo[8.2.1.0$^{3,8}$]trideca-3(8),4,6-trien-13-yl)-amide;
endo-5-chloro-thiophene-2-sulfonic acid (4-chloro-tricyclo[8.2.1.0$^{3,8}$]trideca-3(8),4,6-trien-13-yl)-amide;
endo-4-methyl-N-tricyclo[8.3.1.0$^{3,8}$]tetradeca-3(8),4,6-trien-14-yl-benzenesulfonamide;
endo-thiophene-2-sulfonic acid tricyclo[8.3.1.0$^{3,8}$]tetradeca-3(8),4,6-trien-14-ylamide;
endo-N-(13-methyl-tricyclo[8.2.1.0$^{3,8}$]trideca-3(8),4,6-trien-13-yl)-benzenesulfonamide;
endo-N-(5-nitro-tricyclo[8.2.1.0$^{3,8}$]trideca-3(8),4,6-trien-13-yl)-benzenesulfonamide;
endo-N-(4-nitro-tricyclo[8.2.1.0$^{3,8}$]trideca-3(8),4,6-trien-13-yl)-benzenesulfonamide;
endo-N-(4-amino-tricyclo[8.2.1.0$^{3,8}$]trideca-3(8),4,6-trien-13-yl)-benzenesulfonamide;
endo-N-(5-bromo-tricyclo[8.2.1.0$^{3.8}$]trideca-3(8),4,6-trien-13-yl)-benzenesulfonamide;
endo-N-(5-phenyl-tricyclo[8.2.1.0$^{3,8}$]trideca-3(8),4,6-trien-13-yl)-benzenesulfonamide;
endo-N-(5-thiophen-3-yl-tricyclo[8.2.1.0$^{3,8}$]trideca-3(8),4,6-trien-13-yl)-benzenesulfonamide;
endo-N-[5-(2-methoxy-phenyl)-tricyclo[8.2.1.0$^{3,8}$]trideca-3(8),4,6-trien-13-yl]-benzenesulfonamide;
endo-N-[5-(4-fluoro-phenyl)-tricyclo[8.2.1.0$^{3,8}$]trideca-3(8),4,6-trien-13-yl]-benzenesulfonamide;
endo-N-[5-(3-fluoro-phenyl)-tricyclo[8.2.1.0$^{3,8}$]trideca-3(8),4,6-trien-13-yl]-benzenesulfonamide;
endo-N-(5-benzofuran-2-yl-tricyclo[8.2.1.0$^{3,8}$]trideca-3(8),4,6-trien-13-yl)-benzenesulfonamide;
endo-N-(5-thiophen-2-yl-tricyclo[8.2.1.0$^{3,8}$]trideca-3(8),4,6-trien-13-yl)-benzenesulfonamide;
endo-N-[5-(2-fluoro-phenyl)-tricyclo[8.2.1.0$^{3,8}$]trideca-3(8),4,6-trien-13-yl]-benzenesulfonamide;
endo-N-(5-pyridin-4-yl-tricyclo[8.2.1.0$^{3,8}$]trideca-3(8),4,6-trien-13-yl)-benzenesulfonamide;
endo-N-(5-pyridin-3-yl-tricyclo[8.2.1.0$^{3,8}$]trideca-3(8),4,6-trien-13-yl)-benzenesulfonamide; and
endo-N-[5-(6-methoxy-pyridin-3-yl)-tricyclo[8.2.1.0$^{3,8}$]trideca-3(8),4,6-trien-13-yl]-benzenesulfonamide.

Further compounds in accordance with Formula IV are as shown in the table below. (In all cases, w=1, R$^1$=H and R$^4$ is in the β-position with respect to the ring junction).

| R$^3$ | R$^4$ |
|---|---|
| 5-Cl-2-thienyl | 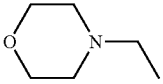 |
| 5-Cl-2-thienyl | CN |
| 5-Cl-2-thienyl | 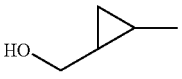 |
| 5-Cl-2-thienyl | 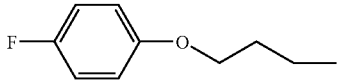 |
| 5-Cl-2-thienyl | 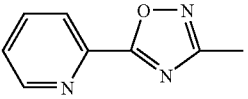 |

-continued

| R$^3$ | R$^4$ |
|---|---|
| 5-Cl-2-thienyl | 2-pyridyl |
| 5-Cl-2-thienyl | 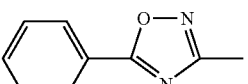 |
| 5-Cl-2-thienyl | 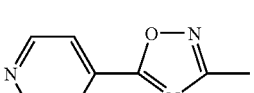 |
| vinyl | H |
| 2-ethoxyethyl | H |
| 2-ethanethioethyl | H |
| 3-chloropropyl | H |
| 2,2,2-trifluoroethyl | H |
| cyclopentyl | H |
| 2-furyl | H |
| 2-thiazolyl | H |
| 3-thienyl | H |
| 2-chloro-5-thiazolyl | H |
| 3-pyridyl | H |
| 6-chloro-3-pyridyl | H |
| n-pentyl | H |
| 3-pyrrolyl | H |
| 1-methyl-3-pyrrolyl | H |
| 5-isothiazolyl | H |

A preferred subclass of the compounds of formula IV is defined by formula V:

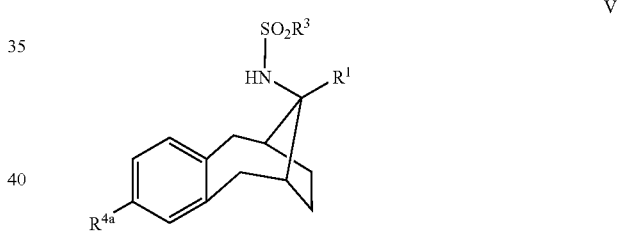

wherein R$^{4a}$ represents —N(R$^9$)$_2$, —NR$^9$COR$^{10}$ or —NR$^9$CO$_2$R$^{10}$, and R$^1$, R$^3$, R$^9$ and R$^{10}$ have the same meanings as before.

In a subset of the compounds of Formula V, R$^1$ represents H.

Examples of compounds within this subclass include:
endo-N-(5-amino-tricyclo[8.2.1.0$^{3,8}$]trideca-3(8),4,6-trien-13-yl)-benzenesulfonamide;
endo-N-(13-benzenesulfonylamino-tricyclo[8.2.1.0$^{3,8}$]trideca-3(8),4,6-trien-5-yl)-benzamide;
endo-N-(13-benzenesulfonylamino-tricydo[8.2.1.0$^{3,8}$]trideca-3(8),4,6-trien-5-yl)-2-phenyl-acetamide;
endo-N-(13-benzenesulfonylamino-tricyclo[8.2.1.0$^{3,8}$]trideca-3(8),4,6-trien-5-yl)-2-phenoxy-acetamide;
endo-N-(13-benzenesulfonylamino-tricyclo[8.2.1.0$^{3,8}$]trideca-3(8),4,6-trien-5-yl)-2-(3,5-difluoro-phenyl)-acetamide;
endo-N-(13-benzenesulfonylamino-tricyclo[8.2.1.0$^{3,8}$]trideca-3(8),4,6-trien-5-yl)-4-fluoro-benzamide;
endo-N-(13-benzenesulfonylamino-tricyclo[8.2.1.0$^{3,8}$]trideca-3(8),4,6-trien-5-yl)-acetamide;
endo-hexanoic acid (13-benzenesulfonylamino-tricyclo[8.2.1.0$^{3,8}$]trideca-3(8),4,6-trien-5-yl)-amide;

endo-3-methyl-pentanoic acid (13-benzenesulfonylamino-tricyclo[8.2.1.0$^{3,8}$]trideca-3(8),4,6-trien-5-yl)-amide;
endo-N-(13-benzenesulfonylamino-tricyclo[8.2.1.0$^{3,8}$]trideca-3(8),4,6-trien-5-yl)-2-cyclopentyl-acetamide;
endo-4-methyl-octanoic acid (13-benzenesulfonylamino-tricyclo[8.2.1.0$^{3,8}$]trideca-3(8),4,6-trien-5-yl)-amide;
endo-5-methyl-hexanoic acid (13-benzenesulfonylamino-tricyclo[8.2.1.0$^{3,8}$]trideca-3(8),4,6-trien-5-yl)-amide;
endo-N-(13-benzenesulfonylamino-tricyclo[8.2.1.0$^{3,8}$]trideca-3(8),4,6-trien-5-yl)-2-methoxy-acetamide;
endo-N-(13-benzenesulfonylamino-tricyclo[8.2.1.0$^{3,8}$]trideca-3(8),4,6-trien-5-yl)-3-phenyl-propionamide;
endo-pyridine-2-carboxylic acid (13-benzenesulfonylamino-tricyclo[8.2.1.0$^{3,8}$]trideca-3(8),4,6-trien-5-yl)-amide;
endo-N-[13-(5-chloro-thiophene-2-sulfonylamino)-tricyclo[8.2.1.0$^{3,8}$]trideca-3(8),4,6-trien-5-yl]-2-phenoxy-acetamide;
endo-(13-benzenesulfonylamino-tricyclo[8.2.1.0$^{3,8}$]trideca-3(8),4,6-trien-5-yl)-carbamic acid phenyl ester;
endo-(13-benzenesulfonylamino-tricyclo[8.2.1.0$^{3,8}$]trideca-3(8),4,6-trien-5-yl)-carbamic acid benzyl ester;
endo-(13-benzenesulfonylamino-tricyclo[8.2.1.0$^{3,8}$]trideca-3(8),4,6-trien-5-yl)-carbamic acid isobutyl ester;
endo-(13-benzenesulfonylamino-tricyclo[8.2.1.0$^{3,8}$]trideca-3(8),4,6-trien-5-yl)-carbamic acid p-tolyl ester;
endo-(13-benzenesulfonylamino-tricyclo[8.2.1.0$^{3,8}$]trideca-3(8),4,6-trien-5-yl)-carbamic acid 4-fluoro-phenyl ester;
endo-(13-benzenesulfonylamino-tricyclo[8.2.1.0$^{3,8}$]trideca-3(8),4,6-trien-5-yl)-carbamic acid 4-methoxy-phenyl ester;
endo-(13-benzenesulfonylamino-tricyclo[8.2.1.0$^{3,8}$]trideca-3(8),4,6-trien-5-yl)-carbamic acid 2,2-dimethyl-propyl ester;
endo-N-[5-[(pyridin-3-ylmethyl)-amino]-tricyclo[8.2.1.0$^{3,8}$]trideca-3(8),4,6-trien-13-yl]-benzenesulfonamide;
endo-N-[5-(4-phenoxy-benzylamino)-tricyclo[8.2.1.0$^{3,8}$]trideca-3(8),4,6-trien-13-yl]-benzenesulfonamide;
endo-N-[5-(4-benzyloxy-benzylamino)-tricyclo[8.2.1.0$^{3,8}$]trideca-3(8),4,6-trien-13-yl]-benzenesulfonamide;
endo-N-[5-(3-methoxy-benzylamino)-tricyclo[8.2.1.0$^{3,8}$]trideca-3(8),4,6-trien-13-yl]-benzenesulfonamide;
endo-N-[5-(4-methoxy-benzylamino)-tricyclo[8.2.1.0$^{3,8}$]trideca-3(8),4,6-trien-13-yl]-benzenesulfonamide;
endo-N-[5-(cyclohexylmethyl-amino)-tricyclo[8.2.1.0$^{3,8}$]trideca-3(8),4,6-trien-13-yl]-benzenesulfonamide;
endo-N-[5-(3-methyl-butylamino)-tricyclo[8.2.1.0$^{3,8}$]trideca-3(8),4,6-trien-13-yl]-benzenesulfonamide;
endo-N-{5-[(2,3-dihydro-benzo[1,4]dioxin-6-ylmethyl)-amino]-tricyclo[8.2.1.0$^{3,8}$]trideca-3(8),4,6-trien-13-yl}-benzenesulfonamide;
endo-N-[5-(4-tert-butyl-benzylamino)-tricyclo[8.2.1.0$^{3,8}$]trideca-3(8),4,6-trien-13-yl]-benzenesulfonamide;
endo-N-[5-(3-phenyl-butylamino)-tricyclo[8.2.1.0$^{3,8}$]trideca-3(8),4,6-trien-13-yl]-benzenesulfonamide;
endo-N-[5-(4-isopropoxy-benzylamino)-tricyclo[8.2.1.0$^{3,8}$]trideca-3(8),4,6-trien-13-yl]-benzenesulfonamide;
endo-N-{5-[(benzofuran-2-ylmethyl)-amino]-tricyclo[8.2.1.0$^{3,8}$]trideca-3(8),4,6-trien-13-yl}-benzenesulfonamide;
endo-N-[5-(3-phenyl-propylamino)-tricyclo[8.2.1.0$^{3,8}$]trideca-3(8),4,6-trien-13-yl]-benzenesulfonamide;
endo-N-[5-(4-pentyl-benzylamino)-tricyclo[8.2.1.0$^{3,8}$]trideca-3(8),4,6-trien-13-yl]-benzenesulfonamide;
endo-N-[5-(3-trifluoromethoxy-benzylamino)-tricyclo[8.2.1.0$^{3,8}$]trideca-3(8),4,6-trien-13-yl]-benzenesulfonamide;
endo-N-[5-(4-cyano-benzylamino)-tricyclo[8.2.1.0$^{3,8}$]trideca-3(8),4,6-trien-13-yl]-benzenesulfonamide;
endo-N-[5-(3-fluoro-benzylamino)-tricyclo[8.2.1.0$^{3,8}$]trideca-3(8),4,6-trien-13-yl]-benzenesulfonamide;
endo-N-[5-(4-fluoro-benzylamino)-tricyclo[8.2.1.0$^{3,8}$]trideca-3(8),4,6-trien-13-yl]-benzenesulfonamide;
endo-N-[5-(3-chloro-benzylamino)-tricyclo[8.2.1.0$^{3,8}$]trideca-3(8),4,6-trien-13-yl]-benzenesulfonamide; and
endo-N-[5-(3-trifluoromethyl-benzylamino)-tricyclo[8.2.1.0$^{3,8}$]trideca-3(8),4,6-trien-13-yl]-benzenesulfonamide.

Further examples of compounds in accordance with formula V include:
endo-5-chloro-thiophene-2-sulfonic acid {5-[2-(4-fluoro-phenoxy)-ethylamino]-tricyclo[8.2.1.0$^{3,8}$]trideca-3(8),4,6-trien-13-yl}-amide;
endo-5-chloro-thiophene-2-sulfonic acid {5-[2-(4-chloro-phenoxy)-ethylamino]-tricyclo[8.2.1.0$^{3,8}$]trideca-3(8),4,6-trien-13-yl}-amide;
endo-5-chloro-thiophene-2-sulfonic acid {5-[4-(4-fluoro-phenyl)-piperazin-1-yl]-tricyclo[8.2.1.0$^{3,8}$]trideca-3(8),4,6-trien-13-yl}-amide;
endo-5-chloro-thiophene-2-sulfonic acid {5-[2-(4-fluoro-phenylamino)-ethylamino]-tricyclo[8.2.1.0$^{3,8}$]trideca-3(8),4,6-trien-13-yl}-amide;
endo-5-chloro-thiophene-2-sulfonic acid {5-[4-(2-methoxy-phenyl)-piperazin-1-yl]-tricyclo[8.2.1.0$^{3,8}$]trideca-3(8),4,6-trien-13-yl}-amide; and
endo-5-chloro-thiophene-2-sulfonic acid [5-(4-pyridin-2-yl-piperazin-1-yl)-tricyclo[8.2.1.0$^{3,8}$]trideca-3(8),4,6-trien-13-yl]-amide.

In preferred compounds in accordance with formula V, $R^1$ represents H and $R^{4a}$ represents $N(R^9)_2$ wherein the two $R^9$ groups complete a piperidine or piperazine ring which is optionally substituted in the 4-position by Ar, or $NHR^{10}$ wherein $R^{10}$ is selected from $C_{6-10}arylC_{1-6}alkyl$ (especially benzyl or substituted benzyl), heteroaryl$C_{1-6}$alkyl, and $C_{1-6}$alkyl which is substituted by $OR^{10}$ or $N(R^{11})_2$ (especially ethyl which is substituted by OAr or $N(R^{12})_2$ wherein the two $R^{12}$ groups complete a heterocyclic ring).

Another preferred subclass of the compounds of formula IV is defined by formula VA:

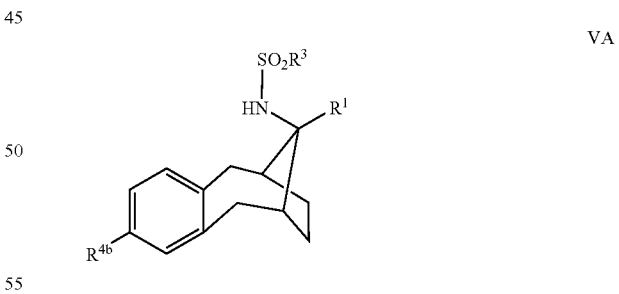

VA wherein $R^{4b}$ represents $C_{2-6}$alkenyl (which is optionally substituted by halogen, CN, $OR^{11}$, —$CO_2R^{11}$, —$COR^{11}$ or —$CON(R^{11})_2$), $C_{6-10}arylC_{2-6}alkenyl$, heteroaryl$C_{2-6}$alkenyl, —CH=CHCH$_2$N(R$^{16}$)$_2$, —OR$^{10}$, —CH$_2$OR$^9$, —NHCOCH$_2$OR$^{10}$ or —NHCOCH$_2$N(R$^{16}$)$_2$; and $R^1$, $R^3$, $R^9$, $R^{10}$, $R^{11}$ and $R^{16}$ have the same meanings as before.

In particular, $R^{4b}$ represents —CH=CH$_2$, —CH=CHCN, —CH=CH—CH$_2$OR$^{11}$, —CH=CH—CO—Ar, —CH=CH—CO$_2$R$^{11}$, —CH=CHAr, —CH=CHCH$_2$N(R$^{16}$)$_2$, —OCH$_2$Ar, —OCH$_2$CH$_2$OR$^{12}$, —OCH$_2$CON(R$^{12}$)$_2$, —OCH$_2$CH$_2$N(R$^{12}$)$_2$, —CH$_2$OR$^9$, —NHCOCH$_2$OR$^{10}$ or —NHCOCH$_2$N(R$^{16}$)$_2$, where Ar and R$^{12}$ have the same meanings as before.

Examples of compounds within this subclass include the compounds of formula VA wherein R$^1$ is H and R$^3$ and R$^{4b}$ are as follows:

| R$^3$ | R$^{4b}$ |
|---|---|
| Ph | 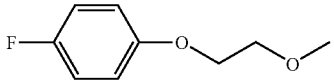 |
| Ph | 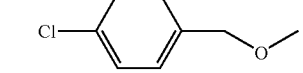 |
| Ph | 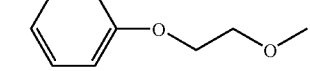 |
| Ph | 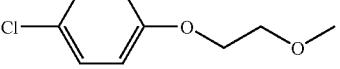 |
| Ph | 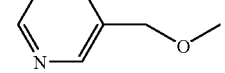 |
| Ph | 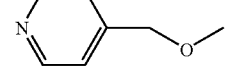 |
| 5-Cl-2-thienyl | 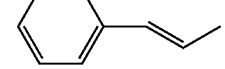 |
| 5-Cl-2-thienyl | 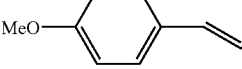 |
| 5-Cl-2-thienyl | 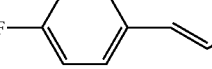 |
| 5-Cl-2-thienyl | 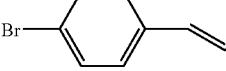 |
| 5-Cl-2-thienyl | 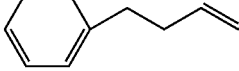 |
| 5-Cl-2-thienyl |  |
| 5-Cl-2-thienyl | 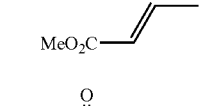 |
| 5-Cl-2-thienyl | 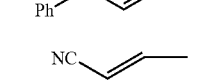 |
| 5-Cl-2-thienyl |  |

-continued

| R$^3$ | R$^{4b}$ |
|---|---|
| 5-Cl-2-thienyl | 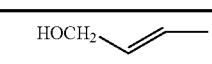 |
| 5-C-2-thienyl | HOCH$_2$— |
| Ph | HOCH$_2$— |
| Ph |  |
| Ph | 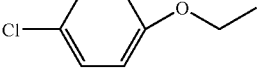 |
| Ph | 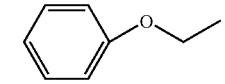 |
| Ph | 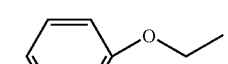 |
| Ph | 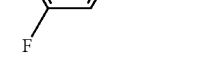 |
| Ph | 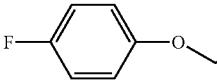 |
| Ph | 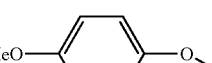 |
| Ph | 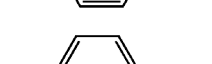 |
| Ph | 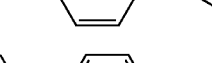 |
| Ph | 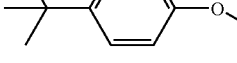 |
| Ph | 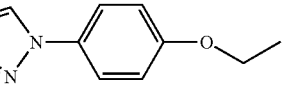 |
| 5-Cl-2-thienyl |  |
| 5-Cl-2-thienyl | 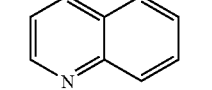 |

-continued

| R³ | R⁴ᵇ |
|---|---|
| 5-Cl-2-thienyl | [4-fluorophenyl-substituted diazabicyclic-CH2-C(O)NHMe] |
| 5-Cl-2-thienyl | [4-phenylpiperazinyl-CH2-C(O)NHMe] |
| 5-Cl-2-thienyl | [piperidinyl-CH2-C(O)NHMe] |
| 5-Cl-2-thienyl | [4-methylpiperazinyl-CH2-C(O)NHMe] |
| 5-Cl-2-thienyl | [morpholinyl-CH2-C(O)NHMe] |
| 5-Cl-2-thienyl | Et₂N-CH2-C(O)NHMe |
| 5-Cl-2-thienyl | [4-phenylpiperidinyl-CH2-C(O)NHMe] |
| 5-Cl-2-thienyl | [4-(2-methoxyphenyl)piperidinyl-CH2-C(O)NHMe] |
| 5-Cl-2-thienyl | [2-(phenoxymethyl)morpholinyl-CH2-C(O)NHMe] |
| 5-Cl-2-thienyl | [4-phenyl-2-(aminomethyl)morpholinyl acetamide derivative] |
| 5-Cl-2-thienyl | [spiro-isobenzofuran-piperidinyl-CH2-C(O)NHMe] |

-continued

| R³ | R⁴ᵇ |
|---|---|
| 5-Cl-2-thienyl | [3-phenyl-imidazo[1,2-a]pyrazinyl-CH2-C(O)NHMe] |
| 5-Cl-2-thienyl | [N-benzyl-N-methyl-amino-CH2-C(O)NHMe] |
| 5-Cl-2-thienyl | [4-(2-methoxyphenyl)piperazinyl-CH2-C(O)NHMe] |

Further suitable compounds in accordance with formula VA are those in which R¹ is H and R³ and R⁴ᵇ are as follows:

| R³ | R⁴ᵇ |
|---|---|
| 5-Cl-2-thienyl | [4-Cl-phenoxy-CH2-C(O)NHMe] |
| 5-Cl-2-thienyl | [4-F-phenoxy-CH2-C(O)NHMe] |
| 5-Cl-2-thienyl | t-Bu-O-C(O)-N[piperidinyl]-O-Me |
| 5-Cl-2-thienyl | [pyridin-4-yl-O-Me] |
| 3-pyridyl | PhCH₂O— |
| 2-Cl-5-thiazolyl | PhCH₂O— |
| 2-thienyl | [4-F-phenyl-O-CH2CH2-O-Me] |
| 4-fluorophenyl | [4-F-phenyl-O-CH2CH2-O-Me] |
| 4-chlorophenyl | [4-F-phenyl-O-CH2CH2-O-Me] |
| 4-nitrophenyl | [4-F-phenyl-O-CH2CH2-O-Me] |

-continued

| R³ | R⁴ᵇ |
|---|---|
| 4-methoxyphenyl | 4-fluorophenyl-O-CH₂CH₂-OMe |
| n-propyl | 4-fluorophenyl-O-CH₂CH₂-OMe |
| 3,5-(bistrifluoromethyl)phenyl | 4-fluorophenyl-O-CH₂CH₂-OMe |
| 2-fluorophenyl | 4-fluorophenyl-O-CH₂CH₂-OMe |
| 2,4-difluorophenyl | 4-fluorophenyl-O-CH₂CH₂-OMe |
| 3-fluorophenyl | 4-fluorophenyl-O-CH₂CH₂-OMe |
| 5-Br-2-thienyl | 4-fluorophenyl-O-CH₂CH₂-OMe |
| 1-Me-1H-imidazol-4-yl | 4-fluorophenyl-O-CH₂CH₂-OMe |
| 1,2-di-Me-1H-imidazol-4-yl | 4-fluorophenyl-O-CH₂CH₂-OMe |
| 4-cyanophenyl | 4-fluorophenyl-O-CH₂CH₂-OMe |
| 3-pyridyl | 4-fluorophenyl-O-CH₂CH₂-OMe |
| n-butyl | 4-fluorophenyl-O-CH₂CH₂-OMe |
| 3-pyridyl | morpholinyl-CH₂CH₂-OMe |
| 5-Cl-2-thienyl | morpholinyl-CH₂CH₂-OMe |
| 5-Cl-2-thienyl | 2-Me-pyrrolidinyl-CH₂CH₂-OMe |

-continued

| R³ | R⁴ᵇ |
|---|---|
| 5-Cl-2-thienyl | 2-(hydroxymethyl)pyrrolidinyl-CH₂CH₂-OMe |
| 5-Cl-2-thienyl | 2-(methoxymethyl)pyrrolidinyl-CH₂CH₂-OMe |
| 5-Cl-2-thienyl | (S)-2-(methoxymethyl)pyrrolidinyl-CH₂CH₂-OMe |
| 5-Cl-2-thienyl | 2-oxa-5-azabicyclic-CH₂CH₂-OMe |
| 5-Cl-2-thienyl | piperidinyl-CH₂CH₂-OMe |
| 5-Cl-2-thienyl | 3-hydroxypyrrolidinyl-CH₂CH₂-OMe |
| 5-Cl-2-thienyl | 4-hydroxypiperidinyl-CH₂CH₂-OMe |
| 5-Cl-2-thienyl | 2-Me-piperidinyl-CH₂CH₂-OMe |
| 5-Cl-2-thienyl | piperidinyl-CH₂-CH=CH-CH₃ |
| 5-Cl-2-thienyl | morpholinyl-CH₂-CH=CH-CH₃ |
| 5-Cl-2-thienyl | imidazolyl-CH₂-CH=CH-CH₃ |
| 5-Cl-2-thienyl | 1,2,4-triazolyl-CH₂-CH=CH-CH₃ |

-continued

| R³ | R⁴ᵇ |
|---|---|
| 5-Cl-2-thienyl | (Me-piperazine-CH2-CH=CH-CH3) |
| 5-Cl-2-thienyl | (Ph-piperazine-CH2-CH=CH-CH3) |
| 5-Cl-2-thienyl | (MeO-CH2CH2-N(Me)-CH2-CH=CH-CH3) |
| 3-pyridyl | (morpholine-CH2-CH=CH-CH3) |
| (morpholine-thiazole-Me) | (morpholine-CH2-CH=CH-CH3) |
| 5-Cl-2-thienyl | (morpholine N-oxide-CH2-CH=CH-CH3) |
| 5-Cl-2-thienyl | (MeOCO-CH=CH-CH3, cis) |
| 5-Cl-2-thienyl | (morpholine-CH2CH2CH2-O-Me) |

Another subclass of the compounds of formula I is defined by formula IIIC:

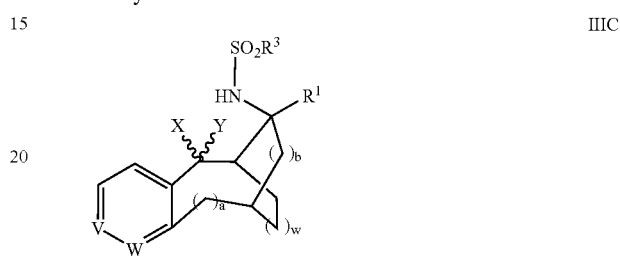

IIIC wherein
V represents CR⁴ or N;
W represents CH or N;
a is 0 or 1;
b is 0 or 1;
w is 1 or 2;

and X, Y, R¹, R³ and R⁴ have the same meanings as before.
Preferably, b is 0, R¹ is H and V and W are not both N.
Examples of compounds within this subclass are as indicated in the following table:

| V | W | a | b | w | X, Y | R³ | R⁴ |
|---|---|---|---|---|------|----|----|
| CR⁴ | CH | 1 | 1 | 1 | H, H | 5-Cl-2-thienyl | H |
| CR⁴ | CH | 0 | 0 | 2 | H, H | 5-Cl-2-thienyl | H |
| CR⁴ | N | 1 | 0 | 1 | H, H | 5-Cl-2-thienyl | H |
| N | CH | 1 | 0 | 1 | H, H | 5-Cl-2-thienyl | — |
| CR⁴ | CH | 1 | 0 | 1 | =CH₂ | 3-pyridyl | H |
| CR⁴ | CH | 1 | 0 | 1 | CH₃, OH | 3-pyridyl | H |
| CR⁴ | CH | 1 | 0 | 1 | =O | 5-Cl-2-thienyl | (4-F-phenyl-O-CH2CH2-O-Me) |
| CR⁴ | CH | 1 | 0 | 1 | =O | 3-pyridyl | (4-F-phenyl-O-CH2CH2-O-Me) |
| CR⁴ | CH | 1 | 0 | 1 | H, OH | 3-pyridyl | (4-F-phenyl-O-CH2CH2-O-Me) |
| CR⁴ | CH | 1 | 0 | 1 | H, CH₃ | 3-pyridyl | (4-F-phenyl-O-CH2CH2-O-Me) |
| CR⁴ | CH | 1 | 0 | 1 | =CH₂ | 3-pyridyl | (4-F-phenyl-O-CH2CH2-O-Me) |

Preferred compounds in accordance with the invention include those of formula IV wherein:

w is 1;

$R^1$ is H;

$R^3$ is selected from n-propyl, n-butyl, phenyl, 2-fluorophenyl, 3-fluorophenyl, 4-fluorophenyl, 2,4-difluorophenyl, 4-chlorophenyl, 2-thienyl, 5-chloro-2-thienyl, 5-bromo-2-thienyl, 3-pyridyl, 6-chloro-2-pyridyl and 5-isothiazolyl; and $R^4$ is in the β-position with respect to the ring junction and is selected from pyridine-2-carboxamido, phenoxyacetamido, 4-chlorophenoxyacetamido, 2,4-dichlorophenoxyacetamido, 4-fluorophenoxyacetimido, morpholin-4-ylacetamido, pyrrolidin-1-ylacetamido, piperidin-1-ylacetamido, 4-phenylpiperazin-1-ylacetamido, 4-(4-fluorophenyl)piperazin-1-ylacetamido, 2-(4-fluorophenoxy)ethoxy, 2-(morpholin-4-yl)ethoxy, 2-(morpholin-4-yl)ethylamino, 2-(4-fluorophenoxy)ethylamino, 2-(4-chlorophenoxy)ethylamino, 3-(4-fluorophenoxy)propenyl, 3-(imidazol-1-yl)propenyl, 3-(morpholin-4-yl)propenyl, 5-(pyridin-2-yl)-1,2,4-oxadiazol-3-yl, 5-(pyridin-3-yl)-1,2,4-oxadiazol-3-yl, 5-(pyridin-4-yl)-1,2,4-oxadiazol-3-yl, 3-(2-aza-5-oxabicyclo[2.2.1]hept-2-yl)propenyl, 2-(2-aza-5-oxabicyclo[2.2.1]hept-2-yl)ethoxy, 3-(4-fluoropiperidin-1-yl)propenyl, 2-(4-fluoropiperidin-1-yl)ethoxy, 3-(4-trifluoromethylpiperidin-1-yl)propenyl and 2-(4-trifluoromethylpiperidin-1-yl) ethoxy;

and the pharmaceutically acceptable salts thereof.

The compounds of the present invention have an activity as inhibitors of γ secretase.

The invention provides pharmaceutical compositions comprising one or more compounds of Formula I or pharmaceutically acceptable salts thereof and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of Formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of Formula I or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to Formula I or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

Compounds of formula IA in accordance with the invention (corresponding to formula I in which $R^1$ and $R^2$ are both H) may be prepared by reaction of the amines (VI) with $R^3SO_2$-Hal, where Hal represents halogen (preferably Cl) and A, B, X, Y, $R^3$, n and m have the same meanings as before:

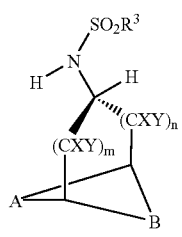

IA

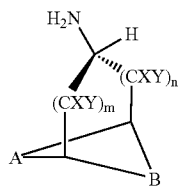

VI

The reaction is advantageously carried out in an aprotic solvent such as dichloromethane in the presence of a base such as pyridine at ambient temperature.

The amines VI may be prepared by reduction of the oximes VII, derived from the ketones VIII:

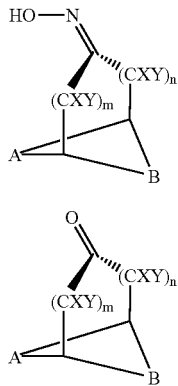

VII

VIII wherein A, B, X, Y, n and m have the same meanings as before.

The reduction of VII to VI may be effected by conventional means, such as hydrogenation in a solvent such as acetic acid in the presence of a catalyst such as $PtO_2$, or reaction with sodium cyanoborohydride in ethanolic solution. Conversion of the ketones VIII to the oximes VII is readily achieved by condensation of the ketones with hydroxylamine hydrochloride in refluxing ethanolic solution in the presence of a mild base such as sodium acetate.

Compounds of formula IB in accordance with the invention (corresponding to formula I in which $R^1$ is an alkyl group and $R^2$ is H) may be prepared by reaction of the sulphonylimine IX with RLi:

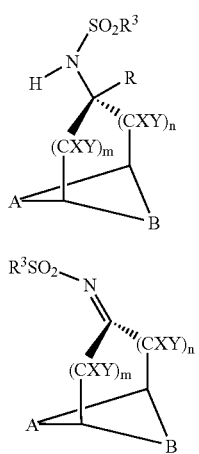

IB

IX wherein R represents $C_{1-4}$alkyl, and A, B, X, Y, $R^3$, n and m have the same meanings as before. The reaction is advantageously carried out at reduced temperature in a hydrocarbon solvent, with quenching by aqueous acid.

The sulphonylimines IX are obtained by condensation of the ketones VIII with a sulphonamide $R^3SO_2NH_2$, where $R^3$ has the same meaning as before. The condensation may be effected by refluxing the reagents in toluene in the presence of an acid catalyst with azeotropic removal of water.

Compounds of formula I in which $R^2$ is other than H may be obtained by appropriate transformations of the compounds of formulae IA, IB and ID, for example by N-alkylation or N-acylation using standard methods. Alternatively, the primary amines VI may be converted to secondary amines by N-alkylation or N-arylation using standard methods, prior to reaction with $R^3SO_2$-Hal.

The ketones VIII, sulphonyl halides $R^3SO_2$-Hal and sulphonamides $R^3SO_2NH_2$ are commercially available or accessible by the application of known synthetic methods to commercially available materials. For example, a convenient route to ketones VIIIA, synthetic precursors of the compounds of formula IV, is illustrated in the following scheme:

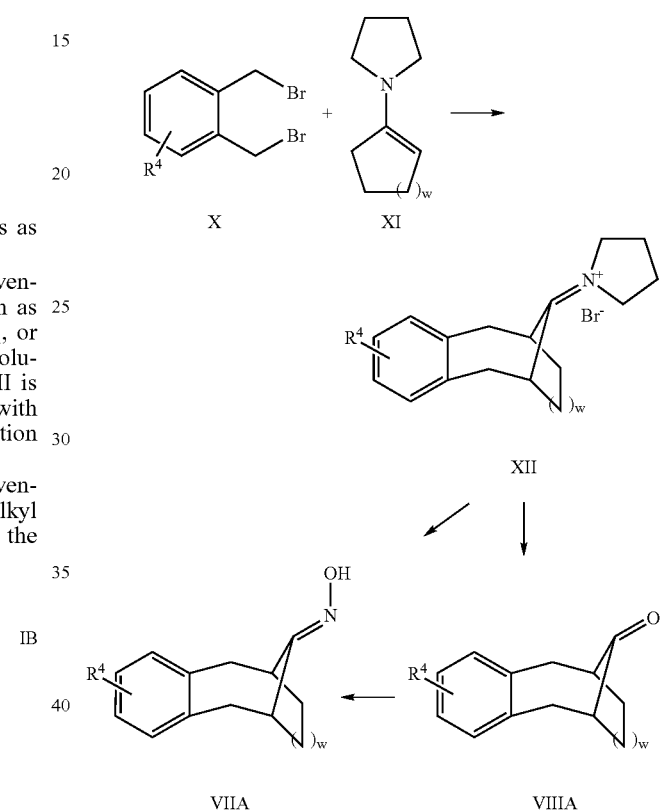

X    XI

XII

VIIA    VIIIA wherein w and $R^4$ have the same meanings as before.

The dibromide X reacts exothermically with the enamine XI in acetonitrile solution to form the salt XII, which may be hydrolysed in aqueous acid to form the ketone VIIIA, which may be converted to the oxime VIIA in the manner described previously. Alternatively, the salt XII may be reacted directly with hydroxylamine hydrochloride under similar conditions to provide oxime VIIA. Although the above illustration is with regard to monosubstituted benzofused derivatives, the process may readily be adapted to provide ketones of formula VIII in which A comprises a different fused ring system.

Individual compounds in accordance with formula I may be converted to different compounds in accordance with formula I by application of known synthetic techniques. Alternatively, such transformations may be carried out on the precursors of the compounds of formula I. For example, a compound in which A or B comprises an olefinic double bond may be converted to the corresponding alkane derivative by catalytic hydrogenation. Similarly, an exocyclic olefinic double bond may be converted to an oxo substituent by ozonolysis. Alternatively, an oxo substituent on A or B may be converted to an exocyclic olefin by means of a Wittig reaction, or an oxo substituent may be converted to a thioxo substituent by treatment with Lawesson's reagent.

Compounds of formula I wherein A or B comprises a —CH$_2$—NR$^{13}$-moiety may be prepared from the corresponding compounds comprising a —CO— moiety as illustrated in the scheme below:

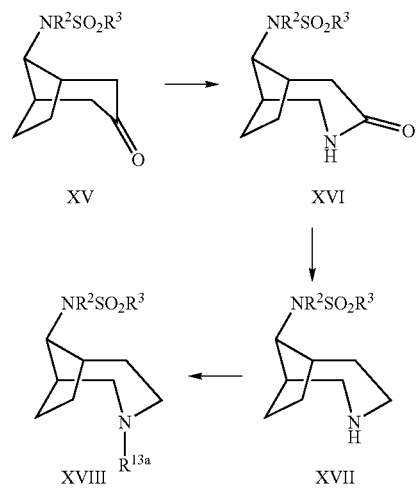

Treatment of ketone XV with hydroxylamine-O-sulfonic acid in refluxing formic acid yields the lactam XVI, which may be reduced to the amine XVII by reaction with aluminium hydride in refluxing THF. If desired, N-alkylation may be carried out by standard methods to provide XVIII where R$^{13a}$ is R$^{13}$ which is other than H and R$^{13}$ has the same meaning as before.

Likewise, compounds of formula I or their precursors comprising aryl or heteroaryl groups may have substituents attached thereto by conventional synthetic means, and said substituents may be converted to other substituents by known techniques.

As an illustration of this principle, compounds of formula IV in which R$^4$ is H may be nitrated under standard conditions (such as reaction with sodium nitrate in trifluoroacetic acid) to provide the nitro derivatives (IV, R$^4$=NO$_2$). Generally, a mixture of positional isomers is obtained, from which the individual isomers may be separated by conventional techniques of chromatography or fractional crystallisation. The nitro derivatives may be reduced to the corresponding anilines (IV, R$^4$=NH$_2$) by conventional methods, such as reaction with tin in hydrochloric acid. The anilines may be converted to the corresponding diazonium salts (e.g. by treatment with sodium nitrite and hydrochloric acid) and thence to a variety of derivatives by displacement of the diazonium group. Examples of substituents R$^4$ introducible by this route include F, Cl, Br, I, OH, CN and SH. A phenol group introduced by this process may be alkylated by standard procedures, for example by reaction with an alkyl halide (such as a phenoxyethyl bromide) in the presence of a base such as potassium carbonate. Such a reaction may be carried out at about 120° C. in DMF. An alternative alkylation method is a Mitsunobu reaction with an alcohol in the presence of diethyl azodicarboxylate and triphenylphosphine.

Alternatively, the anilines IV (R$^4$=NH$_2$) may be reacted with R$^{10}$CO-Hal, R$^{10}$OCO-Hal or R$^{10}$SO$_2$-Hal to form the corresponding amides (R$^4$=—NHCOR$^{10}$), carbamates (R$^4$=—NHCO$_2$R$^{10}$) or sulphonamides (R$^4$=—NHSO$_2$R$^{10}$) respectively, where Hal and R$^{10}$ have the same meanings as before. In another alternative, the anilines may be alkylated, e.g. by reaction with R$^{10}$CHO and sodium cyanoborohydride to form IV (R$^4$=—NHCH$_2$R$^{10}$) where R$^{10}$ has the same meaning as before.

The bromo derivatives IV (R$^4$=Br) may be subjected to substitution by R$^9$R$^{10}$NH to form secondary or tertiary amines IV (R$^4$=—NR$^9$R$^{10}$), where R$^9$ and R$^{10}$ have the same meanings as before. The reaction may be carried out at elevated temperature in a sealed tube in the presence of a Pd$^0$ catalyst. In the case of secondary amines thus formed (i.e. if R$^9$ is hydrogen), subsequent reaction with R$^{10}$CO—Hal, R$^{10}$OCO—Hal or R$^{10}$SO$_2$-Hal provides the corresponding amides, carbamate and sulphonamides respectively, where R$^{10}$ and Hal have the same meanings as before.

Alternatively, the bromo derivatives IV (R$^4$=Br) may react with boronic acids R$^{10}$B(OH)$_2$ to form IV (R$^4$=R$^{10}$), where R$^{10}$ has the same meaning as before, the reaction taking place in the presence of base and a (Ph$_3$P)$_4$Pd$^0$ catalyst.

Compounds of formula IV (or their precursors) in which R$^4$ is alkoxycarbonyl (available by elaboration of the compounds X in which R$^4$ is alkoxycarbonyl as described above) are particularly useful intermediates. Reduction of the alkoxycarbonyl group (e.g. by treatment with diisobutylaluminium hydride [DIBAL-H]) provides the corresponding benzyl alcohol (R$^4$=—CH$_2$OH), which may be converted to the tosylate, mesylate or similar, or to the corresponding bromide, and subjected to nucleophilic displacement by an amine or ArO— where Ar has the same meaning as before, especially by a phenoxide. Alternatively, the benzyl alcohol may be oxidised to the corresponding aldehyde (R$^4$=—CHO) (e.g. by treatment with pyridinium dichromate at room temperature in dichloromethane), and coupled with a variety of ylides to form olefinic derivatives, including propenoic acid derivatives (R$^4$=—CH=CHCO$_2$R where R is alkyl such as methyl or ethyl). Reduction of the propenoic esters (e.g. by treatment with DIBAL-H) provides the corresponding allyl alcohols (R$^4$=—CH=CHCH$_2$OH which may be elaborated in the same way as the benzyl alcohols discussed above. In particular, the alcohol may be converted to the corresponding bromide (R$^4$=—CH=CHCH$_2$Br) by treatment with phosphorus tribromide in dichloromethane at low temperature (e.g. −20° C.), and the bromine atom may be displaced by a variety of nucleophiles, in particular the amines NH(R$^{16}$)$_2$ such as morpholine, piperidine and pyrrolidine, thereby providing the corresponding compounds in which R$^4$ is —CH=CHCH$_2$N(R$^{16}$)$_2$ where R$^{16}$ has the same meaning as before. The displacement is typically carried out at about 80° C. in DMF in the presence of potassium carbonate.

The above mentioned aldehydes (R$^4$=—CHO) may also be reacted with hydroxylamine hydrochloride in refluxing formic acid to provide the corresponding nitriles (R$^4$=—CN), which in turn may be reacted with hydroxylamine hydrochloride and triethylamine in refluxing ethanol to provided the corresponding N-hydroxycarboximidamides (R$^4$=—C(NH$_2$)=NOH), which may be condensed with aryl or heteroaryl carboxylic acids to yield the corresponding compounds in which R$^4$ is 5-aryl- or 5-heteroaryl-1,2, 4-oxadiazol-3-yl.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50-70% confluency in the presence of sterile 10 mM sodium butyrate.
(2) Cells are placed in 96-well plates at 30,000/well/100 μL in minimal essential medium (MEM) (phenol red-free)+ 10% foetal bovine serum (FBS), 50 mM HEPES buffer (pH7.3), 1% glutamine, 0.2 mg/ml G418 antibiotic, 10 mM sodium butyrate.
(3) Make dilutions of the compound plate. Dilute stock solution to 5.5% DMSO/110 μM compound. Mix compounds vigorously and store at 4° C. until use.
(4) Add 10 μL compound/well. Mix plate briefly and leave for 18 h in 37° C. incubator.
(5) Remove 90 μL of culture supernatant and dilute 1:1 with ice-cold 25 mM HEPES (pH.3), 0.1% BSA, 1.0 mM EDTA (+broad spectrum protease inhibitor cocktail; pre-aliquotted into a 96-well plate). Mix and keep on ice or freeze at −80° C.
(6) Add back 100 μL of warm MEM+10% FBS, 50 mM HEPES (pH7.3), 1% glutamine, 0.2 mg/ml G418, 10 mM sodium butyrate to each well, and return plate to 37° C. incubator.
(7) Prepare reagents necessary to determine amyloid peptide levels, for example by ELISA assay.
(8) To determine if compounds are cytotoxic, cell viability following compound administration is assessed by the use of redox dye reduction. A typical example is a combination of redox dye MTS (Promega) and the electron coupling reagent PES. This mixture is made up according to the manufacturer's instructions and left at room temperature.
(9) Quantitate amyloid beta 40 and 42 peptides using an appropriate volume of diluted culture medium by standard ELISA techniques.
(10) Add 15 μL/well MTS/PES solution to the cells; mix and leave at 37° C.
(11) Read plate when the absorbance values are approximately 1.0 (mix briefly before reading to disperse the reduced formazan product).

Alternative assays are described in *Biochemistry*, 2000, 39(30), 8698-8704.

The Examples of the present invention all had an $ED_{50}$ of less than 10 μM, preferably less than 1 μM and most preferably less than 100 nM in at least one of the above assays.

Nomenclature

Many of the compounds of formula I, and in particular those in which A comprises a fused aryl or heteroaryl ring, may be named according to two or more different protocols which are equally valid. Thus, for example, a compound of formula V may treated as a sulphonamide derived from a 5-substituted endo-tricyclo[8.2.1.0$^{3,8}$]trideca-3(8),4,6-trien-13-ylamine:

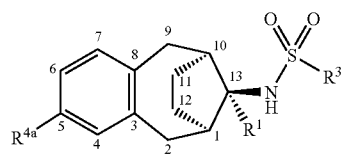

or as a sulphonamide derived from a 2-substituted 11-endo-5,6,7,8,9,10-hexahydro-6,9-methanobenzo[a][8]annulen-11-amine:

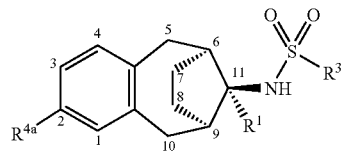

In both cases, "endo" refers to the configuration of the sulphonamido group relative to the ring to which the benzene ring is fused. Such systems are used interchangeably herein.

The following examples illustrate the present invention.

EXAMPLES

General Procedures

All products capable of existing in enantiomeric form were obtained as racemic mixtures unless otherwise stated.

Where stated, purification by mass-directed preparative HPLC refers to preparative reversed phase HPLC using a Platform LCZ mass spectrometer running under MassLynx 3.3/FractionLynx control [Micromass, UK] to trigger fraction collection when a compound of the molecular weight corresponding to the desired compound was detected. A generic acetonitrile/water gradient of 20%→100% with a constant 0.1% trifluoroacetic acid was used for the preparative HPLC, and the mass spectrometer was operated with an APcI probe in positive and negative ionization mode. Solvent was removed from the resulting purified samples by lyophilization.

All examples were analyzed by analytical LC-MS utilizing diode array detection (210-250 nm) and APcI detection (150-850 amu) using a full 5%→95% MeCN gradient with 0.1% aqueous TFA.

1-Tricyclo[8.2.1.0$^{3,8}$]trideca-3(8),4,6-trien-13-ylidene-pyrrolidinium bromide

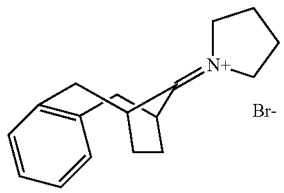

1,2-Bis-bromomethyl-benzene (66.4 g, 0.25 mol) was added to a mixture of 1-cyclopent-1-enyl-pyrrolidine (29.4 g, 0.25 mol) and Hünig's base (87 mL, 0.50 mol) in MeCN (200 mL) with vigorous stirring. An exothermic reaction ensued, bringing the mixture to reflux. The mixture was refluxed for 16 h, cooled, the product was filtered off and washed with MeCN to give the pure title compound as a white crystalline solid (48.14 g, 60%). $^1$H NMR (d$_6$-DMSO, 360 MHz) δ 7.29-7.22 (4 H, m, aromatic), 4.16-4.11 (2 H, m, CH—N+), 4.04-3.99 (2 H, m, CH—N+), 3.60 (2 H, bs, bridgehead CH), 3.05 (4 H, d, benzylic), 2.17-2.05 (4 H, m, N+—C—CH$_2$), 1.92-1.88 (2 H, m), 1.25-1.20 (2 H, m). m/z 240 (M+).

Tricyclo[8.2.1.0$^{3,8}$]trideca-3(8),4,6-trien-13-one oxime

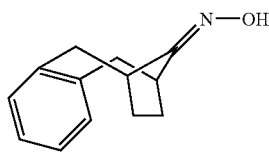

1-Tricyclo[8.2.1.0$^{3,8}$]trideca-3(8),4,6-trien-13-ylidene-pyrrolidinium bromide (48.14 g, 0.15 mol) was suspended in EtOH (200 mL) and H$_2$O (100 mL) and stirred. Hydroxylamine hydrochloride (31.27 g, 0.45 mol) was added, resulting in the starting material dissolving. Sodium acetate trihydrate (61.2 g, 0.45 mol) was added to the solution. After a few minutes a thick white precipitate formed. The mixture was heated to reflux until a clear solution was obtained and then allowed to cool to room temperature. The product oxime crystallized from solution and was filtered off, washing with water. The resulting pure oxime was dried to give 27.18 g (90%) of a pure white crystalline solid. $^1$H NMR (d$_6$-DMSO, 360 MHz) δ 10.17 (1 H, s, N—OH), 7.19-7.12 (4 H, m, aromatic), 3.51 (1 H, bt, bridgehead CH), 3.01-2.87 (2 H, m, benzylic), 2.80 (1 H, bt, bridgehead CH), 2.77 (2 H, t, J=14 Hz, benzylic), 1.68-1.63 (2 H, m), 1.10-1.05 (2 H, m). m/z 202 (M+H$^+$).

A similar procedure may be used to synthesise oximes from the corresponding ketones when they are available.

endo-Tricyclo[8.2.1.0$^{3,8}$]trideca-3(8),4,6-trien-13-ylamine

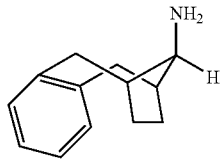

Tricyclo[8.2.1.0$^{3,8}$]trideca-3(8),4,6-trien-13-one oxime (27.18 g, 0.135 mol) was dissolved in AcOH (170 mL), PtO$_2$ (785 mg) was added, and the mixture was hydrogenated in a Parr reactor at 30 psi for 2 h, at which point hydrogen uptake had ceased. The mixture was filtered through Celite®, washing with AcOH, and the filtrate was concentrated by lyophilization to give a white solid. The solid was treated with aqueous 2 N NaOH (200 mL) and extracted into DCM. The organic extracts were dried (MgSO$_4$) and concentrated to give the pure product amine (20.1 g, 80%) [single endo stereoisomer] as a pale yellow oil which crystallized upon standing. $^1$H NMR (d$_6$-DMSO, 360 MHz) δ 7.08-6.99 (4 H, m, aromatic), 3.39 (2 H, d, J=15.0 Hz, benzylic), 3.23 (1 H, t, J=6.1 Hz, CH—N), 2.37 (2 H, dd, J=15.0 & 7.8 Hz, benzylic), 2.15-2.09 (2 H, m, bridgehead CH), 1.73 (2 H, bs, —NH$_2$), 1.64-1.53 (2 H, m), 1.03-0.94 (2 H, m). m/z 188 (M+H$^+$).

The following derivatives were similarly prepared by use of a suitably substituted oxylyl dibromide:

endo-4-Fluoro-tricyclo[8.2.1.0$^{3,8}$]trideca-3(8),4,6-trien-13-ylamine endo-5-Fluoro-tricyclo[8.2.1.0$^{3,8}$]trideca-3(8),4,6-trien-13-ylamine endo-4-Chloro-tricyclo[8.2.1.0$^{3,8}$]trideca-3(8),4,6-trien-13-ylamine endo-5-Chloro-tricyclo[8.2.1.0$^{3,8}$]trideca-3(8),4,6-trien-13-ylamine endo-Tricyclo[8.3.1.0$^{3,8}$]tetradeca-3(8),4,6-trien-14-ylamine

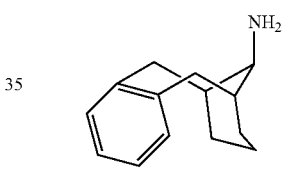

This was synthesized in an analogous manner to endo-tricyclo[8.2.1.0$^{3,8}$]trideca-3(8),4,6-trien-13-ylamine using 1-cyclohex-1-enyl-pyrrolidine as a starting material. m/z 202 (M+H$^+$).

Example 1 endo-4-Methyl-N-tricyclo[8.2.1.0$^{3,8}$]trideca-3(8),4,6-trien-13-yl-benzenesulfonamide

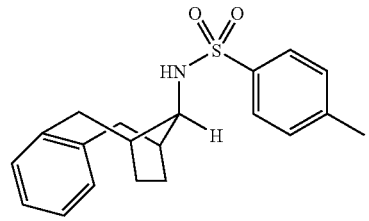

endo-Tricyclo[8.2.1.0$^{3,8}$]trideca-3(8),4,6-trien-13-ylamine (325 mg, 1.74 mmol) was dissolved in DCM (10 mL) and treated with pyridine (300 μL, 3.7 mmol) and p-toluenesulfonyl chloride (497 mg, 2.6 mmol). The mixture was stirred for 16 h, 900 mg of polyamine scavenger resin (4.5 mmol/g) was added to remove excess sulfonyl chloride and the mixture stirred for 24 h. The mixture was filtered, concentrated, dissolved in EtOAc (100 mL) and washed with 2 M aqueous HCl followed by saturated aqueous NaHCO$_3$. The solution was concentrated and recrystallized from EtOAc/diethyl ether to give the pure product (168 mg) as a white crystalline solid.

$^1$H NMR d$_6$-DMSO, 400 MHz) δ 7.88 (1 H. d, J=7.1 Hz, N-H), 7.77 (2 H, d, J=8.2 Hz, tosyl), 7.41 (2 H, d, J=8.2 Hz, tosyl), 7.03 (4 H, s, aromatic), 3.42 (1 H, dd, J=7.1 & 6.2 Hz, CH—N), 3.17 ( 2 H, d, J=15.6 Hz, benzylic), 2.40 (3 H, s, tosyl), 2.35 (2 H, dd, J=15.6 & 7.8 Hz, benzylic), 2.12 (2 H, m, bridgehead CH), 1.49-1.46 (2 H, m), 0.90-0.87 (2 H, m). m/z 342 (M+H$^+$).

Following the procedure of Example 1, and using the appropriate sulfonyl chloride, the following compounds of formula H were prepared. In each case, purification was by mass-directed HPLC.

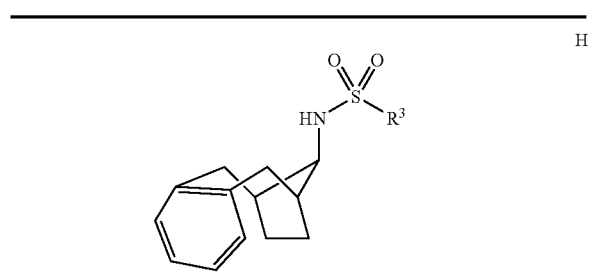

H

| Example | R$^3$ | m/z (M + H$^+$) |
|---|---|---|
| 2 | 4-fluorophenyl | 346 |
| 3 | 4-chlorophenyl | 362 |
| 4 | 4-nitrophenyl | 373 |
| 5 | n-propyl | 294 |
| 6 | 4-bromophenyl | 406 |
| 7 | 4-iodophenyl | 454 |
| 8 | 4,5-dibromo-2-thienyl | 490 |
| 9 | 3-chloro-4-fluorophenyl | 380 |
| 10 | 4-ethylphenyl | 356 |
| 11 | pentafluorophenyl | 418 |
| 12 | 4-trifluoromethylphenyl | 396 |
| 13 | 2,4-difluorophenyl | 364 |
| 14 | 2-chlorophenyl | 362 |
| 15 | 2,5-dichloro-3-thienyl | 402 |
| 16 | 2,3-dichlorophenyl | 396 |
| 17 | 4,5-dichloro-2-thienyl | 402 |
| 18 | 2-cyanophenyl | 353 |
| 19 | 2-thienyl | 334 |
| 20 | 3-fluorophenyl | 346 |
| 21 | 5-bromo-2-thienyl | 412 |
| 22 | 2,6-difluorophenyl | 364 |
| 23 | 4-bromo-5-chloro-2-thienyl | 446 |
| 24 | 3-bromo-5-chloro-2-thienyl | 446 |
| 25 | 2,3,4-trifluorophenyl | 382 |
| 26 | 3,4-difluorophenyl | 364 |
| 27 | 4-cyanophenyl | 353 |
| 28 | phenyl | 328 |
| 29 | 2-fluorophenyl | 346 |
| 30 | 2-pyridyl | 329 |
| 31 | n-butyl | 308 |
| 32 | 5-chloro-2-thienyl | 368 |

Example 33 endo-N-(5-Fluoro-tricyclo[8.2.1.0$^{3,8}$]trideca-3(8),4,6-trien-13-yl)-benzenesulfonamide The title compound was prepared by an analogous route to Example 1 using endo-5-fluoro-tricyclo[8.2.1.0$^{3,8}$] trideca-3(8),4,6-trien-13-ylamine and purified by mass-directed preparative HPLC. m/z 346 (M+H$^+$).

Example 34 endo-5—Chloro-thiophene-2-sulfonic acid (5-fluoro-tricyclo[8.2.1.0$^{3,8}$]trideca-3(8),4,6-trien-13-yl)-amide The title compound was prepared by an analogous route to Example 1 using endo-5-fluoro-tricyclo[8.2.1.0$^{3,8}$] trideca-3(8),4,6-trien-13-ylamine and purified by mass-directed preparative HPLC. m/z 386 (M+H$^+$).

Example 35 endo-5—Chloro-thiophene-2-sulfonic acid (4-fluoro-tricyclo[8.2.1.0$^{3,8}$]trideca-3(8),4,6-trien-13-yl)-amide The title compound was prepared by an analogous route to Example 1 using endo-4-fluoro-tricyclo[8.2.1.0$^{3,8}$] trideca-3(8),4,6-trien-13-ylamine and purified by mass-directed preparative HPLC. m/z 386 (M+H$^+$).

Example 36 endo-5—Chloro-thiophene-2-sulfonic acid (5-chloro-tricyclo[8.2.1.0$^{3,8}$]trideca-3(8),4,6-trien-13-yl)-amide The title compound was prepared by an analogous route to Example 1 using endo-5-chloro-tricyclo[8.2.1.0$^{3,8}$] trideca-3(8),4,6-trien-13-ylamine and purified by mass-directed preparative HPLC. m/z 402 (M+H$^+$).

Example 37 endo-5—Chloro-thiophene-2-sulfonic acid (4-chloro-tricyclo[8.2.1.0$^{3,8}$]trideca-3(8),4,6-trien-13-yl)-amide The title compound was prepared by an analogous route to Example 1 using endo-4-chloro-tricyclo[8.2.1.0$^{3,8}$] trideca-3(8),4,6-trien-13-ylamine and purified by mass-directed preparative HPLC. m/z 402 (M+H$^+$).

Example 38 endo-4-Methyl-N-tricyclo[8.3.1.0$^{3,8}$]tetradeca-3(8), 4,6-trien-14-yl-benzenesulfonamide The title compound was prepared by an analogous route to Example 1 using endo-tricyclo[8.3.1.0$^{3,8}$]tetradeca-3(8), 4,6-trien-14-ylamine and purified by mass-directed preparative HPLC. m/z 356 (M+H$^+$).

Example 39 endo-Thiophene-2-sulfonic acid tricyclo[8.3.1.0$^{3,8}$] tetradeca-3(8),4,6-trien-14-ylamide The title compound was prepared by an analogous route to Example 1 using endo-tricyclo[8.3.1.0$^{3,8}$]tetradeca-3(8), 4,6-trien-14-ylamine and purified by mass-directed preparative HPLC. m/z 348 (M+H$^+$).

Example 40 endo-N-(13-Methyl-tricyclo[8.2.1.0$^{3,8}$]trideca-3(8),4,6-trien-13-yl)-benzenesulfonamide

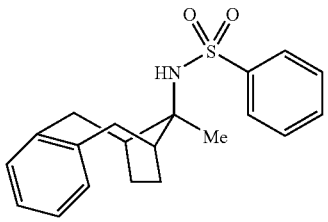

Step 1. Tricyclo[8.2.1.0$^{3,8}$]trideca-3(8),4,6-trien-13-one

1-Tricyclo[8.2.1.0$^{3,8}$]trideca-3(8),4,6-trien-13-ylidene-pyrrolidinium bromide (225 mg, 0.70 mmol) was dissolved in water (5 mL) and 2 M aqueous HCl (5 mL) was added. The mixture was heated at reflux for 16 h, cooled and extracted into DCM. The organic extracts were concentrated to give tricyclo[8.2.1.0$^{3,8}$]trideca-3(8),4,6-trien-13-one (130 mg) as a white crystalline solid. $^1$H NMR (CDCl$_3$, 360 MHz) δ 7.19 (4 H, s, aromatic), 2.99-2.86 (4 H, m, benzylic), 2.61-2.57 (2 H, m, bridgehead H), 1.90-1.80 (2 H, m), 1.33-1.26 (2 H, m).

Step 2. N-Tricyclo[8.2.1.0$^{3,8}$]trideca-3(8),4.6-trien-13-ylidene-benzenesulfonamide Tricyclo[8.2.1.0$^{3,8}$]trideca-3(8),4,6-trien-13-one (130 mg, 0.70 mmol) and benzenesulfonamide (110 mg, 0.70 mmol) were mixed in toluene (6 mL). Amberlyst-15 ion exchange resin (35 mg) was added, and the mixture was heated at reflux under Dean Stark conditions for 36 h. The mixture was concentrated and the crude sulfonylimine was used directly in the next step.

Step 3. endo-N-(13-Methyl-tricyclo[8.2.1.0$^{3,8}$]trideca-3(8),4.6-trien-13-yl)-benzenesulfonamide The crude N-tricyclo[8.2.1.0$^{3,8}$]trideca-3(8),4,6-trien-13-ylidene-benzenesulfonamide above was dissolved in THF (2 mL), cooled to −78° C., and treated dropwise with 1.0 M MeLi in THF/cumene (5.0 mL). The mixture was allowed to slowly warm to 20° C., quenched with water (10 ml) followed by 5 M aqueous HCl (2 mL) and extracted into DCM. The mixture was concentrated and purified by mass-directed preparative HPLC to give 10 mg of the pure product. $^1$H NMR (d$_6$-DMSO, 360 MHz) δ 7.84 (2 H, m, aromatic), 7.58 (1 H, s, N—), 7.50 (3 H, m, aromatic), 6.98 (4 H, m, aromatic), 3.32 (2 H, benzylic), 2.39 (2 H, benzylic), 2.21 (2 H, m, bridgehead H), 1.52 (2 H, m), 0.91 (3 H, s, Me), 0.90 (2 H, m). m/z 342 (M+H$^+$).

Example 41 endo-N-(5-Nitro-tricyclo[8.2.1.0$^{3,8}$]trideca-3(8),4,6-trien-13-yl)-benzenesulfonamide and endo-N-(4-nitro-tricyclo[8.2.1.0$^{3,8}$]trideca-3(8),4,6-trien-13-yl)-benzenesulfonamide

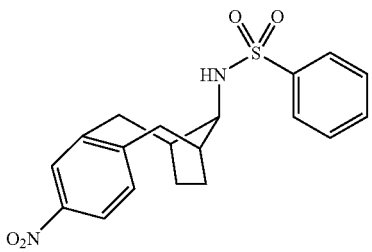

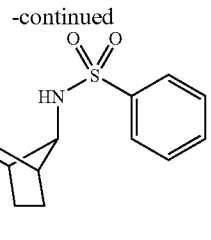

Sodium nitrate (10.1 g, 118.8 mmol) was added portionwise to a stirred solution of endo-N-tricyclo[8.2.1.0$^{3,8}$]trideca-3(8),4,6-trien-13-yl-benzenesulfonamide (Example 28) (13.0 g, 39.8 mmol) in trifluoroacetic acid (260 mL) with ice-cooling. The cooling was removed 10 minutes after the addition was complete. The reaction mixture was stirred at rt for 1 h and then added to ice. Stirring was continued until the ice had melted. The mixture was filtered, the solid washed with water until the washings were neutral and dried under vacuum. The crude product was recrystallized from ethanol four times to give pure endo-N-(5-nitro-tricyclo[8.2.1.0$^{3,8}$]trideca-3(8),4,6-trien-13-yl)-benzenesulfonamide (5.75 g, 39%) as a yellow solid. 1H NMR (CDCl$_3$, 400 MHz) δ 1.02-1.11 (m, 2 H), 1.58-1.66 (m, 2 H), 2.33-2.40 (m, 2 H), 2.57-2.66 (m, 2 H), 3.11-3.18 (m, 2 H), 3.60 (m, 1 H) 5.45 (bd, 1 H), 7.17 (d, 1 H, J=9 Hz) 7.52-7.64 (m, 3 H), 7.90-7.96 (m, 4 H). m/z 373 (M+H$^+$).

endo-N-(4-Nitro-tricyclo[8.2.1.0$^{3,8}$]trideca-3(8),4,6-trien-13-yl)-benzenesulfonamide was isolated pure from the above recrystallization mother liquors by mass-directed preparative HPLC. m/z 373 (M+H$^+$).

Example 42 endo-N-(5-Amino-tricyclo[8.2.1.0$^{3,8}$]tridea-3(8),4,6-trien-13-yl)-benzenesulfonamide

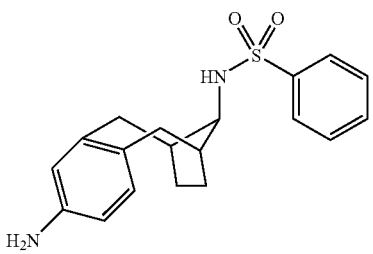

A solution of tin (II) chloride (4.86 g, 25.6 mmol) in concentrated hydrochloric acid (25 mL) was added dropwise to an ice-cooled solution of endo-N-(5-nitro-tricyclo[8.2.1.0$^{3,8}$]trideca-3(8),4,6-trien-13-yl)-benzenesulfonamide (Example 41) (2.8 g, 7.5 mmol) in THF (40 mL). The reaction mixture was stirred at room temperature for 18 h, cooled in an ice-bath and basified carefully with 4N sodium hydroxide solution. The mixture was then extracted with ethyl acetate. The organic phase was washed with brine and concentrated to give an orange oil. The crude product was dissolved in the minimum quantity of ethyl acetate and diluted with diethyl ether. 2M HCl in ether (5.6 mL, 11.2 mmoles) was added with stirring. The mixture was filtered and the solid washed with ethyl acetate and then diethyl ether. The solid was dispersed between DCM and 1 N NaOH solution and mixed thoroughly. The organic phase was separated, dried over sodium sulphate and evaporated to give the title compound as a yellow solid (2.4 g, 93%). $^1$H NMR (CDCl$_3$, 400 MHz) δ 1.13-1.19 (m, 2 H), 1.50-1.58 (m, 2 H), 2.15-2.25 (m, 2 H), 2.30-2.40 (m, 2 H), 2.82-2.92

(m, 2 H), 3.66 (m, 1 H), 5.04 (bd, 1 H), 6.38-6.42 (m, 2 H), 6.79 (d, 1 H, J=9 Hz), 7.50-7.61 (m, 3 H), 7.91-7.94 (m, 2 H). m/z 343 (M+H+).

Example 43 endo-N-(4-Amino-tricyclo[8.2.1.0$^{3,8}$]trideca-3(8),4,6-trien-13-yl)-benzene sulfonamide

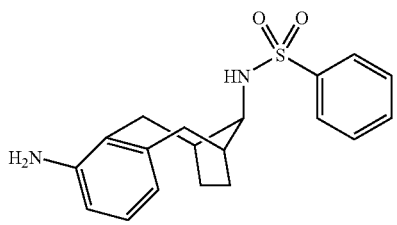

The title compound was prepared from the crude mother liquors resulting from the recrystallization described in Example 41 using an analogous route to Example 42. A pure sample was obtained by mass-directed preparative HPLC as its TFA salt. $^1$H NMR (CDCl$_3$, 400 MHz) δ 0.96-1.09 (m, 2 H), 1.43-1.56 (m, 2 H), 2.19-2.27 (m, 1 H), 2.38-2.49 (m, 2 H), 2.80-2.88 (m, 1 H), 2.95-3.10 (m, 2 H), 3.48-3.41 (m, 1 H), 6.16 (bd, 1 H), 6.93-7.01 (m, 2 H), 7.10 (bd, 1 H), 7.49-7.53 (m, 2 H), 7.57-7.61 (m, 1 H), 7.90-7.94 (m, 2 H). m/z 343 (M+H+).

Example 44 endo-N-(13-Benzenesulfonylamino-tricyclo[8.2.1.0$^{3,8}$]trideca-3(8),4,6-trien-5-yl)-benzamide

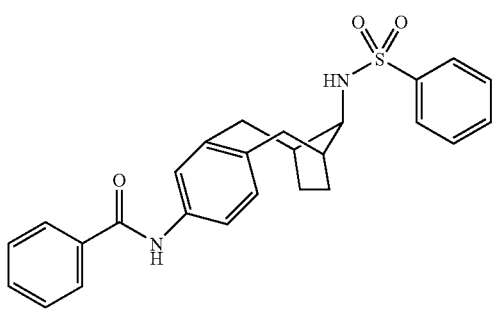

Benzoic acid (5.0 mg, 0.041 mmol) was weighed into a test tube and treated with N,N'-carbonyldiimidazole (4.1 mg, 0.025 mmol) in THF (0.5 mL). The solution was heated at 70° C. for 2 h, cooled, and a solution of endo-N-(5-amino-tricyclo[8.2.1.0$^{3,8}$]trideca-3(8),4,6-trien-13-yl)-benzene-sulfonamide (Example 42) (6.0 mg, 0.0175 mmol) in THF (0.5 mL) was added. The solution was heated at 70° C. for 16 h, concentrated, and the crude product purified by mass-directed preparative HPLC. m/z 447 (M+H+).

Following the procedure of Example 44, and using the appropriate carboxylic acid, the following compounds of formula J were prepared. In each case, purification was by mass-directed HPLC.

| Example | R$^4$ | m/z (M + H+) |
|---|---|---|
| 45 | PhCH$_2$CONH— | 461 |
| 46 | PhOCH$_2$CONH— | 477 |
| 47 | 3,5-difluoro-C$_6$H$_3$-CH$_2$CONH— | 497 |
| 48 | 4-F-C$_6$H$_4$-CONH— | 465 |
| 49 | CH$_3$CONH— | 385 |
| 50 | CH$_3$(CH$_2$)$_4$CONH— | 441 |
| 51 | CH$_3$CH$_2$CH(CH$_3$)CH$_2$CONH— | 441 |
| 52 | cyclopentyl-CH$_2$CONH— | 453 |
| 53 | CH$_3$(CH$_2$)$_3$CH(CH$_3$)(CH$_2$)$_2$CONH— | 483 |
| 54 | (CH$_3$)$_2$CH(CH$_2$)$_3$CONH— | 455 |
| 55 | MeOCH$_2$CONH— | 415 |
| 56 | Ph(CH$_2$)$_2$CONH— | 475 |
| 57 | pyridin-2-yl-CONH— | 448 |

Example 58 endo-N-[13-(5-Chloro-thiophene-2-sulfonylamino)-tricyclo[8.2.1.0$^{3,8}$]trideca-3(8),4,6-trien-5-yl]-2-phenoxy-acetamide The title compound was prepared by an analogous route to Example 44 and purified by mass-directed preparative HPLC. m/z 517 (M+H+).

Example 59 endo-(13-Benzenesulfonylamino-tricyclo[8.2.1.0$^{3,8}$]trideca-3(8),4,6-trien-5-yl)-carbamic acid phenyl ester

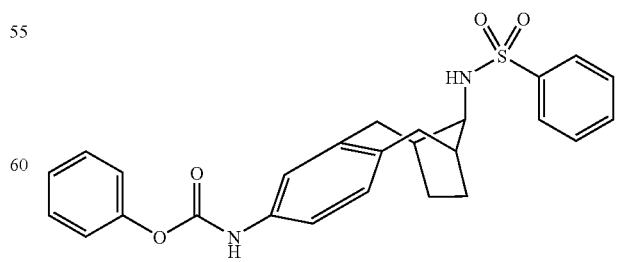

Phenyl chloroformate (10 μL, 0.08 mmol) was added to a test tube and treated with a solution of endo-N-(5-amino-tricyclo[8.2.1.0$^{3,8}$]trideca-3(8),4,6-trien-13-yl)-benzenesulfonamide (Example 42) (6.0 mg, 0.0175 mmol) in THF (0.5 mL) followed by pyridine (10 μL). The solution was allowed to stand at 20° C. for 16 h, concentrated, and the crude product purified by mass-directed preparative HPLC. m/z 463 (M+H$^+$).

Following the procedure of Example 59, and using the appropriate chloroformate, the following compounds of formula J were prepared. In each case, purification was by mass-directed HPLC.

| Example | R$^4$ | m/z (M + H$^+$) |
|---|---|---|
| 60 | PhCH$_2$OCONH— | 477 |
| 61 | (CH$_3$)$_2$CHCH$_2$OCONH— | 443 |
| 62 | Me—C$_6$H$_4$—OCONH— | 477 |
| 63 | F—C$_6$H$_4$—OCONH— | 481 |
| 64 | MeO—C$_6$H$_4$—OCONH— | 493 |
| 65 | (CH$_3$)$_3$CCH$_2$OCONH— | 457 |

Example 66 endo-N-Bicyclo[4.2.1]non-3-en-9-yl-4-methyl-benzenesulfonamide

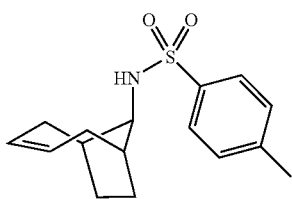

Step 1. Bicyclo[4.2.1]non-3-en-9-one oxime

Hydroxylamine hydrochloride (1.53 g, 22.0 mmol) and sodium acetate (2.99 g, 36.4 mmol) were added to a solution of bicyclo[4.2.1]non-3-en-9-one (*Synthesis*, 1976, 453) (1.0 g, 7.3 mmol) and the resulting solution warmed to reflux overnight. The reaction was then cooled to room temperature and the solvent removed under reduced pressure. The residue was partitioned between EtOAc (50 mL) and NaOH solution (1N aq 50 mL), the organic layer separated, dried over MgSO$_4$, filtered and the solvent removed under reduced pressure to give the title compound (1.02 g, 93%). $^1$H NMR (CDCl$_3$) δ 1.22-1.63 (2H, m), 1.88-1.95 (2H, m), 1.99-2.09 (3H, m), 2.45-2.49 (1H, m), 2.88 (1H, m), 3.55 (1H, m), 5.54 (1H, d, J=2 Hz). m/z 152 (M+H)$^+$.

Step 2. endo-Bicyclo[4.2.1]non-3-en-9-ylamine NaCNBH$_3$ (451 mg, 7.3 mmol) was added to a solution of bicyclo [4.2.1]non-3-en-9-one oxime (550 mg, 3.6 mmol) in MeOH (10 mL) at −30° C. containing methyl orange indicator (20 μl of 0.1% solution) followed by enough HCl (5N, Aq) to turn the solution pink. As the reaction proceeded sufficient HCl was added to maintain a pink colour. After two hours the reaction was allowed to warm to room temperature and poured onto ice/NaOH (4N, aq), and extracted into EtOAc (30 mL), dried over MgSO$_4$, filtered and the solvent removed under reduced pressure. The recovered hydroxylamine was taken up in AcOH (2 mL) an added to a stirred suspension of activated Zn dust (4.72 g 72.6 mmol) in AcOH (50 mL). After 30 min TLC (2N NH$_3$/MeOH: DCM 5:95) showed complete reduction of the hydroxylamine to a more polar product. The solution was filtered through Celite® to remove the zinc and the solvent removed under reduced pressure. The residue was basified with NaHCO$_3$ and extracted into EtOAc (50 mL), dried over MgSO$_4$, filtered and the solvent removed under reduced pressure to afford the title product (220 mg 46%). $^1$H NMR (CDCl$_3$) δ 1.33-1.43 (2H, m), 1.48 (2H bs, NH$_2$), 1.78-1.81 (2H, m), 1.82 (2H, bd, J=16 Hz), 2.09-2.32 (4H, m), 3.39 (1H, t, J=8.0 Hz), 5.48 (2H, d, J=4 Hz). m/z 138 (M+H)$^+$.

Step 3. endo-N-Bocyclo[4.2.1]non-3-en-9-yl-4-methyl-benzenesulfonamide p-Toluenesulphonyl chloride (41.94 mg, 0.22 mmol) was added to a solution of endo-bicyclo[4.2.1]non-3-en-9-ylamine (157 mg, 0.22 mmol) and N-Methyl morpholine (NMM, 48 μL, 0.44 mmol) in dry DCM (2.0 mL). The resulting mixture was stirred for 18 hrs at room temperature, followed by the addition of polyamine resin (100 mg of 2.46 mmol/g) and stirred for a further 18 h. The reaction was then filtered and the resin washed with MeOH (2×5 mL). The filtrates were combined and the solvent removed under reduced pressure. The residue was purified by mass-directed preparative HPLC to afford the title compound. $^1$H NMR (d$_6$-DMSO) δ 1.22 (2H, bd, J=8.0 Hz), 1.62 (2H, m), 1.94 (2H, m), 2.1 (2H, m), 2.29 (1H, m, 2.31 (1H, m), 2.39 (3H, s), 3.34 (1H, m), 5.42 (2H, d, J=4.0 Hz), 7.14 (1H, bd, J=4.0 Hz), 7.39 (2H, d, J=8.0 Hz), 7.76 (2H, d, J=8.0 Hz). m/z 292 (M+H)$^+$.

Example 67 endo-N-Bicyclo[4.2.1]non-3-en-9-yl-4-fluoro-benzenesulfonamide

The title compound was prepared by an analogous route to Example 66 and purified by mass-directed preparative HPLC. $^1$H NMR (d$_6$-DMSO) δ 1.21 (2H, m), 1.6 (2H, m), 1.85 (2H, m), 2.05 (2H, m), 2.20 (2H, m), 3.40 (1H, dd, J=8.0, 4.0 Hz), 5.32 (2H, d, J=4.0 Hz), 7.15 (1H, d, J=4.0 Hz), 7.31 (2H, m), 7.82 (2H, m). m/z 296 (M+H)$^+$.

Example 68 endo-N-Bicyclo[4.2.1]non-3-en-9-yl-benzenesulfonamide

The title compound was prepared by an analogous route to Example 66 and purified by mass-directed preparative HPLC. $^1$H NMR (d$_6$-DMSO) δ 1.23 (2H, m), 1.55 (2H, m), 1.9 (2H, m), 2.1 (2H, m), 2.3 (2H, m), 3.49 (1H, dd, J=8.0, 4.0 Hz), 5.41 (2H, d, J=4.0 Hz), 7.2 (1H, d, J=4.0 Hz), 7.6 (3H, m), 7.84 (2H, m). m/z 278 (M+H)$^+$.

Example 69 endo-Thiophene-2-sulfonic acid bicyclo[4.2.1]non-3-en-9-ylamide

The title compound was prepared by an analogous route to Example 66 and purified by mass-directed preparative HPLC. ¹H NMR (d₆-DMSO) δ 1.25 (2H, m), 1.7 (2H, m), 1.9 (2H, m), 2.2 (2H, m), 2.3 (2H, m), 3.55 (1H, dd, J=8.0, 4.0 Hz), 5.51 (2H, d, J=4.0 Hz), 7.19 (1H, t, J=4.0 Hz), 7.49 (1H, d, J=4.0 Hz), 7.63 (1H, d, J=1.5 Hz), 7.93 (1H, d, J=1.5 Hz). m/z 284 (M+H)⁺.

Example 70 endo-5-Chloro-thiophene-2-sulfonic acid bicyclo[4.2.1]non-3-en-9-ylamide

The title compound was prepared by an analogous route to Example 66 and purified by mass-directed preparative HPLC. ¹H NMR (d₆-DMSO) δ 1.26 (2H, dd, J=8.0, 1.0 Hz), 1.73 (2H, m), 1.97 (2H, m), 2.23-2.33 (4H, m), 3.59 (1H, m), 5.43 (2H, brs), 7.26 (1H, d, J=1.5 Hz), 7.5 (1H, d, J=1.5 Hz), 7.65 (1H, bs). m/z 318 (M+H)⁺.

Example 71 endo-5-Chloro-thiophene-2-sulfonic acid bicyclo[4.2.1]non-9-ylamide

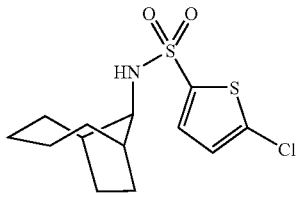

Step 1. Endo-Bicyclo[4.2.1]non-9-ylamine

A solution of bicyclo[4.2.1]non-3-en-9-one oxime (220 mg, 1.46 mmol) in AcOH (50 mL) was hydrogenated over PtO₂ (25 mg) at 50 psi for 4 h. The reaction mixture was filtered through Celite® and the solvent removed under reduced pressure. The residue was partitioned between EtOAc (50 mL) and NaOH solution (1N aq, 50 mL), the organic layer separated, dried over MgSO₄, filtered and the solvent removed under reduced pressure to give the title compound as an oil (201 mg, 98%). ¹H NMR (CDCl₃) δ 1.39-1.65 (8H, bm), 1.70-1.75 (4H, brm), 1.82 (2H, m), 2.17 (2H, m), 3.29 (1H, t, J=8 Hz). m/z 140 (M+H)⁺.

Step 2. endo-5-Chloro-thiophene-2-sulfonic acid bicyclo[4.2.1]non-9-ylamide

5-Chlorothiophene-2-sulphonyl chloride (313 mg, 1.4 mmol) was added in a single portion to a solution of endo-bicyclo[4.2.1]non-9-ylamine (201 mg, 1.4 mmol) and N-methyl morpholine (461 μL, 4.2 mmol) in dry DCM (20 mL). The resulting mixture was stirred at room temperature for 3 h, at which time polyamine resin (500 mg, 2.46 mmol/g) was added and stirring continued for one hour. The reaction mixture was then filtered to remove the resin and the resin pad washed with MeOH (4×20 mL). The filtrates were combined and the solvent removed under reduced pressure to afford a white solid. Recrystallisation from EtOH afforded the pure title compound as white needles. (382 mg, 85%) ¹H NMR (CDCl₃) δ 1.37-1.60 (10H, m), 1.79 (2H, m), 2.29 (2H, m), 3.69 (1H, m), 4.77 (1H, brd, J=8.0 Hz), 6.90 (1H, d, J=4 Hz), 7.40 (1H, d, J=4.0 Hz). m/z 320 (M+H)⁺.

Example 72 endo-8-(5-Chloro-thiophene-2-sulfonylamino)-bicyclo[3.2.1]octane-endo-3-carboxylic acid ethyl ester

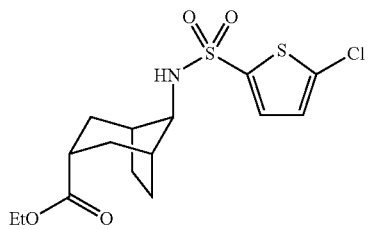

Step 1. 8-Hydroxamino-bicyclo[3.2.1]octane-endo-3-carboxylic acid ethyl ester

3-Bromo-2-bromomethyl-propionic acid ethyl ester (5.48 g, 20 mmol) was added to a mixture of 1-cyclopent-1-enyl-pyrrolidine (2.74 g, 20 mmol) and Hünig's base (3.5 mL) in MeCN (15 mL) with vigorous stirring. An exothermic reaction ensued, bringing the mixture to reflux. The mixture was refluxed for 16 h, cooled, and poured into 100 mL of EtOAc with stirring. The resulting solid (3.33 g) was collected by filtration, dissolved in 0.5 M aqueous HCl (100 mL) and stirred with EtOAc (100 mL) for 48 h. The organic layer was separated and concentrated to give 8-oxo-bicyclo[3.2.1]octane-endo-3-carboxylic acid ethyl ester (1.0 g, 5.1 mmol) as a colourless oil. This was dissolved in EtOH (50 mL), treated with a solution of hydroxylamine hydrochloride (1.04 g, 15 mmol) and sodium acetate trihydrate (2.04 g, 15 mmol) in water (10 mL) and heated at reflux for 16 h. The solution was cooled, concentrated, diluted with water (100 mL) and extracted with DCM. The DCM extracts were dried (MgSO₄), concentrated and purified by flash chromatography (20→30% EtOAc/hexane) to give the oxime (270 mg) as a colourless oil. ¹H NMR (CDCl₃, 360 MHz) δ 9.85 (1 H, bs, N—OH), 4.20 (2 H, q, J=7.1 Hz, CH₂—O), 3.36 (1 H, bs, bridgehead H), 2.63-2.56 (4 H, m), 2.15-2.04 (2 H, m), 1.76-1.69 (4 H, m), 1.30 (3 H, t, J=7.1 Hz, —Me). m/z 212 (M+H)⁺.

Step 2. endo-8-Amino-bicyclo[3.2.1]octane-endo-3-carboxylic acid ethyl ester

8-Hydroxamino-bicyclo[3.2.1]octane-endo-3-carboxylic acid ethyl ester (270 mg, 1.28 mmol) was dissolved in AcOH (5 mL), treated with PtO₂ (34 mg) and stirred under an atmosphere of H₂ for 1 h [catalyst clumps together when reaction complete]. The mixture was filtered, concentrated, basified (aqueous 4 N NaOH) and extracted into DCM to give the title compound which was sufficiently pure for use in the next step. m/z 198 (M+H)⁺.

Step 3. endo-8-(5-Chloro-thiophene-2-sulfonylamino)-bicyclo[3.2.1]octane-endo-3-carboxylic acid ethyl ester endo-8-Amino-bicyclo[3.2.1]octane-endo-3-carboxylic acid ethyl ester (21.2 mg, 0.108 mmol) in DCM (2 mL) was treated with 5-chlorothiophene-2-sulphonyl chloride (43 mg, 2.0 mmol) and pyridine (40 μL, 0.5 mmol). The mixture was stirred for 16 h, diluted with DCM (50 mL) and washed with aqueous 2 M HCl. The organic extracts were dried and purified by flash chromatography (10→25% EtOAc/hexane) to give pure title compound (12.6 mg) as a colourless crystalline solid. ¹H NMR (CDCl₃, 360 MHz) δ 7.42 (1 H, d, J=3.9 Hz, thiophene), 6.93 (1 H, d, J=3.9 Hz, thiophene), 5.29 (1 H, bd, J=6.7 Hz, N—H), 4.16 (2 H, q, J=7.0 Hz, CH$_2$—O), 3.27 (1 H, q, J=6.7 Hz, CH—N), 2.50 (1 H, t, J=8.3 Hz, CH—COOEt), 2.21 (2 H, dd, J=14.9 & 3.0 Hz, CH$_{eq}$—C—COOEt), 2.03 (2 H, bs, bridgehead H), 1.88 (2 H, ddd, J=15.0, 8.4 & 2.3 Hz, CH$_{ax}$—C—COOEt), 1.66-1.51 (4 H, m), 1.28 (3 H, t, J=7.0 Hz, —Me). m/z 378 (M+H)$^+$.

Example 73 endo-N-{5-[(Pyridin-3-ylmethyl)-amino]-tricyclo[8.2.1.0$^{3,8}$]trideca-3(8),4,6-trien-13-yl}-benzenesulfonamide

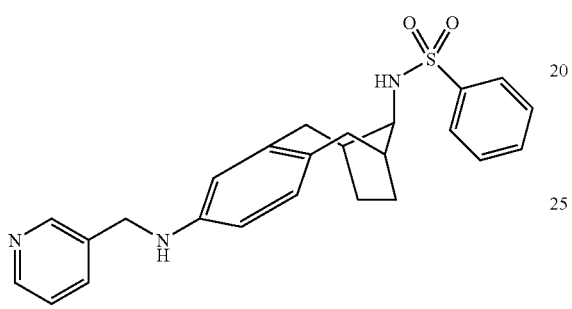

endo-N-(5-Amino-tricyclo[8.2.1.0$^{3,8}$]trideca-3(8),4,6-trien-13-yl)-benzenesulfonamide (Example 42) (25 mg, 0.073 mmol), pyridine-3-carbaldehyde (7.9 mg, 0.073 mmol) and acetic acid (4.4 mg, 0.073 mmol) in 1,2-dichloroethane (0.5 mL) were added to a test-tube. A solution of tetramethylammonium triacetoxyborohydride (27 mg, 0.102 mmol) in 1,2-dichloroethane (0.5 mL) was added and the mixture stirred at room temperature for 64 h. Water (1 mL) was added with stirring, the organic phase was separated and concentrated to dryness. The crude product was purified by mass-directed preparative HPLC. m/z 434 (M+H$^+$).

Following the procedure of Example 73, and using the appropriate aldehyde, the following compounds of formula J were prepared. In each case, purification was by mass-directed HPLC.

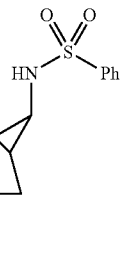
J

| Example | R$^4$ | m/z (M + H$^+$) |
|---|---|---|
| 74 | PhO—C$_6$H$_4$—CH$_2$NH— | 525 |
| 75 | PhCH$_2$O—C$_6$H$_4$—CH$_2$NH— | 539 |
| 76 | 3-MeO—C$_6$H$_4$—CH$_2$NH— | 463 |
| 77 | MeO—C$_6$H$_4$—CH$_2$NH— | 463 |
| 78 | cyclohexyl-CH$_2$NH— | 439 |
| 79 | (CH$_3$)$_2$CHCH$_2$CH$_2$NH— | 413 |
| 80 | 2,3-dihydrobenzo[1,4]dioxin-6-yl-CH$_2$NH— | 491 |
| 81 | t-Bu—C$_6$H$_4$—CH$_2$NH— | 489 |
| 82 | PhCH(CH$_3$)CH$_2$CH$_2$NH— | 475 |
| 83 | i-PrO—C$_6$H$_4$—CH$_2$NH— | 491 |
| 84 | benzofuran-2-yl-CH$_2$NH— | 473 |
| 85 | Ph(CH$_2$)$_3$NH— | 461 |
| 86 | CH$_3$(CH$_2$)$_4$—C$_6$H$_4$—CH$_2$NH— | 503 |
| 87 | 3-CF$_3$O—C$_6$H$_4$—CH$_2$NH— | 517 |

-continued

J

| Example | R⁴ | m/z (M + H⁺) |
|---|---|---|
| 88 | NC-C₆H₄-CH₂NH— | 458 |
| 89 | 3-F-C₆H₄-CH₂NH— | 451 |
| 90 | 4-F-C₆H₄-CH₂NH— | 451 |
| 91 | 3-Cl-C₆H₄-CH₂NH— | 467 |
| 92 | 3-CF₃-C₆H₄-CH₂NH— | 501 |

Example 93 endo-N-(5-Bromo-tricyclo[8.2.1.0$^{3,8}$]trideca-3(8),4,6-trien-13-yl)-benzenesulfonamide

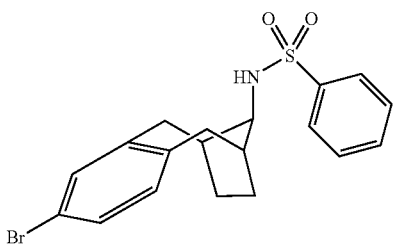

A solution of sodium nitrite (223 mg, 3.23 mmol) in water (4 mL) was added dropwise to a stirred suspension of endo-N-(5-amino-tricyclo[8.2.1.0$^{3,8}$]trideca-3(8),4,6-trien-13-yl)-benzenesulfonamide (Example 42) (465 mg, 1.36 mmol) in water (16 mL) and 2 N HCl (4 mL) with ice-cooling. The reaction mixture was stirred at room temperature for 20 min and then saturated sodium tetrafluoroborate solution (4 mL) was added. The mixture was stirred with ice-cooling for 20 min followed by 30 min at room temperature. The mixture was filtered and the solid washed with water and then DCM. A solution of the filtered solid in acetone (16 mL) was added dropwise to a stirred suspension of copper (I) bromide (5.6 g, 39.15 mmol) in water (16 mL) and conc. HBr (16 mL). The reaction was stirred at room temperature for 3 h and then added to ethyl acetate and water. The organic phase was washed with brine, dried over sodium sulphate and concentrated to give a brown oil. The crude product was purified by flash chromatography over silica eluting with 3:1 DCM: isohexane increasing in polarity to 1% methanol in DCM to give the title compound as a white solid (220 mg, 40%). $^{1}$H NMR (CDCl$_3$, 400 MHz) δ 1.06-1.14 (m, 2 H), 1.54-1.64 (m, 2 H), 2.24-2.29 (m, 2 H), 2.37-2.47 (m, 2 H), 2.94-3.20 (m, 2 H), 3.62 (m, 1 H), 5.22 (bd, 1 H), 6.88 (d, 1 H, J=9 Hz), 7.16 (m, 2 H), 7.51-7.61 (m, 3 H), 7.93 (m, 2 H). m/z 406/408 (M+H⁺).

Example 94 endo-N-[5-(4-Phenyl-piperidin-1-yl)-tricyclo[8.2.1.0$^{3,8}$]trideca-3 (8),4,6-trien-13-yl]-benzenesulfonamide

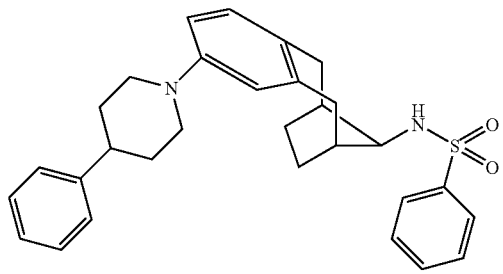

endo-N-(5-Bromo-tricyclo[8.2.1.0$^{3,8}$]trideca-3(8),4,6-trien-13-yl)-benzenesulfonamide (Example 93) (25 mg, 0.062 mmol), sodium tert-butoxide (14 mg, 0.148 mmol), tris(dibenzylidineacetone)dipalladium (0) (1.4 mg, 0.0015 mmol), tri-o-tolylphosphine (1.9 mg, 0.0061 mmol) and 4-phenylpiperidine (11.9 mg, 0.074 mmol) in degassed 1,4-dioxane (1.2 mL) were added to a test-tube and sealed under an atmosphere of nitrogen. The mixture was stirred and heated at 90° C. for 18 h, allowed to cool to room temperature and diluted with ethyl acetate. The mixture was washed with water and brine, the organic phase separated, dried over sodium sulphate and concentrated to dryness. The crude product was purified by mass-directed preparative HPLC. m/z 487 (M+H⁺).

Example 95 endo-N-(5-Phenyl-tricyclo[8.2.1.0$^{3,8}$]trideca-3(8),4,6-trien-13-yl)-benzenesulfonamide

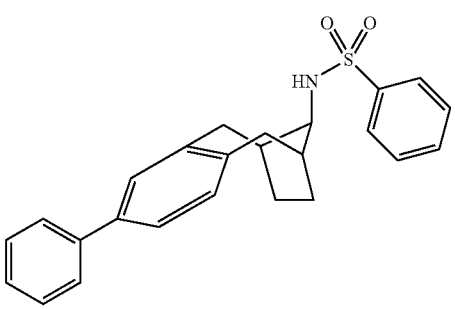

A mixture of endo-N-(5-bromo-tricyclo[8.2.1.0$^{3,8}$]trideca-3(8),4,6-trien-13-yl)-benzenesulfonamide (Example 93) (24 mg, 0.059 mmol), benzeneboronic acid (9 mg, 0.074 mmol) and sodium carbonate (25 mg, 0.296 mmol) in water (0.25 mL) and dimethoxyethane (1 mL) was thoroughly degassed. Tetrakis(triphenylphosphine)palladium (0) (5 mg) was added and the mixture was stirred and heated at reflux under nitrogen for 3 h. The mixture was cooled to room temperature and diluted with water and ethyl acetate. The organic phase was washed with brine, dried over sodium sulphate and concentrated to dryness. The crude product was purified by mass-directed preparative HPLC. $^1$H NMR CDCl$_3$, 400 MHz) δ 1.16-1.21 (m, 2 H), 1.59-1.64 (m, 2 H), 2.30 (m, 2 H), 2.51-2.60 (m, 2 H), 3.00-3.07 (m 2 H), 3.72 (m, 1 H), 5.01 (bd, 1 H), 7.10 (d, 1 H, J=8 Hz), 7.26-7.33 (m, 3 H), 7.39-7.43 (m, 2 H), 7.52-7.63 (m, 5 H), 7.94-7.97 (m, 2 H). m/z 404 (M+H$^+$).

Following the procedure of Example 95, and using the appropriate boronic acid, the following compounds of formula J were prepared. In each case, purification was by mass-directed HPLC.

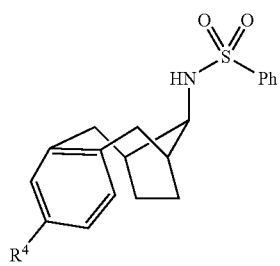

J

| Example | R$^4$ | m/z (M + H$^+$) |
|---|---|---|
| 96 | 3-thienyl | 410 |
| 97 | 2-methoxyphenyl | 434 |
| 98 | 4-fluorophenyl | 422 |
| 99 | 3-fluorophenyl | 422 |
| 100 | benzofuran-2-yl | 444 |
| 101 | 2-thienyl | 410 |
| 102 | 2-fluorophenyl | 422 |
| 103 | 4-pyridyl | 405 |
| 104 | 3-pyridyl | 405 |
| 105 | 6-methoxypyridin-3-yl | 435 |

Example 106 endo-5-Chloro-thiophene-2-sulfonic acid tricyclo[6.2.2.0$^{2,7}$]dodeca-2(7),3,5-trien-9-ylamide

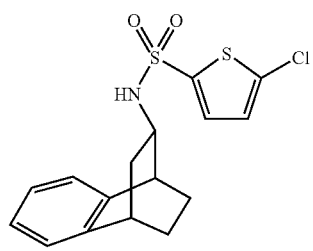

Step 1. Tricyclo[6.2.2.0$^{2,7}$]dodeca-2,4,6-trien-9-one oxime

Tricyclo[6.2.2.0$^{2,7}$]dodeca-2,4,6-trien-9-one (*Can. J. Chem.*, 71, 1290-6, 1993) (440 mg, 2.56 mmol) was dissolved in ethanol (3 mL) and water (1.5 mL) was added, followed by hydroxylamine hydrochloride (484 mg, 6.97 mmol) and sodium acetate trihydrate (948 mg, 6.97 mmol). The reaction was stirred at room temperature overnight. Water (40 mL) was added, a precipitate formed and this was filtered. The precipitate was dissolved in DCM (20 mL) and washed with water. The aqueous washings were extracted into DCM (20 mL) and the organic layer was dried (MgSO$_4$) and concentrated to give the desired oxime (475 mg, 100%). $^1$H NMR (CDCl$_3$, 360 MHz) δ 7.25-7.18 (4 H, m), 3.73-3.70 (1 H, m), 3.34-3.30 (1 H, m), 2.61, (1 H, dd, J=18 & 2.5 Hz), 2.39-2.31 (1 H, m), 2.04-1.96 (1 H, m), 1.87-1.79 (1 H, m), 1.66-1.49 (2 H, m). m/z 188 (M+H$^+$).

Step 2. endo-Tricyclo[6.2.2.0$^{2,7}$]dodeca-2,4,6-trien-9-ylamine

Tricyclo[6.2.2.0$^{2,7}$]dodeca-2,4,6-trien-9-one oxime (20 mg, 0.107 mmol) was dissolved in glacial acetic acid (5 mL), platinum (IV)oxide (5 mg) was added, and the mixture was hydrogenated in a Parr reactor at 32 psi for 4 h. The mixture was filtered, freeze dried and used crude in the next reaction step.

Step 3. endo-5-Chloro-thiophene-2-sulfonic acid tricyclo[6.2.2.0$^{2,7}$]dodeca-2(7),3 5-trien-9-ylamide endo-Tricyclo[6.2.2.0$^{2,7}$]dodeca-2,4,6-trien-9-ylamine (prepared above, 0.107 mmol) was dissolved in CDCl$_3$ (2 mL) and treated with 5-chlorothiophenesulphonyl chloride (46.5 mg, 0.214 mmol) followed by pyridine (200 μL). The reaction was heated at 45° C. for 48 hours. The product was purified by mass-directed preparative HPLC to give the desired product (1.8 mg, 5%) $^1$H NMR (CDCl$_3$, 360 MHz) δ 7.37 (1 H, d, J=4 Hz), 7.27-7.07 (4 H, m), 6.93 (1 H, d, J=4 Hz), 4.01-3.97 (1 H, br d), 3.88-3.79 (1 H, m), 3.02-2.96 (2 H, m), 2.29-2.21 (1 H, m), 1.79-1.58 (2 H, m), 1.49-1.39 (1 H, m), 1.36-1.25 (1 H, m), 1.14-1.08 (1 H, m). m/z 354 (M+H$^+$).

Example 107

5-Chloro-thiophene-2-sulfonic acid (3-methyl-bicyclo[3.2.1]oct-8-yl)-amide

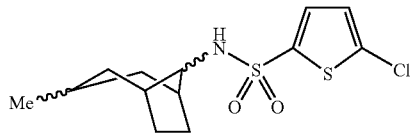

Step 1. 3-Methylene-bicyclo[3.2.1]octan-8-one oxime

3-Methylene-bicyclo[3.2.1]octan-8-one (*Tetrahedron Lett.*, 29, 5663-4, 1988) (408 mg, 3 mmol) was dissolved in ethanol (3 mL) and water (1.5 mL) was added, followed by hydroxylamine hydrochloride (534 mg, 9 mmol) and sodium acetate trihydrate (1.224 g, 9 mmol). The reaction was stirred at room temperature overnight. Water (20 mL) was added and the mixture was extracted into DCM (3×30 mL). The combined organic extracts were dried (Na$_2$SO$_4$) and concentrated to give a viscous yellow oil which was purified by column chromatography on silica using 10→20% ethyl acetate in isohexane to yield the oxime (284 mg, 63%). $^1$H NMR (CDCl$_3$, 360 MHz) δ 4.91-4.87 (2H, m), 3.42-3.38 (1 H, m), 2.66-2.64(1 H, m), 2.55-2.48 (2 H, m), 2.37-2.24 (2 H, m),1.87-1.51 (4 H, m). m/z 152 (M+H$^+$).

Step 2. 3-Methyl-bicyclo[3.2.1]oct-8-ylamine 3-Methylene-bicyclo[3.2.1]octan-8-one oxime (25 mg, 0.165 mmol) was dissolved in ethanol (5 mL), 10% palladium on carbon (15 mg) was added, and the mixture was hydrogenated in a Parr reactor at 40 psi for 2 h and then 50 psi for 20 h. The mixture was filtered and the catalyst was washed with further ethanol (25 mL). The filtrate was evaporated to give the product amine as a mixture of 4 isomers which was used crude in the next step.

Step 3. 5-Chloro-thiophene-2-sulfonic acid (3-methyl-bicyclo[3.2.1]oct-8-yl)-amide 3-Methyl-bicyclo[3.2.1]oct-8-ylamine (prepared in Step 2, 0.165 mmol) was dissolved in DCM (1.5 mL) and treated with 5-chlorothiophenesulphonyl chloride (53.7 mg, 0.248 mmol) followed by pyridine (100 µL). The reaction was stirred at room temperature for 66 h, followed by heating at 60° C. for 18 h. The reaction mixture was evaporated and purified by mass-directed preparative HPLC to give the desired product (5.3 mg, 10%) as a mixture of four isomers. m/z 320 (M+H$^+$).

Example 108 endo-5-Chloro-thiophene-2-sulfonic acid (3-methylene-bicyclo[3.2.1]oct-8-yl)-amide

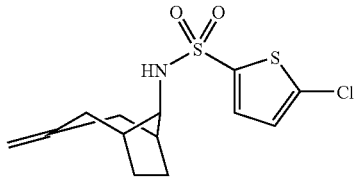

Step 1. endo-N-(3-Methylene-bicyclo[3.2.1]oct-8-yl)-hydroxylamine

Sodium cyanoborohydride (165 mg, 2.62 mmol) was added to a solution of 3-methylene-bicyclo[3.2.1]octan-8-one oxime (200 mg, 1.32 mmol) in methanol (4 mL) containing methyl orange indicator (10 µL of a 0.1% aqueous solution) at −30° C. followed by enough 5 N hydrochloric acid to turn the solution pink. After 90 min the reaction mixture was allowed to warm to 0° C. and the reaction mixture was basified using 4 N sodium hydroxide solution. The mixture was extracted into DCM (3×30 mL) and the combined organic extracts were dried (Na$_2$SO$_4$) and concentrated to give the desired hydroxylamine (185 mg, 91%). $^1$H NMR (CDCl$_3$, 360 MHz) δ 4.73-4.71 (2 H, m), 3.25 (1 H, t, J=4.5 Hz), 2.57-2.53 (2 H, br d), 2.25-2.22 (2 H, m), 1.91-1.85 (2 H, br dd), 1.75-1.66 (2 H, m), 1.55-1.42 (2 H, m). m/z 154 (M+H$^+$).

Step 2. endo-3-Methylene-bicyclo[3.2.1]oct-8-ylamine endo-N-(3-Methylene-bicyclo[3.2.1]oct-8-yl)-hydroxylamine (25 mg, 0.16 mmol) in 50% acetic acid (1 mL) was treated with activated zinc dust (110 mg) and heated at 55° C. for 2 h. The reaction was allowed to cool to room temperature, filtered and basified using 4 N sodium hydroxide solution. The reaction mixture was extracted into DCM (3×30 mL) and the combined organic extracts were dried (Na$_2$SO$_4$) and concentrated. The crude product was used directly in the next step.

Step 3. endo-5-Chloro-thiophene-2-sulfonic acid (3-methylene-bicyclo[3.2.1]oct-8-yl)-amide endo-3-Methylene-bicyclo[3.2.1]oct-8-ylamine (prepared as above, 0.16 mmol) was dissolved in CDCl$_3$ (2.1 mL) and treated with 5-chlorothiophenesulphonyl chloride (53 mg, 0.244 mmol) followed by pyridine (100 µL). The reaction was heated at 50° C. for 18 h followed by 65° C. for a further 24 h. The product was purified by mass-directed preparative HPLC followed by column chromatography on silica using 20% diethyl ether in isohexane as the eluant to give the desired product (14.1 mg, 27%). $^1$H NMR (CDCl$_3$, 360 MHz) δ 7.42 (1 H, d, J=4 Hz), 6.92 (1 H, d, J=4 Hz), 4.92-4.85 (1 H, br d), 4.78-4.75 (2 H, m), 3.47-3.42 (1 H, m), 2.40-2.35 (2 H, br d), 2.15-2.10 (2 H, m), 1.99-1.93 (2 H, br dd), 1.68-1.63 (2 H, m), 1.48-1.41 (2 H, m). m/z 318 (M+H$^+$).

Alternative Procedure for Step 3

A solution of endo-3-methylene-bicyclo[3.2.1]oct-8-ylamine [Step 2] (0.50 g, 3.65 mmol), triethylamine (0.56 ml, 4.03 mmol) and 5-chlorothiophenesulfonyl chloride (0.87 g, 4.03 mmol) in CH$_2$Cl$_2$ (20 ml) was stirred at room temperature for 1 h. The reaction mixture was diluted with CH$_2$Cl$_2$ and washed with water, and dried (MgSO$_4$), filtered and evaporated. Trituration gave endo-5-chloro-thiophene-2-sulfonic acid (3-methylene-bicyclo[3.2.1]oct-8-yl)-amide (1.2 g, ca 100%).

Example 109 endo-5-Chloro-thiophene-2-sulfonic acid (3-oxo-bicyclo[3.2.1]oct-8-yl)-amide

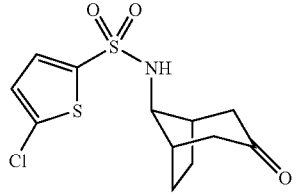

A solution of the sulfonamide from Example 108 (0.60 g, 1.89 mmol) in methanol (12 ml), CH$_2$Cl$_2$ (50 ml) was cooled to −78° C., and treated with ozone until a blue color persisted. The reaction mixture was treated with dimethyl sulfide (0.5 ml) and allowed to warm to room temperature overnight. The reaction mixture was evaporated in vacuo and purified by column chromatography to yield endo-5-Chloro-thiophene-2-sulfonic acid (3-oxo-bicyclo[3.2.1]oct-8-yl)-amide (0.5 g, 83%) as a colorless foam.

$^1$H NMR (CDCl$_3$, 360 MHz), 7.46 (1H, d, J=4.0), 6.97 (1H, d, J=4.0), 5.12 (1H, d, J=3.1), 3.45-3.42 (1H, m), 2.68-2.63 (2H, m), 2.50 (2H, m), 2.26-2.21 (2H, m), 1.87-1.84 (2H, m), 1.62-1.56 (2H, m). m/z=320 (MH$^+$).

Example 110 endo-5-Chloro-thiophene-2-sulfonic acid (4-oxo-3-aza-bicyclo[4.2.1]non-9-yl)-amide

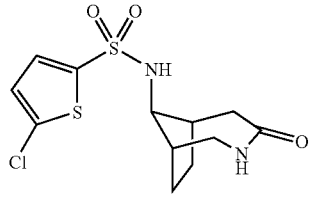

A solution of the ketone from Example 109 (0.80 g, 2.51 mmol) in 98% formic acid (15 ml) was treated with hydroxylamine-O-sulfonic acid (450 mg, 3.98 mmol) and refluxed for 7 h. The reaction mixture was evaporated in vacuo, and diluted with ethyl acetate and brine. The organic layer was separated, dried (MgSO$_4$), filtered and evaporated in vacuo. Purification by column chromatography gave endo-5-Chloro-thiophene-2-sulfonic acid (4-oxo-3-aza-bicyclo[4.2.1]non-9-ylmethyl)-amide (412 mg, 49%). $^1$H NMR (d$_6$-DMSO, 400 MHz) 8.34 (1H, brs), 7.52 (1H, d, J=4.0), 7.26 (1H, d, J=4.0), 7.18 (1H, d, J=7.0), 3.47-3.36

(2H, m), 2.71 (1H, d, J=15.5), 2.64-2.57 (1H, m), 2.11-1.94 (3H, m), 1.76-1.33 (4H, m). m/z=335 (MH⁺).

Example 111 endo-5-Chloro-thiophene-2-sulfonic acid (3-aza-bicyclo[4.2.1]non-9-yl)-amide

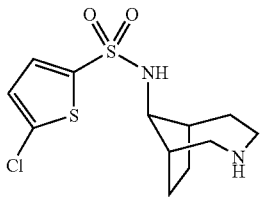

A solution of the lactam from Example 110 (100 mg, 0.29 mmol) in THF (3 ml) was treated with a freshly prepared solution of AlH₃ (H. C. Brown et al, *J. Am. Chem. Soc.*, 1968, 2927) (0.66M in THF, 1.4 ml, 0.92 mmol) and refluxed for 10 min. The reaction mixture was cooled to 0° C., and quenched carefully with ice cold H₂O-THF (1:1) (ca. 1 ml). The reaction mixture was warmed to room temperature and treated with 4 N NaOH solution until a precipitate formed. The supernatant was collected by decantation, and the precipitate was washed several times with ethyl acetate. The combined organic fractions were dried (MgSO₄), filtered and evaporated in vacuo. Purification by column chromatography gave endo-5-chloro-thiophene-2-sulfonic acid (3-aza-bicyclo[4.2.1]non-9-ylmethyl)-amide (60 mg, 63%) as a white solid. ¹H NMR (d₆-DMSO, 400 MHz) 7.54 (1H, d, J=4.0), 7.24 (1H, d, J=4.0), 3.68 (1H, dd, J=7.1, 7.1), 3.5 (2H, obscured), 2.92-2.85 (2H, m), 2.54-2.38 (2H, m), 2.21-2.16 (2H, m), 1.92-1.26 (6H, m). m/z=321 (MH⁺).

Example 112 endo-5-Chloro-thiophene-2-sulfonic acid (3-benzyl-3-aza-bicyclo[4.2.1]non-9-yl)-amide

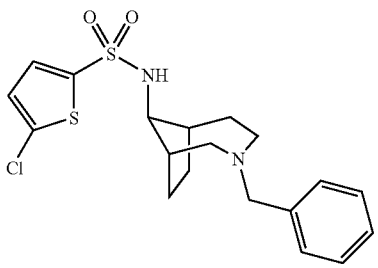

A solution of the amine from Example 111 (35 mg, 0.11 mmol) in CH₂Cl₂ (1 ml) was treated with triethylamine (0.034 ml) and benzyl bromide (0.042 ml). The reaction mixture was stirred for 4 h, then diluted with CH₂Cl₂, washed with water, dried (MgSO₄), filtered and evaporated in vacuo. Purification by column chromatography gave endo-5-Chloro-thiophene-2-sulfonic acid (3-benzyl-3-aza-bicyclo[4.2.1]non-9-ylmethyl)-amide (35 mg, 78%). ¹H NMR (CDCl₃, 400 MHz) 7.41-7.26 (6H, m), 7.04 (1H, d J=3.7), 6.77 (1H, d, J=4.0), 3.83-3.80 (1H, m), 3.58-3.48 (2H, m), 2.84-2.76 (2H, m), 2.38-2.17 (3H, m), 2.09-1.95 (2H, m), 1.82-1.71 (2H, m), 1.54-1.26 (3H, m). m/z=411 (MH⁺).

Example 113 endo-5-chloro-N-(4-thioxo-3-azabicyclo[4.2.1]non-9-yl)thiophene-2-sulfonamide

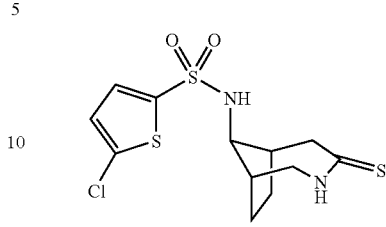

A mixture of the product from Example 110 (250 mg) and Lawesson's reagent (227 mg) in toluene (10 ml) was heated to reflux for 20 mins. On cooling, the mixture was basified with NaOH (1M 10 ml) and extracted with EtOAc (3×20 ml). The combined organic phases were dried and concentrated, then recrystallised from EtOAc/ether to give the title compound as a white solid (58 mg, 22%), (360 MHz ¹H δ, d₆-DMSO) 1.43 (1H, m), 1.56 (1H, m), 1.68 (2H, m), 2.09 (1H, m), 2.15 (1H, m), 2.83 (1H, dd, J=7.2, 14.4), 2.93 (1H, m), 3.04 (1H, d, J=14.4), 3.44 (1H, dd, J=3.6, 10.8), 3.54 (1H, dd, J=2.4, 14.4), 7.22 (1H, d, J=4), 7.53 (1H, d, J=4), 8.39 (1H, d, J=7.2), 9.89 (1H, brs); MS(ES+): MH+351.

Example 114 endo-5-chloro-N-[5,6,7,8,9,10-hexahydro-6,9-methanoimidazo[1,2-α]azocin-11-yl]thiophene-2-sulfonamide

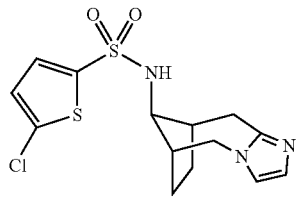

Step 1: endo-N-[4-(benzylthio)-3-azabicyclo[4.2.1]non-3-en-9-yl]-5-chloro thiophene-2-sulfonamide-HBr salt

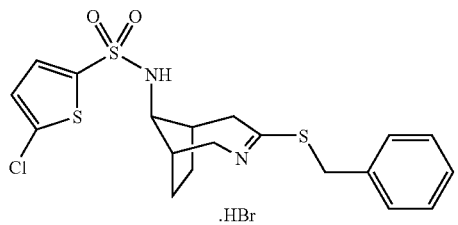

The product from Example 113 (50 mg) was suspended in CHCl₃ (3 ml), benzyl bromide (20 µl) added and the mixture heated to reflux for 8 hrs. Cooled, added ether and filtered. Recrystallisation from EtOAc/ether gave the title sulfide (44 mg, 59%) as a white solid.

Step 2

The above intermediate (30 mg), aminoacetaldehyde dimethyl acetal (10 µl) and triethylamine (24 µl) in THF (1 ml) were heated to reflux for 24 hrs. The cooled mixture was concentrated, added to saturated aqueous NaHCO₃ (5 ml) and extracted with DCM (3×20 ml). The extracts were dried, concentrated and the residue dissolved in DCM (2 ml). TFA (0.2 ml) was added and heated to reflux for 24 hrs. The mixture was concentrated in vacuo, 1M NaOH (5 ml) added and extracted with DCM (3×5 ml). Drying, concentration and column chromatography on silica eluting with 1% NH$_3$ in EtOAc gave the title imidazole (8 mg, 39%) as a white solid, (360 MHz $^1$H d$_6$-DMSO) 1.04 (2H, m), 1.74 (2H, m), 2.32 (1H, dd, J=6.2, 12.2), 2.40 (1H, dd, J=7.1, 13.3), 2.89 (1H, dd, J=6.4, 13.7), 3.04 (1H, d, J=16.5), 3.70 (1H, dd, J=6.3, 6.3), 4.01 (1H, dd, J=5.6, 14.4), 4.18 (1H, d, J=14.7), 7.09 (1H, d, J=0.9), 7.23 (1H, s), 7.30 (1H, d, J=4.1), 7.60 (1H, d, J=4), 8.52 (1H, brs); MS(ES+): M+Na 358.

Example 115

[9-endo]-N-(9-methylbicyclo[4.2.1]non-3-en-9-yl)benzenesulfonamide

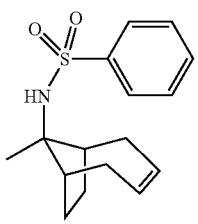

To a solution of bicyclo[4.2.1]non-3-en-9-one (1.55 g), triethylamine (4.8 ml) and benzenesulfonamide (1.79 g) in dry DCM (50 ml) at 0° C. was added TiCl$_4$ (1.0M in DCM, 6.3 ml). The reaction was stirred for 30 min at 0° C. then at RT for 16 h. Filtered through Celite® then concentrated in vacuo, the resulting solid was suspended in ether and heated under reflux for 5 min then filtered. The filtrate was concentrated in vacuo and the crude imine extracted into hexane at reflux, concentrated in vacuo to give an off white solid (1.706 g, 54%). The imine was used without further purification.

A solution of the imine (0.138 g) in dry THF (10 ml) was cooled to −78° C. and MeLi (1.0M in ether, 0.6 ml) was added dropwise. The reaction was stirred at −78° C. for 10 min then at RT for 3 h. The reaction was cooled to 0° C., quenched with water and extracted with EtOAc, washed with brine, dried over MgSO$_4$ and concentrated in vacuo. The product was purified by column chromatography (silica, 15% EtOAc in hexane) to give a white solid (0.108 g, 74%), (360 MHz $^1$H, δ-CDCl$_3$) 1.22 (3H, s), 1.39 (2H, m), 1.88 (2H, m), 2.16 (4H, m), 2.42 (2H, m), 4.71 (1H, brs), 5.53 (2H, m), 7.51 (3H, m), 7.92 (2H, m); ($^{13}$C δ-CDCl$_3$) 26.8, 28.9, 35.2, 47.8, 69.5, 128.8, 129.1, 130.6, 134.0, 145.4. MS(CI+): [M+Na+MeCN]+355.

Example 116

[9-endo]-5-chloro-N-(9-methylbicyclo[4.2.1]non-3-en-9-yl)thiophene-2-sulfonamide

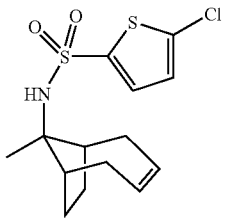

An imine was prepared by a similar procedure to the previous example using 5-chlorothiophene-2-sulfonamide instead of benzenesulfonamide. A solution of the imine (0.158 g) in dry THF (10 ml) was cooled to 0° C. and MeMgCl (3.0M in THF, 0.2 ml) was added dropwise. The reaction was stirred at 0° C. for 30 min then heated euder reflux for 2 h. The reaction was cooled to 0° C., quenched with saturated ammonium chloride solution, extracted with ether, washed with brine, dried over MgSO$_4$ and concentrated in vacuo to give a pale yellow solid (0.150 g, 90%), (360 MHz $^1$H, δ-CDCl$_3$) 1.38 (3H, s), 1.41 (2H, m), 1.92 (2H, m), 2.20 (4H, m), 2.36 (2H, m), 4.80 (1H, brs), 5.53 (2H, m), 6.87 (1H, d, J=3.9), 7.40 (1H, d, J=3.9); ($^{13}$C δ-CDCl$_3$) 26.5, 28.9, 35.1, 47.9, 70.0, 128.1, 129.1, 132.9, 138.5, 144.8.

Example 117

[9-endo]-N-(9-allylbicyclo[4.2.1]non-3-en-9-yl)-5-chlorothiophene-2-sulfonamide

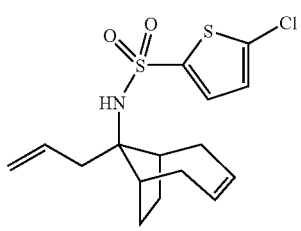

A solution of the imine prepared as described in the previous example (0.158 g) in dry THF (10 ml) was cooled to 0° C. and allylmagnesium bromide (1.0M in ether, 0.6 ml) was added dropwise. The reaction was stirred at 0° C. for 1 h then at RT for 2 h. The reaction was cooled to 0° C., quenched with 2N HCl and extracted with EtOAc, washed with brine, dried over MgSO$_4$ and concentrated in vacuo. The product was recrystallized (hexane/EtOAc) to give a white solid (0.118 g, 66%), (360 MHz $^1$H, δ-CDCl$_3$) 1.42 (2H, m), 1.83 (2H, m), 2.19 (2H, m), 2.35 (4H, m), 2.54 (2H, m), 4.59 (1H, brs), 4.94 (2H, m), 5.34 (1H, m), 5.53 (2H, m), 6.86 (1H, d, J=3.9), 7.39 (1H, d, J=3.9); ($^{13}$C δ-CDCl$_3$) 29.1, 35.0, 41.5, 45.3, 73.1, 119.7, 128.0, 129.0, 133.2, 135.4, 138.8, 144.1. MS(CI+): [M-allyl]+316.

Example 118

(syn, exo)-7-{[(5-Chlorothien-2-yl)sulfonyl]amino}bicyclo[2.2.1]hept-2-yl acetate

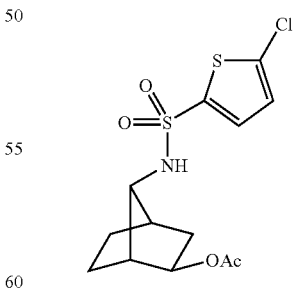

(a) A solution of (syn, exo)-7-azidobicyclo[2.2.1]hept-2-yl acetate (E. Zibral; A. Stuetz, *Tetrahedron*, 1974, 27, 4953-4963) (1.2 g, 6.15 mmol) in EtOAc (20 mL) was hydrogenated over 5% Pd-C at 30 psi H$_2$ for 2 h. The catalyst was removed by filtration and the filtrate was concentrated to give (syn, exo)-7-aminobicyclo[2.2.1]hept-2-yl acetate as a colourless oil (0.95 g, 91%). ¹H NMR (CDCl₃, 400 MHz) δ 1.08-1.12 (2 H, m), 1.56-1.64 (2 H, m), 1.88-1.96 (2 H, m), 2.01-2.04 (4 H, m), 2.10 (1 H, d, J 5), 3.06 (1 H, s), 4.75-4.77 (1 H, m).

(b) The amine was dissolved in dry CH₂Cl₂ (20 mL) and 5-chlorothiophene-2-sulfonyl chloride (1.22 g, 5.62 mmol) and Et₃N (1.2 mL, 8.4 mmol) were added. The solution was stirred at room temperature under N₂ for 60 h. The solution was washed with H₂O (20 mL) and the washings were extracted with CH₂Cl₂ (20 mL). The combined organic extracts were dried (Na₂SO₄), filtered and concentrated. Flash column chromatography, eluting 15% EtOAc-isohexane, then 30% EtOAc-isohexane, gave the product as a pink oil. Trituration and washing with Et₂O gave the title compound as white crystals (1.12 g, 57%). A sample was recrystallised from EtOAc-isohexane. ¹H NMR (CDCl₃, 360 MHz) δ 1.10-1.16 (2 H, m), 1.55-1.64 (2 H, m), 1.68-1.75 (1 H, m), 1.95 (1 H, dd, J 14, 8), 2.07 (3 H, s), 2.13 (1 H, d, J 4), 2.25 (1 H, dd, J 4, 4) 3.46 (1 H, d, J 9), 4.77 (1 H, dd, J 7, 3), 5.19 (1H, d, J 9), 6.93 (1 H, d, J 4), 7.40 (1 H, d, J 4); m/z 374, 372 (M+Na⁺).

Example 119

(syn, exo)-7-1[(5-Chlorothien-2-yl)sulfonyl]amino)bicyclo[2.2.1]hept-2-yl 2-(methylthio)nicotinate

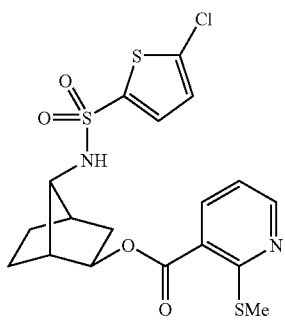

(a) A mixture of the product from Example 118 (0.483 g, 1.38 mmol) and K₂CO₃ (0.19 g, 1.38 mmol) in MeOH (20 mL) was stirred at room temperature for 2.5 h. The mixture was concentrated and the residue was partitioned between water (50 mL) and CH₂Cl₂ (50 mL). The organic layer was dried (Na₂SO₄), filtered and concentrated to give a colourless gum. Trituration and washing with Et₂O gave (syn, exo)-5-chloro-N-(2-hydroxybicyclo[2.2.1]hept-7-yl)thiophene-2-sulfonamide as a white solid (0.337 g, 79%). ¹H NMR (CDCl₃, 360 MHz) δ 0.94-1.09 (2 H, m), 1.47-1.61 (2 H, m), 1.68 (1 H, dd, J 14, 2), 1.82 (1 H, dd, J 14, 7), 1.09 (1 H, d, J 1), 2.01 (1 H, d, J 4),2.23-2.25 (1 H, m) 3.47-3.49 (1 H, m), 3.94 (1 H, d, J 6), 6.25 (1H, d, J 9), 6.91 (1 H, d, J4), 7.40 (1 H, d, J 4); m/z 310, 308 (M+H⁺).

(b) A solution of potassium bis(trimethylsilyl)amide (0.5 M in toluene, 0.25 mL) was added to a solution of (syn, exo)-5-chloro-N-(2-hydroxybicyclo[2.2.1]hept-7-yl)thiophene-2-sulfonamide (0.015 g, 0.05 mmol) in dry THF (0.5 mL) in a septum-sealed glass reaction tube. After 20 min a solution of 2-thiomethyl-3-pyridinecarbonyl chloride (0.06 mmol) in dry THF (0.1 mL) was added. After 3 h at room temperature HCl (0.05 M, 1.5 mL) and CH₂Cl₂ (1.5 mL) were added. The mixture was vortex mixed and the organic layer was separated by filtration through a Teflon membrane. Solvent was removed by evaporation. Purification of half of the sample by preparative HPLC-MS gave the title compound (0.0051 g, 44%).

¹H NMR (h₆-DMSO, 400 MHz, DMSO and H₂O signals suppressed) δ 0.90-1.05 (2 H, m), 1.30-1.50 (2 H, m), 1.75 (1 H, dd, J 13, 7), 1.90-1.96 (1 H, m), 2.09-2.12 (1 H, m), 3.00 (1 H, br s), 4.60-4.65 (1 H, m), 7.12 (1 H, d, J 4), 7.18 (1 H, dd, J 8, 5), 7.38 (1 H, d, J 4), 7.90-7.92 (1 H, m), 8.25 (1 H, dd, J 8, 2), 8.58 (1 H, dd, J 5, 2); m/z 361, 359 (M+H⁺).

Example 120

(syn, exo)-7-{[(5-Chlorothien-2-yl)sulfonyl]amino}bicyclo[2.2.1]hept-2-yl 3,4-dimethoxybenzoate

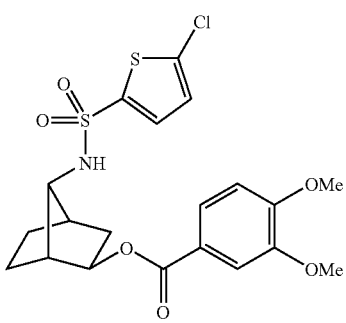

Prepared as for Example 119 using 3,4-dimethoxybenzoyl chloride in place of 2-thiomethyl-3-pyridinecarbonyl chloride. ¹H NMR (h₆-DMSO, 400 MHz, DMSO and H₂O signals suppressed) δ 1.07-1.20 (2 H, m), 1.46-1.62 (2 H, m), 1.92 (1 H, dd, J 13.4, 7.6), 2.01-2.07 (2 H, m), 2.22 (1 H, br s), 3.07 (1 H, br s), 3.83 (6 H, br s), 4.79 (1 H, dd, J 7.3, 2.6), 7.05 (1 H, d, J 8.4), 7.21 (1 H, d, J 4.0), 7.47 (1 H, d, J 4.0), 7.54 (1 H, d, J 1.7), 7.63 (1 H, dd, J 8.4, 1.8), 8.01(1 H, br s); m/z 496, 494 (M+Na⁺).

Example 121

(syn, exo)-7-(5-Chlorothiophene-2-sulfonylamino)-bicyclo[2.2.1]hept-2-yl 2-nitrobenzoate

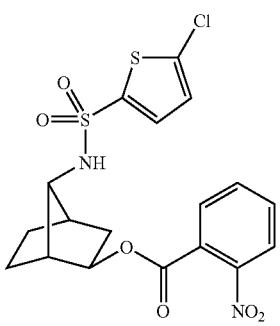

Prepared as for Example 119 using 2-nitrobenzoyl chloride in place of 2-thiomethyl-3-pyridinecarbonyl chloride. ¹H NMR (h₆-DMSO, 400 MHz, DMSO and H₂O signals suppressed) δ 1.07-1.21 (2 H, m), 1.46-1.63 (2 H, m), 1.92 (1 H, dd, J 13.6, 7.6), 2.04-2.07 (2 H, m), 2.24 (1 H, br s), 3.07 (1 H, br s), 4.77-4.80 (1 H, m), 7.21 (1 H, d, J 4.0), 7.46 (1H, d, J 4.0), 7.80-7.86 (2 H, m), 7.95-8.03 (3 H, m); m/z 479, 481 (M+Na⁺).

Example 122

(syn, exo)-7-{[(5-Chlorothien-2-yl) sulfonyl]amino}bicyclo[2.2.1]hept-2-yl methyl carbonate

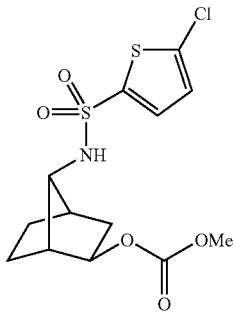

Prepared as for Example 119 using methyl chloroformate in place of 2-thiomethyl-3-pyridinecarbonyl chloride.

$^1$H NMR ($_{h6}$-DMSO, 400 MHz, DMSO and H$_2$O signals suppressed) δ 0.90-1.00 (2 H, m), 1.30-1.45 (2 H, m), 1.70 (1 H, dd, J 14, 7), 1.82-1.90 (1 H, m), 2.05-2.10 (1 H, m), 2.22 (1 H, d, J 5), 3.56 (3 H, s), 4.30-4.35 (1 H, m), 7.23 (1 H, d, J 4), 7.45 (1 H, d, J 4), 7.82 (1 H, d, J 5). m/z 390, 388 (M+Na$^+$).

Example 123

(syn, exo)-7-(5-Chlorothiophene-2-sulfonylamino)bicyclo[2.2.1]hept-2-yl methanesulfonate

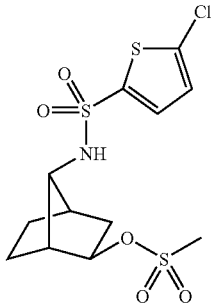

To a solution of (syn, exo)-5-chloro-N-(2-hydroxybicyclo[2.2.1]hept-7-yl)thiophene-2-sulfonamide) [Example 119 step (a)] (48 mg, 0.16 mmol) in CH$_2$Cl$_2$ (3 mL) were added Et$_3$N (33 μL, 0.24 mmol), methanesulfonyl chloride (14 μL, 0.18 mmol) and 4-(dimethylamino)pyridine (10 mg, 0.08 mmol). The mixture was stirred at room temperature under N$_2$ for 18 h. The mixture was then partitioned between H$_2$O and EtOAc. The layers were separated and the aqueous phase extracted a second time with EtOAc. The combined organic extracts were dried (MgSO$_4$) and concentrated. Purification by flash chromatography (15% EtOAc/hexane) afforded the title compound as a white solid (54 mg, 90%). $^1$H NMR (CDCl$_3$, 400 MHz) δ 1.10-1.17 (2 H, m), 1.56-1.73 (2 H, m), 1.98-2.09 (2 H, m), 2.39 (1 H br s), 2.44 (1 H, br d, J 4.8), 3.05 (3 H, s), 3.44 (1 H, d, J 7.0), 4.72 (1 H, dd, J 7.0, 3.3), 5.29 (1 H, d, J 7.0), 6.95 (1 H, d, J 4.0), 7.43 (1 H, d, J 4.0); m/z 292, 290 ([M—OSO$_2$Me]$^+$).

Example 124

(syn, exo)-7-(5-Chlorothiophene-2-sulfonylamino)bicyclo[2.2.1]hept-2-yl toluene-4-sulfonate

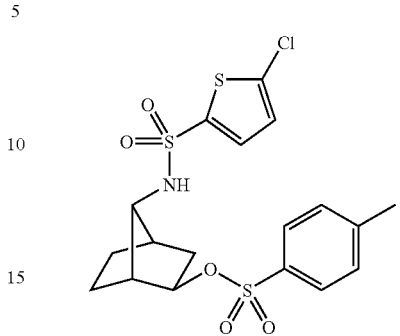

Prepared as for Example 123 using toluene-4-sulfonyl chloride in place of methanesulfonyl chloride. $^1$H NMR (CDCl$_3$, 400 MHz) δ 0.98-1.08 (2 H, m), 1.49-1.66 (2 H, m), 1.78-1.88 (2 H, m), 2.21 (1 H, br d, J 4.6), 2.29 (1 H, br s), 2.47 (3 H, s), 3.43 (1 H, d, J 7.7), 4.55 (1 H, dd, J 6.8, 3.5), 5.17 (1 H, d, J 7.7), 6.93 (1 H, d, J 3.9), 7.36-7.40 (3 H, m), 7.75-7.78 (2 H, m); m/z 462, 460 ([M+H]$^+$); 292, 290 ([M—OSO$_2$PhMe]$^+$).

Example 125

(syn)-5-Chloro-N-(2-methylenebicyclo[2.2.1]hept-7-yl)thiophene-2-sulfonamide

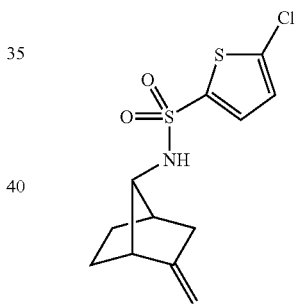

(a) Pyridinium dichromate absorbed on alumina (20% wt/wt 0.5 g) was added to a stirred solution of (syn, exo)-5-chloro-N-(2-hydroxybicyclo[2.2.1]hept-7-yl)thiophene-2-sulfonamide) [Example 119 step (a)] (0.121 g, 0.393 mmol) in dry CH$_2$Cl$_2$ (4 mL) at room temperature. After 3.5 h, further pyridinium dichromate-alumina (0.5 g) was added. After a further 4.5 h, the mixture was diluted with CH$_2$Cl$_2$ (10 mL) and filtered through a pad of silica gel, eluting with EtOAc (200 mL). The filtrate was concentrated to give (syn)-5-chloro-N-(2-oxobicyclo[2.2.1]hept-7-yl)thiophene-2-sulfonamide as a white powder (0.100 g, 83%). $^1$H NMR (CDCl$_3$, 360 MHz) δ 1.52-1.55 (2 H, m), 1.87-1.92 (3 H, m), 2.42 (1 H, dd, J 18, 4), 2.54-2.56 (1 H, m), 2.77-2.79 (1 H, m), 3.50-3.52 (1 H, m), 4.94 (1 H, s), 6.96 (1 H, d, J 4), 7.41 (1 H, d, J 4); m/z 330 and 328 (M+Na$^+$), 308 and 306 (M+H$^+$).

(b) A mixture of (syn)-5-chloro-N-(2-oxobicyclo[2.2.1]hept-7-yl)thiophene-2-sulfonamide (0.100 g, 0.313 mmol), methyl(triphenylphosphonium) bromide (0.125 g, 0.35 mmol) and potassium tert-butoxide (1M in THF, 1.0 mL) in dry toluene (2 mL) was refluxed under N$_2$ for 4 h. The mixture was cooled, diluted with 1M citric acid (15 mL) and extracted with EtOAc (2×15 mL). The extracts were dried (Na$_2$SO$_4$), filtered and concentrated. Flash column chromatography, eluting with 10% then 20% EtOAc-isohexane, gave the title compound as a pale yellow solid (0.027 g, 28%). $^1$H NMR (CDCl$_3$, 360 MHz) δ 1.30-1.34 (2 H, m), 1.69-1.73 (2 H, m), 1.96 (1 H, d, J 15), 2.26-2.35 (2 H, m), 2.41 (1 H, d, J 3), 3.42 (1 H, d, J 6), 4.55 (1 H, d, J 6), 4.83 (1 H, s), 4.95 (1 H, s), 6.92 (1 H, d, J 4), 7.39 (1 H, d, J 4); m/z 306 and 304 (M+H$^+$).

Example 126

(syn, endo)-7-{[(5-Chlorothien-2-yl)sulfonyl]amino}bicyclo[2.2.1]hept-2-yl acetate

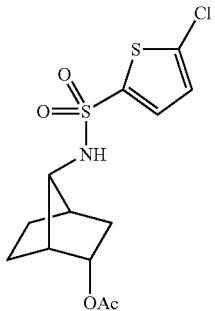

(a) Sodium hydride (55% wt/wt dispersion in oil; 1.75 g, 40 mmol) was added portionwise to a stirred solution of (endo)-2-hydroxybicyclo[2.2.1]heptan-7-one dimethyl acetal (M. E. Jung, J. P. Hudspeth, *J. Am. Chem. Soc.* 1977, 5508) (6.07 g, 36 mmol) and benzyl bromide (5.1 mL, 43 mmol) in dry DMF (100 mL) at room temperature under N$_2$. The gently effervescent mixture was warmed to 50° C. for 3.25 h. The mixture was cooled, diluted with H$_2$O (300 mL) and NH$_4$Cl (100 mL), and extracted with Et$_2$O (4×100 mL). The extracts were dried (Na$_2$SO$_4$), filtered and concentrated. Flash column chromatography, eluting with 20% EtOAc-isohexane, gave (endo)-2-benzyloxybicyclo[2.2.1]heptan-7-one dimethyl acetal as an orange oil (7.25 g, 78%). $^1$H NMR (CDCl$_3$, 360 MHz) δ 1.03 (1 H, dd, J 12, 2), 2.23 (1 H, ddd, J 12, 8, 4), 2.84 (1 H, dd, J 4, 4), 3.14 (3 H, s), 3.16 (3 H, s), 3.17-3.19 (1 H, m), 4.30-4.35 (1 H, m), 4.45 (1 H, d, J 12), 4.48 (1 H, d, J 12), 6.02 (1 H, dd, J 6, 3), 6.35 (1 H, ddd, J 6, 3, 1), 7.26-7.33 (5 H, m).

(b) 50% H$_2$SO$_4$ (30 mL) was added dropwise to a vigorously stirred solution of (endo)-2-benzyloxybicyclo[2.2.1]heptan-7-one dimethyl acetal (7.13 g, 27.4 mmol) in CH$_2$Cl$_2$ (300 mL) at room temperature. After 3.5 h, further 50% H$_2$SO$_4$ (30 mL) was added. After 24 h, conc H$_2$SO$_4$ (10 mL) was added and stirring was continued for 2 h. The mixture was diluted with H$_2$O (100 mL) and neutralised with NaHCO$_3$ (s). The mixture was further diluted with H$_2$O (200 mL) and extracted with CH$_2$Cl$_2$ (2×150 mL). The extracts were dried (Na$_2$SO$_4$), filtered and concentrated. The residual oil was filtered through a plug of silica, eluting with 20% EtOAc-isohexane, to give (endo)-2-benzyloxybicyclo[2.2.1]heptan-7-one (6.20 g, 100%). $^1$H NMR (CDCl$_3$, 400 MHz) δ 1.28 (1 H, dd, J 13, 3), 2.32 (1 H, ddd, J 13, 8, 4), 2.91-2.94 (1 H, m), 3.30-3.32 (1 H, m), 4.33-4.37 (1 H. m), 4.47 (1 H, d, J 12), 4.53 (1 H, d, J 12), 6.35-6.37 (1 H, m), 6.68-6.71 (1 H, m), 7.27-7.37 (5 H, m).

(c) A solution of (endo)-2-benzyloxybicyclo[2.2.1]heptan-7-one (3.0 g, 14 mmol), hydroxylamine hydrochloride (2.1 g, 30 mmol) and sodium acetate (2.5 g, 30 mmol) in EtOH—H$_2$O (3:1, 50 mL) was stirred under N$_2$ at room temperature for 18 h. The mixture was diluted with water (200 mL) and extracted with CH$_2$Cl$_2$ (2×100 mL). The extracts were dried (Na$_2$SO$_4$), filtered and concentrated. Flash column chromatography, eluting 50% EtOAc-isohexane, gave (eado)-2-benzyloxybicyclo[2.2.1]heptan-7-one oxime as a straw-coloured liquid (3.02 g, 94%). $^1$H NMR (CDCl$_3$, 400 MHz) 1:1 mixture of oxime isomers δ 1.19-1.27 (1 H, m), 2.19-2.29 (1 H, m), 3.11-3.12 and 3.72-7.74 (1 H, 2×m), 3.41-3.43 and 4.15-4.16 (1 H, 2×m), 4.26-4.30 (1 H, m), 4.45-4.54 (2 H, m), 6.12-6.14 and 6.19-6.22 (1 H, 2×m), 6.44-6.46 and 6.52-6.54 (1 H, 2×m), 7.25-7.36 (5 H, m) 7.60-8.10 (1 H, br s); m/z 230 (M+H$^+$).

(d) Lithium aluminium hydride (1M in THF, 14 mL) was added to a stirred solution of (endo)-2-benzyloxybicyclo[2.2.1]heptan-7-one oxime (3.0 g, 13.1 mmol) in dry THF (60 mL) at −78° C. under N$_2$. After 45 min the mixture was warmed to room temperature and stirred for 1 h. The reaction was recooled to −78° C. and further lithium aluminium hydride (1M in THF, 14 mL) was added. The orange solution was warmed to room temperature and stirred for a further 18 h. The reaction was quenched by cautious addition of saturated aqueous ammonium chloride (10 mL) then poured into saturated aqueous ammonium chloride (100 mL) and diluted with water (100 mL). Saturated aqueous Rochelle salt (100 mL) and EtOAc (200 mL) were added. After standing for 15 min the two phases were separated and the aqueous phase was extracted with EtOAc (2×100 mL). The combined organic extracts were dried (Na$_2$SO$_4$), filtered and concentrated. Flash column chromatography, eluting with 90:9:1 CH$_2$Cl$_2$—MeOH—NH$_3$ (aq), gave (syn, endo)-7-amino-2-benzyloxybicyclo[2.2.1]heptane as a pale yellow oil (0.67 g, 24%). $^1$H NMR (CDCl$_3$, 360 MHz) δ 1.15 (1 H, ddd, J 13, 3, 2), 1.30-1.50 (2 H, br s), 2.23 (1 H, ddd, J 12, 8, 4), 2.48-2.50 (1 H, m), 2.84-2.87 (1 H, m), 2.99 (1 H, d, J 2), 4.41 (1 H, ddd, J 8, 4, 3), 4.47 (2 H, s), 6.01 (1 H, dd, J 6, 3), 6.31 (1 H, ddd, J 6, 3, 1), 7.25-7.37 (5 H, m); m/z 216 (M+H$^+$).

(e) A solution of (syn, endo)-7-amino-2-benzyloxybicyclo[2.2.1]heptane (0.66 g, 3.07 mmol), di-tert-butyldicarbonate (0.74 g, 3.4 mmol) and triethylamine (0.84 mL, 6 mmol) in dry CH$_2$Cl$_2$ (10 mL) was stirred at room temperature under N$_2$ for 18 h. The solution was poured into water (100 mL) and extracted with CH$_2$Cl$_2$ (100 mL). The extract was dried (Na$_2$SO$_4$), filtered and concentrated. Flash column chromatography, eluting with 10% EtOAc-isohexane, gave (syn, endo)-7-(tert-butyloxycarbonyl)amino-2-benzyloxybicyclo[2.2.1]heptane as a white solid (0.885 g, 92%). $^1$H NMR (CDCl$_3$, 360 MHz) δ 1.15-1.21 (1 H, m), 1.43 (9 H, s), 2.05-2.12 (1 H, m), 2.70 (1 H, br s), 3.10 (1 H, br s), 3.55 (1 H, br s), 4.45-4.48 (1 H, m), 4.44-4.49 (2 H, m), 6.02-6.04 (1 H, m), 6.31-6.33 (1 H, m), 7.26-7.24 (5 H, m).

(f) A mixture of (syn, endo)-7-(tert-butyloxycarbonyl)amino-2-benzyloxybicyclo[2.2.1]heptane (0.74 g, 2.35 mmol), ammonium formate (1.6 g, 24 mmol) and 5% palladium on carbon (0.2 g) in MeOH (20 mL) was refluxed under N$_2$. After 18 h, further ammonium formate (1.6 g) and palladium catalyst (0.2 g) were added. After 3 days the mixture was cooled, filtered and concentrated. The material was redissolved in MeOH (30 mL) with 5% palladium on carbon (0.5 g) and hydrogenated at 40 psi H$_2$ in a Parr apparatus. When H$_2$ uptake was complete (ca. 2 h) the mixture was filtered and the filtrate was concentrated to give (syn, endo)-7-(tert-butyloxycarbonyl)amino-2-hydroxybicyclo[2.2.1]heptane as a white solid (0.471 g, 88%). $^1$H NMR (CDCl$_3$, 400 MHz) δ 1.05-1.11 (1 H, m), 1.35-1.40 (1

H, m), 1.45 (9 H, s), 1.50-1.55 (1 H, m), 1.65-1.75 (1 H, m), 1.80-1.95 (1 H, m), 2.10-2.20 (2 H, 1 m), 2.30-2.35 (1 H, m), 3.70-3.75 (1 H, m), 4.45-4.50 (1 H, m).

(g) A solution of (syn, endo)-7-(tert-butyloxycarbonyl) amino-2-hydroxybicyclo[2.2.1]heptane (0.147 g, 0.647 mmol), acetyl chloride (0.055 mL, 0.78 mmol) and Et$_3$N (0.28 mL, 2 mmol) in dry CH$_2$Cl$_2$ (5 mL) was stirred for 18 h at RT under N$_2$. The mixture was diluted with H$_2$O (20 mL) and extracted with CH$_2$Cl$_2$ (2×25 mL). The extracts were dried (Na$_2$SO$_4$), filtered and concentrated. Flash column chromatography, eluting with 20% EtOAc, gave the partly purified ester as a colourless oil (0.109 g). This material was dissolved in Et$_2$O (1 mL) with 2M HCl in Et$_2$O (4 mL) and heated gently for 5 min. After stirring for 1.5 h at room temperature the solution was concentrated to give a yellow solid (0.058 g). The solid was resuspended in CH$_2$Cl$_2$ (2 mL) and 5-chlorothiophene-2-sulfonyl chloride (0.13 g, 0.6 mmol) and Et$_3$N (0.14 mL, 1.0 mmol) were added. After stirring for 18 h at room temperature, the mixture was diluted with CH$_2$Cl$_2$ (20 mL), washed with 1M citric acid (20 mL), dried (Na$_2$SO$_4$), filtered and concentrated. Flash column chromatography, eluting 20% EtOAc-isohexane, gave (syn, endo)-7-{[(5-chlorothien-2-yl)sulfonyl]amino}bicyclo[2.2.1]hept-2-yl acetate (0.034 g, 24%) as a colourless gum that solidified to a white powder on trituration with Et$_2$O.

$^1$H NMR (CDCl$_3$, 400 MHz) δ 1.17-1.26 (1 H, m), 1.34-1.47 (2 H, m), 1.64-1.82 (2 H, m), 2.05 (3 H, s), 2.23-2.34 (2 H, m), 2.40-2.50 (1 H, m), 3.36-3.39 (1 H, m), 4.88-4.90 (1 H, m), 5.14-5.17 (1 H, m), 6.94 (1 H, d, J 4); 7.41 (1 H, d, J4); m/z 390, 388 (M+Na$^+$), 374, 372 (M+Na+), 352, 350 (M+H$^+$).

Example 127

(syn)-5-Chloro-N-(5,6,7,8,9,10-hexahydro-5,9-methanobenzo[α][8]annulen-11-yl)thiophene-2-sulfonamide

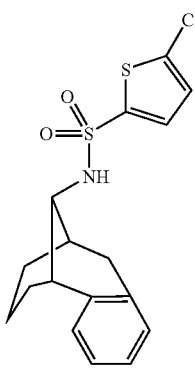

(5,6,7,8,9,10-Hexahydro-5,9-methanobenzo[α][8]annulen-11-one (Muratake and Natsume, *Tetrahedron Lett.*, 1997, 7581) was converted to the oxime and then to the corresponding amine as described in the general procedures. The amine (0.062 g) was dissolved in dry CH$_2$Cl$_2$ (1 mL) and Et$_3$N (0.14 mL, 1 mmol) and and 5-chlorothiophene-2-sulfonyl chloride (0.086 g, 0.4 mmol) were added. The solution was stirred at room temperature under N$_2$ for 26 h, then diluted with CH$_2$Cl$_2$ (10 mL), washed with H$_2$O (10 mL), dried, filtered and concentrated. Preparative thin layer chromatography, eluting with 10% EtOAc-isohexane, gave the title compound as a white solid (0.033 g, 27%). $^1$H NMR (CDCl$_3$, 400 MHz) δ 0.95-1.10 (1 H, m), 1.20-1.30 (1 H, m), 1.60-1.80 (4 H, m), 2.29-2.35 (1 H, m), 2.65 (1 H, d, J 18), 2.85-2.90 (1 H, m), 3.10 (1 H, dd, J 18, 8), 3.65-3.70 (1 H, m), 4.55 (1 H, d, J 8), 6.92 (1 H, d, J 4), 7.10-7.18 (3 H, m), 7.37 (1 H, d, J 4); m/z 392, 390 (M+Na$^+$), 370, 368 (M+H$^+$).

Example 128 endo-5-Chloro-thiophene-2-sulfonic acid (5-amino-tricyclo[8.2.1.0$^{3,8}$]trideca-3(8),4,6-trien-13-yl)-amide

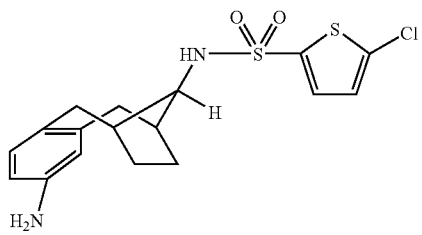

(a) N-(5-Nitro-tricyclo[8.2.1.0$^{3,8}$]trideca-3(8),4,6-trien-13-one oxime

5-Nitro-tricyclo[8.2.1.0$^{3,8}$]trideca-3(8),4,6-trien-13-one (*J. Org. Chem.* 1982, 47, 4329-4334) was converted to the oxime as described in the General Procedures.

m/z 247 (M+H)$^+$.

(b) endo-N-(5-Nitro-tricyclo[8.2.1.0$^{3,8}$]trideca-3(8),4,6-trien-13-yl)-hydroxylamine The oxime was reduced to the hydroxylamine using sodium cyanoborohydride by the procedure of Example 108 step 1 m/z 249 (M+H$^+$).

(c) endo-Tricyclo[8.2.1.0$^{3,8}$]trideca-3(8),4,6-triene-5 13-diamine

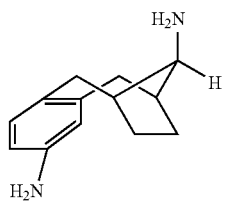

Activated zinc dust (excess) was added to a rapidly stirring solution of N-(5-nitro-tricyclo[8.2.1.0$^{3,8}$]trideca-3 (8),4,6-trien-13-yl)-hydroxylamine (2.0 g) in 1:1 tetrahydrofuran:2N aqueous HCl (100 mL). After two hours the reaction mixture was filtered and reduced to half volume under reduced pressure. The residue was basified to pH 9 with 4N NaOH and extracted into ether (4×100 mL). The organic extracts were combined, dried over MgSO$_4$, filtered and the solvent removed under reduced pressure to afford the title compound as a clear oil. (1.6 g). m/z 203 (M+H$^+$).

(d) endo-(5-Amino-tricyclo[8.2.1.0³,⁸]trideca-3(8),4,6-trien-13-yl)-carbamic acid tert-butyl ester

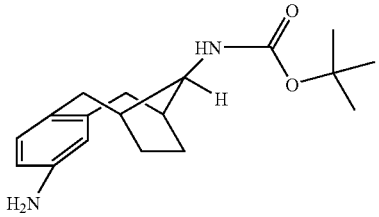

A solution of di-tertbutyldicarbonate (864 mg) in dichloromethane (20 mL) was added over four hours to a stirred solution of tricyclo[8.2.1.0³,⁸]trideca-3(8),4,6-triene-5,13-diamine (800 mg) in dichloromethane (50 mL) at −20° C. After a further two hours the solution was warmed to room temperature and the solvent removed under reduced pressure. The residual oil was purified by chromatography on silica gel (30% EtOAc/isohexane) to afford the product as a white solid (500 mg). ¹H NMR (CDCl₃ 400 MHz) δ 1.20-1.25 (2H, m), 1.46 (9H, s), 1.65-1.69 (2H, m), 2.40-2.46 (4H, m), 2.86-2.90 (2H, m), 4.05 (1H, brs), 5.29 (1H, brs), 6.41-6.44 (2H, m), 6.84 (1H, d, J=5.0 Hz).

(e) endo-(13-tert-Butoxycarbonylamino-tricyclo[8.2.1.0³,⁸]trideca-3(8),4,6-trien-5-yl) carbamic acid allyl ester

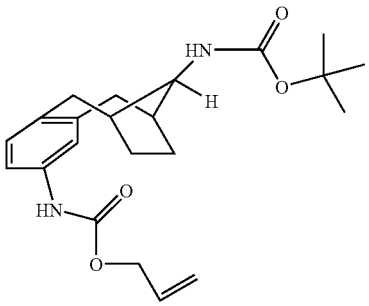

Allyl chloroforimate (75 µL) was added to a stirred solution of (5-amino-tricyclo[8.2.1.0³,⁸]trideca-3(8),4,6-trien-13-yl)-carbamic acid tert-butyl ester (213 mg) in dry dichloromethane (10 mL) containing 4-methylmorpholine (140 mg). After one hour the reaction was dilute with citric acid (10% aq, 20 mL) and the organic layer separated, dried over MgSO₄, filtered and the solvent removed under reduced pressure to afford the title compound as a white solid. (264 mg). ¹H NMR (CDCl₃ 400 MHz) δ 1.17-1.24 (2H, m), 1.46 (9H, s), 1.67-1.70 (2H, m), 2.45-2.59 (4H, m), 2.93-3.00 (2H, m), 4.00 (1H, brs), 4.65 (2H, dd, J=4.0 and 1.0 Hz), 5.25 (1H, dd, J=8.0 and 1.0 Hz), 5.37 (1H, dd, J=16.0 and 1.0 Hz), 5.96 (1H, m), 6.57 (1H, brs), 7.02 (1H, d, J=8.0 Hz), 7.10 (2H, m).

(f) endo-[13-(5-Chloro-thiophene-2-sulfonylamino)-tricyclo[8.2.1.0³,⁸]trideca-3(8) 4,6-trien-5-yl]-carbamic acid allyl ester

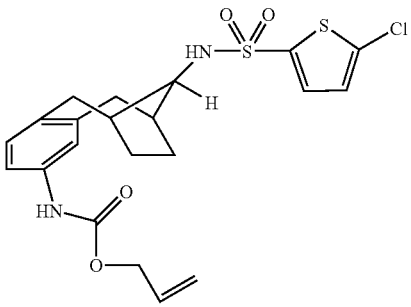

Dry HCl gas was passed through a cooled solution of (13-tert-butoxycarbonylamino-tricyclo[8.2.1.0³,⁸]trideca-3(8),4,6-trien-5-yl) carbamic acid allyl ester (264 mg) in dry ether for ten minutes. At the end of this time a white precipitate had formed which was filtered off to afford the amine hydrochloride. (204 mg) m/z 286 (M+H⁺). The recovered material was re-suspended in dry dichloromethane and treated with 4-methylmorpholine (160 µL) and 5-chlorothiophene-2-sulfonyl chloride (159 mg). After 18 hours a polyamine scavenger resin ( 1.0 g, Novobiochem 4.61 mmol/g) was added and the solution stirred for a further six hours. The reaction was filtered to remove the resin and the resin pad washed sequentially with dichloromethane, methanol, ether 20 mL each). The filtrate and washings were combined and the solvent removed under reduced pressure. The residue was partitioned between dichloromethane and water, the organic layer separated, dried, MgSO₄, filtered and the solvent removed under reduced pressure. Chromatography on silica gel (20% EtOAc/isohexane) afforded the title compound as a white solid. (180 mg). ¹H NMR (CDCl₃ 400 MHz) δ 1.17-1.25 (2H, m), 1.62-1.65 (2H, m), 2.34-2.37 (2H, m), 2.50-2.56 (2H, m), 2.95 (1H, d, J=12 Hz), 3.00 (1H, d, J=12 Hz), 3.74 (1H, dt, J=8.0 and 1.0 Hz), 4.65 (2H, m), 5.24 (1H, d, J=8.0 Hz), 5.27 (1H, d, J=12 Hz), 5.37 (1H, d, J=16 Hz), 5.95 (1H, m), 6.55 (1H, brs), 6.93 (1H, d, J=4.0 Hz), 6.98 (1H, d, J=8.0 Hz), 7.08 (2H, m), 7.44 (1H, d, J=4.0 Hz). m/z 466 (M+H⁺).

(g) endo-5-Chloro-thiophene-2-sulfonic acid (5-amino-tricyclo[8.2.1.0³,⁸]trideca-3(8),4,6-trien-13-yl)-amide

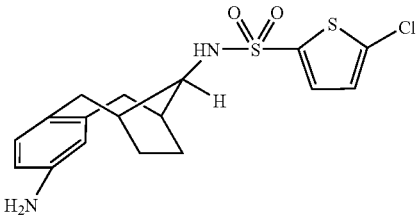

A catalytic amount of Pd(PPh₃)₄ was added to a stirred solution of [13-(5-chloro-thiophene-2-sulfonylamino)-tricyclo[8.2.1.0³,⁸]trideca-3(8),4,6-trien-5-yl]-carbamic acid allyl ester (140 mg) in dichloromethane containing 10% PhSiH₃. The resulting mixture was stirred at room temperature for two hours at which time the solvent was removed under reduced pressure. The residue was purified by chromatography on silica gel (20% EtOAc/isohexane ) to afford the title compound as a white solid. (74 mg).

¹H NMR (CDCl₃ 400 MHz) δ 1.16-1.19 (2H, m), 1.56-1.66 (2H, m), 2.26-2.52 (4H1, m), 2.76 (1H, d, J=12.0 HzO, 2.85 (1H, d, J=12.0 Hz), 3.72 (1H, dt, J=4.0 and 1.0 Hz), 5.29 (1H, d, J=8.0 Hz), 6.42 (2H, m), 6.81 (1H, d, J=8.0 Hz), 6.92 (1H, d, J=4.0 Hz), 7.44 (1H, d, J=4.0 Hz). m/z 382 (M+H⁺).

Example 129 endo-N-[13-(5-Chloro-thiophene-2-sulfonylamino)-tricyclo[8.2.1.0³,⁸]trideca-3(8),4,6-trien-5-yl]-2-pyrrolidin-1-yl-acetamide

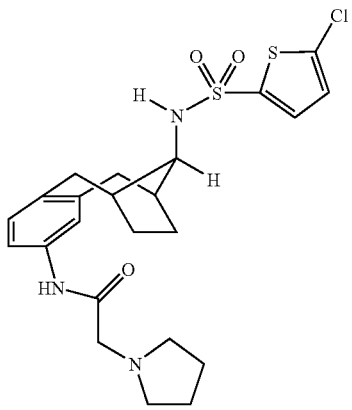

(a) endo-2-Chloro-N-[13-(5-chloro-thiophene-2-sulfonylamino)-tricyclo[8.2.1.0³,⁸]trideca-3(8),4,6-trien-5-yl]-acetamide Chloroacetyl chloride (75 µL) was added to a stirred solution of endo 5-chloro-thiophene-2-sulfonic acid (5-amino-tricyclo[8.2.1.0³,⁸]trideca-3(8),4,6-trien-13-yl)-amide (Example 128) (360 mg) in dichloromethane (15 mL) containing 4-methylmorpholine (131 µL). After 30 minutes at room temperature the reaction mixture was poured into 1N HCl (30 mL), and the organic layer separated off. The aqueous layer was then extracted with dichloromethane (2×15 mL) and the combined organic layers dried over MgSO₄, filtered and the solvent removed under reduced pressure to afford the product as a gum (430 mg) which was used without further purification. ¹H NMR (CDCl₃ 400 MHz) δ 1.13-1.17 (2H, m), 1.61-1.68 (2H, m), 2.36-2.39 (2H, m), 2.51-2.59 (2H, m), 2.99 (1H, d, J=12.0 Hz), 3.04 (1H, d, J=12.0 Hz), 3.72 (1H, dt, J=8.0 and 4.0 Hz), 4.12 (2H, s), 5.23 (1H, s), 6.94 (1H, d, J=4.0 Hz), 7.04 (1H, d, J=8.0 Hz), 7.28 (2H, m), 7.44 (1H, d, J=4.0 Hz), 8.16 (1H, brs).

(b) endo-N-[13-(5-Chloro-thiophene-2-sulfonylamino)-tricyclo[8.2.1.0³,⁸]trideca-3(8),4,6-trien-5-yl]-2-pyrrolidin-1-yl-acetamide A solution of the chloroacetamide from step (a) (257 mg) in dichloromethane (5 mL) was added rapidly to a solution of pyrrolidine (142 mg) in dichloromethane (20 mL). The resulting mixture was stirred at room temperature for 3 hours at which point the solvent was removed under reduced pressure. The residue was partitioned between dichloromethane and NaHCO₃ (aq), the organic layer separated, dried, MgSO₄, filtered and the solvent removed under reduced pressure. Crystallization from methanol afforded the title compound as a white solid. (124 mg). ¹H NMR (CDCl₃ 400 MHz) δ 1.15-1.19 (2H, m), 1.50-1.62 (3H, m), 1.84-1.87 (4H, m), 2.35-2.38 (2H, m), 2.52-2.56 (2H, m), 2.70 (4H, brm), 2.95 (1H, d, J=12.0 Hz), 3.01 (1H, d, J=12.0 Hz), 3.27 (2H, s), 3.74 (1H, dt, J=8.0 and 4.0 Hz), 6.93 (1H, d, J=8.0 Hz), 7.01 (1H, d, J=8.0 Hz), 7.32 (2H, m), 7.44 (1H, d, J=4.0 Hz), 9.05 (1H, s). m/z 494 (M+H⁺)

The following compounds in accordance with formula A below were prepared by the method of Example 129, substituting the appropriate amine for pyrrolidine in step (b). In all cases, purification was by mass directed HPLC.

A

| Example | R | m/z (M + H⁺) |
|---|---|---|
| 130 | F-phenyl-piperazinyl | 604 |
| 131 | F-phenyl-diazabicyclic | 616 |
| 132 | phenyl-piperazinyl | 586 |
| 133 | piperidinyl | 509 |
| 134 | Me-piperazinyl | 524 |
| 135 | morpholinyl | 511 |
| 136 | Et₂N | 497 |
| 137 | 4-phenyl-piperidinyl | 581 |
| 138 | 2-OMe-phenyl-piperidinyl | 615 |

-continued

| Example | R | m/z (M + H⁺) |
|---|---|---|
| 139 | PhO-CH₂-(morpholine-N-Me) | 617 |
| 140 | Ph-N(morpholine)-CH₂-NH-Me | 616 |
| 141 | spiro[isobenzofuran-piperidine]-N-Me | 613 |
| 142 | 3-phenyl-imidazo[1,2-a]pyrazine-CH₂- piperazine-N-Me | 623 |
| 143 | Ph-CH₂-N(Me)- | 545 |
| 144 | 2-OMe-phenyl-piperazine-N-Me | 616 |

Example 145 endo-N-{5-[2-(4-Fluoro-phenoxy)-ethoxy]-tricyclo[8.2.1.0³,⁸]trideca-3(8),4,6-trien-13-yl}-benzenesulfonamide (a) endo-N-(5-Hydroxy-tricyclo[8.2.1.0³,⁸]trideca-3(8),4,6-trien-13-yl)-benzenesulfonamide Endo-N-(5-Amino-tricyclo[8.2.1.0³,⁸]trideca-3(8),4,6-trien-13-yl)-benzenesulfonamide (Example 42) (1.0 g, 2.92 mmol) in 2:1 water: concentrated sulphuric acid (100 mL) was stirred at 0° C. for one hour to give an even dispersion. Sodium nitrite (0.242 g, 3.51 mmol) in the minimum quantity of water was added below the surface of the reaction mixture, and stirred with ice cooling for one hour. The cold reaction mixture was added to water (400 mL) which had been pre-heated to 80° C., then allowed to cool to room temperature and extracted with ethyl acetate. The organic extract was washed with brine and concentrated to give a brown oil. The crude product was purified by flash chromatography on silica gel (isohexane:ethyl acetate) to give a yellow solid. 656 mg. ¹H NMR (CDCl₃, 400 MHz) δ 7.93 (2H, m), 7.59 (1H, m), 7.53 (2H, m), 6.86 (1H, d, J=7.8 Hz), 6.54 (2H, m), 5.08 (1H, d, J=7.9 Hz), 3.65 (1H, m), 2.83-2.92 (2H, m), 2.32-2.42 (2H, m), 2.18-2.24 (2H, m), 1.56 (2H, m), 1.12 (2H, m). m/z 344 (M+H⁺).

(b) endo-N-{5-[2-(4-Fluoro-phenoxy)-ethoxy]-tricyclo[8.2.1.0³,⁸]trideca-3(8),4,6-trien-13-yl}-benzenesulfonamide The phenol from step (a) (200 mg, 0.583 mmol), 4-fluorophenoxyethyl bromide (134 mg, 0.612 mmol) and potassium carbonate (800 mg) in DMF (10 mL) were stirred and heated at 45° C. for 64 hours, then allowed to cool to room temperature and diluted with ethyl acetate and 1M hydrochloric acid. The organic phase was washed with water, brine and concentrated to give an orange oil. The crude product was purified twice by flash chromatography on silica gel (isohexane:ethyl acetate). The chromatographed material was further purified by mass-directed preparative HPLC to give a white solid 65 mg. ¹H NMR (CDCl₃, 400 MHz) δ 7.93 (2H, m), 7.60 (1H, m), 7.53 (2H, m), 6.96 (3H, m), 6.88 (2H, m), 6.64 (2H, m), 4.95 (1H, d, J=7.9 Hz), 3.68 (1H, m), 2.89-2.99 (2H, m), 2.38-2.47 (2H, m), 2.22-2.27 (2H, m), 1.13 (2H, m). m/z 482 (M+H⁺).

The following compounds, in accordance with formula B below, were prepared by the method of Example 145, substituting the appropriate bromoalkyl derivative for 4-fluorophenoxyethyl bromide in step (b). In each case, purification was by mass directed HPLC.

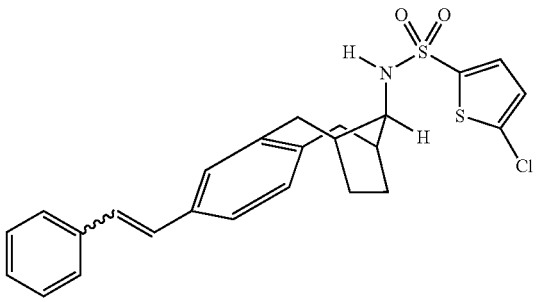

| Example | R | m/z (M + H⁺) |
|---|---|---|
| 146 | 4-Cl-benzyl | 468/470 |
| 147 | phenoxyethyl | 464 |
| 148 | 4-Cl-phenoxypropyl | 498/500 |
| 149 | 3-pyridyl-methyl | 435 |
| 150 | 4-pyridyl-methyl | 435 |

Example 151 endo-5-Chloro-thiophene-2-sulfonic acid (5-hydroxymethyl-tricyclo[8.2.1.0³,⁸]trideca-3(8),4,6-trien-13-yl)-amide

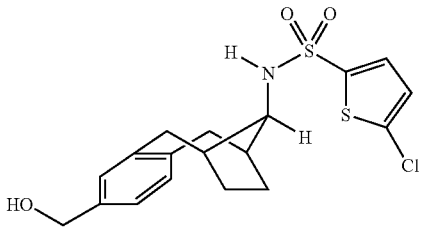

(a) endo-13-(5-Chloro-thiophene-2-sulfonylamino)-tricyclo[8.2.1.0³,⁸]trideca-3(8),4,6-triene-5-carboxylic acid methyl ester This intermediate was prepared as in Example 1 using methyl 3,4-bis(bromomethyl)benzoate as the starting material for the precursor amine, and reacting said amine with 5-chlorothiophene-2-sulfonyl chloride.

¹H NMR (CDCl₃, 400 MHz) δ 7.74 (2H, m), 7.45 (1H, d, J=4.0 Hz), 7.13 (1H, d, J=8.3 Hz), 6.94 (1H, d, J=4.0 Hz), 5.16 (1E, d, J=7.2 Hz), 3.89 (3H, s), 3.72 (1H, m), 3.04-3.11 (2H, m), 2.63-2.70 (2H, m) 2.41-2.44 (2H, m) 1.64-1.69 (2H, m) 1.12-1.15 (2H, m). m/z 426/428 (M+H⁺).

Step (b) 1M DIBAL-H in toluene (28.8 mL, 28.8 mmol) was added to a stirred solution the intermediate ester (3.07 g, 7.21 mmol) in toluene (60 mL) at such a rate to maintain the reaction temperature below −70° C., and stirred at this temperature for 2 hours. The reaction mixture was quenched with methanol at −78° C. and allowed to warm to room temperature. The mixture was diluted with ethyl acetate and washed with 1M hydrochloric acid, saturated sodium bicarbonate solution, brine and the organic phase was concentrated to give a white solid. 2.79 g. ¹H NMR (CDCl₃, 400 MHz) δ 7.44 (1H, d, J=4.1 Hz), 7.06 (3H, m), 6.94 (1H, d, J=3.9 Hz), 5.19 (1H, d, J=7.6 Hz), 4.62 (2H, s), 3.74 (1H, m) 2.99-3.04 (2H, m), 2.54-2.61 (2H, m), 2.39 (2H, m), 1.62-1.68 (2H, m), 1.16 (2H, m).

Example 152 endo-5-Chloro-thiophene-2-sulfonic acid (5-styryl-tricyclo[8.2.1.0³,⁸]trideca-3(8),4,6-trien-13-yl)-amide (a) endo-5-Chloro-thiophene-2-sulfonic acid (5-formyl-tricyclo[8.2.1.0³,⁸]trideca-3(8),4,6-trien-13-yl)-amide Pyridinium dichromate (1.77 g, 4.7 mmol) was added to a stirred solution of endo-5-chloro-thiophene-2-sulfonic acid (5-hydroxymethyl-tricyclo[8.2.1.0³,⁸]trideca-3(8),4,6-trien-13-yl)-amide (Example 151) (1.25 g, 3.1 mmol) in DCM (50 mL). The mixture was stirred at room temperature for two hours and then filtered through silica washing thoroughly with ethyl acetate. The solution was concentrated to give an orange oil. The crude product was purified by flash chromatography on silica gel (isohexane:ethyl acetate) to give a colourless oil 1.10 g. ¹H NMR (CDCl₃, 400 MHz) δ 9.93 (1H, s), 7.59 (2H, m), 7.45 (1H, d, J=4.0 Hz), 7.23 (1H, d, J=7.5 Hz), 6.94 (1H, d, J=4.1 Hz), 5.41 (1H, d, J=6.8 Hz), 3.71 (1H, m), 3.11-3.17 (2H, m), 2.65-2.72 (2H, m), 2.44-2.47 (2H, m), 1.64-1.70 (2H, m), 1.12-1.15 (2H, m).

Step (b)

1M Potassium t-butoxide in THF (0.379, 0.379 mmol) was added dropwise to a stirred suspension of benzyltriphenylphosphonium chloride (147 mg, 0.379 mmol) in THF (0.5 mL). Stirred at room temperature for 30 minutes. The ylide mixture was then added to a stirred solution of the formyl intermediate from step (a) (50 mg, 0.126 mmol) in THF (0.5 mL) and stirred at room temperature for one hour. The reaction mixture was quenched with 2M hydrochloric acid and extracted with ethyl acetate. The organic phase was concentrated to dryness, and the crude product purified by mass-directed preparative HPLC. ¹H NMR (CDCl₃, 400 MHz) [1:1 mixture of cis and trans isomers] δ 7.50 (1H, d, J=7.2 Hz), 7.44 (1H, m), 7.35 (1H, t, J=7.8 Hz), 7.18-7.28 (4H,m), 7.06 (2H, m), 6.94 ( 2H, m), 6.54 (1H, m), 5.09 (1H, d, J=7.7 Hz), 3.76 (1H, m), 2.90-3.07 (2H, m), 2.51-2.65 (2H, m), 2.31-2.42 (2H, m), 1.63-1.68 (2H, m), 1.15-1.26 (2H, m) for cis isomer. m/z 470/472 (M+H⁺).

The following compounds, in accordance with formula C below, were prepared by the method of Example 152, using the appropriate alkyltriphenylphosphonium bromide in step (b):

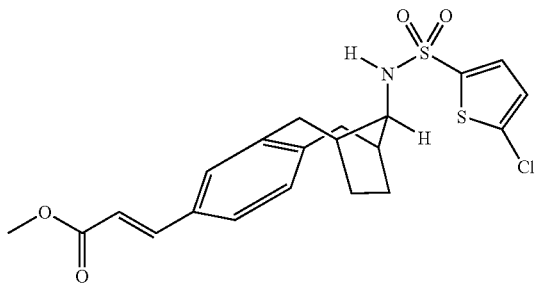

| Example | R | m/z (M + H+) |
|---|---|---|
| 153* | 4-MeO-C6H4-CH=CH- | 500/502 |
| 154* | 4-F-C6H4-CH=CH- | 488/490 |
| 155* | 4-Br-C6H4-CH=CH- | 548/550/562 |
| 156* | Ph-CH2-CH2-CH=CH- | 498/500 |
| 157 | CH2=CH- | 394/396 |

*mixture of cis and trans isomers

Example 158 endo-3-[13-(5-Chloro-thiophene-2-sulfonylamino)-tricyclo[8.2.1.0$^{3,8}$]trideca-3(8),4,6-trien-5-yl]-acrylic acid methyl ester

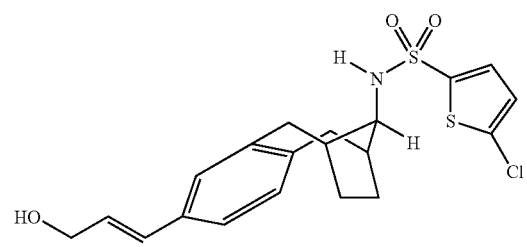

A solution of endo-5-chloro-thiophene-2-sulfonic acid (5-formyl-tricyclo[8.2.1.0$^{3,8}$]trideca-3(8),4,6-trien-13-yl)-amide [Example 152 step (a)] (2.33 g, 5.88 mmol) in DCM (20 mL) was added to a stirred solution of methyl (triphenylphosphoranylidine)acetate (5.90 g, 17.65 mmol) in DCM (40 mL), then stirred at room temperature for 18 hours. Reaction mixture was quenched with 2M hydrochloric acid and the organic phase concentrated to dryness. The crude product was purified by flash chromatography on silica gel eluting with 3:1 isohexane:ethyl acetate to give a white solid 2.1 g. $^1$H NMR (CDCl$_3$, 400 MHz) a 10:1 mixture of trans and cis isomers δ 7.62 (1H, d, J=16.0 Hz), 7.45 (1H, d, J=4.0 Hz), 7.24 (2H, m), 7.08 (1H, d, J=7.7 Hz), 6.94 (1H, d, J=3.9 Hz), 6.38 (1H, d, J=16.0 Hz), 5.18 (1H, d, J=6.2 Hz), 3.73 (1H, m), 3.05 (2H, d, J=16.2 Hz), 2.57-2.64 (2H, m), 2.40 (2H, m), 1.67 (2H, m), 1.17 (2H,m) for trans isomer.
m/z 452/454 (M+H$^+$).

Following the procedure of Example 158, and using the appropriate ylide, there were also prepared:

Example 159 endo-5-Chloro-thiophene-2-sulfonic acid [5-(3-oxo-3-phenyl-propenyl)-tricyclo[8.2.1.0$^{3,8}$]trideca-3(8),4,6-trien-13-yl]-amide m/z 498/500 (M+H$^+$); and

Example 160 endo-5-Chloro-thiophene-2-sulfonic acid [5-(2-cyano-vinyl)-tricyclo[8.2.1.0$^{3,8}$]trideca-3(8),4,6-trien-13-yl]-amide m/z 419/421 (M+H$^+$).

Example 161 endo-5-Chloro-thiophene-2-sulfonicacid [5-(3-hydroxypropenyl)tricyclo[8.2.1.0$^{3,8}$]trideca-3(8),4,6-trien-13-yl]-amide

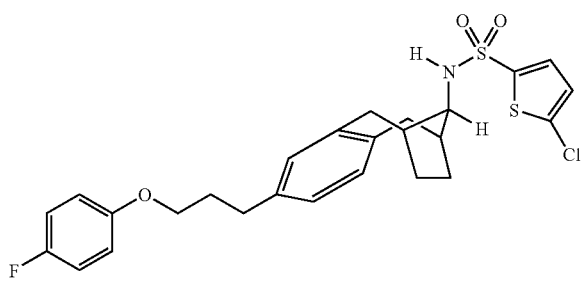

1M DIBAL-H in toluene (18.6 mL, 18.6 mmol) was added to a stirred solution of endo-3-[13-(5-Chloro-thiophene-2-sulfonylamino)-tricyclo[8.2.1.0$^{3,8}$]trideca-3(8),4,6-trien-5-yl]-acrylic acid methyl ester (Example 158) (2.10 g, 4.65 mmol) in toluene (80 mL) at such a rate to maintain the reaction temperature below −70° C. After stirring at this temperature for 2 hours, the reaction mixture was quenched with methanol at −78° C. and allowed to warm to room temperature. The mixture was diluted with ethyl acetate and washed with 1M hydrochloric acid, saturated sodium bicarbonate solution, brine and the organic phase was concentrated to give a white solid. 1.90 g. $^1$H NMR (CDCl$_3$, 400 MHz) 10:1 mixture of trans and cis isomers δ 7.44 (1H, d, J=3.9 Hz), 7.11 (2H, m), 7.01 (1H, d, J=7.8 Hz), 6.93 (1H, d, J=4.0 Hz), 6.54 (1H, d, J=15.9 Hz), 6.29-6.36 (1H, m), 5.11 (1H, d, J=7.6 Hz), 4.30 (1H, d, J=5.3 Hz), 3.75 (1H, m), 3.01 (2H, m), 2.54-2.61 (2H, m) 2.38 (2H, m), 1.64 (2H, m), 1.16 (2H, m) for trans isomer.

Example 162 endo-5-Chloro-thiophene-2-sulfonic acid {5-[3-(4-fluoro-phenoxy)-propyl]-tricyclo[8.2.1.0$^{3,8}$]trideca-3(8),4,6-trien-13-yl}-amide (a) endo-5-Chloro-thiophene-2-sulfonic acid [5-(3-hydroxypropenyl)-tricyclo[8.2.1.0$^{3,8}$]trideca-3(8),4,6-trien-13-yl]-amide (Example 161) (50 mg, 0.118 mmol) and platinum dioxide (5 mg) in glacial acetic acid (5 mL) were stirred at room temperature under a balloon of hydrogen for three hours. The mixture was filtered through Celite® and concentrated to dryness. The crude product was purified by flash chromatography on silica gel (isohexane:ethyl acetate) to give a colourless oil 18 mg. $^1$H NMR (CDCl$_3$, 400 MHz) δ 7.44 (1H, d, J=4.0 Hz), 6.89-6.99 (4H,m), 5.13 (1H, d, J=7.8 Hz), 3.75 (1H, m), 3.66 (2H, t, J=6.5 Hz), 2.98-3.02 (2H, m), 2.62 (2H, t, J=7.4 Hz), 2.51-2.59 (2H, m), 2.37 (2H, m), 1.82-1.89 (2H, m), 1.63 (2H, m), 1.17 (2H, m).

(b) Methanesulphonyl chloride (5.6 mg, 0.049 mmol) in DCM (0.1 mL) was added dropwise to an ice-cooled solution of the 3-hydroxypropyl derivative from step (a) (19 mg, 0.045 mmol) and triethylamine (6.8 mg, 0.067 mmol) in DCM (0.9 mL). After stirring at 0° C. for 90 minutes, more triethylamine (3.4 mg) and methanesulphonyl chloride (2.8 mg) were added and stirred for a further hour at 0° C. After dilution with DCM and washing with 0.1M hydrochloric acid and water (×2), the organic phase was concentrated to give the crude mesylate as a colourless oil (17 mg) which was used immediately in the next step. The mesylate (17 mg, 0.0334 mmol), 4-fluorophenol (3.8 mg, 0.0334 mmol, tris (3,6-dioxaheptyl)amine (109 mg, 0.337 mmol) and potassium carbonate (7.0 mg, 0.051 mmol) in toluene (1 mL) were stirred and heated at 100° C. for 18 hours, cooled to room temperature and diluted with ethyl acetate. Washed with 1M hydrochloric acid, 5% sodium bicarbonate solution and brine. The organic phase was concentrated to dryness. The crude product was purified by flash chromatography on silica gel (isohexane:ethyl acetate) to give a colourless oil. This was further purified by mass-directed preparative HPLC to give the title compound (4.3 mg). $^1$H NMR (CDCl$_3$, 400 MHz) δ 7.44 (1H, d, J=4.0 Hz), 6.90-6.99 (6H, m), 6.81 (2H, m), 5.05 (1H, d, J=7.8 Hz), 3.90 (2H, t, J=6.3 Hz), 3.76 (1H, m),2.95-3.01 (2H, m), 2.72 (2H, t, J=7.7 Hz), 2.49-2.59 (2H, m), 2.36 (2H, m), 2.05 (2H, m), 1.63 (2H, m), 1.16 (2H, m). m/z 520/522 (M+H$^+$).

Example 163 endo-N-(5-Hydroxymethyl-tricyclo[8.2.1.0$^{3,8}$] trideca-3,5,7-trien-13-yl)benzenesulfonamide

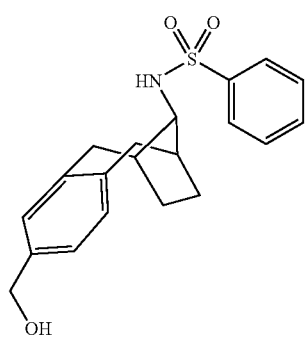

Lithium Aluminium Hydride (300 µl of 1.0M in THF) was added dropwise to a solution of endo-13-(benzenesulfonylamino)-tricyclo[8.2.1.0$^{3,8}$]trideca-3(8),4,6-triene-5-carboxylic acid methyl ester* (116 mg, 0.3 mmol) in dry THF (5 mL) stirring under a nitrogen atmosphere at 0° C. with stirring. The reaction was allowed to warm to room temperature and stirring continued for 1 hour. Water (2.0 mL) and 1.0M sodium hydroxide solution (2.0 mL) were added to the reaction mixture and stirred for 30 minutes. Reaction mixture was extracted into dichloromethane, dried with anhydrous magnesium sulphate, filtered and the solvent removed by evaporation to yield a colourless oil. Purified by mass-directed preparative HPLC. $^1$H NMR (CDCl$_3$, 400 MHz) δ 1.08-1.13 (2H, m), 1.55-1.58 (2H, m), 2.27 (2H, m), 2.46-2.53 (2H, m), 2.95-3.00 (2H, dd, J=16 Hz and 4 Hz), 3.66-3.71 (1H, q), 4.61 (2H,s), 5.01 (1H, d, J=8 Hz), 7.01-7.06 (3H, m), 7.51-7.55 (2H, m), 7.58-7.62 (1H, m), 7.92-7.95 (2H, m). m/z 380 (M+Na$^+$).

* prepared as in Example 151 step (a), using benzenesulfonyl chloride.

Example 164 endo-N-(5-Bromomethyl-tricyclo[8.2.1.0$^{3,8}$]trideca-3,5,7-trien-13-yl)benzenesulfonamide

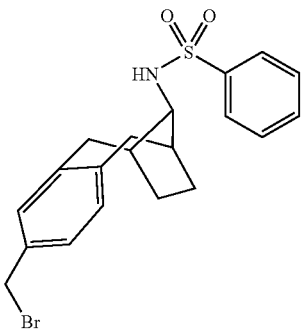

endo-N-(5-Hydroxymethyl-tricyclo[8.2.1.0$^{3,8}$]trideca-3,5,7-trien-13-yl)-benzenesulfonamide (Example 163) (107 mg, 0.3 mmol) and carbon tetrabromide (1.05 eq. 104 mg) were combined in dry diethyl ether (10 mL) and cooled to 0° C. under nitrogen. To this was added triphenyl phosphine (1.05 eq. 83 mg) and the reaction was continued at 0° C. for 1 hour. Reaction was then allowed to warm to room temperature, after 4 hours a further 1 equivalent of carbon tetrabromide and triphenyl phosphine was added and the reaction progressed for 5 hours. Solvent was removed by evaporation and the crude product purified by flash chromatography (10→20% EtOAc in isohexane), and then further purified by mass-directed preparative HPLC. $^1$H NMR (CDCl$_3$, 400 MHz) δ 1.08-1.13 (2H, m), 1.56-1.61 (2H, m), 2.25-2.30 (2H, m), 2.44-2.53 (2H, m), 2.94-2.99 (2H, dd, J=16 Hz and 4 Hz), 3.66-3.71 (1H, q), 4.42 (2H, s), 4.93 (1H, d, J=8 Hz), 6.99-7.09 (3H, m), 7.51-7.62 (3H, m), 7.92-7.95 (2H, m). m/z 421 (M+H$^+$).

Example 165 endo-N-[5-(4-Chloro-phenoxymethyl)-tricyclo[8.2.1.0$^{3,8}$]trideca-3,5,7-trien-13-yl]benzenesulfonamide

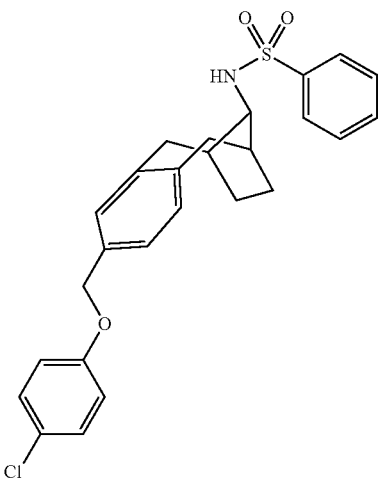

4-Chlorophenol (12.2 mg, 0.095 mmol), sodium hydride 60% w/w in mineral oil (3.8 mg, 0.095 mmol) and dry DMF (1.5 mL) were combined in a test tube and stirred at room temperature for 30 minutes. To this was added endo-N-(5- bromomethyl-tricyclo[8.2.1.0³,⁸]trideca-3,5,7-trien-13-yl)-benzenesulfonamide (Example 164) (20 mg, 0.0475 mmol) and the reaction continued at room temperature for 2 hours. Reaction mixture was then heated to 60° C. for 4 hours. Solvent was removed by evaporation and the crude product was purified by mass-directed preparative HPLC. m/z 468 (M+H⁺).

The following compounds in accordance with formula D below were prepared by the method of Example 165, substituting the appropriate phenol for 4-chlorophenol:

D

| Example | R | m/z (M + H⁺) |
|---|---|---|
| 166 | phenyl | 434 |
| 167 | 3-F-phenyl | 452 |
| 168 | 4-F-phenyl | 452 |
| 169 | 4-MeO-phenyl | 464 |
| 170 | 4-F₃C-phenyl | 502 |
| 171 | 4-tBu-phenyl | 490 |
| 172 | 4-(1,2,4-triazol-1-yl)-phenyl | 501 |
| 173 | quinolin-5-yl | 485 |

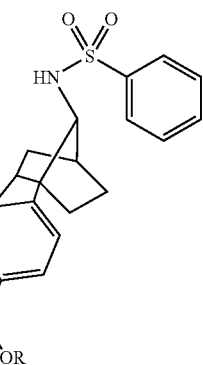

-continued

D

| Example | R | m/z (M + H⁺) |
|---|---|---|
| 174 | 4-F₃CO-phenyl | 518 |
| 175 | 4-(4-acetylpiperazin-1-yl)-phenyl | 560 |

Example 176 endo-5-Chloro-thiophene-2-sulfonic acid (5-cyano-tricyclo[8.2.1.0³,⁸]trideca-3,5,7-trien-13-yl)amide

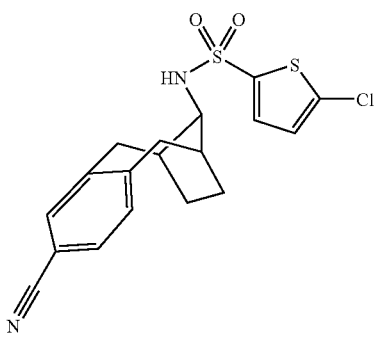

The compound of Example 152 step (a) (100 mg, 0.253 mmol), hydroxylamine hydrochloride (23 mg, 0.328 mmol) and formic acid (5 mL) were combined and heated to reflux under nitrogen for 2 hours. Reaction mixture was allowed to cool to room temperature and then poured onto iced water (20 mL), neutralized with aqueous sodium hydroxide with the temperature maintained at 0° C. The solution was then extracted with diethyl ether, and the combined organic solution dried over anhydrous magnesium sulphate. Filtered and evaporated to yield a white solid. Purified by mass-directed preparative HPLC. ¹H NMR (CDCl₃, 400 MHz) δ 1.07-1.15 (2H, m), 1.65-1.72 (2H, m), 2.41-2.48 (2H, m), 2.57-2.67 (2H, m), 3.07-3.15 (2H, t, J=16 Hz), 3.66-3.71 (1H, q, J=6 Hz), 5.28-5.30 (1H, d, J=6 Hz), 6.95 (1H, d, J=4 Hz), 7.17 (1H, m), 7.35-7.38 (2H, m), 7.45 (1H, d, J=4 Hz). m/z 393 (M+H⁺).

Example 177 endo-5-Chloro-thiophene-2-sulfonic acid [5-(5-pyridin-2-yl-[1,2,4]oxadiazol-3-yl)-tricyclo[8.2.1.0$^{3,8}$]trideca-3,5,7-trien-13-yl]amide

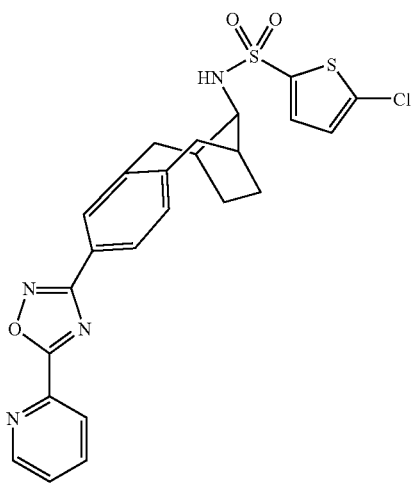

(a) endo-13-(5-Chloro-thiophene-2-sulfonylamino)-N-hydroxy-tricyclo[8.2.1.0$^{3,8}$]trideca-3,5,7-triene-5-carboxamidine

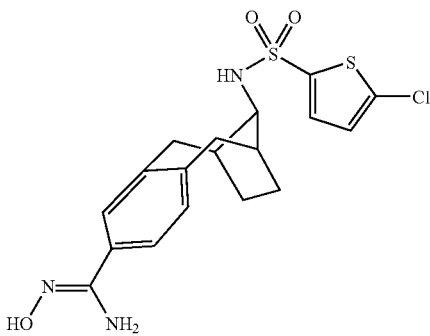

endo-5-Chloro-thiophene-2-sulfonic acid (5-cyano-tricyclo[8.2.1.0$^{3,8}$]trideca-3,5,7-trien-13-yl)-amide (Example 176) (50 mg, 0.127 mmol), triethylamine (32 µl, 0.229 mmol), hydroxylamine hydrochloride (13 mg, 0.19 mmol) and ethanol (5 mL) were combined and heated to reflux under nitrogen overnight. The solvent was removed by evaporation and the residue was partitioned between 1M HCl solution and ethyl acetate. The organic layer was separated, dried over anhydrous magnesium sulphate, filtered and evaporated to give a pale gum which was used without further purification. m/z 426 (M+H$^+$).

(b) The product of step (a) (15 mg, 0.0352 mmol), sodium hydride 60% w/w (1.5 mg) and THF (1.5 mL) were combined in a test tube and stirred at room temperature for 1 hour. To this was added ethyl picolinate (5.3 mg, 0.0352 mmol) and the reaction was heated to 65° C. for 3 hours and then allowed to cool to room temperature. Water (2 mL) and 1M HCl solution (2 mL) were added to the reaction and the whole mixture was extracted with 3×3 mL of ethyl acetate. The combined organic layers were dried over anhydrous magnesium sulphate, filtered and evaporated to give a yellow gum. Purified by mass-directed preparative HPLC. $^1$H NMR (CDCl$_3$, 400 MHz) δ 1.16-1.25 (2H, m), 1.66-1.73 (2H, m), 2.45 (2H, m), 2.64-2.76 (2H, m), 3.08-3.15 (2H, m), 3.73-3.78 (1H, q, J=6 Hz), 5.27 (1H, d, J=6 Hz), 6.95 (1H, d, J=4 Hz), 7.22 (2H, d, J=8Hz), 7.46 (1H, d, J=4 Hz), 7.54 (1H, m), 7.92-7.96 (3H, m), 8.29-8.31 (1H, m). m/z 513 (M+H$^+$).

Example 178 endo-5-Chloro-thiophene-2-sulfonic acid [5-(5-phenyl-[1,2,4]oxadiazol-3-yl)-tricyclo[8.2.1.0$^{3,8}$]trideca-3,5,7-trien-13-yl]amide

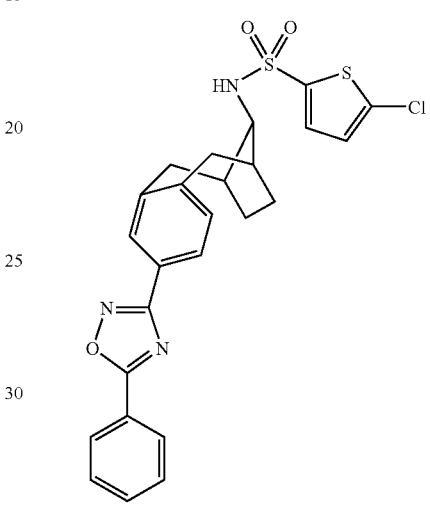

Prepared by the method of Example 177, substituting benzoic anhydride for ethyl picolinate. Pale gum, m/z 512 (M+H$^+$).

Example 179

[11-endo]-N-(5,6,7,8,9,10-hexahydro-6,9-methanobenzo[a][8]annulen-11-yl)ethenesulfonamide

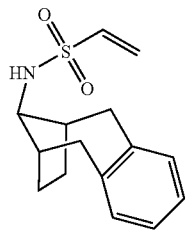

To a solution of the amine* (700 mg) in dry DCM (8 ml) under nitrogen was added triethylamine (1.2 ml) and slowly, 2-chloroethanesulfonyl chloride (0.4 ml). The reaction was stirred at room temperature for 18 h. The reaction was then diluted with DCM, washed with water, brine, dried over MgSO$_4$, filtered and evaporated in vacuo. The crude product was purified by flash chromatography (silica, 5% methanol in DCM) to give a white solid (400 mg, 40%).

(360 MHz, $^1$H, CDCl$_3$) 1.21 (2H, m), 1.77 (2H, m), 2.48 (2H, m), 2.64 (2H, m), 3.07 (2H,d, J=14), 3.75 (1H, m), 4.74 (1H, br), 5.96 (1H, d, J=3.5), 6.32 (1H, d, J=15), 6.61 (1H, m), 7.01 (4H, s)

* [11-endo]-5,6,7,8,9,10-hexahydro-6,9-methanobenzo[a][8]annulen-11-amine, also known as endo-tricyclo[8.2.1.0$^{3,8}$]trideca-3(8),4,6-trien-13-ylamine (General Procedures).

Example 180

[11-endo]-2-ethoxy-N-(5,6,7,8,9,10-hexahydro-6,9-methanobenzo[a][8]annulen-11-yl)ethanesulfonamide

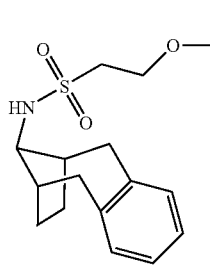

To [11-endo]-N-(5,6,7,8,9,10-hexahydro-6,9-methanobenzo[a][8]annulen-11-yl)ethenesulfonamide (Example 179) (100 mg) in ethanol (2 ml) was added finely ground potassium hydroxide (6 mg). The reaction was stirred at room temperature for 36 h. Solvent removed in vacuo and the residue partitioned between water and EtOAc. Organic phase was washed with brine, dried over MgSO$_4$, filtered and evaporated in vacuo. Purified by flash column chromatography (silica, 25% EtOAc in iso-hexane) to give a colourless oil (37 mg, 32%).

(360 MHz, $^1$H, CDCl$_3$) 1.20 (4H, m), 1.69 (3H, m), 2.48-2.63 (4H, m), 3.16 (2H, d, J=16.0), 3.33 (2H, t, J-6.0), 3.54 (2H, m), 3.85 (3H, m), 4.97 (1H, d, J=6.0), 7.08 (4H, s)

Example 181

[11-endo]-2-ethylsulfide-N-(5,6,7,8,9,10-hexahydro-6,9-methanobenzo[a][8]annulen-11-yl)ethanesulfonamide

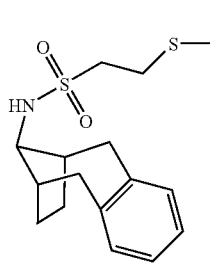

To [11-endo]-N-(5,6,7,8,9,10-hexahydro-6,9-methanobenzo[a][8]annulen-11-yl)ethenesulfonamide (Example 179) (80 mg) in ethanethiol (1 ml) was added finely ground potassium hydroxide (6 mg). The reaction stirred at room temperature for 18 h. Reaction was diluted with water and the products extracted with EtOAc (×3). Organic phase was washed with brine, dried over MgSO$_4$, filtered and evaporated in vacuo. Purified by flash column chromatography (silica, 25% EtOAc in iso-hexane) to give a colourless glassy solid (65 mg, 70%).

(360 MHz, $^1$H, CDCl$_3$) 1.20 (5H, m), 1.69 (2H, m), 2.44-2.69 (6H, m), 2.96 (2H, m), 3.10 (2H, d, J=16.1), 3.32 (2H, m), 3.85 (1H, m), 4.87 (1H, d), 7.08 (4H, s)

Example 182

[11-endo]-3-chloro-N-(5,6,7,8,9,10-hexahydro-6,9-methanobenzo[a][8]annulen-11-yl)propanesulfonamide

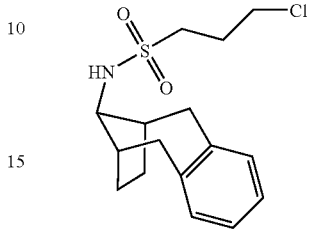

To a solution of the [11-endo]-5,6,7,8,9,10-hexahydro-6,9-methanobenzo[a][8]annulen-11-amine (2.5 g) in dry DCM (20 ml) at 0° C. and under nitrogen were added triethylamine (2 ml) and 3-chloropropanesulfonyl chloride (1.6 ml) over 10 min. The reaction was allowed to warm to room temperature and stirred for 18 h., then washed with water (×2), brine, dried over MgSO$_4$, filtered and evaporated. Crude product was purified by flash column chromatography (silica, DCM) to give a white solid (1.6 g, 45%).

(360 MHz, $^1$H, CDCl$_3$) 1.21 (2H, quin), 1.71 (2H, m), 2.33 (2H, m), 2.50 (2H, m), 2.68 (2H, m), 3.05 (2H, d, J=15.9), 3.27 (2H, t, J=7.7), 3.71 (2H, t, J=7.7), 3.89 (1H, m), 4.72 (1H, br), 7.01 (4H, s) MS(ES+) [MH]+328, [M—Cl(CH$_2$)$_3$SONH]+171

Example 183

[11-endo]-2,2,2-trifluoro-N-(5,6,7,8,9,10-hexahydro-6,9-methanobenzo[a][8]annulen-11-yl)ethanesulfonamide

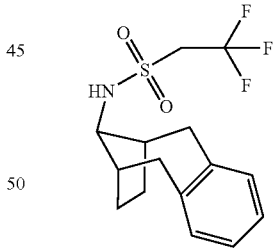

To a solution of the [11-endo]-5,6,7,8,9,10-hexahydro-6,9-methanobenzo[a][8]annulen-11-amine (100 mg) in dry DCM (2 ml) under nitrogen were added 4-methylmorpholine (0.1 ml) and 2,2,2-trifluoroethanesulfonyl chloride (100 mg), and the reaction stirred at room temperature for 18 h., diluted with DCM, washed with water and brine, dried over MgSO$_4$, filtered and evaporated. The crude product was purified by flash column chromatography (silica, DCM) to give a white solid (98 mg, 57%)

(360 MHz, $^1$H, CDCl$_3$) 1.25 (2H, m), 1.73 (2H, m), 2.50 (2H, m), 2.73 (2H, m), 3.01 (2H, d, J=15.1), 3.90 (3H, m), 5.06 (1H, br), 7.11 (4H, s) MS(ES+) [M-SO$_2$CF$_3$]+188, [M-NHSO$_2$CF$_3$]+171

Example 184

[11-endo]-N-(5,6,7,8,9,10-hexahydro-6,9-methanobenzo[a][8]annulen-11-yl)cyclopentanesulfonamide

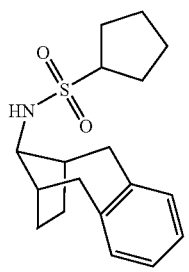

To a solution of the [11-endo]-5,6,7,8,9,10-hexahydro-6,9-methanobenzo[a][8]annulen-11-amine (100 mg) in dry DCM (2 ml) under nitrogen were added 4-methylmorpholine (0.1 ml) and cyclopentylsulfonyl chloride (89 mg) (prepared from cyclopentanethiol via a literature procedure; *Chemistry Letters*, 1992, 1483). The reaction was stirred at room temperature for 18 h., diluted with DCM, washed with water and brine, dried over MgSO$_4$, filtered and evaporated. The crude product was purified by flash column chromatography (silica, DCM) to give a white solid (80 mg, 52%).

(360 MHz, $^1$H, CDCl$_3$) 1.21 (2H, m), 1.62 (2H, m), 1.84 (4H, m), 2.07 (4H, m), 2.47 (2H, m), 2.65 (2H, dd, J=7.9, 7.8), 3.06 (2H, d, J=15.5), 3.53 (1H, m), 3.91 (1H, m), 4.55 (1H, br), 7.09 (4H, s)

Example 185

[11-endo]-N-(5,6,7,8,9,10-hexahydro-6,9-methanobenzo[a][8]annulen-11-yl)-furan-2-sulfonamide

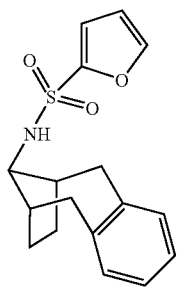

To a solution of the [11-endo]-5,6,7,8,9,10-hexahydro-6,9-methanobenzo[a][8]annulen-11-amine (100 mg) in dry DCM (2 ml) under nitrogen were added 4-methylmorpholine (0.1 ml) and furan-2-sulfonyl chloride (90 mg) (prepared from furan via a literature procedure; *Synthesis*, 1986, 852). After stirring at room temperature for 18 h., the reaction was diluted with DCM, washed with water and brine, dried over MgSO$_4$, filtered and evaporated. The crude product was purified by flash column chromatography (silica, DCM) to give a white solid (120 mg, 58%).

(360 MHz, 1H, CDCl$_3$) 1.16 (2H, m), 1.63 (2H, m), 2.31 (2H, m), 2.57 (2H, dd, J=7.8, 7.8). 3.01 (2H, d, J=15.3), 3.78 (1H, q), 5.12 (1H, d, J=8.1), 6.53 (1H, m), 7.06 (5H, m), 7.59 (1H, m). MS(EI+): [MH]+318, [M-furanSO$_2$NH]+171

Example 186

[11-endo]-N-(5,6,7,8,9,10-hexahydro-6,9-methanobenzo[a][8]annulen-11-yl)-1,3-thiazole-2-sulfonamide

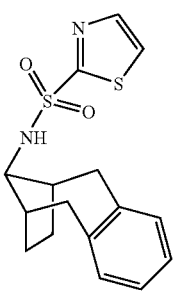

To a solution of the [11-endo]-5,6,7,8,9,10-hexahydro-6,9-methanobenzo[a][8]annulen-11-amine (100 mg) in dry DCM (2 ml) under nitrogen were added 4-methylmorpholine (0.1 ml) and thiazole-2-sulfonyl chloride (99 mg) (prepared from thiazole via a literature procedure; *Synthesis*, 1986, 852). After stirring at room temperature for 18 h., the reaction was diluted with DCM, washed with water and brine, dried over MgSO$_4$, filtered and evaporated. The crude product was purified by flash column chromatography (silica, DCM) to give a white solid (50 mg, 45%).

(360 MHz, $^1$H, CDCl$_3$) 1.15 (2H, m), 1.63 (2H, m), 2.38 (2H, m), 2.56 (2H, dd, J=7.9, 7.9), 3.05 (2H, d, J=15.8), 3.91 (1H, quar, J=7.6), 5.45 (1H, br), 7.06 (4H, m), 7.65 (1H, d, J=3.1), 8.00 (1H, d, J=3.1) MS(CI+) [MH]+335, [M-thiazoleSO$_2$NH]+171

Example 187

[11-endo]-N-(5,6,7,8,9,10-hexahydro-6,9-methanobenzo[a][8]annulen-11-yl)-thiophene-3-sulfonamide

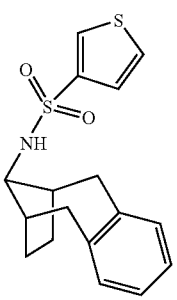

To a solution of the [11-endo]-5,6,7,8,9,10-hexahydro-6,9-methanobenzo[a][8]annulen-11-amine (100 mg) in dry DCM (2 ml) under nitrogen were added 4-methylmorpholine (0.1 ml) and thiophene-3-sulfonyl chloride (100 mg) (prepared from 3-bromothiophene via a literature procedure; *Synthesis*, 1986, 852). After stirring at room temperature for 18 h., the reaction was diluted with DCM, washed with water and brine, dried over MgSO$_4$, filtered and evaporated. The crude product was purified by flash column chromatography (silica, DCM) to give a white solid, (82 mg, 52%).

(360 MHz, ¹H, CDCl₃) 1.13 (2H, m), 1.62 (2H, m), 2.30 (2H, m), 2.51 (2H, dd, J=7.8,7.8), 2.99 (2H, d, J=15.9), 3.73 (1H, m), 5.04 (1H, d, J=7.7), 7.07 (4H, m), 7.42 (2H, m), 8.01 (1H, m)

MS(ES+) [MH]+334, [M-thiopheneSO₂]+188, [M-thiopheneSO₂NH]+171

Example 188

[1-endo]-2-chloro-N-(5,6,7,8,9,10-hexahydro-6,9-methanobenzo[a][8]annulen-11-yl)-1,3-thiazole-5-sulfonamide

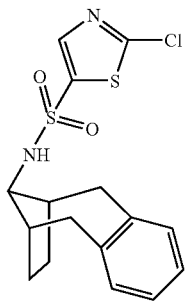

To a solution of the [11-endo]-5,6,7,8,9,10-hexahydro-6,9-methanobenzo[a][8]annulen-11-amine (100 mg) in dry DCM (2 ml) under nitrogen were added 4-methylmorpholine (0.1 ml) and 2-chloro-thiazole-5-sulfonyl chloride (120 mg) (prepared from 2-chlorothiazole via a literature procedure; Synthesis, 1986, 852). After stirring at room temperature for 18 h., the reaction was diluted with DCM, washed with water and brine, dried over MgSO₄, filtered and evaporated. The crude product was purified by flash column chromatography (silica, DCM) to give a white solid (95 mg, 48%).

(360 MHz, ¹H, CDCl₃) 1.21 (2H, m), 1.68 (2H, m), 2.42 (2H, m), 2.60 (2H, dd, J=8.0, 8.0), 3.01 (2H, d, J=15.8), 3.81 (1H, quar, J=7.6), 5.16 (1H, br), 7.08 (4H, s), 8.02 (1H, s)

MS (ES+) [MH]+369, [M-chlorothiazoleSO₂]+188, [M-chlorothiazoleSO₂NH] 171

Example 189

[11-endo]-N-(5,6,7,8,9,10-hexahydro-6,9-methanobenzo[a][8]annulen-11-yl)-pyridyl-3-sulfonamide

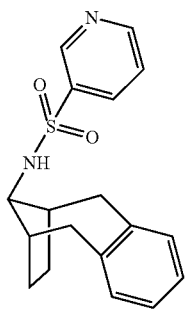

To a solution of the [11-endo]-5,6,7,8,9,10-hexahydro-6,9-methanobenzo[a][8]annulen-11-amine (120 mg) in dry DCM (3 ml) under nitrogen were added 4-methylmorpholine (0.1 ml) and pyridine-3-sulfonyl chloride (117 mg) (prepared from pyridine-3-sulfonic acid via a literature procedure; J. Org. Chem., 1989, 54, 389). After stirring at room temperature for 18 h., the reaction was diluted with DCM, washed with wate and, brine, dried over MgSO₄, filtered and evaporated. The crude product was purified by flash column chromatography (silica, DCM) to give a white solid (152 mg, 72%).

(360 MHz, ¹H, CDCl₃) 1.15 (2H, m), 1.62 (2H, m), 2.32 (2H, m), 2.54 (2H, dd, J=7.9, 7.9), 2.97 (2H, d, J=15.8), 3.74 (1H, quar, J=7.5), 5.08 (1H, br), 7.06 (4H, m), 7.49 (1H, m), 8.22 (1H, dd, J=4.1,4.1), 8.88 (1H, s), 9.15 (1H, s). MS(ES+) [MH]+329, [M-pyridylSO₂]+186

Example 190 endo-5-Chloro-thiophene-2-sulfonic acid [5-(3-piperidin-1-yl-propenyl)-tricyclo[8.2.1.0³,⁸]trideca-3(8),4,6-trien-13-yl]-amide

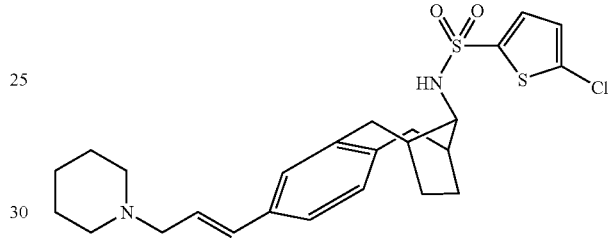

(a) endo-5-Chloro-thiophene-2-sulfonic acid [5-(3-bromo-propenyl)-tricyclo[8.2.1.0³,⁸]trideca-3(8),4,6-trien-13-yl]-amide A solution of 1M phosphorous tribromide in DCM (29 μL, 0.0294 mmol) was added to a stirred solution of 5-chlorothiophene-2-sulfonic acid [5-(3-hydroxy-propenyl)-tricyclo[8.2.1.0³,⁸]trideca-3(8),4,6-trien-13-yl]-amide (Example 161) (25 mg, 0.0589 mmol) in DCM (1ml) at −20° C. The mixture was allowed to warm to ~10° C. gradually at which point it was diluted with DCM and water. The organic phase was washed with dilute sodium bicarbonate solution, dried and concentrated under reduced pressure to give a white solid 24 mg. ¹H NMR (CDCl₃, 360 MHz) δ 7.44 (1H, d, J=3.9 Hz), 7.10 (2H, m), 7.03 (1H, d, J=6.9 Hz), 6.94 (1H, d, J=4.0 Hz), 6.57 (1H, d, J=15.6 Hz), 6.31-6.39 (1H, m), 5.09 (1H, br d, J=7.5 Hz), 4.15 (2H, d, J=7.6 Hz), 3.74 (1H, m), 3.10 (2H, d, J=16.2 Hz), 2.54-2.61 (2H, m), 2.39 (2H, m), 1.65 (2H, m), 1.17 (2H, m)

(b) The recovered bromide (24 mg, 0.0492 mmol), piperidine (40 mg, 0.4705 mmol) and potassium carbonate (17 mg, 0.125 mmol) in DMF (1 ml) were stirred at 80° C. for 18 hours. The mixture was allowed to cool to rt. and concentrated under reduced pressure. The residue was treated with acetic acid (gl.) with stirring and then concentrated under reduced pressure. The crude product was purified by mass-directed preparative HPLC. ¹H NMR (CDCl₃, 400 MHz) δ 7.45 (1H, d, J=4.0 Hz), 7.09 (2H, m), 7.03 (1H, d, J=7.6 Hz), 6.94 (1H, d, J=3.9 Hz), 6.62 (1H, d, J=15.8 Hz), 6.19 (1H, m), 5.33 (1H, d, J=7.2 Hz), 3.74 (3H, m), 3.63 (2H, br d, J=11.7 Hz), 3.04 (2H, m), 2.68-2.47 (6H, m), 2.40 (2H, m), 2.00 (1H, m), 1.89 (2H, m), 1.65 (2H, m), 1.38 (1H, m), 1.15 (2H, m). m/z 491/493 (M+H⁺).

The following compounds in accordance with formula E were prepared by the method of example 190, substituting the appropriate amine for piperidine in step (b). In all cases, purification was by mass-directed HPLC.

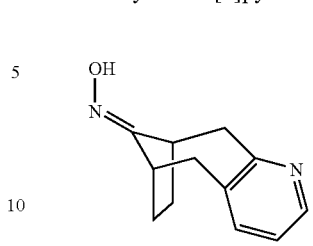

| Example | R | m/z (M + H⁺) |
|---|---|---|
| 191 | morpholin-4-yl-methyl | 493/495 |
| 192 | imidazol-1-yl-methyl | 474/476 |
| 193 | 1,2,4-triazol-1-yl-methyl | 475/477 |
| 194 | 4-methylpiperazin-1-yl-methyl | 506/508 |
| 195 | 4-phenylpiperazin-1-yl-methyl | 568/570 |
| 196 | MeOCH₂CH₂N(Me)CH₂- | 495/497 |

Example 197 endo-5-Chloro-N-[5,6,7,8,9,10-hexahydro-6,9-methanocycloocta[b]pyridin-11-yl]thiophene-2-sulfonamide trifluoroacetate

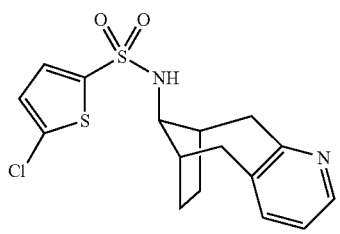

Step (a) (6S/R,9R/.S,11E/Z)-5,6,7,8,9,10-hexahydro-6,9-methanocycloocta[b]pyridin-11-one oxime Diisopropylethylamine (6.6 mL, 38 mmol) and 1-pyrrolidinocyclopentene (2.8 mL, 19 mmol) were added to a stirred solution of freshly prepared 2,3-bis(chloromethyl)pyridine [K. Tsuda et al; *Pharm. Bull.* 1, 1953, 142 ] (2.6 g, 15 mmol) in dry acetonitrile (50 mL) at 0° C. under nitrogen. The reaction was stirred for 15 minutes at this temperature, then 1 hour at room temperature. The mixture was then stirred and heated at reflux for 2 hours. The reaction was allowed to cool, the volatiles removed in vacuo, and the residue taken up in water (40 mL). Concentrated hydrochloric acid was added to give pH 1, and the mixture heated at reflux for 24 hours. The reaction was cooled to 0° C. and basified with 4N aqueous sodium hydroxide, and the dark mixture extracted with dichloromethane (×4). The combined extracts were dried (Na₂SO₄), filtered and evaporated, and the residue purified by chromatography on silica gel, eluting with 80% ethyl acetate/hexanes to 100% ethyl acetate to give (6S/R,9R/S)-5,6,7,8,9,10-hexahydro-6,9-methanocycloocta[b]pyridin-11-one (700 mg) as a dark oil (~75% pure); MS (ES+) 188 ([MH]⁺). This material was used without further purification.

A solution of the above ketone (840 mg), hydroxylamine hydrochloride (625 mg, 9 mmol) and sodium acetate trihydrate (1.2 g, 8.8 mmol) in ethanol/water (2:1, 15 mL) was stirred and heated at reflux for 45 minutes. The reaction was allowed to cool and the ethanol was removed in vacuo. The residue was basified with 4N aqueous sodium hydroxide. This aqueous mixture was extracted with dichloromethane (×4). The combined extracts were dried (Na₂SO₄), filtered and evaporated. The residue was purified by chromatography on silica, eluting with 75% ethyl acetate/hexanes to 100% ethyl acetate to give the title oxime (487 mg, 50%) as a colourless foam; MS (ES+) 203 ([MH]⁺).

Step (b)

The oxime from step (a) was converted to the corresponding amine by sequential treatment with sodium cyanoborohydride and activated zinc as described in Example 108 steps 1 and 2. The product, a yellow oil; MS (ES+) 189 [MH]⁺, was used without further purification. 5-Chlorothiophene-2-sulfonyl chloride (150 mg, 0.7 mmol) was added to a solution of a portion of the above amine (~100 mg, 0.5 mmol) and 4-(dimethylamino)pyridine (84 mg, 0.7 mmol) in dry dichloromethane (5 mL) at room temperature under nitrogen. After stirring at this temperature overnight, the mixture was partitioned between dichloromethane and saturated aqueous sodium hydrogen carbonate. The aqueous layer was extracted with dichloromethane (×2). The combined extracts were dried (Na₂SO₄), filtered. The residue was purified by chromatography on silica gel eluting with 30% ethyl acetate/dichloromethane to give the sulphonamide (140 mg, colourless solid). A portion of this material was further purified by preparative HPLC to give the title compound (7 mg) as a colourless solid; (400 MHz ¹H, δ-d₆-DMSO) 0.89-0.96 (2H,m), 1.65-1.73 (2H, m); 2.33-

2.45 (2H, m); 2.76 (1H, dd, J=16.4, 7.4), 2.99 (1H, dd, J=16.4, 7.5), 3.22 (1H, d, J=16.2), 3.40 (1H, d, J=16.5), 3.57 (1H, q, J=6.2), 7.29 (1H, d, J=4.0), 7.57 (1H, d, J=4.0), 7.65 (1H, br t, J=6), 8.15 (1H, d, J=7.6), 8.45 (1H, d, J=6.1), 8.55 (1H, d, J=5.2); MS (ES+) 369, 371 ([MH]+).

Example 198 endo-5-Chloro-N-[5,6,7,8,9,10-hexahydro-6,9-methanocyclooctа[c]pyridin-11-yl]thiophene-2-sulfonamide

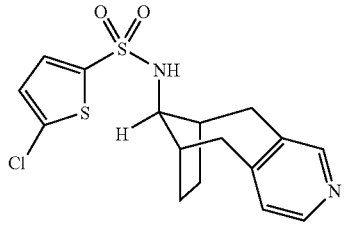

This material was prepared according to the procedure described in Example 197, substituting 3,4-bis(chloromethyl)pyridine for 2,3-bis(chloromethyl)pyridine in step (a).

The final product was purified by preparative tlc (10% ethyl acetate-dichloromethane) to give 5-chloro-N-[(6S/R,9S/R,11R/S)-5,6,7,8,9,10-hexahydro-6,9-methanocyclooctа[c]pyridin-11-yl]thiophene-2-sulfonamide (59 mg) as a colourless foam; (360 MHz $^1$H, δ-d$_6$-DMSO) 0.85-0.94 (2H,m), 1.22-1.29 (1H, m); 1.50-1.56 (2H, m); 2.27-2.32 (2H, m), 2.51-2.58 (1H, m), 3.05-3.16 (2H, m), 3.59-3.65 (1H, m), 7.20 (1H, br s), 7.28 (1H, d, J=4.0), 7.52 (1H, d, J=4.0), 8.25 (2H, br s), 8.36 (1H, d, J=7); MS (ES+) 369, 371 ([MH]+).

Example 199

[N-(11-endo)]-N-(5,6,7,8,9,10-hexahydro-6,9-methanobenzo[a][8]annulen-11-yl)pyrrolidine-1-sulfonamide

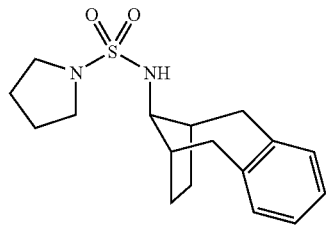

A mixture of [11-endo]-5,6,7,8,9,10-hexahydro-6,9-methanobenzo[a][8]annulen-11-amine (180 mg, 0.96 mmol), 1-pyrrolidinesulfonyl chloride (FR 2678935 A1) (320 mg, 1.9 mmol) and triethylamine (300 μL, 2.2 mmol) in dry acetonitrile (3 mL) was stirred and heated at reflux overnight under a nitrogen atmosphere. After cooling to room temperature the reaction mixture was partitioned between dichloromethane and saturated aqueous sodium hydrogen carbonate. The aqueous layer was further extracted with dichloromethane (×2). The combined organic extracts were dried (Na$_2$SO$_4$), filtered and evaporated. The residue was purified by chromatography on silica gel eluting with 20% ethyl acetate/hexanes to give the title compound (44 mg, 14%) as a cream solid, δ (1H, 360 MHz, CDCl$_3$) 1.15-1.21 (2H, m), 1.66-1.72 (2H, m), 1.92-1.98 (4H, m), 2.46-2.51 (2H, m), 2.61 (2H, dd, J=16.1, 7.6), 3.09 (2H, d, J=16.0), 3.33-3.37 (4H, m), 3.78-3.84 (1H, m), 4.63 (1H, br d, J=8), 7.09 (4H, br s).

Example 200 endo-5-chloro-N-[2-(5-pyridin-4-yl-1,2,4-oxadiazol-3-yl)-5,6,7,8,9,10-hexahydro-6,9-methanobenzo[a][8]annulen-11-yl]thiophene-2-sulfonamide

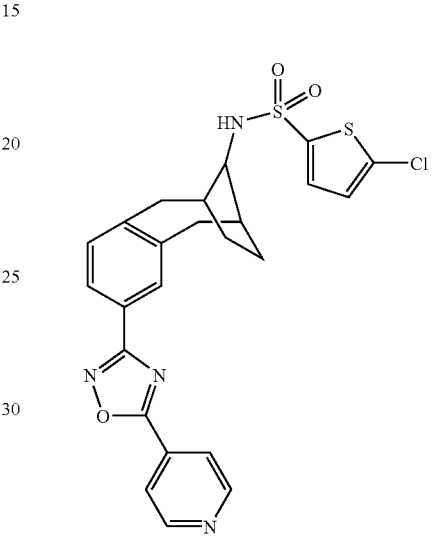

Step 1

Potassium t-butoxide (1.0M in THF; 1.33 ml, 1.33 mmol) was added to a solution of 5-chloro-N-(2-cyano-5,6,7,8,9,10-hexahydro-6,9-methanobenzo[a][8]annulen-11-yl) thiophene-2-sulfonamide (Example 176) (350 mg, 0.89 mmol) in THF (10 ml) and stirred for 20 mins. Chloromethyl methyl ether (108 μl, 1.42 mmol) was added and the reaction stirred overnight at RT. More reagents were added as necessary until the reaction was complete by NMR. The reaction mixture was poured into water (25 ml) and extracted with ethyl acetate (2×25 ml). The combined organic layers were washed with brine, dried over MgSO$_4$ and evaporated to give 5-chloro-N-(2-cyano-5,6,7,8,9,10-hexahydro-6,9-methanobenzo[a][8]annulen-11-yl)-N-(methoxymethyl) thiophene-2-sulfonamide (388 mg, quant.).

$^1$H NMR (400 MHz, CDCl$_3$) δ 7.49 (d, J 4, 1H), 7.40-7.35 (m, 2H), 7.17 (d, J 7.7, 1H), 6.95 (d, J 4, 1H), 4.88 (q, J 9, 2H), 3.48-3.39 (m, 2H), 3.36 (s, 3H), 3.36-3.33 (m, 1H), 2.81-2.77 (m, 2H), 2.68-2.58 (m, 2H), 1.62-1.59 (m, 2H), 1.14-1.11 (m, 2H).

Step 2

The nitrile from Step 1 (388 mg, 0.89 mmol) was converted to the corresponding N-hydroxycarboximide as described in Example 177 step (a). Yield (396 mg, 95%).

$^1$H NMR (400 MHz, DMSO) δ 9.50 (s, 1H), 7.67 (d, J 4.2, 1H), 7.39-7.36 (m, 2H), 7.31 (d, J 4.2, 1H), 7.02 (d, J 7.8, 1H), 5.72 (s, 2H), 4.84 (s, 2H), 3.28 (s, 3H), 3.28-3.23 (m, 3H), 2.73 (m, 2H), 2.59-2.53 (m, 2H), 1.55-1.53 (m, 2H), 1.02 (d, J 10.2, 2H).

Step 3

Isonicotinic acid (29 mg, 0.24 mmol) was dissolved in DMF (4 ml) under nitrogen and carbonyl diimidazole (38 mg, 0.24 mmol) added. The reaction was stirred at RT for 1 h. A solution of the product from step 2 (120 mg, 0.26 mmol) in DMF (2 ml) was added and the reaction stirred for 4 h. The reaction mixture was poured into water (25 ml) and extracted with ethyl acetate (2×25 ml). The combined organic layers were washed with water (3×25 ml), citric acid (10% aq; 25 ml), NaHCO$_3$ (sat. aq; 25 ml) and brine, dried over Na$_2$SO$_4$ and evaporated. Without further purification, 75 mg of the residue was dissolved in DMF (2 ml) and toluene (4 ml), p-toluenesulphonic acid (5 mg) was added and the reaction heated to 70° C. for 3 h. The cooled reaction mixture was poured into NaHCO$_3$ (25 ml) and extracted with ethyl acetate (25 ml). The organic layer was washed with water (3×25 ml) and brine, dried over Na$_2$SO$_4$ and evaporated to give 5-chloro-N-(methoxymethyl)-N-[2-(5-pyridin-4-yl-1,2,4-oxadiazol-3-yl)-5,6,7,8,9,10-hexahydro-6,9-methanobenzo[a][8]annulen-11-yl]thiophene-2-sulfonamide (67 mg, 92%).

$^1$H NMR (400 MHz, DMSO) δ 8.88 (s, 2H), 8.07 (d, J 5, 2H), 7.89 (d, J 7.9, 2H), 7.51 (d, J 4.1, 1H), 7.26-7.22 (m, 1H), 6.96 (d, J 4.1, 1H), 4.92 (q, J 10, 2H), 3.51-3.45 (m, 2H), 3.37 (s, 3H), 3.39-3.36 (m, 1H), 2.79-2.78 (m, 2H), 2.75-2.65 (m, 2H), 1.70-1.60 (m, 2H), 1.26-1.21 (m, 2H).

Step 4

Trifluoroacetic acid (0.5 ml) was added to a solution of the product from step 3 (65 mg, 0.12 mmol) in DCM (2 ml) and stirred for 1 h at RT. Ethyl acetate (20 ml) was added and washed with Na$_2$CO$_3$ (10% aq; 20 ml) and brine, dried over Na$_2$SO$_4$ and evaporated. The residue was purified by flash column chromatography on silica, eluting with 1:1 isohexane:EtOAc, to give the title product (30 mg, 49%).

$^1$H NMR (400 MHz, CDCl$_3$) δ 9.90 (d, J 1.6, 2H), 8.08 (dd, J 1.6, 4.4, 2H), 7.90 (s, 1H), 7.90-7.88 (m, 1H), 7.47 (d, J 3.9, 1H), 7.26-7.23 (m, 1H), 6.97 (d, J 3.9, 1H), 5.05 (d, J 7.4, 1H), 3.77 (q, J 6.4, 1H), 3.14-3.10 (m, 2H), 2.78-2.67 (m, 2H), 2.49-2.44 (m, 2H), 1.72-1.68 (m, 2H), 1.24-1.20 (m, 2H). m/z 513, 514, 515, 516.

Example 201 endo-5-chloro-N-[2-(5-pyridin-3-yl-1,2,4-oxadiazol-3-yl)-5,6,7,8,9,10-hexahydro-6,9-methanobenzo[a][8]annulen-11-yl]thiophene-2-sulfonamide

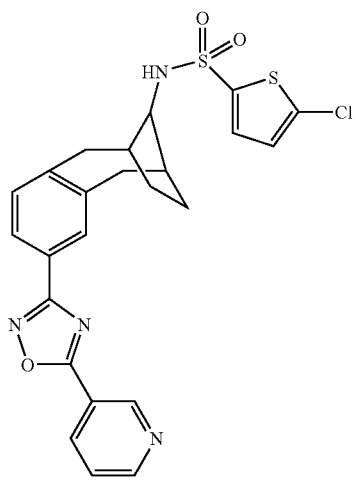

Prepared as described in Example 200, substituting nicotinic acid for isonicotinic acid in step 3.

$^1$H NMR (400 MHz, DMSO) δ 9.34 (d, J 0.8, 1H), 8.90 (dd, J 1.2, 4.7, 1H), 8.57-8.54 (m, 1H), 8.42 (d, J 7, 1H), 7.83 (s, 1H), 7.82-7.79 (m, 1H), 7.73-7.69 (m, 1H), 7.57 (d, J 3.9, 1H), 7.33 (d, J 7.8, 1H), 7.29 (d, J 3.9, 1H), 3.63-3.57 (m,1H), 3.27-3.23 (m, 2H), 2.69-2.57 (m, 2H), 2.36-2.29 (m, 2H), 1.65-1.60 (m, 2H), 1.02-0.97 (m, 2H). m/z 513, 514, 515, 516.

Example 202 endo-N-(5,6,7,8,9,10-hexahydro-6,9-methanobenzo[a][8]annulen-11-yl)pentanesulfonamide

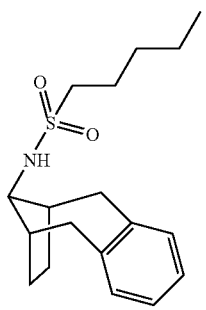

Prepared as described in Example 184, substituting n-pentanesulfonyl chloride for cyclopentanesulfonyl chloride. The crude product was purified by flash column chromatography (silica, 20% EtOAc in iso-hexane) to give a glassy solid (30%).

(360 MHz, $^1$H, CDCl$_3$) 0.92 (3H, q, J=7), 1.20 (2H, m), 1.41 (4H, m), 1.71 (2H, m), 1.86 (2H, m), 2.44 (2H, m), 2.64 (2H, dd, J=7.5, 7.5), 3.09 (4H, m), 3.85 (1H, quar, J=6.3), 4.82 (1H, d, J=8.3), 7.09 (4H, m)

Example 203 endo-N-(5,6,7,8,9,10-hexahydro-6,9-methanobenzo[a][8]annulen-11-yl)-isothiazole-5-sulfonamide

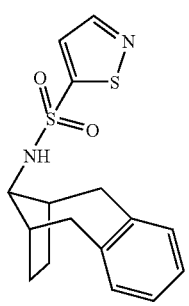

Prepared as in Example 202 using isothiazole-5-sulfonyl chloride (prepared from 5-bromoisothiazole by the method described in *Synthesis*, 1986, 852). The crude product was purified by flash column chromatography (silica, 3:1 iso-hexane/ethyl acetate) to give a white solid (53%).

(360 MHz, 1H, CDCl$_3$) 1.15 (2H, m), 1.61 (2H, m), 2.38 (2H, m), 2.55 (2H, dd, J=7.6, 7.6), 3.00 (2H, d, J=16), 3.85 (1H, quar, J=6.9), 4.75 (1H, d, J=7.3), 5.29 (1H, d, J=7.0), 7.09 (4H, m), 7.67 (1H, s), 8.52 (1H, s) MS (ES+) [MH]+ 335, [M-isothiazoleSO$_2$NH]+171

Example 204 endo-N-(5,6,7,8,9,10-hexahydro-6,9-methanobenzo[a][8]annulen-11-yl)-pyrrole-3-sulfonamide

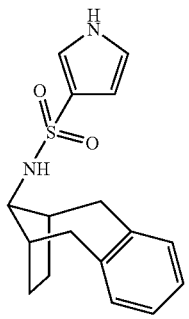

Prepared as in Example 202 using 1-triisopropylsilylpyrrole-3-sulfonyl chloride (prepared from the corresponding 3-bromide by the method described in *Synthesis*, 1986, 852), followed by removal of the silyl group by treatment with t-butylammonium fluoride in dry THF at 0° C. under $N_2$. Purified by flash chromatography ($SiO_2$, 50% ethyl acetate in isohexane) to give a white solid.

(360 MHz, $^1$H, $CDCl_3$) 1.13 (2H, m), 1.61 (2H, m), 2.35 (2H, m), 2.52 (2H, dd, J=6.7, 6.8), 3.07 (2H, d, J=14), 3.70 (1H, quar, J=6.0), 4.82 (1H, d, J=6.8), 6.55 (1H, m), 6.85 (1H, m), 7.06 (4H, m), 7.36 (1H, m). 8.60 (11, br). MS (ES+) [MH]+317, [M-pyrroleSO$_2$NH]+171

Example 205 endo-1-methyl-N-(5,6,7,8,9,10-hexahydro-6,9-methanobenzo[a][8]annulen-11-yl)-pyrrole-3-sulfonamide

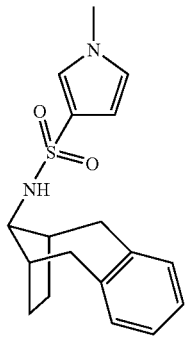

Prepared from the product of Example 204 by treatment with sodium hydride and iodomethane.

(360 MHz, $^1$H, $CDCl_3$) 1.14 (2H, m), 1.61 (2H, m), 2.36 (2H, m), 2.53 (2H, dd, J=7.6, 7.6), 3.08 (2H, d, J=16), 3.69 (4H, m), 4.75 (1H, d, J=7.3), 6.45 (1H, m), 6.63 (1H, m), 7.06 (4H, m), 7.16 (1H, m) MS (ES+) [MH]+330

Example 206 endo-6-chloro-N-(5,6,7,8,9,10-hexahydro-6,9-methanobenzo[a][8]annulen-11-yl)-pyridine-3-sulfonamide

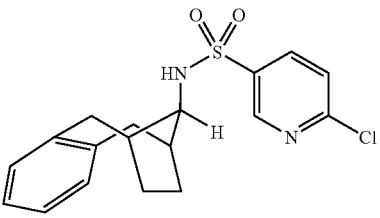

Prepared as in Example 1 using 6-chloropyridine-3-sulfonyl chloride.

$^1$H NMR (CDCl3, 360 MHz) δ 8.92 (1 H,d, J=2.5 Hz, PyH), 8.15 (1 H, dd, J=2.5 & 8.4 Hz, PyH), 7.50 (1H, d, J=8.4 Hz), 7.10-7.03 (4H, m, aromatic), 5.17 (1H, d, J=7.9 Hz, NH), 3.72 (1H,q, J=6.3 & 14.2 Hz), 2.96 (2H, d, J=16 Hz, aliph), 2.59-2.52 (2H, in, aliph), 2.35-2.29 (2H, m, aliph), 1.65-1.59 (2H, m, aliph), 1.19-1.13 (2H, m, aliph), m/z 362.

Example 207 endo-5-chloro-N-(2-pyridin-2-yl-5,6,7,8,9,10-hexahydro-6,9-methanobenzo[a][8]annulen-11-yl)thiophene-2-sulfonamide

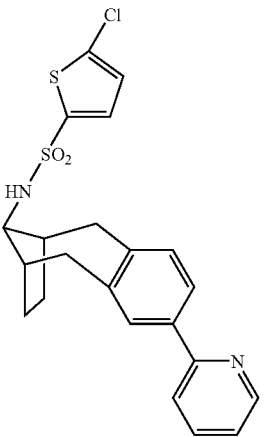

Step 1

[6S/R,9R/S] 2-Hydroxy-5,6,7,8,9,10-hexahydro-6,9-methanobenzo[a][8]annulen-11-one (J.Org.Chem 1982, 47, 4329) was converted to the oxime and thence to the 11-amine by the process described in the General Procedures. The amine (10.90 g) and di-tert-butyl dicarbonate (24 g) in dry THF (400 ml) were stirred at r.t. under nitrogen for 4 hours. Unsymm-N,N-dimethyl ethylenediamine (6 ml) was added and the mixture was stirred for a further 1.5 hours. Water (500 ml) was added and the mixture was extracted with ethyl acetate (2×200 ml). The organic layers were washed with 0.2M citric acid (200 ml), brine (100 ml), dried and concentrated. The residue was filtered through charcoal, eluting with dichloromethane, and the filtrate concentrated to give [6S/R,9R/S,11S/R] tert-butyl 2-hydroxy-5,6,7,8,9,10-hexahydro-6,9-methanobenzo[a][8]annulen-11-ylcarbamate (17.7 g, quantitative) as a beige solid.

Step 2

The product of step 1 (0.463 g), diisopropylethylamine (0.32 ml) and N-phenylbis(trifluoromethanesulfonamide) (0.65 g) in acetonitrile (20 ml) were stirred at 0° C. under nitrogen, warming slowly to room temperature. After 18 hours the suspension was diluted with ethyl acetate (50 ml) and washed with water (50 ml), 1M citric acid (50 ml), dried and concentrated. Flash column chromatography, eluting with 5% then 10% ethyl acetate-isohexane, gave [6S/R,9R/S,11S/R]11-[(tert-butoxycarbonyl)amino]-5,6,7,8,9,10-hexahydro-6,9-methanobenzo[a][8]annulen-2-yl trifluoromethanesulfonate (0.497 g,75%) as a white powder Step 3

The product from step 2 (0.076 g), dipalladium (0) tris(dibenzylideneacetone) (0.008 g) and tri(2-furyl)phosphine (0.008 g) in dry DMF (1 ml) were stirred at 80° C. under nitrogen, followed by addition of 2-pyridylzinc bromide (0.5M in THF, 0.2 ml). After 18 hours the mixture was poured into 1M citric acid (5 ml), neutralised with saturated aqueous sodium hydrogencarbonate and extracted with ethyl acetate (20 ml). The organic extract was dried and concentrated. Flash column chromatography, eluting with 20% ethyl acetate-isohexane, gave [6S/R,9R/S, 1SMR] tert-butyl 2-pyridin-2-yl-5,6,7,8,9,10-hexahydro-6,9-methanobenzo [a][8]annulen-11-ylcarbamate (0.012 g, 19%) as an oil.

Step 4

The product of step 3 (0.020 g) and trifluoroacetic acid (1 ml) in dichloromethane (1 ml) was stood at room temperature for 1.5 hours then evaporated to dryness. The residue was redissolved in dry dichloromethane (1 ml) and triethylamine (1 ml) and 2-chlorothiophene-5-sulfonyl chloride (0.015 ml) were added. After 18 hours the mixture was diluted with water (5 ml) and extracted with dichloromethane (2×5 ml). The extracts were dried and concentrated. Preparative thin layer chromatography, eluting with 30% ethyl acetate-isohexane, gave the title compound (0.004 g, 16%) as a white solid. (360 MHz 1H, δ-CDCl$_3$) 1.20-1.26 (2H, m), 1.65-1.70 (2H, m), 2.40-2.45 (2H, m), 2.63-2.77 (2H, m), 3.07 (2H, d. J=16), 3.75-3.81 (1H, m), 5.04 (1H, d, J=7), 6.95 (1H, d, J=4), 7.17-7.23 (2H, m), 7.46 (1H, d, J=4), 7.67-7.76 (4H, m), 8.67 (1H, d, J=5). M/z (ES+) 445, 447 (M+H$^+$).

Example 208 endo-5-chloro-N-(2-(pyridin-4-yloxy)-5,6,7,8,9,10-hexahydro-6,9-methanobenzo[a][8]annulen-11-yl) thiophene-2-sulfonamide

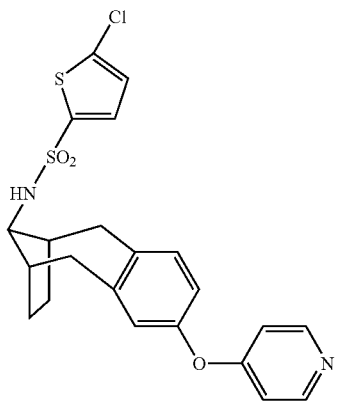

Step 1

Sodium hydride (55% in oil, 0.26 g) was added to a stirred solution of [6S8R,9R/S] 2-Hydroxy-5,6,7,8,9,10-hexahydro-6,9-methanobenzo[a][8]annulen-11-one (0.50 g; J. Org. Chem 1982, 47, 4329) in dry DMF at room temperature under nitrogen. When effervescence had subsided, 4-bromopyridine hydrochloride (0.57 g) was added and the mixture was stirred at 80° C. for 18 hours. The mixture was diluted with water (100 ml), acidified with 1M hydrochloric acid and washed with EtOAc (20 ml). The aqueous layer was basified with 4M sodium hydroxide and extracted with dichloromethane-methanol (9:1, 2×100 mL). The extracts were dried and concentrated. Flash column chromatography, eluting with 90:9:1 dichloromethane-methanol-ammonia, gave a brown oil that was filtered through charcoal, eluting with dichloromethane, and concentrated to give [6S/R,9R/S]2-(pyridin-4-yloxy)-5,6,7,8,9,10-hexahydro-6,9-methanobenzo[a][8]annulen-11-one (0.27 g) as a beige solid.

Step 2

The ketone from step 1 was converted to the oxime as described in the General Procedures, and this was reduced to the amine as described in Example 66, step 2. Treatment of the amine (0.04 g) with 5-chlorothiophene-2-sulfonyl chloride by the procedure of Example 66 step 3 gave the title compound. Purification by flash column chromatography, eluting with 5% methanol-dichloromethane, gave a beige solid that was washed with ethyl acetate to give the final product (0.010 g, 12%) as an off-white powder. (400 MHz $^1$H, δ-d$_6$-DMSO) 0.98-1.06 (2H, m), 1.57-1.66 (2H, m), 2.23-2.32 (2H, m), 2.43-2.50 (2H, m), 3.15-3.22 (2H, m), 3.55-3.62 (1H, m), 6.84-6.90 (31, m), 6.91-6.96 (1H, m), 7.19 (1H, d, J=8), 7.29 (1H, d, J=4), 7.56 (1H, d, J=4), 8.32-8.38 (1H, broad m), 8.44-8.48 (2H, m). m/z (ES+) 461, 463 (M+H$^+$).

Example 209 endo-Thiophene-2-sulfonic acid{5-[2-(4-fluoro-phenoxy)-ethoxy]-tricyclo[8.2.1.0$^{3,8}$]trideca-3(8),4,6-trien-13-yl}-amide

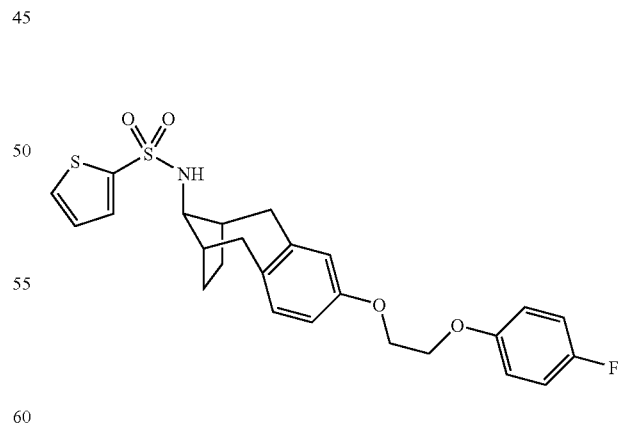

Step 1. 5-[2-(4-fluoro-phenoxy)-ethoxy]-tricyclo[8.2.1.0$^{3,8}$]trideca-3(8),4,6-trien-one A mixture of 2-hydroxy-5,6,7,8,9,10-hexahydro-6,9-methanobenzo[a][8]annulen-11-one (21.7 g; J. Org. Chem 1982, 47, 4329), K$_2$CO$_3$ (17.7 g) and 1-(2-Bromo-ethoxy)-

4-fluoro-benzene (40.3 g) in DMF (400 ml) were stirred for 72 hours at 120° C. The reaction was then cooled to room temperature and the solvent removed in vacuo. The residue was then washed with saturated NaHCO₃ solution and the organics extracted with EtOAc (3×200 ml). The organics were then combined, dried (MgSO₄) and the solvent removed in vacuo yielding a dark brown oil which was purified by flash chromatography on silica eluting 20% EtOAc in isohexane giving the title alkylated ketone (15.97 g, 44%). MS (ES+) 341 [M+H]⁺.

Step 2

The ketone from step 1 was converted to the oxime and thence to the corresponding amine as described in the General Procedures. The amine (0.3 g) was reacted with thiophene-2-sulfonyl chloride by the procedure of Example 1 to provide the title compound which was purified by flash chromatography on silica eluting 20% EtOAc in isohexane. The product isolated from this purification was then recrystallized from EtOAc and isohexane yielding 250 mg of the desired sulfonamide as a white crystalline solid. (400 MHz ¹H, δ-CDCl₃), 1.16-1.18 (21, d), 1.60-1.65 (2H, m), 2.31-2.32 (2H, m), 2.44-2.53 (2H, benzylic, m), 2.92-2.96 (1H, benzylic, d), 2.99-3.03 (1H, benzylic, d), 3.76 (1H, CH—N, m), 4.26 (4E, s), 5.01 (1H, NH—SO₂ s), 6.68 (2H, aromatic, m), 6.88 (2H, aromatic, m), 6.97 (3H, aromatic, m), 7.10 (1H, thiophenyl, m), 7.60 (1H, thiophenyl, m), 7.66 (1H, thiophenyl, m). MS (ES+) 488 [M+H]⁺.

Following the procedure of Example 209, using the appropriate alkyl halide in step 1 and the appropriate sulfonyl chloride in step 2, the following compounds of formula VA were prepared, wherein R¹ is H and R³ and R⁴ᵇ are as indicated:

| Example | R³ | R⁴ᵇ | m/z [M + H]⁺ |
|---|---|---|---|
| 210 | 4-fluorophenyl | 2-(4-fluorophenoxy)ethoxy | 500 |
| 211 | 4-chlorophenyl | 2-(4-fluorophenoxy)ethoxy | 516 |
| 212 | 4-nitrophenyl | 2-(4-fluorophenoxy)ethoxy | 527 |
| 213 | 4-methoxyphenyl | 2-(4-fluorophenoxy)ethoxy | 512 |
| 214 | n-propyl | 2-(4-fluorophenoxy)ethoxy | 448 |
| 215 | 3,5-bis(trifluoromethyl)phenyl | 2-(4-fluorophenoxy)ethoxy | 618 |
| 216 | 2-fluorophenyl | 2-(4-fluorophenoxy)ethoxy | 500 |
| 217 | 2,4-difluorophenyl | 2-(4-fluorophenoxy)ethoxy | 518 |
| 218 | 3-fluorophenyl | 2-(4-fluorophenoxy)ethoxy | 500 |
| 219 | 5-bromo-2-thienyl | 2-(4-fluorophenoxy)ethoxy | 568 |
| 220 | 1-methyl-1H-imidazol-5-yl | 2-(4-fluorophenoxy)ethoxy | 486 |
| 221 | 1,2-dimethyl-1H-imidazol-5-yl | 2-(4-fluorophenoxy)ethoxy | 500 |
| 222 | 4-cyanophenyl | 2-(4-fluorophenoxy)ethoxy | 507 |
| 223 | 3-pyridyl | 2-(4-fluorophenoxy)ethoxy | 483 |
| 224 | n-butyl | 2-(4-fluorophenoxy)ethoxy | 462 |
| 225 | 5-chloro-2-thienyl | 2-(4-fluorophenoxy)ethoxy | 523 |
| 226 | 3-pyridyl | benzyloxy | 435 |
| 227 | 2-chlorothiazol-5-yl | benzyloxy | — |

Example 228 endo-5-Chloro-thiophene-2-sulfonic acid [5-(2-morpholin-4-yl-ethoxy)-tricyclo[8.2.1.0$^{3,8}$]trideca-3(8),4,6-trien-13-yl]-amide

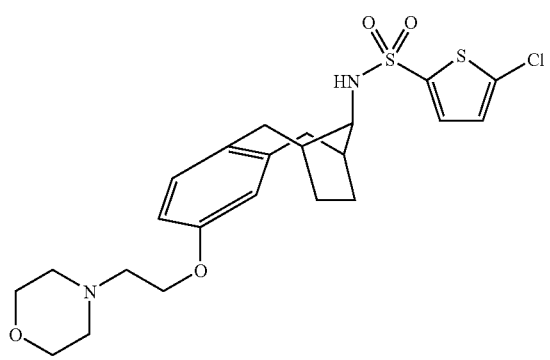

Step 1 endo-[13-(5-Chloro-thiophene-2-sulfonylamino)-tricyclo[8.2.1.0$^{3,8}$]trideca-3(8),4,6-trien-5-yloxy]-acetic acid ethyl ester was prepared by the method of Example 209 using ethyl bromoacetate in step 1 and 5-chlorothiophene-2-sulfonyl chloride in step 2.

Step 2: endo-[13-(5-Chloro-thiophene-2-sulfonylamino)-tricyclo[8.2.1.0$^{3,8}$]trideca-3(8),4,6-trien-5-yloxy]-acetic acid.

Lithium hydroxide monohydrate (84 mg) was added to a stirred solution of the ester from step 1 ( 870 mg) in THF:H$_2$O (20 ml 1:1) and the resulting solution stirred at room temperature for 16 hours. After this time the solvent was removed under reduced pressure and the residue partitioned between 2N HCl (aq.) and DCM, the organic layer separated, dried over MgSO$_4$, filtered and the solvent removed under reduced pressure to afford the acid as a white powder. (820 mg).

Step 3

HBTU (17.08 mg) was added to a stirred solution of the acid from step 2 (20 mg), morpholine (3.94 mg) and diisopropylethylamine (15 µl) in acetonitrile (2.0 ml). After 18 hours the reaction was quenched by the addition of water (2 ml) and solvent removed by lyophilisation. The residue was taken up in DMSO (1.0 ml) and purified by purified by mass-directed preparative HPLC m/z 512 (M+H$^+$). The recovered amide intermediate was taken up in dry THF (0.5 ml) and treated with BH$_3$:THF (0.5 ml/1.0 M) for 4 hours. The reaction was then quenched with 1N HCl (0.5 ml) and the solvents removed under reduced pressure. The residue was taken up in DMSO (1.0 ml) and purified by mass-directed preparative HPLC m/z 498 (M+H$^+$). $^1$H NMR (CDCl$_3$ 400 MHz) (TFA salt) δ 1.19 (2H, m), 1.62 (2H, m), 2.36 (2H, m), 2.48-2.61 (6H, m), 2.78 (2H, t, J=8.0 Hz), 2.93 (1H, d, J=16.0 Hz), 3.00 (1H, d, J=16 Hz), 3.74 (5H, m), 4.06 (2H, t, J=8.0 Hz), 5.10 (1H, d, J=12.0 Hz), 6.61 (2H, m), 6.94 (2H, m), 7.44 (2, m).

The following compounds in accordance with formula F below were prepared by the above method, substituting the appropriate amine for morpholine in the amide formation step. In all cases, purification was by mass directed HPLC.

| Example No | NR$_2$ | m/z (M + H)$^+$ |
|---|---|---|
| 229 | pyrrolidinyl | 610 |
| 230 | 2-(hydroxymethyl)pyrrolidinyl | 626 |
| 231 | 2-(methoxymethyl)pyrrolidinyl | 640 |
| 232 | 2-(methoxymethyl)pyrrolidinyl | 640 |
| 233 | morpholinyl | 624 |
| 234 | piperidinyl | 496 |
| 235 | 3-hydroxypyrrolidinyl | 498 |
| 236 | 4-hydroxypiperidinyl | 512 |
| 237 | 2-methylpiperidinyl | 510 |

Example 238 endo-Pyridine-3-sulfonic acid [5-(3-morpholin-4-yl-propenyl)-tricyclo[8.2.1.0$^{3,8}$]trideca-3(8),4,6-trien-13-yl]-amide

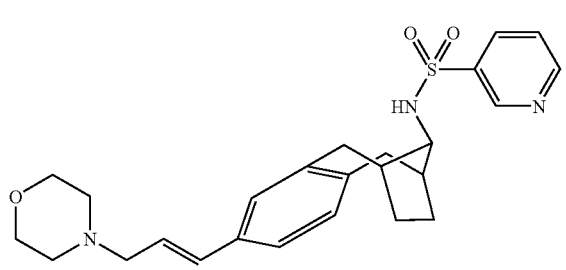

Step 1 endo-13-Amino-tricyclo[8.2.1.0$^{3,8}$]trideca-3(8),4,6-triene-5-carboxylic acid methyl ester was prepared as described in the General Procedures using methyl 3,4-bis(bromomethyl)benzoate as starting material, and converted to the BOC derivative as described in Example 207 step 1. The methyl ester was reduced to the benzyl alcohol as in Example 151 step (b), then oxidised to the aldehyde as in Example 152 step (a), and converted to the 3-hydroxypropenyl derivative by the procedures of Example 158 and Example 161.

Step 2

1-Bromo-N,N,2-trimethylpropenylamine (171 mg, 0.962 mmol) in DCM (0.5 ml) was added to a stirred suspension of the alcohol of step 1 (300 mg, 0.875 mmol) in DCM (4.5 ml) with ice cooling. After stirring at room temperature for 1 hour, morpholine (3 ml) was added, with stirring for a further 30 minutes. The mixture was diluted with DCM and washed with water. The organic phase was dried over sodium sulphate, filtered and concentrated to dryness. The crude product was purified by column chromatography on silica eluting with 20:1 DCM: methanol to give [5-(3-morpholin-4-yl-propenyl)-tricyclo[8.2.1.0$^{3,8}$]trideca-3(8),4,6-trien-13-yl]-carbamic acid tert-butyl ester as a colourless oil 156 mg (43%).

Step 3

The BOC group was removed by treatment with trifluoroacetic acid as described in Example 207 step 4. The resulting amine (32 mg, 0.103 mmol), pyridine-3-sulphonyl chloride (27 mg, 0.154 mmol), triethylamine (15 mg, 0.154 mmol) and DMAP (cat.) in DCM (3 ml) were stirred at room temperature for 18 hours at which point more pyridine-3-sulphonyl chloride (20 mg) and triethylamine (30 mg) were added and the mixture stirred for a further 6 hours. The mixture was diluted with DCM and washed with 1M sodium hydroxide (aq). The organic phase was dried over sodium sulphate, filtered and concentrated to dryness. The crude product was purified twice by column chromatography firstly on silica eluting with 20:1 DCM: 2M ammonia in methanol and then on silica eluting with 40:1 DCM: 2M ammonia in methanol. Finally the product was purified by mass-directed preparative HPLC to give the title compound 20 mg (43%).

$^1$H NMR (CDCl$_3$, 400 MHz) δ 9.14 (1 H, s), 8.82 (1 H, m), 8.22 (1 H, m), 7.49 (1 H, m), 7.10 (1 H, d, J=7.8 Hz), 7.05 (1 H, s), 6.99 (1 H, m), 6.45 (1 H, d, J=15.8 Hz), 6.16-6.23 (1 H, m), 5.21 (1 H, d, J=7.8 Hz), 3.72 (5 H, m), 3.13 (2 H, d, J=7.6 Hz), 2.94-2.99 (2 H, dd, J=16.1 +6.6 Hz), 2.50 (6 H, m), 2.31 (2 H, m), 1.62 (2 H, m), 1.14 (2 H, m).

Example 239 endo-2-Morpholin-4-yl-thiazole-5-sulfonic acid [5-(3-morpholin-4-yl-propenyl)-tricyclo[8.2.1.0$^{3,8}$]trideca-3(8),4,6-trien-13-yl]-amide

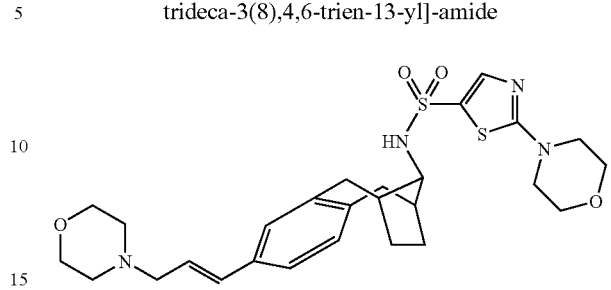

Prepared as described in Example 238, using 2-morpholin-4-yl-thiazole-5-sulfonyl chloride in step 3. m/z 545 (M+H$^+$).

Example 240 endo-Pyridine-3-sulfonic acid [5-(2-morpholin-4-yl-ethoxy)-tricyclo[8.2.1.0$^{3,8}$]trideca-3(8),4,6-trien-13-yl]-amide

Step 1

Diethyl azodicarboxylate (1.07 g, 6.16 mmol) in DCM (5 ml) was added at a dropwise rate to a stirred solution of 2-hydroxy-11-oxo-5,6,7,8,9,10-hexahydro-6,9-methanobenzocyclooctene (J. Org. Chem. 1982 4329, 829 mg, 4.10 mmol), triphenylphosphine (1.61 g, 6.16 mmol) and 4-(2-hydroxyethyl)morpholine (806 mg, 6.16 mmol) in DCM (45 ml). The mixture was stirred at room temperature for 2 hours and then concentrated to dryness. The crude product was purified by column chromatography on silica eluting with 40:1 DCM: 2M ammonia in methanol. The chromatographed material was taken up in the minimal volume of ethyl acetate and diluted with diethyl ether. 1M HCl in diethyl ether was added. The precipitate was filtered washing the solid with ethyl acetate and diethyl ether. The white solid was taken up in DCM and washed with 1M sodium hydroxide (aq). The organic phase was dried over sodium sulphate, filtered and concentrated to dryness to give 5-(2-morpholin-4-yl-ethoxy)-tricyclo[8.2.1.0$^{3,8}$]trideca-3(8),4,6-trien-13-one as a colourless oil 740 mg (57%).

Step 2

The ketone from step 1 was converted to the amine as described in the General Procedures, then reacted with pyridine-3-sulfonyl chloride by the process of Example 237 step 3 to provide the title compound which was isolated as its dihydrochloride salt.

$^1$H NMR (CDCl$_3$+[CD$_3$OD], 400 MHz) δ 9.34 (1 H, s), 8.98 (1 H, s), 8.73 (1 H, br d, J=7.2 Hz), 7.98 (1 H, m), 6.97 (1 H, d, J=7.9 Hz), 6.63 (2 H, m), 4.46 (2 H, m), 4.15 (2 H, br t, J=12.3 Hz), 4.03 (2 H, m), 3.59 (1 H, m), 3.50 (2 H, m), 3.39 (1 H, br d, J=16.2 Hz), 3.06-3.16 (4 H, m), 2.47 (2 H, m), 2.33 (2 H, m), 1.61 (2 H, m), 1.14 (2H, m).

Example 241 endo-4-[13-(5-Chloro-thiophene-2-sulfonylamino)tricyclo[8.2.1.0³,⁸]trideca-3(8),4,6-trien-5-yloxy]-piperidine-1-carboxylic acid tert-butyl ester

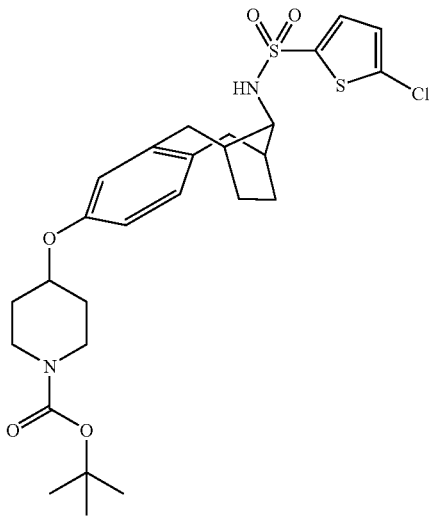

Prepared as in Example 240, using tert-butyl-4-hydroxy-1-piperidinecarboxylate in step 1 and 5-chlorothiophene-2-sulfonyl chloride in step 2.

$^1$H NMR (CDCl$_3$, 360 MHz) δ 7.43 (1 H, d, J=3.9 Hz), 6.92-6.95 (2 H, m), 6.63 (2 H, m), 5.33 (1 H, br d, J=7.6 Hz), 4.39 (1 H, m), 3.65-3.75 (3 H, m), 3.28-3.37 (2 H, m), 2.93-3.05 (2 H, m), 2.44-2.54 (2 H, m), 2.35 (2 H, m), 1.89 (2 H, m), 1.72 (2 H, m), 1.63 (2 H, m), 1.18 (2 H, m). m/z 567/569 (M+H$^+$).

Example 242 endo-5-Chloro-thiophene-2-sulfonic acid {5-[3-(4-oxy-morpholin-4-yl)-propenyl]-tricyclo[8.2.1.0³,⁸]trideca-3(8),4,6-trien-13-yl}-amide

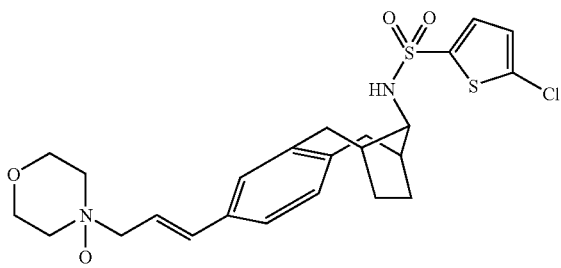

endo-5-Chloro-thiophene-2-sulfonic acid [5-(3-morpholin-4-yl-propenyl)-tricyclo[8.2.1.0³,⁸]trideca-3(8),4,6-trien-13-yl]-amide (Example 191) (20 mg, 0.041 mmol) and m-chloroperoxybenzoic acid (7 mg, 0.041 mmol) in DCM (2 ml) were stirred at room temperature for 18 hours. The mixture was diluted with DCM and washed with sodium bicarbonate solution (aq, sat.). The organic phase was dried over sodium sulphate, filtered and concentrated to dryness. The crude product was purified by mass-directed preparative HPLC and further purified by reverse-phase preparative HPLC to provide 1.5 mg of the titile compound. $^1$H NMR (CDCl$_3$, 400 MHz) δ 7.45 (1 H, d, J=4.1 Hz), 7.15 (2 H, m), 7.08 (1 H, d, J=8.2 Hz), 6.95 (1 H, d, J=4.0 Hz), 6.81 (1 H, d, J=15.8 Hz), 6.30-6.37 (1 H, m), 5.07(1 H, br d, J=7.2 Hz), 4.55 (2 H, d, J=7.4 Hz), 4.31 (2 H, t, J=11.7 Hz), 3.94 (4 H, m), 3.74 (1 H, m), 3.39 (2 H, m), 3.05 (2 H, d, J=16.1 Hz), 2.58-2.65 (2 H, m), 2.43 (2 H, m), 1.69 (2 H, m), 1.17 (2 H, m).

Example 243 endo-5-Chloro-N-[2-(morpholin-4-ylmethyl)-5,6,7,8,9,10-hexahydro-6,9-methanobenzo[a][8]annulen-11-yl]thiophene-2-sulfonamide

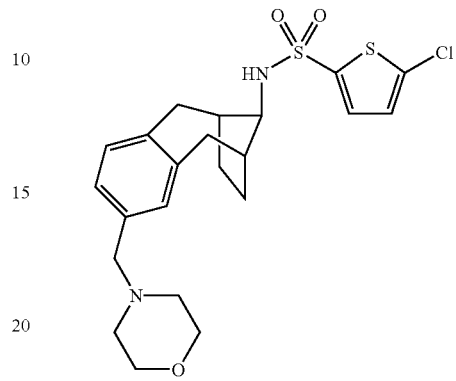

Step 1

To a solution of the alcohol described in Example 151 (173 mg, 0.43 mmol) in CH$_2$Cl$_2$ (10 ml) under N$_2$ was added triethylamine (73 μl, 0.52 mmol) followed by methanesulphonyl chloride (37 μl, 0.48 mmol). The mixture was stirred at room temperature for 17 h. The mixture was then diluted with water and extracted with CH$_2$Cl$_2$ (×3). The combined organic extracts were dried (MgSO$_4$) and concentrated. Purification by flash chromatography (20%EtOAc/hexane) afforded endo-5-chloro-N-[2-(chloromethyl)-5,6,7,8,9,10-hexahydro-6,9-methanobenzo[a][8]annulen-11-yl]thiophene-2-sulfonamide (78 mg, 43% yield).

Step 2

Morpholine (38 μl, 0.44 mmol) was added to a solution of the chloromethyl compound (36 mg, 86 mmol) in THF (3 ml) under N$_2$. The resulting mixture was stirred at room temperature for 2 h and then heated at 65° C. for 1.5 h. The mixture was concentrated in vacuo and a pure sample of the title compound as its trifluoroacetate salt was obtained by mass-directed preparative HPLC. 1H NMR (CDCl$_3$, 400 MHz) δ 1.10-1.16 (2H, m), 1.65-1.69 (2H, m), 2.39-2.44 (2H, m), 2.53-2.66 (21, m), 2.82 (2H, br s), 3.06 (2H, dd, J=16.2, 4.9 Hz), 3.41-3.48 (2H, m), 3.72 (1H, dd, J=12.9, 6.4 Hz), 3.95-3.96 (4H, m), 4.10 (2H, app dd, J=23.0, 12.8 Hz), 5.16 (1H, d, J=7.0 Hz), 6.95 (1H, d, J=4.0 HzO, 7.07-7.13 (3H, m), 7.45 (1H, d, J=4.0 Hz); m/z 469, 467 ([M+H]$^+$).

Example 244

Methyl endo-(2Z)-3-(11-{[(5-chlorothien-2-yl)sulfonyl]amino}-5,6,7,8,9,10-hexahydro-6,9-methanobenzo[a][8]annulen-2-yl)prop-2-enoate

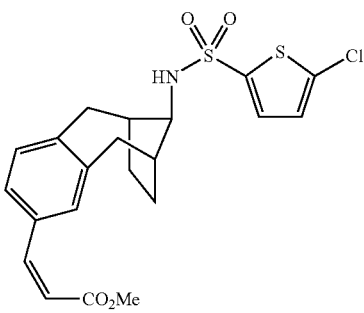

Potassium bis(trimethylsilyl)amide solution (0.48 ml of a 0.5 M solution in toluene) was added dropwise to a solution of 18-crown-6 (150 mg, 0.57 mmol) and bis(2,2,2-trifluoroethyl)(methoxycarbonylmethyl)phosphonate (26 μl, 0.12 mmol) in THF (2 ml) at −78° C. under $N_2$. A solution of the aldehyde described in Example 152 (45 mg, 0.11 mmol) in THF (2 ml) was then added dropwise. The mixture was stirred at −78° C. for 1.5 h and then partitioned between aqueous $NH_4Cl$ solution and $Et_2O$. The layers were separated and the aqueous phase extracted a second time with $Et_2O$. The combined organic extracts were dried ($MgSO_4$) and concentrated. Chromatography on silica (eluting with 20% EtOAc/hexane) provided the title compound as a white solid. $^1H$ NMR ($CDCl_3$, 400 MHz) δ 1.18-1.26 (2H, m), 1.64-1.68 (2H, m), 2.39 (2H, br s), 2.56-2.64 (2H, m), 3.02 (2H, br d, J=16.6 Hz), 3.71 (3H, s), 3.71-3.76 (1H, m), 5.07 (1H, d, J=7.6 Hz), 5.90 (1H, d, J=12.7 Hz), 6.86 (1H, d, J=12.7 Hz), 6.94 (1H, d, J=3.9 Hz), 7.06 (1H, d, J=7.9 Hz), 7.33 (1H, br s), 7.40 (1H, dd, J=7.8, 1.5 Hz), 7.45 (1H, d, J=4.0 Hz).

Example 245 endo-5-chloro-N-{2-[2-(hydroxymethyl)cyclopropyl]-5,6,7,8,9,10-hexahydro-6,9-methanobenzo[a][8]annulen-11-yl}thiophene-2-sulfonamide

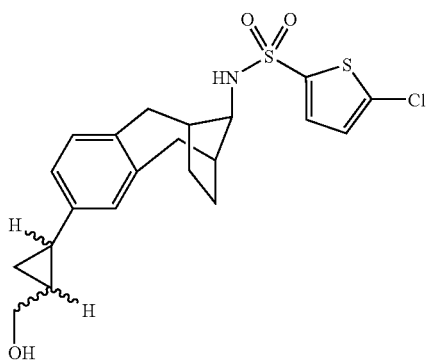

A solution of the allylic alcohol from Example 161 (155 mg, 0.37 mmol) in $CH_2Cl_2$ (10 ml) was placed under $N_2$ and cooled to −15° C. Diethylzinc solution (1.83 ml of a 1.0 M solution in hexanes, 1.83 mmol) was added dropwise with care and this was followed by addition of diiodomethane (0.15 ml, 1.86 mmol). The reaction mixture was allowed to warm to room temperature over 3 h and then stirred for a further 2 h. The reaction mixture was quenched by addition of satd. $NH_4Cl$ solution and then $Et_2O$ and 1M HCl (aq.) were added. The layers were separated and the organic extract washed sequentially with $Na_2SO_3$ (sat. aq.), $NaHCO_3$ (sat. aq.) and brine before being dried ($MgSO_4$) and concentrated. Trituration with $Et_2O$ afforded the cyclopropyl alcohols as a mixture of diastereomers (155 mg, 97%). $^1H$ NMR ($CDCl_3$, 400 MHz) δ 0.87-0.95 (2H, m), 1.15-1.20 (2H, m), 1.37-1.46 (1H, m), 1.61-1.67 (2H, m), 1.73-1.77 (1H, m), 2.34-2.38 (2H, m), 2.49-2.57 (2H, m), 2.93-3.00 (2H, m), 3.61 (2H, d, J=6.7 Hz), 3.75 (1H, app dd, J=13.9, 6.4 Hz), 5.04 (1H, d, J=7.8 Hz), 6.76-6.78 (2H, m), 6.93-6.96 (2H, m), 7.44 (1H, d, J=4.0 Hz).

Example 246 endo-5-Chloro-N-[2-(3-morpholin-4-ylpropoxy)-5,6,7,8,9,10-hexahydro-6,9-methanobenzo[a][8]annulen-11-yl]thiophene-2-sulfonamide

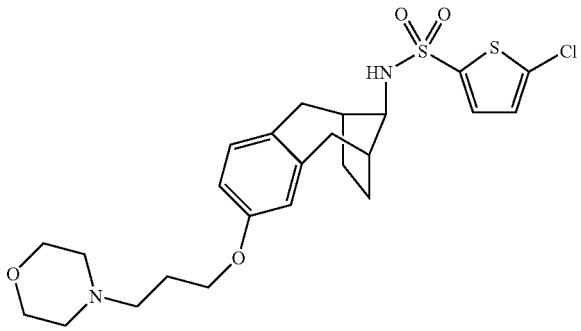

N-(3-Hydroxypropyl)morpholine was prepared as described in *Tetrahedron Letters* 1994, 35, 761. A Mitsunobu reaction with 2-hydroxy-11-oxo-5,6,7,8,9,10-hexahydro-6,9-methanobenzocyclooctene was carried out in an analogous manner to that described in Example 240 step 1. The ketone functionality was converted to the primary amine by oxime formation and reduction as described in the General Procedures. Sulphonylation with 5-chlorothiophene-2-sulphonyl chloride was then carried out as described in Example 1 to give, after trituration with EtOAc/hexane, the title compound as a white solid. $^1H$ NMR ($CDC_3$, 400 MHz) δ 1.15-1.24 (2H, m), 1.61-1.65 (2H, m), 1.91-1.98 (2H, m), 2.31-2.40 (2H, m), 2.46-2.54 (8H, m), 2.97 (2H, dd, J=27.1, 16.1 Hz), 3.71-3.77 (5H, m), 3.97 (2H, t, J=6.3 Hz), 5.18 (1H, d, J=7.8 Hz), 6.60-6.62 (2H, m), 6.90-6.96 (2H, m), 7.44 (1H, d, J=4.0 Hz); m/z 511, 513 ([M+H]$^+$).

Example 247 endo-5-Chloro-thiophene-2-sulfonic acid (3-methoxyimino-bicyclo[3.2.1]oct-8-yl)-amide

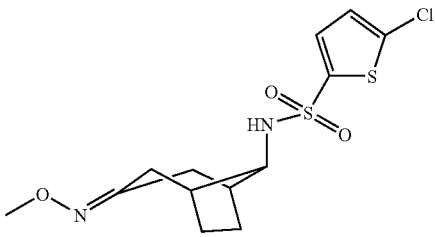

A solution of the endo-5-Chloro-thiophene-2-sulfonic acid (3-oxo-bicyclo[3.2.1]oct-8-yl)-amide (Example 109) (10 mg) in ethanol (0.5 ml) was added to a solution of methoxylamine hydrochloride (8.4 mg) and sodium acetate trihydrate (13.6 mg) in water (0.25 ml) and stirred at room temperature for 18 hours. Water (2 ml) was added and the aqueous layer was extracted with dichloromethane (2×2 ml). The combined organics were evaporated and purified by mass-directed preparative HPLC. m/z 349 (M+H$^+$). $^1H$ NMR (CDCl$_3$, 360 MHz) δ 1.4-1.6 (m, 2 H), 1.7-1.8 (m, 2 H), 2.03-2.35 (m, 4 H), 2.43-2.50 (m, 2 H), 2.90-2.96 (m, 2 H), 3.42-3.47 (m, 1 H), 3.82 (s. 3H), 4.94 (d, 1 H, J=5.4 Hz), 6.94 (d, 1H, J=4.0 Hz), 7.43 (d, 1H, J=4.0 Hz).

Example 248 endo-Butane-1-sulfonic acid (3-methylene-bicyclo[3.2.1]oct-8-yl)-amide

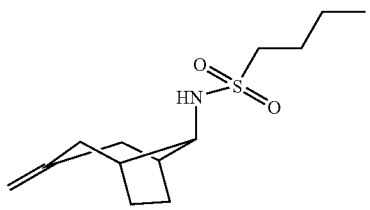

A solution of endo-3-methylene-bicyclo[3.2.1]oct-8-ylamine [Example 108, Step 2] (25 mg, 0.18 mmol) in dichloromethane (0.8 ml) containing N,N-diisopropylethylamine (0.2 ml) was added to a stirred solution of 1-butanesulphonyl chloride in dichloromethane (1 ml) at 0° C. and allowed to warm to room temperature over 18 hours. The solution was evaporated and purified by mass-directed preparative HPLC. m/z 258 (M+H$^+$). $^1$H NMR (CDCl$_3$, 400 MHz) δ 0.96 (s, 3 H, J=7.4 Hz), 1.42-1.52 (m, 2 H), 1.68-1.73 (m, 2 H), 1.78-1.87 (m, 2 H), 1.99-2.04 (m, 2 H), 2.18-2.22 (m, 2 H), 2.38-2.44 (m, 2H), 3.02-3.08 (m, 2H), 3.54-3.60 (m, 1 H), 4.54 (d, 1H, J=7.5 Hz), 4.77-4.80 (m, 2 H).

Following the procedure of Example 248 using the appropriate sulphonyl chloride, the following compounds of formula G were prepared and purified by mass-directed preparative HPLC:

G

| Example | R | m/z (M + H$^+$) |
|---------|---|----------------|
| 249 | phenyl | 278 |
| 250 | 2-thienyl | 284 |
| 251 | 4-methylphenyl | 292 |
| 252 | 4-fluorophenyl | 296 |
| 253 | 2-fluorophenyl | 296 |
| 254 | 3-fluorophenyl | 296 |
| 255 | 4-chlorophenyl | 312 |
| 256 | 4-bromophenyl | 356 |
| 257 | 5-bromo-2-thienyl | 362 |
| 258 | 4-iodophenyl | 404 |

Example 259 endo-5-Chloro-thiophene-2-sulfonic acid (3-benzylidene-bicyclo[3.2.1]oct-8-yl)-amide

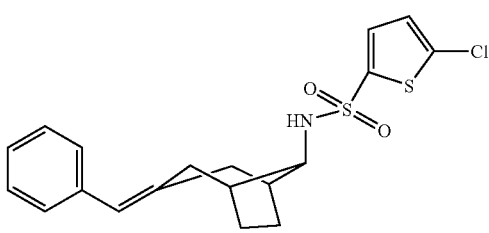

Step 1 endo-3-Methylene-bicyclo[3.2.1]oct-8-ylamine (example 108 step 2) was converted to the BOC derivative as described in Example 207 step 1. This compound (305 mg), tetrabutylammonium chloride (360 mg), sodium hydrogen carbonate (220 mg), iodobenzene (505 mg) and palladium acetate (90 mg) were combined in DMF (10 ml) and heated at 100° C. for 80 hours. The reaction mixture was evaporated and endo-3-benzylidene-bicyclo[3.2.1]oct-8-yl)-carbamic acid tert-butyl ester was isolated, after column chromatography on silica using 10% ethyl acetate in isohexane as the eluant, as a mixture of isomers including the desired compound and endo-(3-benzyl-bicyclo[3.2.1]oct-2-en-8-yl)-carbamic acid tert-butyl ester (220 mg).

Step 2

The product from step 1 (120 mg) in dichloromethane (4 ml) was treated with trifluoroacetic acid (4 ml) and stirred at room temperature for 1 hour. The reaction mixture was evaporated, basified using saturated potassium carbonate solution (4 ml) and extracted using dichloromethane (6×1 ml) The dichloromethane solution was treated with N,N-dimethylethylenediamine (0.4 ml), cooled to 0° C. and treated with 5-chlorothiophene sulphonyl chloride in dichloromethane (2 ml) at 0° C. The reaction mixture was allowed to warm to room temperature over 18 hours. The reaction mixture was washed with 1N hydrochloric acid (2 ml), evaporated and purified by chromatography on silica using 5-10% ethyl acetate in isohexane as eluant followed by mass-directed preparative HPLC to give the desired compound (7.5 mg)

$^1$H NMR (CDCl$_3$, 360 MHz) δ 1.28-1.37 (m, 1 H), 1.50-1.73 (m,3H), 2.0-2.25 (m, 2H) 2.30-2.40 (m, 1H) 2.50-2.56 (m, 1H), 2.61-2.66 (m, 1H), 3.46 (dd, 1H, J1=11.2 Hz, J2=5 Hz), 5.11 (d, J=6.7 Hz), 6.38 (s, 1H), 6.93 (d, 1H, J=4 Hz), 7.15-7.21 (m, 3H), 7.28-7.33 (m, 2H), 7.44 (d, 1H, J=4 Hz).

Example 260 endo-5-Chloro-thiophene-2-sulfonic acid {5-[2-(4-fluorophenoxy)-ethylamino]-tricyclo[8.2.1.0$^{3,8}$]trideca-3(8),4,6-trien-13-yl}-amide

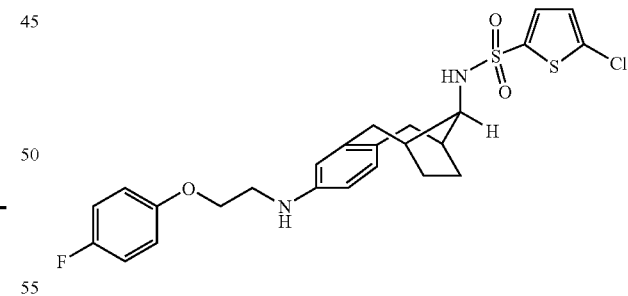

endo-N-[13-(5-Chloro-thiophene-2-sulfonylamino)-tricyclo[8.2.1.0$^{3,8}$]trideca-3(8),4,6-trien-5-yl]-2-(4-fluorophenoxy)-acetamide was prepared by the method of Example 44, substituting 4-fluorophenoxyacetic acid for benzoic acid. The amide (35 mg) was treated with borane-tetrahydrofuran complex in tetrahydrofuran (1M, 1.5 ml) and stirred at room temperature for 18 hours. Methanol (1 ml) was added and the mixture was stirred at room temperature overnight. The reaction mixture was evaporated and purified to give the desired compound (27 mg) by mass-directed preparative HPLC m/z 521 (M+H$^+$). $^1$H NMR (CDCl$_3$, 360 MHz) δ

0.90-1.07 (m, 2H), 1.52-1.60 (m,2H), 2.27-2.45(m,4H), 2.83-2.92 (m,2H), 3.40-3.46 (m, 1H), 3.54-3.66 (m,2H), 4.06-4.18 (m, 2H), 6.20 (br d,1H), 6.82-6.99(m,8H), 7.43 (d, 1H, J=4.1 Hz).

Example 261 endo-5-Chloro-thiophene-2-sulfonic acid {5-[2-(4-chlorophenoxy)-ethylamino]-tricyclo[8.2.1.0$^{3,8}$]trideca-3(8),4,6-trien-13-yl}-amide

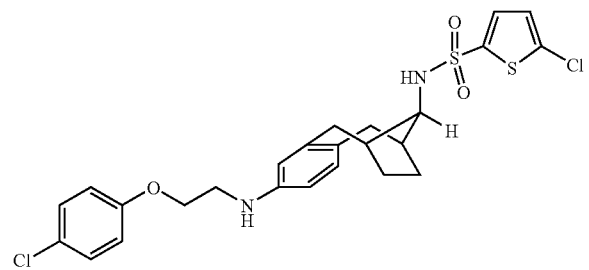

Prepared as for Example 260, using 4-chlorophenoxyacetic acid in the first step, and purified by mass-directed preparative HPLC. m/z 537 (M+H$^+$).

Example 262 endo-5-Chloro-thiophene-2-sulfonic acid {5-[4-(4-fluorophenyl)-piperazin-1-yl]-tricyclo[8.2.1.0$^{3,8}$]trideca-3(8),4,6-trien-13-yl}-amide

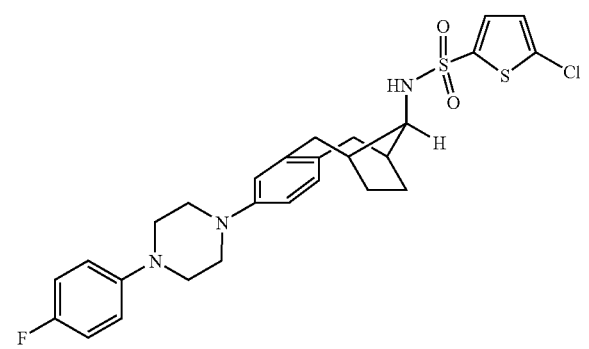

Step 1

5-Amino-tricyclo[8.2.1.0$^{3,8}$]trideca-3(8),4,6-trien-13-one (ref. *J. Org. Chem.*, 1982, 47, 4329-4334) (7.45 g, 37 mmol) in 40% sulphuric acid was cooled to 0° C. and treated with sodium nitrite (3.06 g, 44 mmol) in water (16 ml) keeping the temperature below 5° C. Meanwhile copper(1) bromide (57 g) in water was treated with 48% hydroboinic acid at 0° C. The diazonium solution was added to this solution, keeping the temperature below 5° C. After addition the reaction mixture was allowed to warm to room temperature and stirred at room temperature overnight. Water (500 ml) was added and the aqueous mixture extracted using dichloromethane (9×200 ml). The combined organics were washed with brine (200 ml), dried using sodium sulphate, filtered and the filtrate evaporated. 5-Bromo-tricyclo[8.2.1.0$^{3,8}$]trideca-3(8),4,6-trien-13-one (5.1 g) was purified by column chromatography on silica using 9:1 to 5:1 isohexane:ethyl acetate as the eluant.

Step 2

An oven dried flask was charged with caesium carbonate (912 mg), rac-2,2'-bis(diphenylphospino)-1,1'-binaphthyl (racemic BINAP) (56 mg), and palladium (II) acetate (13.6 mg) and flushed with nitrogen. A solution of the bromo-derivative of step 1 (530 mg, 2 mmol) and 1-(4-fluorophenyl)-piperazine (432 mg, 2.4 mmol) in toluene (4 ml) was added via canula and the mixture degassed using nitrogen. The reaction was stirred at room temperature for 30 minutes and then heated at 80° C. for 18 hours. After cooling to room temperature, ether was added and a precipitate formed. This was filtered and the filtrate was evaporated and purified by column chromatography on silica using 9:1 to 5:1 isohexane:ethyl acetate as the eluant to give 5-[4-(4-fluorophenyl)-piperazin-1-yl]-tricyclo[8.2.1.0$^{3,8}$]trideca-3(8),4,6-trien-13-one (290 mg, 40%). m/z 365 (M+H$^+$).

Step 3

The ketone from step 2 was converted to the oxime as described in Example 107 step 1 and reduced to the amine as described in Example 108 steps 1 and 2. The amine (250 mg, 0.68 mmol) in dichloromethane (2 ml) and pyridine (0.5 ml) was cooled to 0° C. and treated with 5-chlorothiophene sulphonyl chloride (223 mg, 1.03 mmol) followed by a catalytic amount of 4-dimethylaminopyridine. The mixture was allowed to warm to room temperature and stirred at room temperature for 18 hours. Water (25 ml) was added and the aqueous layer extracted using dichloromethane (3×30 ml). The combined organics were dried using sodium sulphate, filtered and the filtrate evaporated to dryness. The residue was purified by column chromatography on silica using 4:1 isohexane:ethyl acetate followed by purification on alumina using 5:1 to 4:1 isohexane: ethyl acetate to give the title compound (124 mg). m/z 546 (M+H$^+$).

$^1$H NMR (CDCl$_3$, 360 MHz) δ 1.20-1.29 (m, 2H), 1.60-1.67 (m,2H), 2.31-2.43(m,4H), 2.51(d,1H,J=16.2 Hz), 2.53 (d,1H,J=16.2 Hz), 2.93 (d,1H,J=16.3 Hz), 3.04(d,1H,J=16.4 Hz), 3.74-3.80 (m,1H), 5.02 (d,1H, J=7.9 Hz), 6.91-7.02(m, 4E), 7.44 (d, 1H, J=4.1 Hz).

Example 263 endo-5-Chloro-thiophene-2-sulfonic acid {5-[4-(2-methoxyphenyl)-piperazin-1-yl]-tricyclo[8.2.1.0$^{3,8}$]trideca-3(8),4,6-trien-13-yl}-amide

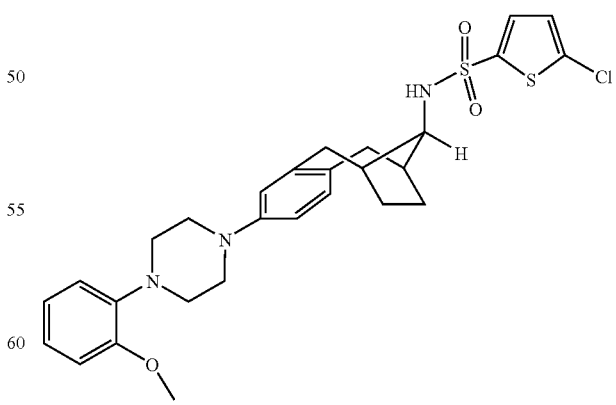

Prepared as for Example 262, using 1-(2-methoxyphenyl)piperazine in step 2, and purified by mass-directed preparative HPLC. m/z 558 (M+H$^+$).

Example 264 endo-5-Chloro-thiophene-2-sulfonic acid [5-(4-pyridin-2-yl-piperazin-1-yl)-tricyclo[8.2.1.0³,⁸]trideca-3(8),4,6-trien-13-yl]-amide

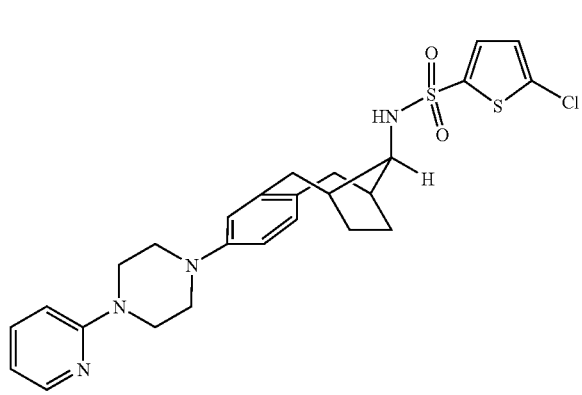

Prepared as for Example 262, using 1-(2-pyridyl)piperazine in step 2, and purified by mass-directed preparative HPLC. m/z 529 (M+H⁺).

Example 265 endo-5-Chloro-thiophene-2-sulfonic acid {5-[2-(4-fluorophenylamino)-ethylamino]-tricyclo[8.2.1.0³,⁸]trideca-3(8),4,6-trien-13-yl}-amide

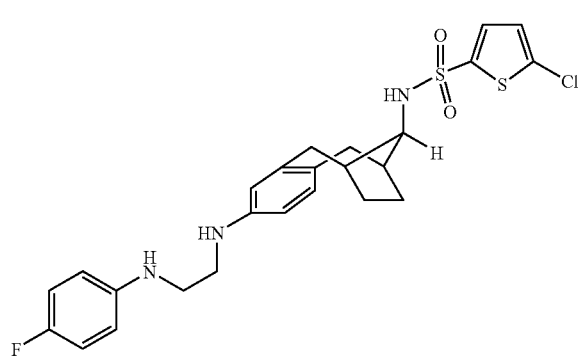

Step 1: Endo-2-[13-(5-chloro-thiophene-2-sulfonylamino)-tricyclo[8.2.1.0³,⁸]trideca-3(8),4,6-trien-5-ylamino]-N-(4-fluorophenyl)-acetamide The amine from Example 128 step (g) (100 mg) in dichloroethane was treated with N,N-diisopropylethylamine (0.4 ml) followed by α-chloro-4-fluoroacetamlide (50 mg) and heated at 65° C. for 40 hours. Further α-chloro-4-fluoroacetamlide (100 mg) was added and the mixture heated for a further 8 days. The mixture was evaporated and purified by column chromatography on silica using 2:1 to 1:1 isohexane: ethyl acetate as the eluant to give the title compound (48 mg) m/z 534 (M+H⁺).

Step 2

The product from Step 1 was reduced to the title compound by the process described in Example 260. m/z 520 (M+H⁺).

Example 266 endo-5-Chloro-thiophene-2-sulfonic acid [5-(2-morpholin-4-ylethylamino) tricyclo[8.2.1.0³,⁸]trideca-3(8),4,6-trien-13-yl]-amide

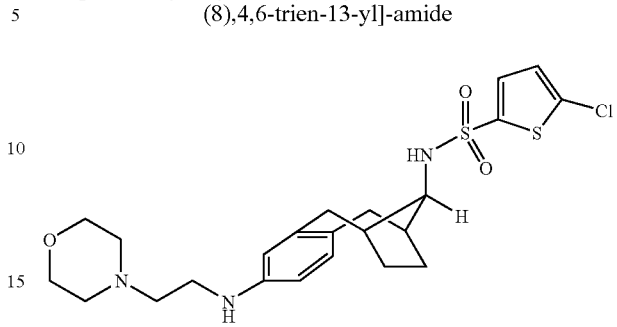

Step 1

The amine from Example 128 step G (100 mg) in dichloroethane was treated with N,N-diisopropylethylamine (0.4 ml) followed by 4-(2-chloroacetyl)morpholine (63 mg, 0.39 mmol) ) in dichloroethane (1 ml) and was heated at 70° C. for 72 hours. The mixture was evaporated and purified by column chromatography on silica using 1:1 isohexane:ethyl acetate as the eluant to give endo-5-chlorothiophene-2-sulfonic acid [5-(2-morpholin-4-yl-2-oxoethyl amino)-tricyclo[8.2.1.0³,⁸]trideca-3(8),4,6-trien-13-yl]-amide (63 mg) m/z 510 (M+H⁺).

Step 2

The product from step 1 was reduced as described in Example 260 to give the title compound. m/z 496 (M+H⁺).

Example 267 endo-Pyridine-3-sulfonic acid (2-hydroxy-2-methyl-tricyclo-[8.2.1.0³,⁸]trideca-3(8),4,6-trien-13-yl)-amide

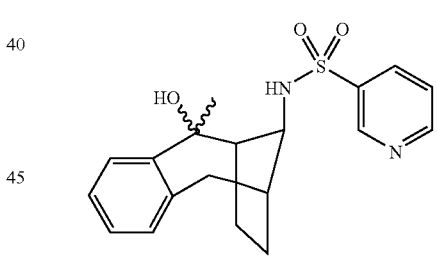

Step 1

Chromium trioxide (2.61 g, 26.12 mmol) was dissolved in a solution of sulfuric acid (100 ml) and water (225 ml). endo-Tricyclo[8.2.1.0³,⁸]trideca-3(8),4,6-trien-13-ylamine (General Procedures) (as the acetic acid salt, 3.23 g, 13.06 mmol) was added, and the mixture was heated to reflux for 2.5 h. After cooling in an ice-water bath, sodium hydroxide (73 g, 1.83 mol) was added slowly over 30 min [CARE!], and ammonium hydroxide was added to pH 10. The mixture was extracted with DCM (3×120 ml), the combined organic extracts were dried (Na₂SO₄) and concentrated under reduced pressure to give a yellow oil (1.77 g), which was converted to the BOC derivative as follows:

The crude amino ketone (1.77 g) was dissolved in DCM (30 ml), and di-tertbutyldicarbonate (9.60 g, 43.97 mmol), triethylamine (2.45 ml, 17.59 mmol) and DMAP (100 mg) were added. After stirring at room temperature for 96 h, the mixture was quenched with 1 M HCl (10 ml). The aqueous phase was extracted with DCM (3×20 ml) and the combined organic phases were washed with saturated NaHCO₃ (aq), dried (Na₂SO₄) and concentrated under reduced pressure. The orange oil was purified by flash chromatography (isohexane/diethyl ether 7:3) to give endo-(2-oxo-tricyclo[8.2.1.0³,⁸]trideca-3(8),4,6-trien-13-yl)-carbamic acid tert-butyl ester as a white foam (920 mg, 23%). m/z 202.

Step 2

The product of step 1 (920 mg, 3.05 mmol) was treated with TFA (10 ml) in DCM (15 ml) for 1 h. The volatiles were removed under reduced pressure, and the residue was dissolved in DCE (15 ml). Thiethylamine (1.27 ml, 9.16 mmol), DMAP (50 mg), and 3-pyridylsulfonyl chloride were added, and the mixture was heated to reflux for 16 h. After cooling to room temperature, the precipitate was filtered, washing the residue with EtOAc (50 ml). The filtrate was concentrated, and the orange oil was subjected to flash chromatography (gradient elution from EtOAc/isohexane 1:1 to 1:0) to give endo-pyridine-3-sulfonic acid (2-oxo-tricyclo[8.2.1.0³,⁸]trideca-3(8),4,6-trien-13-yl)-amide as a white solid (334 mg, 30%). m/z 343 (M+H)⁺.

Step 3

To a stirred suspension of the product of step 2 (150 mg, 0.44 mmol) in THF (20 ml) was added 3 M MeMgBr in diethyl ether (409 µl, 1.23 mmol). The mixture was heated to reflux for 3 h and then quenched with EtOH (1 ml). The volatiles were removed under reduced pressure and the residue was partitioned between pH 7 buffer (10 ml) and EtOAc (20 ml). The aqueous phase was extracted with EtOAc (4×20 ml) and the combined organic phases were washed with brine (30 ml), dried (Na₂SO₄) and concentrated to dryness. Purification by flash chromatography (gradient elution from EtOAc/isohexane 2:3-1:0) gave white solids: Major diastereoisomer (110 mg, 70%). ¹H NMR (CDCl₃, 360 MHz) δ 9.16 (1H, s), 8.77-8.79 (1H, m), 8.26-8.20 (11H, m), 7.91 (2H, d, J=8.5 Hz), 7.49 (1H, dd, J=8.0, 4.9 Hz), 7.31 (1H, dd, J=6.8, 1.9 Hz), 7.19-7.10 (2H, m), 3.74-3.69 (1H, m), 3.54 (1H, d, J=15.5 Hz), 2.52 (1H, dd, J=15.5, 8.2 Hz), 2.41-2.35 (1H, m), 2.05 (1H, t, J=6.6 Hz), 1.91-1.67 (4H, br s), 1.47-1.57 (2H, m), 1.06-0.99 (1H, m), 0.81-0.74 (1H, m). m/z 359 (M+H)⁺.

Minor diastereoisomer (11 mg, 7%). 1H NMR (CDCl₃, 360 MHz) δ 9.15 (1H, s), 8.77-8.79 (1H, m), 8.23-8.20 (1H, m), 7.72 (1H, dd, J=7.8, 1.0 Hz), 7.51 (1H, dd, J=8.0, 4.9 Hz), 7.22 (1H, t, J=7.5 Hz), 7.12 (1H, td, 7.4, 1.2 Hz), 7.01 (1H, d, J=7.4 Hz), 5.22 (1H, d, J=7.5 Hz), 3.68-3.63 (1H, m), 3.04 (1H, d, J=16.2 Hz), 2.62 (1H, dd, J=16.1, 7.9 Hz), 2.38-2.30 (2H, m), 1.90 (1H, br s), 1.68-1.61 (2H, m), 1.58 (3H, m), 1.22-1.13 (2H, m). m/z 359, (M+H)⁺.

Example 268 endo-Pyridine-3-sulfonic acid (2-methylene-tricyclo[8.2.1.0³,⁸]-trideca-3(8),4,6-trien-13-yl)-amide

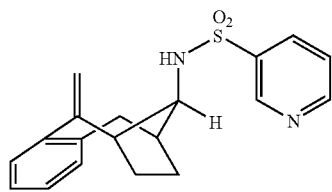

The product from Example 267 (20 mg, 55.8 µmol) was treated with TFA (1 ml) in DCM (5 ml) for 1 h. Concentration under reduced pressure gave a yellow foam, which was dissolved in DCM (20 ml) and washed with saturated NaHCO₃ (aq) (10 ml). The aqueous phase was extracted with DCM (2×20 mL) and the combined organic phases were dried (Na₂SO₄) and concentrated under reduced pressure to give a cream solid which was purified by flash chromatography (eluent: EtOAc/isohexane 1:1) to give a white solid (17 mg, 89%). ¹H NMR (CDCl₃, 360 MHz) δ 9.16 (1H, s), 8.77-8.79 (1H, m), 8.23-8.20 (1H, m), 7.49 (1H, dd, J=8.0, 4.9 Hz), 7.22-7.14 (3H, m), 7.08-7.04 (1H, m), 5.22 (1H, d, J=1.7 Hz), 5.08 (1H, d, J=8.8 Hz), 4.89 (1H, d, J=1.7 Hz), 3.84-3.79 (1H, m), 2.95 (1H, d, J=15.9 Hz), 2.76 (1H, t, J=6.8 Hz), 2.48 (1H, dd, J=15.9, 7.2 Hz), 2.41-2.35 (1H, m), 1.80-1.69 (2H, m), 1.13-1.35 (2H, m). m/z 341 (M+H)⁺.

Example 269 endo-5-Chloro-thiophene-2-sulfonic acid {6-[2-(4-fluoro-phenoxy)-ethoxy]-2-oxo-tricyclo[8.2.1.0³,⁸]trideca-3(8),4,6-trien-13-yl}-amide

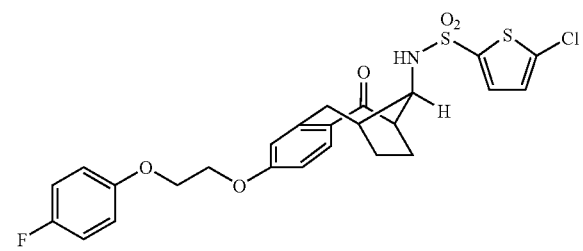

The product of Example 225 was oxidised to the title compound using chromium trioxide in sulphuric acid as described in Example 267 step 1. The product was purified by flash chromatography (gradient elution from EtOAc/isohexane 1:4-1:1) to give a white foam (41 mg, 35%). ¹H NMR (CDCl₃, 360 MHz) δ 7.51 (1H, d, J=8.6 Hz), 7.46 (1H, d, J=4.0 Hz), 7.02-6.95 (3H, m), 6.91-6.85 (2H, m), 6.80 (1H, dd, 8.6, 2.4 Hz), 6.72 (1H, d, J=2.2 Hz), 5.27 (1H, d, J=6.2 Hz), 4.35-4.27 (4H, m), 3.90-3.85 (1H, m), 3.39 (1H, d, J=15.0 Hz), 2.99 (1H, t, J=7.7 Hz), 2.80-2.73 (2H, m), 2.04-1.95 (1H, m), 1.92-1.82 (1H, m), 1.77-1.59 (2H, m). m/z 536 (M+H)⁺.

Example 270 endo-Pyridine-3-sulfonic acid {6-[2-(4-fluoro-phenoxy)-ethoxy]-2-oxo-tricyclo[8.2.1.0³,⁸]trideca-3(8),4,6-trien-13-yl}-amide

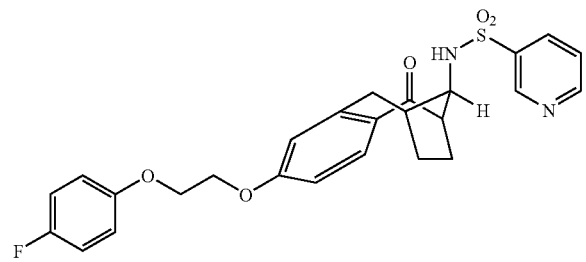

Prepared by oxidation of the product of Example 223 as described in

Example 269. Purification by flash chromatography (eluant: EtOAc/isohexane 1:1) gave a white solid. m/z=497 (M+H)⁺.

Example 271

Pyridine-3-sulfonic acid (6-[2-(4-fluoro-phenoxy)-ethoxy]-2-hydroxy-tricyclo[8.2.1.0^{3,8}]trideca-3(8),4,6-trien-13-yl)-amide

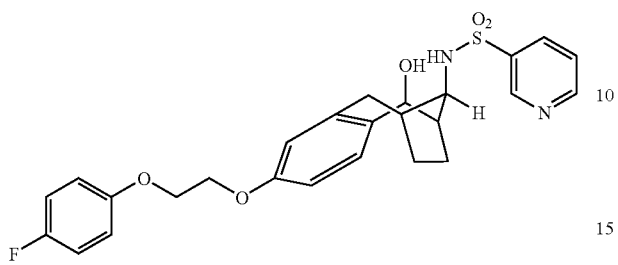

The product from Example 270 (18 mg, 36.2 μmol) in methanol (5 ml) was treated with NaBH$_4$ (22 mg, 0.59 mmol) at room temperature for 3 h. The solvent was removed under reduced pressure and the residue was partitioned between EtOAc (10 ml) and pH 7 buffer (5 ml). The aqueous phase was extracted with EtOAc (3×10 ml), and the combined organic phases were washed (brine), dried (Na$_2$SO$_4$) and concentrated under reduced pressure to give a white solid. Purification by flash chromatography (gradient elution from EtOAc/isohexane 1:1-1:0) gave a white solid (13.7 mg, 76%). $^1$H NMR (CDCl$_3$, 360 MHz) δ 9.15 (1H, s), 8.78-8.81 (1H, m), 8.24-8.21 (1H, m), 7.74 (1H, d, J=7.4 Hz), 7.48 (1H, dd, J=7.9, 4.8 Hz), 7.05-6.95 (3H, m), 6.91-6.87 (2H, m), 6.75-6.69 (2H, m), 4.78 (1H, d, J=6.8 Hz), 4.28 (4H, s), 3.79-3.73 (11, m), 3.50 (1H, d, J=14.8 Hz), 2.56-2.38 (3H, m), 1.73-1.48 (2H, m), 1.25-1.17 (2H, m), 0.93-0.88 (1H, m). m/z 499 (M+H)$^+$.

Example 272 endo-Pyridine-3-sulfonic acid {6-[2-(4-fluoro-phenoxy)-ethoxy]-2-methyl-tricyclo[8.2.1.0^{3,8}]trideca-3(8),4,6-trien-13-yl}-amide

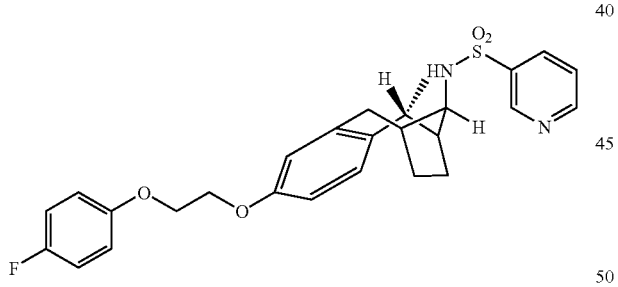

Step 1 endo-5-[2-(4-Fluoro-phenoxy)-ethoxy]-tricyclo[8.2.1.0^{3,8}]trideca-3(8),4,6-trien-13-ylamine (1.00 g, 2.93 mmol) (Example 209 step 2) was oxidised to the 2-oxo derivative by the procedure of Example 267 step 1. Trituration of the crude product with Et$_2$O furnished a cream solid (282 mg, 27%). m/z 356 (M+H)$^+$.

Step 2

To a stirred suspension of Ph$_3$PCH$_3$Br (377 mg, 1.06 mmol) in anhydrous dioxane (3.5 ml) at 0° C. was added, dropwise, 1.6 M n-BuLi in diethyl ether (555 μl, 0.88 mmol). Stirring was continued for a further 30 min., prior to warming to room temperature. The ketone from step 1 (150 mg, 0.423 mmol) was added, and after stirring at room temperature for a further 30 min., the mixture was heated to reflux for 90 min., and then stirred at room temperature for a further 16 h. The solvent was removed under reduced pressure, and the residue was partitioned between CHCl$_3$ (20 ml) and water (10 ml). The layers were separated and the aqueous phase was extracted with CHCl$_3$ (4×20 ml), and the combined organic phases were dried (Na$_2$SO$_4$) and concentrated to give an orange oil. Purification by flash chromatography (CHCl$_3$/MeOH/ammonium hydroxide 95:3:0.3) gave the 2-methylene derivative as a cream solid (115 mg, 77%). m/z 354 (M+H)$^+$.

Step 3

The product of step 2 (25 mg, 70.7 μmol) and 10% Pd/C (25 mg) were stirred in methanol (3 ml) under an atmosphere of H$_2$ for 4 h. The mixture was filtered and concentrated under reduced pressure to give the 2-methyl derivative as a white solid (25 mg, 100%). Sulfonylation of this compound with pyridine-3-sulfonyl chloride by the procedure of Example 1 gave the title compound. $^1$H NMR (CDCl$_3$, 400 MHz) δ9.17 (1H, d, J=2.0 Hz), 8.84 (1H, s), 8.24-8.21 (1H, m), 7.52-7.48 (1H, m), 7.04 (1H, d, J=8.5 Hz), 6.99-6.95 (2H, m), 6.90-6.86 (2H, m), 6.71 (1H, dd, J=8.5, 2.8 Hz), 6.66 (1H, d, J=2.8 Hz), 5.42 (1H, d, J=6.9 Hz), 4.26 (4H, s), 3.66-3.61 (1H, m), 3.04-2.99 (2H, m), 2.44-2.38 (1H, m), 2.26 (1H, q, J=7.1 Hz), 1.98 (1H, t, J=6.4 Hz), 1.55-1.35 (2H, m), 1.11 (3H, d, J=7.1 Hz), 1.10-1.03 (1H, m), 0.96-0.88 (1H, m). m/z 497 (M+H)$^+$.

Example 273 endo-Pyridine-3-sulfonic acid {6-[2-(4-fluoro-phenoxy)-ethoxy]-2-methylene-tricyclo[8.2.1.0^{3,8}]trideca-3(8),4,6-trien-13-yl}amide

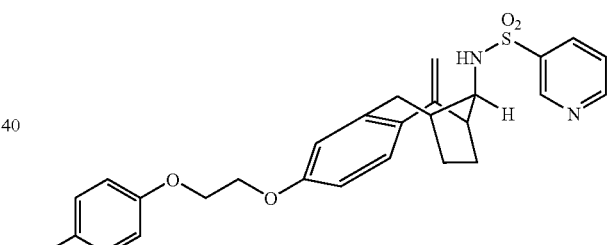

Prepared by reacting the product of Example 272 step 2 with pyridine-3-sulfonyl chloride by the procedure of Example 1. m/z 495 (M+H)$^+$.

Example 274

Enantiomers of endo-5-chloro-thiophene-2-sulfonic acid [5-(3-morpholin-4-yl-propenyl)-tricyclo[8.2.1.0^{3,8}]trideca-3(8),4,6-trien-13-yl]-amide

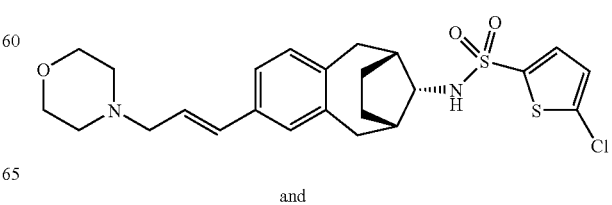

and

-continued

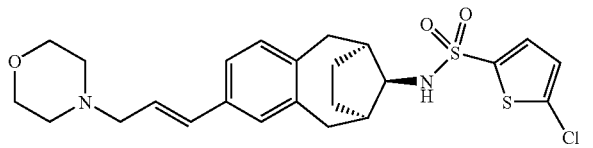

A 25 mg/ml solution in ethanol of racemic endo-5-chloro-thiophene-2-sulfonic acid [5-(3-morpholin-4-yl-propenyl)-tricyclo[8.2.1.0$^{3,8}$]trideca-3(8),4,6-trien-13-yl]-amide (Example 191) was purified by chiral HPLC. The HPLC system was a Chiralcel OD column (250×10 mm i.d.), using 8% ethanol in isohexane, with a flow rate of 5 ml/min and detection at 260 nm. Loadings of 80 μl onto the column (i.e. 2 mg of material) were achieved The two enantiomers were eluted with retention times of 15 minutes for enantiomer A and 22 minutes for enantiomer B. Enantiomer A TFA salt: $^1$H NMR (CDCl$_3$, 400 MHz) δ 7.45 (1 H, d, J=3.9 Hz), 7.10 (2 H, m), 7.04 (1 H, d, J=7.6 Hz), 6.95 (1 H, d, J=4.0 Hz), 6.66 (1 H, d, J=15.9 Hz), 6.13-6.21 (1 H, m), 5.15 (1 H, br d, J=7.2 Hz), 3.99 (4 H, m), 3.78 (2 H, d, J=7.4 Hz), 3.72 (1 H, m), 3.56 (2H, m), 3.04(21H, m), 2.87 (2 H, m), 2.55-2.63 (2 H, m), 2.42 (2 H, m), 1.67 (2 H, m), 1.17 (2 H, m). m/z 493/495 (M+H$^+$).

Enantiomer B TFA salt: $^1$H NMR (CDCl$_3$, 400 MHz) δ 7.45 (1 H, d, J=3.9 Hz), 7.10 (2 H, m), 7.04 (1 H, d, J=7.9 Hz), 6.95 (1 H, d, J=3.9 Hz), 6.67(1 H, d, J=15.6 Hz), 6.14-6.23 (1 H, m), 5.20 (1 H, br d, J=7.2 Hz), 3.99 (4 H, m), 3.78 (2 H, br d, J=6.9 Hz), 3.72 (1 H, m), 3.56 (2 H, m), 3.04 (2 H, m), 2.87 (2 H, m), 2.55-2.63 (2 H, m), 2.41 (2 H, m), 1.66 (2 H, m), 1.17 (2 H, m). m/z 493/495 (M+H$^+$).

What is claimed is:

1. A compound of formula II:

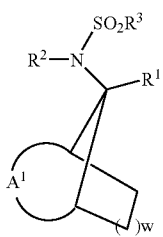

II wherein:
w is 1 or 2; and
A$^1$ represents —CH$_2$CH$_2$CH$_2$CH$_2$—, —CH$_2$CH=CHCH$_2$— or —CH$_2$CXYCH$_2$—;
X represents halogen, R$^9$, —OR$^9$, —SR$^9$, —S(O)$_t$R$^{10}$ where t is 1 or 2, —OSO$_2$R$^9$, —N(R$^9$)$_2$, —COR$^9$, —CO$_2$R$^9$, —OCOR$^{10}$, —OCO$_2$R$^{10}$, —CON(R$^9$)$_2$, —SO$_3$N(R$^9$)$_2$, —OSO$_2$N(R$^9$)$_2$, —NR$^9$COR$^{10}$, —NR$^9$CO$_2$R$^{10}$ or —NR$^9$SO$_2$R$^{10}$;
Y represents H or C$_{1-6}$alkyl;
or X and Y together represent =O, =S, =N—OR$^{11}$ or =CHR$^{11}$;
R$^1$ represents H, C$_{1-4}$alkyl, or C$_{2-4}$alkenyl;
R$^2$ represents H;
R$^3$ represents C$_{1-16}$alkyl, C$_{3-10}$cycloalkyl, C$_{2-16}$alkenyl, C$_{2-16}$alkynyl, C$_{6-10}$arylC$_{1-6}$alkyl, heteroarylC$_{1-6}$alkyl, C$_{6-10}$arylC$_{2-6}$alkenyl, heteroarylC$_{2-6}$alkenyl, C$_{6-10}$aryl, bi(C$_{6-10}$aryl), heteroaryl, bi(heteroaryl) or heterocyclyl; wherein the alkyl, cycloalkyl, alkenyl and alkynyl groups represented by R$^3$ or forming part of a group represented by R$^3$ optionally bear up to 3 substituents independently selected from halogen, CN, NO$_2$, —OR$^7$, —SR$^7$, —S(O)$_t$R$^8$ where t is 1 or 2, —N(R$^7$)$_2$, —COR$^7$, —CO$_2$R$^7$, —OCOR$^8$, —CON(R$^7$)$_2$, —NR$^7$COR$^8$, —C$_{1-6}$alkylNR$^7$COR$^8$, —NR$^7$CO$_2$R$^8$ and —NR$^7$SO$_2$R$^8$; and the aryl, heteroaryl and heterocyclic groups represented by R$^3$ or forming part of a group represented by R$^3$ optionally bear up to 5 substituents independently selected from R$^8$, halogen, CN, NO$_2$, —OR$^7$, —SR$^7$, —S(O)$_t$R$^8$ where t is 1 or 2, —N(R$^7$)$_2$, —COR$^7$, —CO$_2$R$^7$, —OCOR$^8$, —CON(R$^7$)$_{2,7}$, —NR$^7$COR$^8$, —C$_{1-6}$alkylNR$^7$COR$^8$, —NR$^7$CO$_2$R$^8$ and —NR$^7$SO$_2$R$^8$;
R$^7$ represents H or R$^8$; or two R$^7$ groups together with a nitrogen atom to which they are mutually attached may complete a pyrrolidine, piperidine, piperazine or morpholine ring;
R$^8$ represents C$_{1-10}$alkyl, perfluoroC$_{1-6}$alkyl, C$_{3-10}$cycloalkyl, C$_{3-6}$cycloalkylC$_{1-6}$alkyl, C$_{2-10}$alkenyl, C$_{2-10}$alkynyl, Ar or —C$_{1-6}$alkylAr;
R$^9$ represents H or R$^{10}$; or two R$^9$ groups together with a nitrogen atom to which they are mutually attached may complete a pyrrolidine, piperidine, piperazine or morpholine ring which is optionally substituted by R$^{12}$, —COR$^{12}$ or —SO$_2$R$^{12}$;
R$^{10}$ represents C$_{1-10}$alkyl, perfluoroC$_{1-6}$alkyl, C$_{3-10}$cycloalkyl, C$_{3-6}$cycloalkylC$_{1-6}$alkyl, C$_{2-10}$alkenyl, C$_{2-10}$alkynyl, C$_{6-10}$aryl, heteroaryl, heterocyclyl, C$_{6-10}$arylC$_{1-6}$alkyl, heteroarylC$_{1-6}$alkyl, C$_{6-10}$arylC$_{2-6}$alkenyl, or heteroarylC$_{2-10}$alkenyl, wherein the alkyl, cycloalkyl, alkenyl and alkynyl groups optionally bear one substituent selected from halogen, CF$_3$, NO$_2$, CN, —OR$^{11}$, —SR$^{11}$, —SO$_2$R$^{12}$, —COR$^{11}$, —CO$_2$R$^{11}$, —CON(R$^{11}$)$_2$, —OCOR$^{12}$, —N(R$^{11}$)$_2$ and —NR$^{11}$COR$^{12}$; and the aryl, heteroaryl and heterocyclic groups optionally bear up to 3 substituents independently selected from halogen, NO$_2$, CN, R$^{12}$, —OR$^{11}$, —SR$^{11}$, —SO$_2$R$^{12}$, —COR$^{11}$, —CO$_2$R$^{11}$, —CON(R$^{11}$)$_2$, —OCOR$^{12}$, —N(R$^{11}$)$_2$ and —NR$^{11}$COR$^{12}$;
R$^{11}$ represents H, C$_{1-6}$alkyl, perfluoroC$_{1-6}$alkyl, C$_{3-7}$cycloalkyl, C$_{2-6}$alkenyl, C$_{2-6}$alkynyl, Ar, —C$_{1-6}$alkylAr or ArOC$_{1-6}$alkyl;
R$^{12}$ represents C$_{1-6}$alkyl, perfluoroC$_{1-6}$alkyl, C$_{3-7}$cycloalkyl, C$_{2-6}$alkenyl, C$_{2-6}$alkynyl, Ar, —C$_{1-6}$alkylAr or ArOC$_{1-6}$alkyl; or two R$^{12}$ groups together with a nitrogen atom to which they are mutually attached may complete a heterocyclic ring system selected from the group consisting of pyrrolidine, piperidine, piperazine, morpholine, thiomorpholine, 2,5-diazabicyclo[2.2.1]heptane and 2-aza-5-oxabicyclo[2.2.1]heptane, said ring system bearing 0-2 substituents selected from halogen, CN, NO$_2$, C$_{1-6}$alkyl, perfluoroC$_{1-6}$alkyl, C$_{3-7}$cycloalkyl, C$_{2-6}$alkenyl, C$_{2-6}$alkynyl, Ar, —C$_{1-6}$alkylAr or ArOC$_{1-6}$alkyl, OR$^{11}$, NHR$^{11}$, and COR$^{11}$;
Z$^2$ completes an imidazole ring;
X represents halogen, R$^9$, —OR$^9$, —SR$^9$, —S(O)$_t$R$^{10}$ where t is 1 or 2, —OSO$_2$R$^9$, —N(R$^9$)$_2$, —COR$^9$, —CO$_2$R$^9$, —OCOR$^{10}$, —OCO$_2$R$^{10}$, —CON(R$^9$)$_2$, —SO$_3$N(R$^9$)$_2$, —OSO$_2$N(R$^9$)$_2$, —NR$^9$COR$^{10}$, —NR$^9$CO$_2$R$^{10}$ or —NR$^9$SO$_2$R$^{10}$;
Y represents H or C$_{1-6}$alkyl;
or X and Y together represent =O, =S, =N—OR$^{11}$ or =CHR$^{11}$;
R$^1$ represents H, C$_{1-4}$alkyl, or C$_{2-4}$alkenyl;
R$^2$ represents H;
R$^3$ represents C$_{1-16}$alkyl, C$_{3-10}$cycloalkyl, C$_{2-16}$alkenyl, C$_{2-16}$alkynyl, C$_{6-10}$arylC$_{1-6}$alkyl, heteroarylC$_{1-6}$alkyl, C$_{6-10}$arylC$_{2-6}$alkenyl, heteroarylC$_{2-6}$alkenyl, C$_{6-10}$aryl, bi(C$_{6-10}$aryl), heteroaryl, bi(heteroaryl) or heterocyclyl; wherein the alkyl, cycloalkyl, alkenyl and alkynyl groups represented by $R^3$ or forming part of a group represented by $R^3$ optionally bear up to 3 substituents independently selected from halogen, CN, NO$_2$, —OR$^7$, —SR$^7$, —S(O)$_t$R$^8$ where t is 1 or 2, —N(R$^7$)$_2$, —COR$^7$, —CO$_2$R$^7$, —OCOR$^8$, —CON(R$^7$)$_2$, —NR$^7$COR$^8$, —C$_{1-6}$alkylNR$^7$COR$^8$, —NR$^7$CO$_2$R$^8$ and —NR$^7$SO$_2$R$^8$; and the aryl, heteroaryl and heterocyclic groups represented by $R^3$ or forming part of a group represented by $R^3$ optionally bear up to 5 substituents independently selected from $R^8$, halogen, CN, NO$_2$, —OR$^7$, —SR$^7$, —S(O)$_t$R$^8$ where t is 1 or 2, —N(R$^7$)$_2$, —COR$^7$, —CO$_2$R$^7$, —CON(R$^7$)$_2$, —NR$^7$COR$^8$, —C$_{1-6}$alkylNR$^7$COR$^8$, —NR$^7$CO$_2$R$^8$ and —NR$^7$SO$_2$R$^8$;

$R^7$ H or $R^8$; or two $R^7$ groups together with a nitrogen atom to which they are mutually attached may complete a pyrrolidine, piperidine, piperazine or morpholine ring;

$R^8$ represents C$_{1-10}$alkyl, perfluoroC$_{1-6}$alkyl, C$_{3-10}$cycloalkyl, C$_{3-6}$cycloalkylC$_{1-6}$alkyl, C$_{2-10}$alkenyl, C$_{2-10}$alkynyl, Ar or —C$_{1-6}$alkylAr;

$R^9$ H or $R^{10}$; or two $R^9$ groups together with a nitrogen atom to which they are mutually attached may complete a pyrrolidine, piperidine, piperazine or morpholine ring which is optionally substituted by $R^{12}$, —COR$^{12}$ or —SO$_2$R$^{12}$;

$R^{10}$ represents C$_{1-10}$alkyl, perfluoroC$_{1-6}$alkyl, C$_{3-10}$cycloalkyl, C$_{3-6}$cycloalkylC$_{1-6}$alkyl, C$_{2-10}$alkenyl, C$_{2-10}$alkynyl, C$_{6-10}$aryl, heteroaryl, heterocyclyl, C$_{6-10}$arylC$_{1-6}$alkyl, heteroarylC$_{1-6}$alkyl, C$_{6-10}$arylC$_{2-6}$alkynyl, or heteroarylC$_{2-6}$alkenyl, wherein the alkyl, cycloalkyl, alkenyl and alkynyl groups optionally bear one substituent selected from halogen, CF$_3$, NO$_2$, CN, —OR$^{11}$, —SR$^{11}$, —SO$_2$R$^{12}$, —COR$^{11}$, —CO$_2$R$^{11}$, —CON(R$^{11}$)$_2$, —OCOR$^{12}$, —N(R$^{11}$)$_2$ and —NR$^{11}$COR$^{12}$; and the aryl, heteroaryl and heterocyclic groups optionally bear up to 3 substituents independently selected from halogen, NO$_2$, CN, $R^{12}$, —OR$^{11}$, —SR$^{11}$, —SO$_2$R$^{12}$, —COR$^{11}$, —CO$_2$R$^{11}$, —CON(R$^{11}$)$_2$, —OCOR$^{12}$, —N(R$^{11}$)$_2$ and —NR$^{11}$COR$^{12}$;

$R^{11}$ represents H, C$_{1-6}$alkyl, perfluoroC$_{1-6}$alkyl, C$_{3-7}$cycloalkyl, C$_{2-6}$alkenyl, C$_{2-6}$alkynyl, Ar, —C$_{1-6}$alkylAr or ArOC$_{1-6}$alkyl;

Ar represents phenyl or heteroaryl either of which optionally bears up to 3 substituents independently selected from halogen, CF$_3$, NO$_2$, CN, OCF$_3$, C$_{1-6}$alkyl and C$_{1-6}$alkoxy;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom is other than C;

or a pharmaceutically acceptable salt thereof.

2. A compound according to claim 1 wherein w is 1; $R^1$ and $R^2$ are both H; Y is H or together with X represents =O, =N—OR$^{11}$ or =CH$_2$; and X is selected from H, C$_{1-6}$alkyl, —CO$_2$R$^9$, —OCOR$^{10}$, —OCO$_2$R$^{10}$, —OSO$_2$R$^9$, and —CON(R$^9$)$_2$, or together with Y represents =O, =N—OR$^{11}$ or =CH$_2$.

3. A compound of formula IIA:

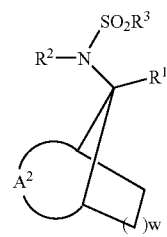

IIA wherein:
w is 1 or 2; and
$A^2$ represents —CH$_2$—NR$^{13}$—CXY—CH$_2$— or

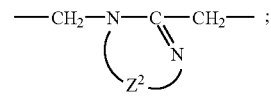

$R^{12}$ represents C$_{1-6}$alkyl, perfluoroC$_{1-6}$alkyl, C$_{3-7}$cycloalkyl, C$_{2-6}$alkenyl, C$_{2-6}$alkynyl, Ar, —C$_{1-6}$alkylAr or ArOC$_{1-6}$alkyl; or two $R^{12}$ groups together with a nitrogen atom to which they are mutually attached may complete a heterocyclic ring system selected from the group consisting of pyrrolidine, piperidine, piperazine, morpholine, thiomorpholine, 2,5-diazabicyclo[2.2.1]heptane and 2-aza-5-oxabicyclo[2.2.1]heptane, said ring system bearing 0-2 substituents selected from halogen, CN, NO$_2$, C$_{1-6}$alkyl, perfluoroC$_{1-6}$alkyl, C$_{3-7}$cycloalkyl, C$_{2-6}$alkenyl, C$_{2-6}$alkynyl, Ar, —C$_{1-6}$alkylAr or ArOC$_{1-6}$alkyl, OR$^{11}$, NHR$^{11}$, and COR$^{11}$;

$R^{13}$ represents $R^9$, —COR$^{10}$, —CO$_2$R$^{10}$, —SO$_2$R$^{10}$, —CON(R$^9$)$_2$ or —SO$_2$N(R$^9$)$_2$;

Ar represents phenyl or heteroaryl either of which optionally bears up to 3 substituents independently selected from halogen, CF$_3$, NO$_2$, CN, OCF$_3$, C$_{1-6}$alkyl and C$_{1-6}$alkoxy;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom is other than C;

or a pharmaceutically acceptable salt thereof.

4. A compound of formula III:

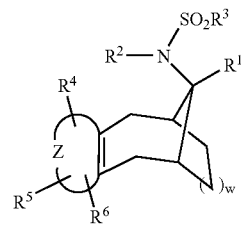

III wherein w is 1 or 2;
Z completes an aromatic ring;
$R^1$ represents H, C$_{1-4}$alkyl, or C$_{2-4}$alkenyl;

$R^2$ represents H;

$R^3$ represents $C_{1-16}$alkyl, $C_{3-10}$cycloalkyl, $C_{2-16}$alkenyl, $C_{2-16}$alkynyl, $C_{6-10}$aryl$C_{1-6}$alkyl, heteroaryl$C_{1-6}$alkyl, $C_{6-10}$aryl$C_{2-6}$alkenyl, heteroaryl$C_{2-6}$alkenyl, $C_{6-10}$aryl, bi($C_{6-10}$aryl), heteroaryl, bi(heteroaryl) or heterocyclyl; wherein the alkyl, cycloalkyl, alkenyl and alkynyl groups represented by $R^3$ or forming part of a group represented by $R^3$ optionally bear up to 3 substituents independently selected from halogen, CN, $NO_2$, $-OR^7$, $-SR^7$, $-S(O)_tR^8$ where t is 1 or 2, $-N(R^7)_2$, $-COR^7$, $-CO_2R^7$, $-OCOR^8$, $-CON(R^7)_2$, $-NR^7COR^8$, $-C_{1-6}$alkyl$NR^7COR^8$, $-NR^7CO_2R^8$ and $-NR^7SO_2R^8$; and the aryl, heteroaryl and heterocyclic groups representented by $R^3$ or forming part of a group represented by $R^3$ optionally bear up to 5 substituents independently selected from $R^8$, halogen, CN, $NO_2$, $-OR^7$, $-SR^7$, $-S(O)_tR^8$ where t is 1 or 2, $-N(R^7)_2$, $-COR^7$, $-CO_2R^7$, $-OCOR^8$, $-CON(R^7)_2$, $-NR^7COR^8$, $-C_{1-6}$alkyl$NR^7COR^8$, $-NR^7CO_2R^8$ and $-NR^7SO_2R^8$, wherein the $R^3$ heteroaryl group is a cyclic or polycyclic system of up to 10 ring atoms selected from C, N, O and S, wherein at least one of the constituent rings is aromatic and wherein at least one ring atom is other than C;

$R^4$, $R^5$ and $R^6$ independently represent $R^9$, halogen, CN, $NO_2$, $-OR^9$, $-SR^9$, $-S(O)_tR^{10}$ where t is 1 or 2, $-N(R^9)_2$, $-COR^9$, $-CO_2R^9$, $-OCOR^{10}$, $-CON(R^9)_2$, $-SO_2N(R^9)_2$, $-NR^9COR^{10}$, $-NR^9CO_2R^{10}$, $-NR^9SO_2R^{10}$, $-CH=CHCH_2N(R^{16})_2$, $-CH_2OR^{10}$, $-CH_2N(R^{16})_2$, $-NHCOCH_2OR^{10}$ or $-NHCOCH_2N(R^{16})_2$;

$R^7$ represents H or $R^8$; or two $R^7$ groups together with a nitrogen atom to which they are mutually attached may complete a pyrrolidine, piperidine, piperazine or morpholine ring;

$R^8$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, Ar or $-C_{1-6}$alkylAr;

$R^9$ represents H or $R^{10}$; or two $R^9$ groups together with a nitrogen atom to which they are mutually attached may complete a pyrrolidine, piperidine, piperazine or morpholine ring which is optionally substituted by $R^{12}$, $-COR^{12}$ or $-SO_2R^{12}$;

$R^{10}$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, $C_{6-10}$aryl$C_{2-6}$alkenyl, or heteroaryl$C_{2-6}$alkenyl, wherein the alkyl, cycloalkyl, alkenyl and alkynyl groups optionally bear one substituent selected from halogen, $CF_3$, $NO_2$, CN, $-OR^{11}$, $-SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$; and the aryl, heteroaryl and heterocyclic groups optionally bear up to 3 substituents independently selected from halogen, $NO_2$, CN, $R^{12}$, $-OR^{11}$, $-SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$, wherein the $R^{10}$ heteroaryl group is selected from the group consisting of pyridinyl, pyridazinyl, pyrimidinyl, pyrazinyl, pyrrolyl, furyl, thienyl, oxazolyl, isoxazolyl, thiazolyl, isothiazolyl, oxadiazolyl, thiadiazolyl, 1,2,4-triazine, 1,3,5-triazine, 1,2,3,4-tetrahydroisoquinoline, imidazor[2,1-b]thiazole and benzo[1,4]dioxin;

$R^{11}$ represents H, $C_{1-6}$alkyl, perfluoro$C_{1-6}$alkyl, $C_{3-7}$cycloalkyl, $C_{2-6}$alkenyl, $C_{2-6}$alkynyl, Ar, $-C_{1-6}$alkylAr or ArO$C_{1-6}$alkyl;

$R^{12}$ represents $C_{1-6}$alkyl, perfluoro$C_{1-6}$alkyl, $C_{3-7}$cycloalkyl, $C_{2-6}$alkenyl, $C_{2-6}$alkynyl, Ar, $-C_{1-6}$alkylAr or ArO$C_{1-6}$alkyl; or two $R^{12}$ groups together with a nitrogen atom to which they are mutually attached may complete a heterocyclic ring system selected from the group consisting of pyrrolidine, piperidine, piperazine, morpholine, thiomorpholine, 2,5-diazabicyclo[2.2.1]heptane and 2-aza-5-oxabicyclo[2.2.1]heptane, said ring system bearing 0-2 substituents selected from halogen, CN, $NO_2$, $C_{1-6}$alkyl, perfluoro$C_{1-6}$alkyl, $C_{3-7}$cycloalkyl, $C_{2-6}$alkenyl, $C_{2-6}$alkynyl, Ar, $-C_{1-6}$alkylAr or ArO$C_{1-6}$alkyl, $OR^{11}$, $NHR^{11}$, and $COR^{11}$;

each $R^{16}$ independently represents H or $R^{10}$, or two $R^{16}$ groups together with the nitrogen to which they are mutually attached complete a mono- or bicyclic heterocyclic ring system of 5-10 ring atoms selected from C, N, O and S, said ring system optionally having an additional aryl or heteroaryl ring fused thereto, said heterocyclic system and/or additional fused ring bearing 0-3 substituents independently selected from halogen, $NO_2$, CN, $R^{12}$, $-OR^{11}$, $-SR^{11}$, $-SO_2R^{12}$, $-COR^{11}$, $-CO_2R^{11}$, $-CON(R^{11})_2$, $-OCOR^{12}$, $-N(R_{11})_2$ and $-NR^{11}COR^{12}$;

Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy;

"heterocyclyl" at every occurrence thereof means a cyclic or polycyclic system of up to 10 ring atoms selected from C, N, O and S, wherein none of the constituent rings is aromatic and wherein at least one ring atom is other than C; and or a pharmaceutically acceptable salt thereof.

5. A compound according to claim 4 of formula IV:

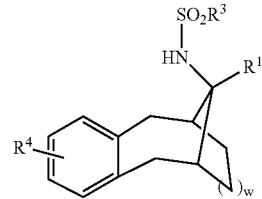

IV or a pharmaceutically acceptable salt thereof.

6. A compound according to claim 5 of formula V:

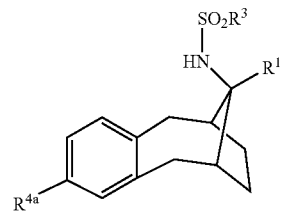

V wherein $R^{4a}$ represents $-N(R^9)_2$, $-NR^9COR^{10}$ or $-NR^9CO_2R^{10}$;

or a pharmaceutically acceptable salt thereof.

7. A compound according to claim 5 of formula VA:

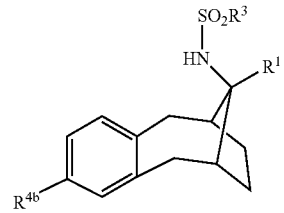

VA wherein $R^{4b}$ represents $C_{2-6}$alkenyl (which is optionally substituted by halogen, CN, $OR^{11}$, —$CO_2R^{11}$, —$COR^{11}$ or —$CON(R^{11})_2$), $C_{6-10}$aryl$C_{2-6}$alkenyl, heteroaryl$C_{2-6}$alkenyl, —CH=CHCH$_2$N($R^{16}$)$_2$, —$OR^{10}$, —CH$_2$OR$^9$, —NHCOCH$_2$OR$^{10}$ or —NHCOCH$_2$N($R^{16}$)$_2$;

or a pharmaceutically acceptable salt thereof.

8. A compound according to claim 7 wherein $R^{4b}$ represents —CH=CH$_2$, —CH=CHCN, —CH=CH—CH$_2$OR$^{11}$, —CH=CH—CO—Ar, —CH=CH—CO$_2$R$^{11}$, —CH=CHAr, —CH=CHCH$_2$N(R$^{16}$)$_2$, —OCH$_2$Ar, —OCH$_2$CH$_2$OR$^{12}$, —OCH$_2$CON(R$^{12}$)$_2$, —OCH$_2$CH$_2$N(R$^{12}$)$_2$, —CH$_2$OR$^9$, —NHCOCH$_2$OR$^{10}$ or —NHCOCH$_2$N(R$^{16}$)$_2$.

9. A compound of formula IIIC:

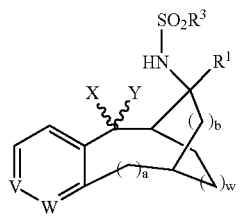

IIIC wherein

X represents halogen, $R^9$, —$OR^9$, —$SR^9$, —$S(O)_tR^{10}$ where t is 1 or 2, —$OSO_2R^9$, —$N(R^9)_2$, —$COR^9$, —$CO_2R^9$, —$OCOR^{10}$, —$OCO_2R^{10}$, —$CON(R^9)_2$, —$SO_2N(R^9)_2$, —$OSO_2N(R^9)_2$, —$NR^9COR^{10}$, —$NR^9CO_2R^{10}$ or —$NR^9SO_2R^{10}$;

Y represents H or $C_{1-6}$alkyl;

or X and Y together represent =O, =S, =N—OR$^{11}$ or =CHR$^{11}$;

$R^1$ represents H, $C_{1-4}$alkyl, or $C_{2-4}$alkenyl;

$R^2$ represents H;

$R^3$ represents $C_{1-16}$alkyl, $C_{3-10}$cycloalkyl, $C_{2-16}$alkenyl, $C_{2-16}$alkynyl, $C_{6-10}$aryl$C_{1-6}$alkyl, heteroaryl$C_{1-6}$alkyl, $C_{6-10}$aryl$C_{2-6}$alkenyl, heteroaryl$C_{2-6}$alkenyl, $C_{6-10}$aryl, bi($C_{6-10}$aryl), heteroaryl, bi(heteroaryl) or heterocyclyl; wherein the alkyl, cycloalkyl, alkenyl and alkynyl groups represented by $R^3$ or forming part of a group represented by $R^3$ optionally bear up to 3 substituents independently selected from halogen, CN, NO$_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkylNR$^7$COR$^8$, —$NR^7CO_2R^8$ and —$NR^7SO_2R^8$; and the aryl, heteroaryl and heterocyclic groups represented by $R^3$ or forming part of a group represented by $R^3$ optionally bear up to 5 substituents independently selected from $R^8$, halogen, CN, NO$_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkylNR$^7$COR$^8$, —$NR^7CO_2R^8$ and —$NR^7SO_2R^8$, wherein the $R^3$ heteroaryl group is a cyclic or polycyclic system of up to 10 ring atoms selected from C, N, O and S, wherein at least one of the constituent rings is aromatic and wherein at least one ring atom is other than C;

$R^4$ represents halogen, CN, NO$_2$, —$OR^9$, —$SR^9$, —$S(O)_tR^{10}$ where t is 1 or 2, —$N(R^9)_2$, —$COR^9$, —$CO_2R^9$, OCOR$^{10}$, —$CON(R^9)_2$, —$SO_2N(R^9)_2$, —$NR^9COR^{10}$, —$NR^9CO_2R^{10}$, —$NR^9SO_2R^{10}$, —CH=CHN(R$^{16}$)$_2$, —CH$_2$OR$^{10}$, —CH$_2$N(R$^{16}$)$_2$, —NHCOCH$_2$OR$^{10}$, or —NHCOCH$_2$N(R$^{16}$)$_2$;

$R^7$ represents H or $R^8$; or two $R^7$ groups together with a nitrogen atom to which they are mutually attached may complete a pyrrolidine, piperidine, piperazine or morpholine ring;

$R^8$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, Ar or —$C_{1-6}$alkylAr;

$R^9$ H or $R^{10}$; or two $R^9$ groups together with a nitrogen atom to which they are mutually attached may complete a pyrrolidine, piperidine, piperazine or morpholine ring which is optionally substituted by $R^{12}$, —COR$^{12}$ or —SO$_2$R$^{12}$;

$R^{10}$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, $C_{6-10}$aryl$C_{2-6}$alkenyl, or heteroaryl$C_{2-6}$alkenyl, wherein the alkyl, cycloalkyl, alkenyl and alkynyl groups optionally bear one substituent selected from halogen, CF$_3$, NO$_2$, CN, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$; and the aryl, heteroaryl and heterocyclic groups optionally bear up to 3 substituents independently selected from halogen, NO$_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$, wherein the $R^{10}$ heteroaryl group is selected from the group consisting of pyridinyl, pyridazinyl, pyrimidinyl, pyrazinyl, pyrrolyl, furyl, thienyl, oxazolyl, isoxazolyl, thiazolyl, isothiazolyl, oxadiazolyl, thiadiazolyl, 1,2,4-triazine, 1,3,5-triazine, 1,2,3,4-tetrahydroisoquinoline, imidazo[2,1-b]thiazole and benzo[1,4]dioxin;

$R^{11}$ represents H, $C_{1-6}$alkyl, perfluoro$C_{1-6}$alkyl, $C_{3-7}$cycloalkyl, $C_{2-6}$alkenyl, $C_{2-6}$alkynyl, Ar, —$C_{1-6}$alkylAr or ArOC$_{1-6}$alkyl;

$R^{12}$ represents $C_{1-6}$alkyl, perfluoro$C_{1-6}$alkyl, $C_{3-7}$cycloalkyl, $C_{2-6}$alkenyl, $C_{2-6}$alkynyl, Ar, —$C_{1-6}$alkylAr or ArOC$_{1-6}$alkyl; or two $R^{12}$ groups together with a nitrogen atom to which they are mutually attached may complete a heterocyclic ring system selected from the group consisting of pyrrolidine, piperidine, piperazine, morpholine, thiomorpholine, 2,5-diazabicyclo[2.2.1]heptane and 2-aza-5-oxabicyclo[2.2.1]heptane, said ring system bearing 0-2 substituents selected from halogen, CN, NO$_2$, $C_{1-6}$alkyl, perfluoro$C_{1-6}$alkyl, $C_{3-7}$cycloalkly, $C_{2-6}$alkenyl, $C_{2-6}$alkynyl, Ar, —$C_{1-6}$alkylAr or ArOC$_{1-6}$alkyl, OR$^{11}$, NHR$^{11}$, and COR$^{11}$ $R^{13}$ represents $R^9$, —$COR^{10}$, —$CO_2R^{10}$, —$SO_2R^{10}$, —$CON(R_9)_2$ or —$SO_2N(R^9)_2$;

each $R^{16}$ independently represents H or $R^{10}$, or two $R^{16}$ groups together with the nitrogen to which they are mutually attached complete a mono- or bicyclic heterocyclic ring system of 5-10 ring atoms selected from C, N, O and S, said ring system optionally having an additional aryl or heteroaryl ring fused thereto, said heterocyclic system and/or additional fused ring bearing 0-3 substituents independently selected from halogen, NO$_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

V represents CR$^4$ or N;

W represents CH or N;

a is 0 or 1;

b is 0; and w is 1 or 2;

or a pharmaceutically acceptable salt thereof.

10. A compound according to claim 5 wherein:

w is 1;

$R^1$ is H;

$R^3$ is selected from n-propyl, n-butyl, phenyl, 2-fluorophenyl, 3-fluorophenyl, 4-fluorophenyl, 2,4-difluorophenyl, 4-chlorophenyl, 2-thienyl, 5-chloro-2-thienyl, 5-bromo-2-thienyl, 3-pyridyl, 6-chloro-2-pyridyl and 5-isothiazolyl; and $R^4$ is selected from pyridine-2-carboxamido, phenoxyacetamido, 4-chlorophenoxyacetamido, 2,4-dichlorophenoxyacetamido, 4-fluorophenoxyacetimido, morpholin-4-ylacetamido, pyrrolidin-1-ylacetamido, piperidin-1-ylacetamido, 4-phenylpiperazin-1-ylacetamido, 4-(4-fluorophenyl)piperazin-1-ylacetamido, 2-(4-fluorophenoxy)ethoxy, 2-(morpholin-4-yl)ethoxy, 2-(morpholin-4-yl)ethylamino, 2-(4-fluorophenoxy)ethylamino, 2-(4-chlorophenoxy)ethylamino, 3-(4-fluorophenoxy)propenyl, 3-(imidazol-1-yl)propenyl, 3-(morpholin-4-yl)propenyl, 5-(pyridin-2-yl)-1,2,4-oxadiazol-3-yl, 5-(pyridin-3-yl)-1,2,4-oxadiazol-3-yl, 5-(pyridin-4-yl)-1,2,4-oxadiazol-3-yl, 3-(2-aza-5-oxabicyclo[2.2.1]hept-2-yl)propenyl, 2-(2-aza-5-oxabicyclo[2.2.1]hept-2-yl)ethoxy, 3-(4-fluoropiperidin-1-yl)propenyl, 2-(4-fluoropiperidin-1-yl)ethoxy, 3-(4-trifluoromethylpiperidin-1-yl)propenyl and 2-(4-trifluoromethylpiperidin-1-yl)ethoxy.

\* \* \* \* \*

UNITED STATES PATENT AND TRADEMARK OFFICE
CERTIFICATE OF CORRECTION

PATENT NO. : 7,365,196 B2 Page 1 of 2
APPLICATION NO. : 10/239233
DATED : April 29, 2008
INVENTOR(S) : Patrice Charles Belanger et al.

It is certified that error appears in the above-identified patent and that said Letters Patent is hereby corrected as shown below:

On the Title page,
Change Item (73) Assignees from "Merck Sharp & Dohme Ltd., Hoddesdon, Hertfordshire (GB); Merck Frosst Canada & Co., Kirkland, Quebec (CA)" to --Merck Sharp & Dohme, Ltd., Hoddesdon, Hertfordshire (GB); Merck Frosst Canada Ltd., Kirkland, Quebec (CA)--

Column 126, line 52, cancel the text beginning with "$Z^2$ completes" to and ending "or $ArOC_{1-6}$alkyl;" in column 127, line 45.

Column 128, line 25, insert the following text:

--$Z^2$ completes an imidazole ring;
X represents halogen, $R^9$, $-OR^9$, $-SR^9$, $-S(O)_tR^{10}$ where t is 1 or 2, $-OSO_2R^9$, $-N(R^9)_2$, $-COR^9$, $-CO_2R^9$, $-OCOR^{10}$, $-OCO_2R^{10}$, $-CON(R^9)_2$, $-SO_2N(R^9)_2$, $-OSO_2N(R^9)_2$, $-NR^9COR^{10}$, $-NR^9CO_2R^{10}$ or $-NR^9SO_2R^{10}$;
Y represents H or $C_{1-6}$alkyl;
or X and Y together represent =O, =S, =N-$OR^{11}$ or =$CHR^{11}$;
$R^1$ represents H, $C_{1-4}$alkyl, or $C_{2-4}$alkenyl;
$R^2$ represents H;
$R^3$ represents $C_{1-16}$alkyl, $C_{3-10}$cycloalkyl, $C_{2-16}$alkenyl, $C_{2-16}$alkynyl, $C_{6-10}$aryl$C_{1-6}$alkyl, heteroaryl$C_{1-6}$alkyl, $C_{6-10}$aryl$C_{2-6}$alkenyl, heteroaryl$C_{2-6}$alkenyl, $C_{6-10}$aryl, bi($C_{6-10}$aryl), heteroaryl, bi(heteroaryl) or heterocyclyl; wherein the alkyl, cycloalkyl, alkenyl and alkynyl groups represented by $R^3$ or forming part of a group represented by $R^3$ optionally bear up to 3 substituents independently selected from halogen, CN, $NO_2$, $-OR^7$, $-SR^7$, $-S(O)_tR^8$ where t is 1 or 2, $-N(R^7)_2$, $-COR^7$, $-CO_2R^7$, $-OCOR^8$, $-CON(R^7)_2$, $-NR^7COR^8$, $-C_{1-6}$alkyl$NR^7COR^8$, $-NR^7CO_2R^8$ and $-NR^7SO_2R^8$; and the aryl, heteroaryl and heterocyclic groups represented by $R^3$ or forming part of a group represented by $R^3$ optionally bear up to 5 substituents independently selected from $R^8$, halogen, CN, $NO_2$, $-OR^7$, $-SR^7$, $-S(O)_tR^8$ where t is 1 or 2, $-N(R^7)_2$, $-COR^7$, $-CO_2R^7$, $-OCOR^8$, $-CON(R^7)_2$, $-NR^7COR^8$, $-C_{1-6}$alkyl$NR^7COR^8$, $-NR^7CO_2R^8$ and $-NR^7SO_2R^8$;
$R^7$ represents H or $R^8$; or two $R^7$ groups together with a nitrogen atom to which they are mutually attached may complete a pyrrolidine, piperidine, piperazine or morpholine ring;
$R^8$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, Ar or $-C_{1-6}$alkylAr;

UNITED STATES PATENT AND TRADEMARK OFFICE
CERTIFICATE OF CORRECTION

PATENT NO. : 7,365,196 B2
APPLICATION NO. : 10/239233
DATED : April 29, 2008
INVENTOR(S) : Patrice Charles Belanger et al.

It is certified that error appears in the above-identified patent and that said Letters Patent is hereby corrected as shown below:

$R^9$ represents H or $R^{10}$; or two $R^9$ groups together with a nitrogen atom to which they are mutually attached may complete a pyrrolidine, piperidine, piperazine or morpholine ring which is optionally substituted by $R^{12}$, $-COR^{12}$ or $-SO_2R^{12}$;

$R^{10}$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, $C_{6-10}$aryl$C_{2-6}$alkenyl, or heteroaryl$C_{2-6}$alkenyl, wherein the alkyl, cycloalkyl, alkenyl and alkynyl groups optionally bear one substituent selected from halogen, $CF_3$, $NO_2$, CN, $-OR^{11}$, $-SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$; and the aryl, heteroaryl and heterocyclic groups optionally bear up to 3 substituents independently selected from halogen, $NO_2$, CN, $R^{12}$, $-OR^{11}$, $-SR^{11}$, $-SO_2R^{12}$, $-COR^{11}$, $-CO_2R^{11}$, $-CON(R^{11})_2$, $-OCOR^{12}$, $-N(R^{11})_2$ and $-NR^{11}COR^{12}$;

$R^{11}$ represents H, $C_{1-6}$alkyl, perfluoro$C_{1-6}$alkyl, $C_{3-7}$cycloalkyl, $C_{2-6}$alkenyl, $C_{2-6}$alkynyl, Ar, -$C_{1-6}$alkylAr or ArO$C_{1-6}$alkyl;--

Signed and Sealed this

Seventeenth Day of November, 2009

David J. Kappos
*Director of the United States Patent and Trademark Office*